(12) United States Patent
Baik et al.

(10) Patent No.: US 11,613,558 B2
(45) Date of Patent: *Mar. 28, 2023

(54) PEPTIDES AND PHARMACEUTICAL COMPOSITIONS FOR TREATING EYE DISEASES

(71) Applicant: Yuyu Pharma, Inc., Seoul (KR)

(72) Inventors: Taegon Baik, Seoul (KR); Jong-Yun Choi, Chungcheongbuk-do (KR); Gyoung-Wook Min, Gyeonggi-do (KR); Chun-Ho Park, Yongin-Si (KR)

(73) Assignee: Yuyu Pharma, Inc., Seoul (KR)

( * ) Notice: Subject to any disclaimer, the term of this patent is extended or adjusted under 35 U.S.C. 154(b) by 240 days.

This patent is subject to a terminal disclaimer.

(21) Appl. No.: 16/683,962

(22) Filed: Nov. 14, 2019

(65) Prior Publication Data

US 2020/0270306 A1 Aug. 27, 2020

Related U.S. Application Data

(60) Provisional application No. 62/767,183, filed on Nov. 14, 2018, provisional application No. 62/767,180, filed on Nov. 14, 2018.

(51) Int. Cl.
| | | |
|---|---|---|
| *C07K 7/06* | (2006.01) | |
| *A61P 27/04* | (2006.01) | |
| *A61K 9/00* | (2006.01) | |
| *A61K 38/00* | (2006.01) | |

(52) U.S. Cl.
CPC .............. *C07K 7/06* (2013.01); *A61K 9/0048* (2013.01); *A61P 27/04* (2018.01); *A61K 38/00* (2013.01)

(58) Field of Classification Search
None
See application file for complete search history.

(56) References Cited

U.S. PATENT DOCUMENTS

| | | |
|---|---|---|
| 6,037,135 A | 3/2000 | Kubo et al. |
| 9,695,218 B2 | 7/2017 | Yang et al. |
| 2014/0309400 A1 | 10/2014 | Combette et al. |
| 2016/0215018 A1 | 7/2016 | Yang et al. |
| 2019/0002528 A1 | 1/2019 | Yang et al. |
| 2019/0111112 A1 | 4/2019 | Yang |
| 2020/0270306 A1 | 8/2020 | Baik et al. |
| 2021/0024577 A1 | 1/2021 | Baik et al. |

FOREIGN PATENT DOCUMENTS

| | | | |
|---|---|---|---|
| KR | 20100087188 A | 8/2010 | |
| KR | 101438744 B1 | 9/2014 | |
| KR | 20160079983 A | 7/2016 | |
| KR | 101795653 B1 | 11/2017 | |
| KR | 10-2018-0074928 A | 7/2018 | |
| WO | WO-2012/166610 A1 | 12/2012 | |
| WO | WO-2015/088096 A1 | 6/2015 | |
| WO | WO-2016/104964 A1 | 6/2016 | |
| WO | WO-2017/018613 A1 | 2/2017 | |
| WO | WO 2017/101748 * | 6/2017 | ............... C07K 7/04 |
| WO | WO-2017/175963 A1 | 10/2017 | |
| WO | WO-2018/225961 A1 | 12/2018 | |
| WO | WO-2020/099925 A2 | 5/2020 | |
| WO | WO-2021/191689 A2 | 9/2021 | |

OTHER PUBLICATIONS

Extended European Search Report for EP Application No. EP 18812841 dated Mar. 3, 2021.
Kim et al., "Effects of chondrocyte-derived extracellular matrix in a dry eye mouse model," Mol Vision, 21: 1210-1223 (2015).
International Search Report and Written Opinion for International Application No. PCT/IB2019/001220 dated May 7, 2020.
International Search Report and Written Opinion for International Application No. PCT/KR2018/005673 dated Oct. 24, 2018.
Shankar et al., "Structural determinants of calcium signaling by RGD peptides in rat osteoclasts: integrin-dependent and-independent actions," Experimental Cell Research, 219: 364-371 (1995).
International Preliminary Report on Patentability for International Application No. PCT/IB2019/001220 dated May 18, 2021.
International Search Report and Written Opinion for International Application No. PCT/IB2021/000423 dated Nov. 17, 2021.
Lee et al., "Anti-inflammatory effect of hydroxyproline-GQDGLAGPK in desiccation stress-induced experimental dry eye mouse," Sci Rep, 7(7413): 1-12 (2017).

* cited by examiner

*Primary Examiner* — Kevin S Orwig
(74) *Attorney, Agent, or Firm* — Foley Hoag LLP; David P. Halstead; Laura A. Wzorek

(57) ABSTRACT

The present invention relates to novel peptides and a pharmaceutical compositions comprising the same. The peptide compounds and compositions disclosed herein are useful as therapeutic agents for treating eye diseases. When administered to the eyes, the peptide compounds and compositions disclosed herein increase the amount of tear secretion and promotes recovery of a damaged cornea.

24 Claims, 61 Drawing Sheets
Specification includes a Sequence Listing.

| No. | Lot Number | Peptide Name | Sequence | M.W. | Purity (%) | Amount (mg) | Solubility (0.5mg/ml) |
|---|---|---|---|---|---|---|---|
| 1 | K161389 | YDE-001 | OGQEGLAGPK (O : Hydroxyproline) | 969.1 | >99.7% | 5.0mg 10.0mg | Water |
| 2 | K161390 | YDE-002 | OGQNGLAGPK (O : Hydroxyproline) | 954.0 | >99.7% | 5.0mg 10.0mg | Water |
| 3 | K161391 | YDE-003 | OGQQGLAGPK (O : Hydroxyproline) | 968.1 | >99.7% | 5.0mg 10.0mg | Water |
| 4 | K161392 | YDE-004 | OGQHGLAGPK (O : Hydroxyproline) | 977.1 | >99.7% | 5.0mg 10.0mg | Water |
| 5 | K161393 | YDE-005 | OGQKGLAGPK (O : Hydroxyproline) | 968.1 | >99.5% | 5.0mg 10.0mg | Water |
| 6 | K161394 | YDE-006 | OGQSGLAGPK (O : Hydroxyproline) | 927.0 | >98.9% | 5.0mg 10.0mg | Water |
| 7 | K161395 | YDE-007 | OGQTGLAGPK (O : Hydroxyproline) | 941.0 | >98.0% | 5.0mg 10.0mg | Water |
| 8 | K161396 | YDE-008 | OGQAGLAGPK (O : Hydroxyproline) | 911.0 | >98.8% | 5.0mg 10.0mg | Water |
| 9 | K161397 | YDE-009 | OGQVGLAGPK (O : Hydroxyproline) | 939.1 | >98.1% | 5.0mg 10.0mg | Water |
| 10 | K161398 | YDE-010 | OGQIGLAGPK (O : Hydroxyproline) | 953.1 | >99.0% | 5.0mg 10.0mg | Water |
| 11 | K161399 | YDE-011 | OGQLGLAGPK (O : Hydroxyproline) | 953.1 | >98.3% | 5.0mg 10.0mg | Water |
| 12 | K161400 | YDE-012 | OGQFGLAGPK (O : Hydroxyproline) | 987.1 | >98.9% | 5.0mg 10.0mg | Water |
| 13 | K161401 | YDE-013 | OGQYGLAGPK (O : Hydroxyproline) | 1003.1 | >98.7% | 5.0mg 10.0mg | Water |
| 14 | K161402 | YDE-014 | OGQWGLAGPK (O : Hydroxyproline) | 1026.2 | >98.5% | 5.0mg 10.0mg | Water |

Fig. 1

| 15 | K161403 | YDE-015 | OGQDVLAGPK (O : Hydroxyproline) | 997.1 | >99.1% | 5.0mg 10.0mg | Water |
|---|---|---|---|---|---|---|---|
| 16 | K161404 | YDE-016 | OGQDILAGPK (O : Hydroxyproline) | 1011.1 | >99.4% | 5.0mg 10.0mg | Water |
| 17 | K161405 | YDE-017 | OGQDLLAGPK (O : Hydroxyproline) | 1011.1 | >98.0% | 5.0mg 10.0mg | Water |
| 18 | K161406 | YDE-018 | OGQDALAGPK (O : Hydroxyproline) | 969.1 | >99.6% | 5.0mg 10.0mg | Water |
| 19 | K161407 | YDE-019 | OGQDFLAGPK (O : Hydroxyproline) | 1045.2 | >99.6% | 5.0mg 10.0mg | Water |
| 20 | K161408 | YDE-020 | OGQDYLAGPK (O : Hydroxyproline) | 1061.2 | >99.2% | 5.0mg 10.0mg | Water |
| 21 | K161409 | YDE-021 | OGQDWLAGPK (O : Hydroxyproline) | 1084.2 | >98.1% | 5.0mg 10.0mg | Water |
| 22 | K161410 | YDE-022 | OGQDHLAGPK (O : Hydroxyproline) | 1035.1 | >98.3% | 5.0mg 10.0mg | Water |
| 23 | K161411 | YDE-023 | OGQDSLAGPK (O : Hydroxyproline) | 985.1 | >96.1% | 5.0mg 10.0mg | Water |
| 24 | K161412 | YDE-024 | OGQDTLAGPK (O : Hydroxyproline) | 999.1 | >98.9% | 5.0mg 10.0mg | Water |
| 25 | K161413 | YDE-025 | OGQD-Sar-LAGPK (Sar : me-Gly) (O : Hydroxyproline) | 969.1 | >95% | 5.0mg 10.0mg | Water |
| 26 | K161414 | YDE-026 | OGQS*GLAGPK (S* : homo-Ser) (O : Hydroxyproline) | 941.1 | >95% | 5.0mg 10.0mg | Water |
| 27 | K161415 | YDE-027 | OGQD*GLAGPK (D* : D(OMe)) (O: Hydroxyproline) | 969.1 | >95% | 5.0mg 10.0mg | Water |
| 28 | K161416 | YDE-028 | OGQN*GLAGPK (N* : N(NMe)) (O : Hydroxyproline) | 968.1 | >95% | 5.0mg 10.0mg | Water |

Fig. 1, continued

| Items<br>Groups | Body weights at<br>ELGE surgery* | First test material<br>topical eye drop [A] | 24 hrs after last<br>treatment [B]* | Body weight gains<br>[B-A] |
|---|---|---|---|---|
| Control | | | | |
| Sham | 213.63±21.04 | 305.50±33.53 | 340.50±38.46 | 35.00±11.19 |
| ELGE | 215.50±16.10 | 302.63±20.42 | 339.13±20.01 | 36.50±9.97 |
| Reference | | | | |
| DS | 220.50±8.70 | 304.50±13.11 | 340.63±10.20 | 36.13±5.38 |
| Test materials (0.3% solutions) | | | | |
| YY-102 | 211.88±12.89 | 302.00±20.70 | 337.75±25.96 | 35.75±6.84 |
| YDE-01 | 212.63±11.30 | 302.25±24.57 | 341.00±24.98 | 38.75±9.50 |
| YDE-02 | 210.38±10.89 | 302.00±15.96 | 338.00±22.39 | 36.00±12.29 |
| YDE-03 | 212.50±14.84 | 301.00±20.63 | 339.38±22.93 | 38.38±7.74 |
| YDE-04 | 217.50±16.25 | 302.50±19.66 | 338.50±21.44 | 36.00±10.97 |
| YDE-05 | 212.50±16.75 | 303.50±17.77 | 341.50±17.53 | 38.00±3.12 |
| YDE-06 | 212.38±19.00 | 306.38±25.31 | 345.13±21.06 | 38.75±6.14 |
| YDE-07 | 219.13±4.73 | 310.50±9.99 | 349.88±12.28 | 39.38±4.83 |
| YDE-08 | 213.38±13.99 | 307.00±15.73 | 345.63±17.87 | 38.63±7.01 |
| YDE-09 | 215.63±13.69 | 304.25±18.58 | 341.38±25.47 | 37.13±10.34 |
| YDE-10 | 216.00±12.99 | 305.25±13.82 | 343.63±16.36 | 38.38±6.44 |
| YDE-11 | 219.88±13.42 | 309.13±20.36 | 347.00±27.91 | 37.88±13.66 |
| YDE-12 | 222.13±9.98 | 311.00±15.57 | 349.88±21.70 | 38.88±9.08 |
| YDE-13 | 217.63±4.69 | 305.13±7.66 | 343.25±11.44 | 38.13±7.20 |
| YDE-14 | 216.75±15.53 | 301.25±20.11 | 339.75±26.99 | 38.50±9.94 |
| YDE-15 | 214.88±14.74 | 302.13±16.57 | 340.00±16.44 | 37.88±12.69 |
| YDE-16 | 213.50±18.31 | 299.50±16.42 | 337.38±20.50 | 37.88±7.57 |
| YDE-17 | 214.63±11.81 | 306.63±17.54 | 346.25±19.26 | 39.63±10.51 |
| YDE-18 | 213.88±13.34 | 307.88±13.27 | 347.38±23.02 | 39.50±14.68 |
| YDE-19 | 218.88±11.29 | 307.25±12.85 | 345.38±21.71 | 38.13±9.83 |
| YDE-20 | 217.88±9.61 | 300.75±16.79 | 339.25±15.68 | 38.50±3.71 |
| YDE-21 | 216.38±15.31 | 301.38±20.89 | 340.13±21.53 | 38.75±8.14 |
| YDE-22 | 219.38±10.85 | 304.13±14.56 | 343.50±21.37 | 39.38±9.30 |
| YDE-23 | 219.00±12.54 | 308.25±15.64 | 346.00±15.26 | 37.75±6.94 |
| YDE-24 | 212.13±18.41 | 298.38±25.85 | 334.00±31.75 | 35.63±10.29 |
| YDE-25 | 213.13±13.39 | 303.63±21.87 | 342.50±19.82 | 38.88±5.84 |
| YDE-26 | 213.63±14.71 | 305.75±23.07 | 343.25±29.09 | 37.50±9.38 |
| YDE-27 | 214.75±13.73 | 306.63±25.44 | 345.38±26.40 | 38.75±10.02 |
| YDE-28 | 212.75±13.36 | 297.63±21.12 | 336.38±22.02 | 38.75±7.63 |

Fig. 5

| Groups | Items | Body weights at ELGE surgery* | First test material topical eye drop [A] | 24 hrs after last treatment [B]* | Body weight gains [B-A] |
|---|---|---|---|---|---|
| Control | | | | | |
| Sham | | 242.38±7.73 | 320.25±9.91 | 363.38±27.21 | 43.13±19.71 |
| ELGE | | 243.88±3.83 | 329.25±18.90 | 367.50±19.89 | 38.25±11.40 |
| Reference | | | | | |
| DS | | 246.63±15.68 | 330.50±23.33 | 369.63±37.46 | 39.13±25.56 |
| YY-101 | | 241.25±4.37 | 318.88±10.91 | 356.25±18.16 | 37.38±7.82 |
| YY-102 | | 242.38±11.46 | 318.75±15.20 | 361.25±23.56 | 42.50±9.41 |
| Test materials (0.3% solutions) | | | | | |
| YDE-029 | | 242.25±16.63 | 327.38±18.75 | 373.75±28.50 | 46.38±12.49 |
| YDE-030 | | 243.25±10.26 | 315.88±14.96 | 355.50±29.68 | 39.63±16.61 |
| YDE-031 | | 241.00±15.82 | 316.75±27.58 | 359.00±39.87 | 42.25±14.96 |
| YDE-032 | | 242.75±9.32 | 324.25±14.59 | 365.38±16.16 | 41.13±10.12 |
| YDE-033 | | 243.50±11.96 | 327.50±17.57 | 377.13±26.59 | 49.63±16.27 |
| YDE-034 | | 243.88±8.68 | 322.63±17.15 | 361.63±19.08 | 39.00±4.99 |
| YDE-035 | | 240.88±11.29 | 321.00±22.17 | 358.50±29.18 | 37.50±20.36 |
| YDE-036 | | 242.25±14.01 | 329.38±21.07 | 378.38±24.20 | 49.00±10.81 |
| YDE-037 | | 244.50±10.94 | 324.88±17.36 | 369.13±21.43 | 44.25±8.83 |
| YDE-039 | | 242.88±7.14 | 325.25±15.51 | 363.25±28.35 | 38.00±15.41 |
| YDE-040 | | 241.13±13.39 | 319.25±14.10 | 357.00±27.93 | 37.75±19.37 |
| YDE-041 | | 244.75±14.49 | 322.88±22.47 | 366.13±37.43 | 43.25±16.97 |
| YDE-042 | | 239.13±8.29 | 323.38±8.28 | 372.38±19.46 | 49.00±13.54 |
| YDE-043 | | 246.25±7.92 | 324.00±14.31 | 361.25±19.20 | 37.25±13.63 |

| Items | Tear volumes (mm) after test material topical eye drop | | |
|---|---|---|---|
| Groups | -1 day | 7 days | 14 days |
| Control | | | |
| Sham | 8.34±0.73 | 8.56±0.76 | 8.63±0.93 |
| ELGE | 3.54±0.78a | 2.65±0.85a | 3.27±1.06a |
| Reference | | | |
| DS | 3.53±0.66a | 4.10±1.07ac | 4.80±0.94ac |
| Test materials (0.3% solutions) | | | |
| YY-102 | 3.58±0.93a | 4.59±1.43ac | 5.77±1.99ac |
| YDE-01 | 3.55±0.93a | 4.88±1.62ac | 5.92±2.19ac |
| YDE-02 | 3.59±0.75a | 3.84±1.16a | 5.01±1.67ac |
| YDE-03 | 3.56±0.74a | 4.13±1.76ac | 4.88±1.57ac |
| YDE-04 | 3.57±0.59a | 3.42±1.06a | 5.19±1.84ac |
| YDE-05 | 3.56±0.86a | 3.85±0.93a | 5.08±1.91ac |
| YDE-06 | 3.56±0.63a | 3.44±1.69a | 5.35±1.68ac |
| YDE-07 | 3.53±0.68a | 3.91±1.28a | 5.45±1.26ac |
| YDE-08 | 3.54±0.82a | 4.37±1.25ac | 6.10±2.36ac |
| YDE-09 | 3.56±0.78a | 3.76±1.21a | 4.54±1.11a |
| YDE-10 | 3.52±0.61a | 3.42±1.31a | 4.35±1.36a |
| YDE-11 | 3.56±0.88a | 4.22±1.45ac | 6.16±2.16ac |
| YDE-12 | 3.55±0.71a | 3.68±0.99a | 5.67±1.86ac |
| YDE-13 | 3.55±0.49a | 5.27±1.50ac | 5.49±1.92ac |
| YDE-14 | 3.55±0.66a | 3.81±1.21a | 5.62±1.85ac |
| YDE-15 | 3.54±0.73a | 4.03±2.19ac | 6.65±2.13ac |
| YDE-16 | 3.56±0.93a | 4.39±1.13ac | 5.98±2.27ac |
| YDE-17 | 3.54±0.91a | 4.00±1.22ac | 4.89±1.50a |
| YDE-18 | 3.58±0.68a | 3.75±1.34a | 4.99±1.60ac |
| YDE-19 | 3.58±0.63a | 4.84±1.39ac | 4.52±1.07a |
| YDE-20 | 3.56±0.86a | 3.41±1.47a | 4.20±1.39a |
| YDE-21 | 3.55±0.72a | 4.08±1.33ac | 4.90±1.13a |
| YDE-22 | 3.50±0.75a | 3.19±0.67a | 4.10±0.99a |
| YDE-23 | 3.51±0.72a | 5.32±2.30ac | 5.78±2.23ac |
| YDE-24 | 3.53±0.63a | 3.85±1.30a | 5.72±1.36ac |
| YDE-25 | 3.56±0.75a | 3.21±0.72a | 4.72±2.19a |
| YDE-26 | 3.57±0.57a | 4.32±1.47ac | 6.01±1.83ac |
| YDE-27 | 3.57±0.64a | 2.82±0.86a | 3.95±1.53a |
| YDE-28 | 3.56±0.91a | 4.04±0.99ac | 4.73±1.18a |

Fig. 10

| Groups | Items | Tear volumes (mm) after test material topical eye drop | | |
|---|---|---|---|---|
| | | -1 day | 7 days | 14 days |
| Control | | | | |
| Sham | | 10.90±1.69 | 10.38±1.08 | 10.28±0.69 |
| ELGE | | 4.81±1.09[a] | 4.37±0.83[b] | 4.70±0.65[b] |
| Reference | | | | |
| DS | | 4.74±1.30[a] | 5.72±1.28[be] | 6.56±1.15[bd] |
| YY-101 | | 4.86±1.08[a] | 5.36±0.68[be] | 6.25±0.68[bd] |
| YY-102 | | 4.94±0.71[a] | 5.77±1.01[be] | 6.60±0.64[bd] |
| Test materials (0.3% solutions) | | | | |
| YDE-029 | | 4.72±1.05[a] | 5.33±1.43[b] | 6.03±1.71[b] |
| YDE-030 | | 4.93±1.15[a] | 5.69±1.79[b] | 6.65±2.17[b] |
| YDE-031 | | 4.70±0.69[a] | 5.63±1.97[b] | 5.91±0.85[be] |
| YDE-032 | | 4.94±1.04[a] | 5.58±0.80[be] | 5.03±0.93[b] |
| YDE-033 | | 4.77±1.32[a] | 4.99±1.20[b] | 4.54±1.16[b] |
| YDE-034 | | 4.88±1.07[a] | 6.16±1.01[bd] | 6.43±1.86[b] |
| YDE-035 | | 4.92±1.18[a] | 4.96±0.96[b] | 6.25±0.79[bd] |
| YDE-036 | | 4.83±1.07[a] | 4.95±1.05[b] | 5.13±1.03[b] |
| YDE-037 | | 4.68±0.83[a] | 4.98±0.66[b] | 5.80±0.96[be] |
| YDE-039 | | 4.81±1.27[a] | 6.04±1.01[bd] | 6.44±1.96[be] |
| YDE-040 | | 4.77±0.91[a] | 5.77±1.05[be] | 8.63±1.53[cd] |
| YDE-041 | | 4.87±1.19[a] | 5.01±1.26[b] | 6.25±2.15[b] |
| YDE-042 | | 4.83±0.84[a] | 6.30±1.08[bd] | 7.97±1.48[bd] |
| YDE-043 | | 4.86±0.81[a] | 5.90±1.06[bd] | 8.16±1.42[bd] |

| Groups | Items | Fluorescent stained cornea areas (%) |
|---|---|---|
| Control | | |
| | Sham | 2.62±1.71 |
| | ELGE | 57.34±12.83a |
| Reference | | |
| | DS | 35.40±13.32a |
| Test materials (0.3% solutions) | | |
| | YY-102 | 27.48±14.37ac |
| | YDE-01 | 25.49±11.62ac |
| | YDE-02 | 38.26±11.25ac |
| | YDE-03 | 40.45±6.46ac |
| | YDE-04 | 35.05±11.74ac |
| | YDE-05 | 37.98±11.53ac |
| | YDE-06 | 33.23±13.20ac |
| | YDE-07 | 32.79±10.77ac |
| | YDE-08 | 20.32±11.87ac |
| | YDE-09 | 41.50±7.86ac |
| | YDE-10 | 49.29±12.06a |
| | YDE-11 | 18.11±11.61ac |
| | YDE-12 | 31.01±11.38ac |
| | YDE-13 | 32.24±7.84ac |
| | YDE-14 | 31.15±10.87ac |
| | YDE-15 | 15.95±6.48ac |
| | YDE-16 | 24.57±10.34ac |
| | YDE-17 | 39.76±7.42ac |
| | YDE-18 | 38.19±10.96ac |
| | YDE-19 | 40.39±12.57ac |
| | YDE-20 | 47.84±13.47a |
| | YDE-21 | 37.00±10.49ac |
| | YDE-22 | 47.82±10.01a |
| | YDE-23 | 26.51±8.18ac |
| | YDE-24 | 30.63±10.41ac |
| | YDE-25 | 47.10±11.45a |
| | YDE-26 | 22.63±11.23ac |
| | YDE-27 | 50.24±11.94a |
| | YDE-28 | 41.17±10.25ac |

Fig. 15

| Groups | Items Fluorescent stained cornea areas (%) |
|---|---|
| Control | |
| Sham | 1.53±0.65 |
| ELGE | 66.71±10.02[b] |
| Reference | |
| DS | 30.03±10.97[bd] |
| YY-101 | 33.80±11.11[bd] |
| YY-102 | 27.89±7.10[bd] |
| Test materials (0.3% solutions) | |
| YDE-029 | 63.45±11.57[b] |
| YDE-030 | 30.60±13.61[bd] |
| YDE-031 | 33.35±11.01[bd] |
| YDE-032 | 58.90±19.81[b] |
| YDE-033 | 60.55±21.22[b] |
| YDE-034 | 32.17±12.94[bd] |
| YDE-035 | 27.62±6.51[bd] |
| YDE-036 | 57.87±22.91[b] |
| YDE-037 | 36.30±9.75[bd] |
| YDE-039 | 29.94±11.40[bd] |
| YDE-040 | 18.33±9.41[bd] |
| YDE-041 | 46.38±26.65[b] |
| YDE-042 | 20.72±11.37[bd] |
| YDE-043 | 19.04±7.36[bd] |

Fig. 17

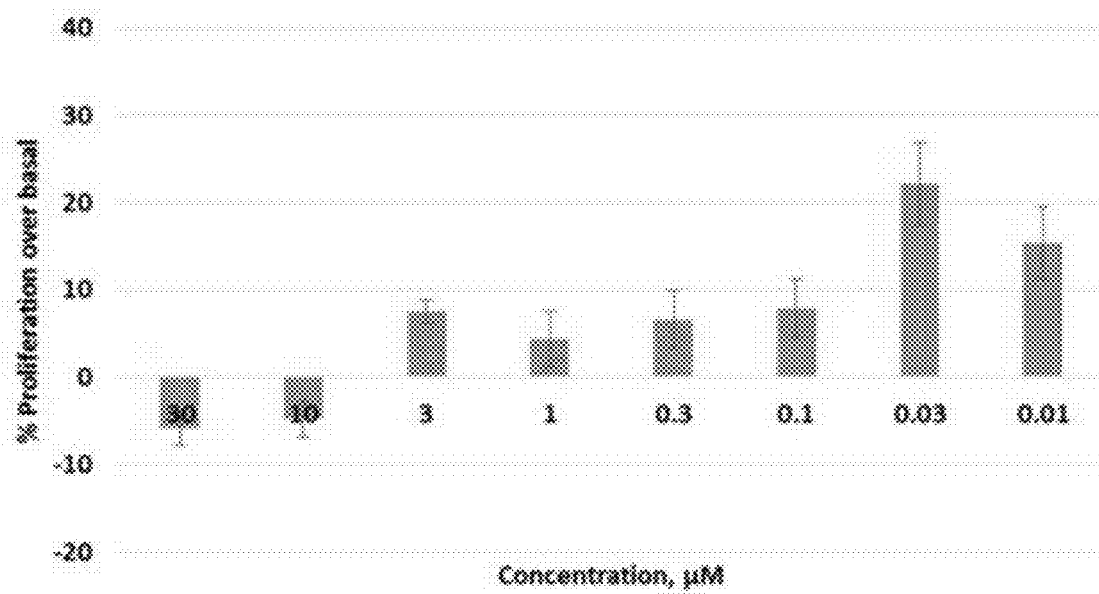
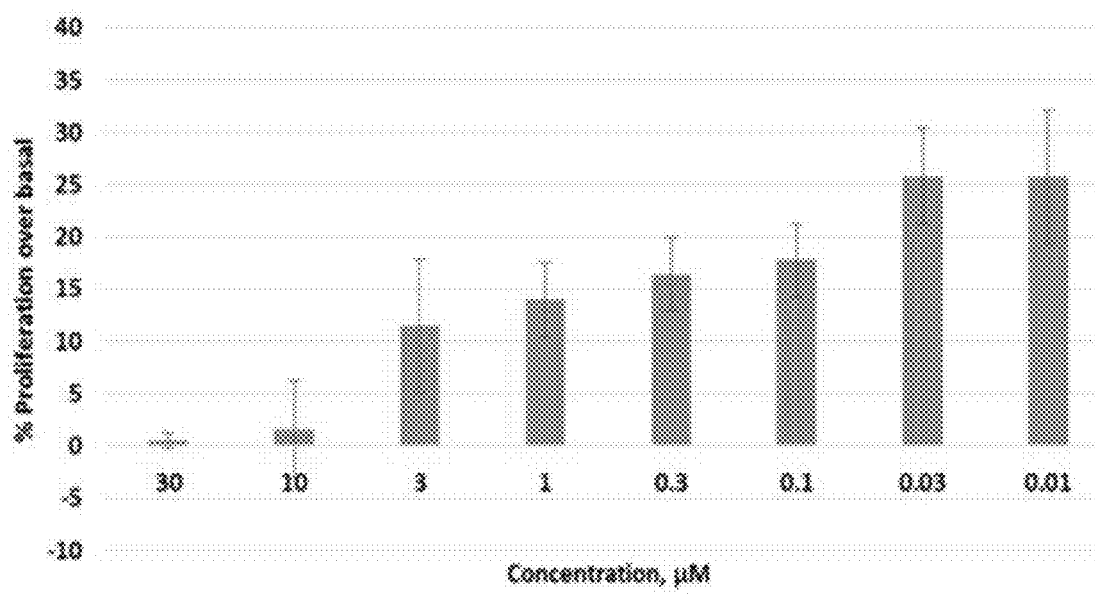
Fig. 37

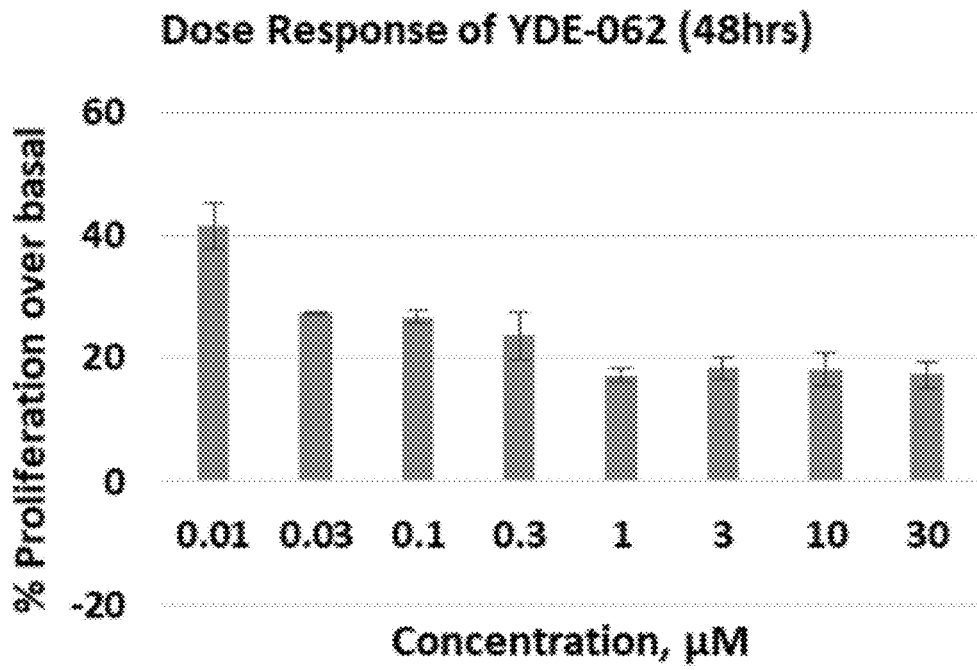
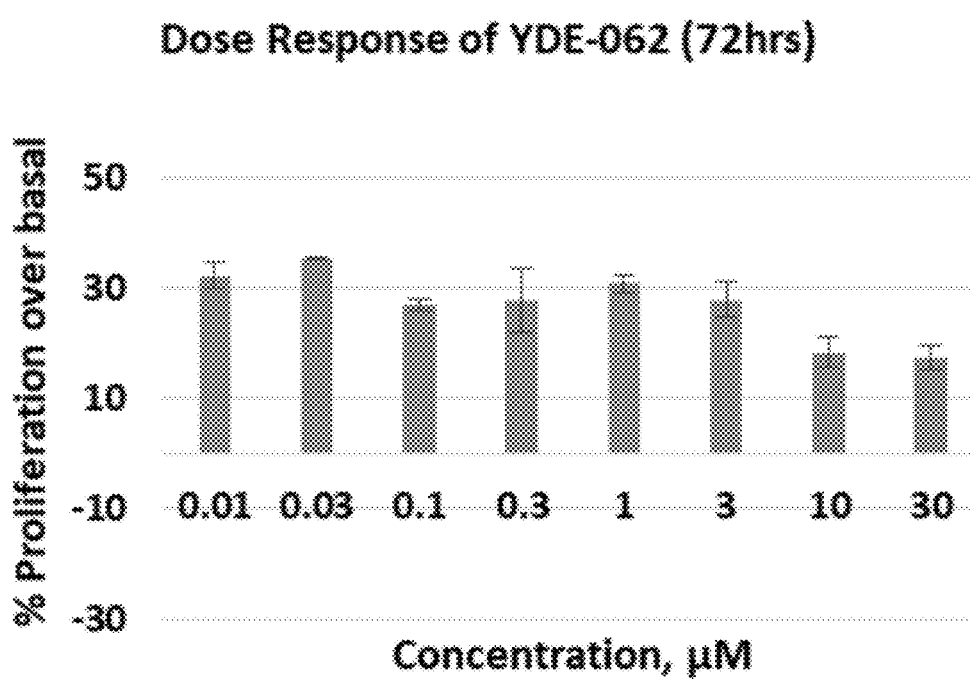
Fig. 68

PEPTIDES AND PHARMACEUTICAL COMPOSITIONS FOR TREATING EYE DISEASES

RELATED APPLICATIONS

This application claims the benefit of priority to U.S. Provisional Patent Application Ser. No. 62/767,180, filed Nov. 14, 2018; and U.S. Provisional Patent Application Ser. No. 62/767,183, filed Nov. 14, 2018; the contents of each of which are hereby incorporated by reference.

SEQUENCE LISTING

The instant application contains a Sequence Listing which has been submitted electronically in ASCII format and is hereby incorporated by reference in its entirety. Said ASCII copy, created on Mar. 29, 2020, is named YUH-00201_SL.txt and is 38,933 bytes in size.

TECHNICAL FIELD

The present invention relates to peptides and pharmaceutical compositions for treating eye diseases.

BACKGROUND

Dry eye syndrome or keratoconjunctivitis sicca may be defined, in a broad sense, as damage to the ocular surface due to tear secretion disorders (Joossen C et al., *Exp. Eye Res.*, 146:172-8, 2016). Dry eye syndrome is known to cause tear secretion disorders and damage and discomfort to the eyeball due to a combination of various factors. Although the onset of dry eye syndrome is closely related to age, the incidence thereof is increasing in younger age groups due to a long-term exposure to a dry environment as the use of contact lenses, computers, and smart devices (Stern M E et al., *Int. Rev. Immunol.*, 32: 19-41, 2013).

Specifically, dry eye syndrome reduces the mucus secretion of the corneal and conjunctival epithelia and that of the mucus-secreting goblet cells, resulting in a sharp decrease in the lubrication of the eyeball. In addition, dry eye syndrome causes damage to the corneal surface, thereby increasing the penetration of a fluorescein dye into the cornea. These symptoms of dry eye syndrome can be evaluated as changes in the tear secretion through the Schirmer test, which uses cobalt chloride paper. Further, the damage to the cornea that may accompany dry eye syndrome can be easily evaluated using a general fluorescent dye and a slit-lamp fluorophotometer.

In the meantime, most of the treatments for dry eye syndrome are confined to symptom therapies, the treatment efficiency of which is often very low. Currently, artificial tears are the first choice for the treatment of dry eye syndrome. Artificial tears as a representative symptom therapy merely supplement the insufficient tears; moreover, they suffer from the disadvantage that they need to be administered to the eyes frequently (Kim C S et al., *Nutrients* 8. pii: E750, 2016). Sodium hyaluronate and eye drops derived from autologous serum have been developed and used in patients suffering from dry eye syndrome. In addition, such synthetic compounds as rebamipide (OPC-127959) and diquafosol sodium, which promote the secretion of tears and mucus, have been developed and used. Long-term use of these drugs, however, may give rise to various side effects such as ocular hyperemia and corneal calcification (Bernauer W et al., *Br. J. Ophthalmol.*, 90:285-8, 2006). Therefore, there has been a demand for the development of a safe and effective therapeutic agent for treating dry eye syndrome.

SUMMARY OF INVENTION

In certain aspects, the invention provides a compound represented by Formula (I):

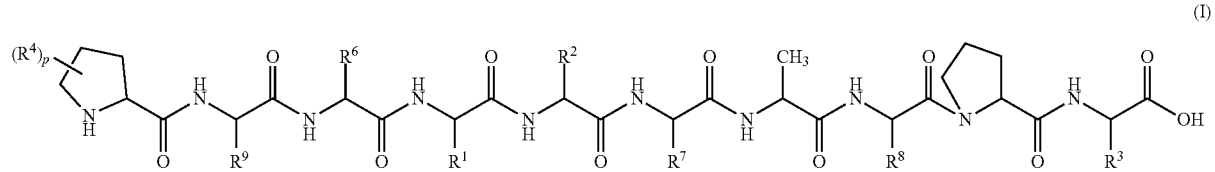

or a pharmaceutically acceptable salt thereof; wherein:

$R^1$, $R^2$, and $R^3$ are each independently H or substituted or unsubstituted alkyl, alkoxy, haloalkyl, alkenyl, alkynyl, aryl, arylalkyl, arylalkenyl, arylalkynyl, heteroalkyl, cycloalkyl, heterocycloalkyl, heteroaryl, or heteroarylalkyl;

$R^4$, independently for each occurrence, is selected from substituted or unsubstituted alkyl, aryl, arylalkyl, heterocycloalkyl, oxo, $-OR^b$, $-CH_2OR^b$, halo, hydroxyl, and hydroxyalkyl;

$R^b$ is substituted or unsubstituted alkyl, aryl, arylalkyl, or heterocycloalkyl;

p is 0, 1, or 2;

$R^6$ is hydrogen or substituted or unsubstituted alkyl; and $R^7$, $R^8$, and $R^9$ are each independently hydrogen or alkyl;

wherein the compound is not:

(SEQ ID NO: 101)

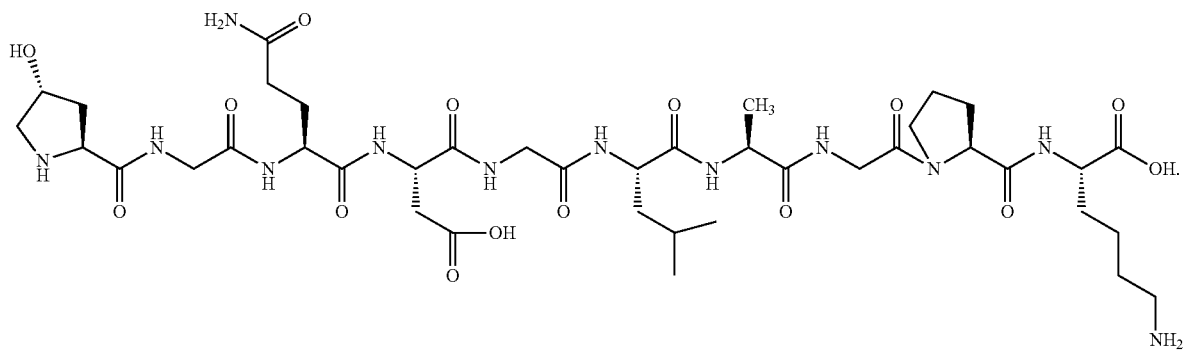

In further embodiments, the invention provides a peptide having an amino acid sequence represented by HyP-Gly-Gln-Xaa-Gly-Leu-Ala-Gly-Pro-Lys (SEQ ID NO: 108);
or a pharmaceutically acceptable salt and/or stereoisomer thereof;
wherein Xaa is selected from Glu, Asn, Gln, His, Lys, Ser, Thr, Ala, Val, Ile, Leu, Phe, Tyr, Trp, homo-Ser, Asp(Me), and Asn(Me); and
at least one amino acid residue in the peptide is a D-amino acid residue.

In further embodiments, the invention provides a peptide having an amino acid sequence represented by HyP-Gly-Gln-Asp-Xaa-Leu-Ala-Gly-Pro-Lys; (SEQ ID NO: 109)
or a pharmaceutically acceptable salt and/or stereoisomer thereof;
wherein Xaa is selected from Val, Ile, Leu, Ala, Phe, Tyr, Trp, Ser, Thr, and (N-Me)Gly; and
at least one amino acid residue in the peptide is a D-amino acid residue.

In further embodiments, the invention provides a peptide having an amino acid sequence represented by HyP-Gly-Gln-Leu-Gly-Leu-Ala-Gly-Pro-Xaa (SEQ ID NO: 110); or a pharmaceutically acceptable salt and/or stereoisomer thereof;
wherein Xaa is selected from Tyr, Leu, Glu, Gln, Ala, and Nle(6-OH); and
at least one amino acid residue in the peptide is a D-amino acid residue.

In further embodiments, the invention provides a peptide having an amino acid sequence represented by Xaa-Gly-Gln-Leu-Gly-Leu-Ala-Gly-Pro-Lys (SEQ ID NO: 111);
or a pharmaceutically acceptable salt and/or stereoisomer thereof;
wherein Xaa is selected from:

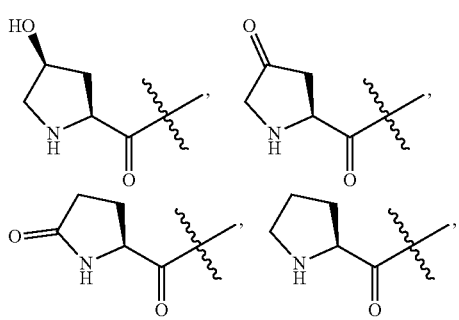

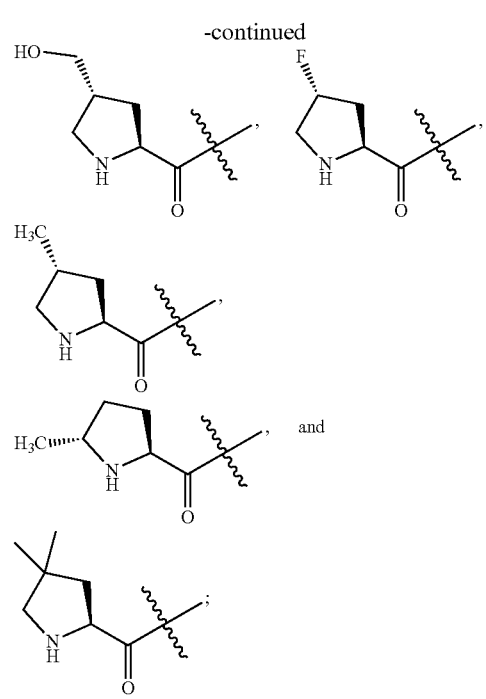

and
at least one amino acid residue in the peptide is a D-amino acid residue.

In further aspects, the invention provides a compound represented by Formula (V):

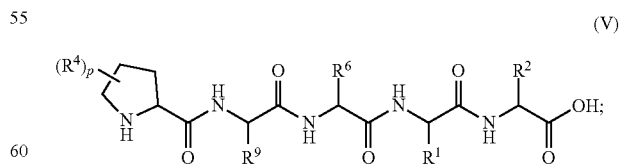

or a pharmaceutically acceptable salt thereof; wherein:
$R^1$ and $R^2$ are each independently H or substituted or unsubstituted alkyl, alkoxy, haloalkyl, alkenyl, alkynyl, aryl, arylalkyl, arylalkenyl, arylalkynyl, heteroalkyl, cycloalkyl, heterocyclyl, or heterocyclylalkyl;

R⁴, independently for each occurrence, is selected from substituted or unsubstituted alkyl, aryl, arylalkyl, heterocyclyl, oxo, —OR$^b$, —CH$_2$OR$^b$, halo, hydroxyl, and hydroxyalkyl;
R$^b$ is substituted or unsubstituted alkyl, aryl, arylalkyl, or heterocyclyl;
p is 0, 1, or 2;
R⁶ is hydrogen or substituted or unsubstituted alkyl; and
R⁹ is hydrogen or alkyl.

In further aspects, the invention provides a compound represented by Formula (VI):

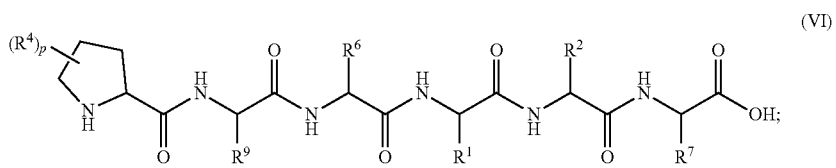

(VI)

or a pharmaceutically acceptable salt thereof; wherein:
R¹ and R² are each independently H or substituted or unsubstituted alkyl, alkoxy, haloalkyl, alkenyl, alkynyl, aryl, arylalkyl, arylalkenyl, arylalkynyl, heteroalkyl, cycloalkyl, heterocyclyl, or heterocyclylalkyl
R⁴, independently for each occurrence, is selected from substituted or unsubstituted alkyl, aryl, arylalkyl, heterocyclyl, oxo, —OR$^b$, —CH$_2$OR$^b$, halo, hydroxyl, and hydroxyalkyl;
R$^b$ is substituted or unsubstituted alkyl, aryl, arylalkyl, or heterocyclyl;
p is 0, 1, or 2;
R⁶ is hydrogen or substituted or unsubstituted alkyl;
R⁷ is hydrogen or alkyl; and
R⁹ is hydrogen or alkyl.

In still further aspects, the invention provides a compound represented by Formula (VII):

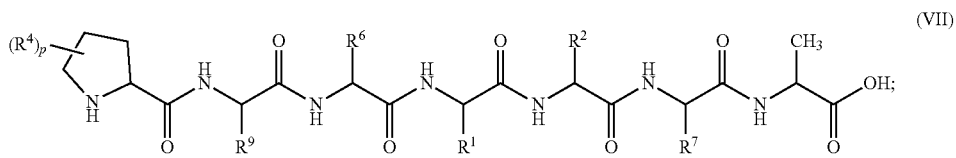

(VII)

or a pharmaceutically acceptable salt thereof; wherein:
R¹ and R² are each independently H or substituted or unsubstituted alkyl, alkoxy, haloalkyl, alkenyl, alkynyl, aryl, arylalkyl, arylalkenyl, arylalkynyl, heteroalkyl, cycloalkyl, heterocyclyl, or heterocyclylalkyl;
R⁴, independently for each occurrence, is selected from substituted or unsubstituted alkyl, aryl, arylalkyl, heterocyclyl, oxo, —OR$^b$, —CH$_2$OR$^b$, halo, hydroxyl, and hydroxyalkyl;
R$^b$ is substituted or unsubstituted alkyl, aryl, arylalkyl, or heterocyclyl;

p is 0, 1, or 2;
R⁶ is hydrogen or substituted or unsubstituted alkyl;
R⁷ is hydrogen or alkyl; and
R⁹ is hydrogen or alkyl.

In still further aspects, the invention provides compounds represented by Formula (IX):

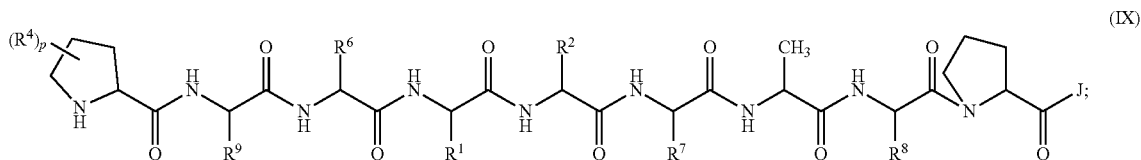

or a pharmaceutically acceptable salt thereof;
wherein:
R¹ and R² are each independently H or substituted or unsubstituted alkyl, alkoxy, haloalkyl, alkenyl, alkynyl, aryl, arylalkyl, arylalkenyl, arylalkynyl, heteroalkyl, cycloalkyl, heterocyclyl, or heterocyclylalkyl;

R⁴, independently for each occurrence, is selected from substituted or unsubstituted alkyl, aryl, arylalkyl, heterocyclyl, oxo, —OR$^b$, —CH$_2$OR$^b$, halo, hydroxyl, and hydroxyalkyl;

R$^b$ is substituted or unsubstituted alkyl, aryl, arylalkyl, or heterocyclyl;

p is 0, 1, or 2;
R⁶ is hydrogen or substituted or unsubstituted alkyl;
R⁷, R⁸, and R⁹ are each independently hydrogen or alkyl;
J is OH or —NR$^x$R$^y$; and
R$^x$ and R$^y$ are each independently selected from H, optionally substituted alkyl, optionally substituted alkoxylalkyl, or R$^x$ and R$^y$ taken together with the intervening nitrogen atom form a ring.

The present invention also provides compounds represented by Formula (X-am):

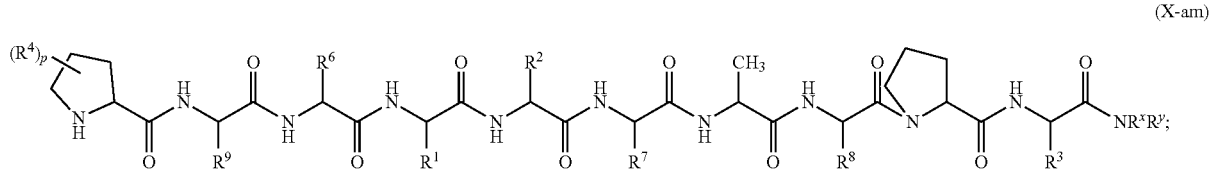

or a pharmaceutically acceptable salt thereof;
wherein:
R¹, R², and R³ are each independently H or substituted or unsubstituted alkyl, alkoxy, haloalkyl, alkenyl, alkynyl, aryl, arylalkyl, arylalkenyl, arylalkynyl, heteroalkyl, cycloalkyl, heterocyclyl, or heterocyclylalkyl;

R⁴, independently for each occurrence, is selected from substituted or unsubstituted alkyl, aryl, arylalkyl, heterocyclyl, oxo, —OR$^b$, —CH$_2$OR$^b$, halo, hydroxyl, and hydroxyalkyl;

$R^b$ is substituted or unsubstituted alkyl, aryl, arylalkyl, or heterocyclyl;

p is 0, 1, or 2;

$R^6$ is hydrogen or substituted or unsubstituted alkyl;

$R^7$, $R^8$, and $R^9$ are each independently hydrogen or alkyl;

J is OH or —$NR^xR^y$; and $R^x$ and $R^y$ are each independently selected from H, optionally substituted alkyl, optionally substituted alkoxylalkyl, or $R^x$ and $R^y$ taken together with the intervening nitrogen atom form a ring.

The invention also provides the following compounds (SEQ ID NOS 102 and 112, respectively in order of appearance):

BRIEF DESCRIPTION OF THE DRAWINGS

FIG. 1 is a diagram showing the sequence and characteristics of the peptides prepared according to an embodiment of the present invention.

[Formula 8]

(SEQ ID NO: 102)

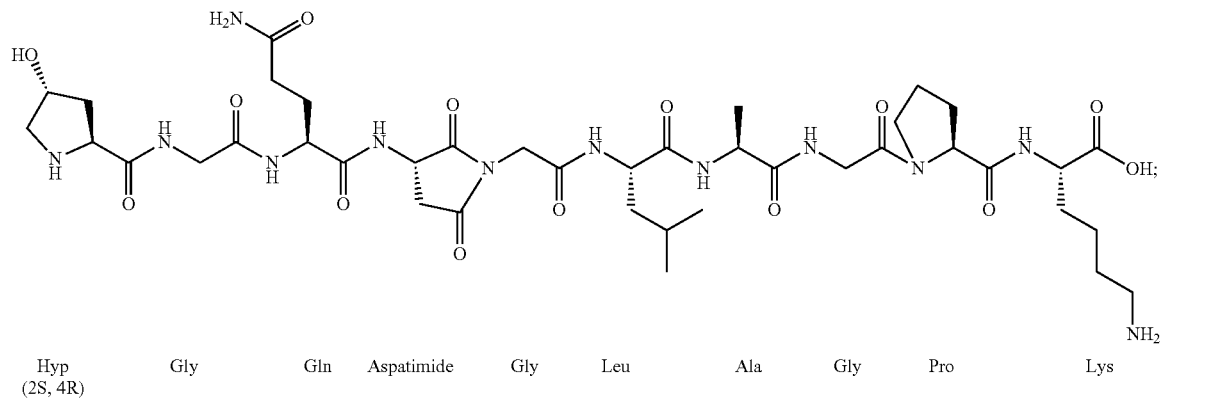

Hyp (2S, 4R)   Gly   Gln   Aspatimide   Gly   Leu   Ala   Gly   Pro   Lys

[Formula 10]

(SEQ ID NO: 112)

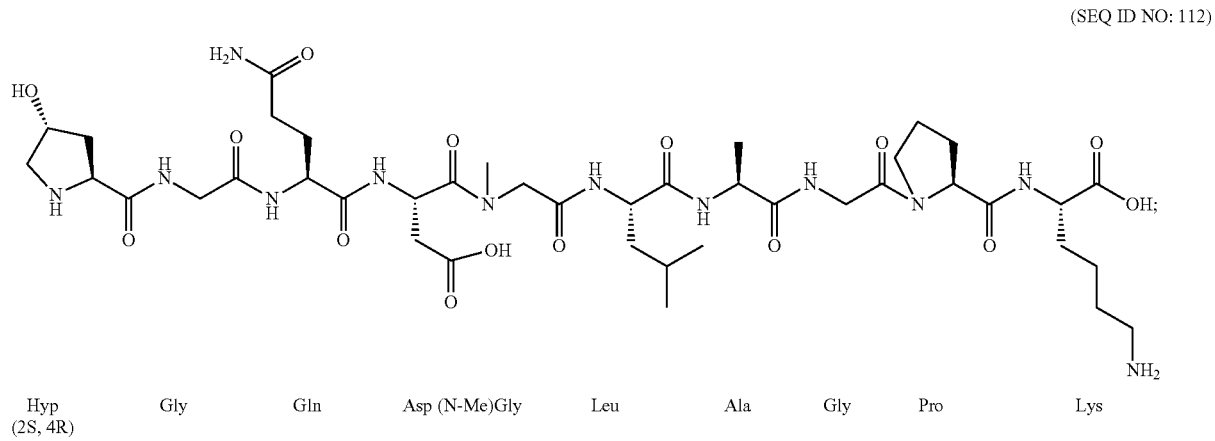

Hyp (2S, 4R)   Gly   Gln   Asp   (N-Me)Gly   Leu   Ala   Gly   Pro   Lys and pharmaceutically acceptable salts thereof.

Also provided by the invention are pharmaceutical compositions comprising a pharmaceutically acceptable carrier and a compound of the invention.

The invention also provides methods of treating eye disease, such as eye disease is selected from retinopathy, keratitis, dry-macular degeneration, wet-macular degeneration, dry eye syndrome, heratoconjunctivitis sicca and keratoconjunctival epithelium disorder, by administering a compound of the invention, or a pharmaceutical composition comprising the same.

FIG. 5 is a diagram showing a change in the body weight of a rat model whose eyes have been administered with YDE-001 to YDE-028.

Figures 6, 7:
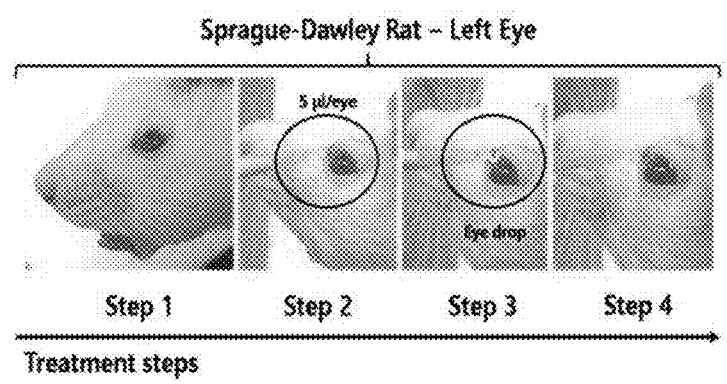

FIG. 6 is a diagram showing a change in the body weight of a rat model whose eyes have been administered with YDE-029 to YDE-043.

FIG. 7 is a photograph showing a procedure of administering an agent to the eyes of a rat model.

Figure 8:
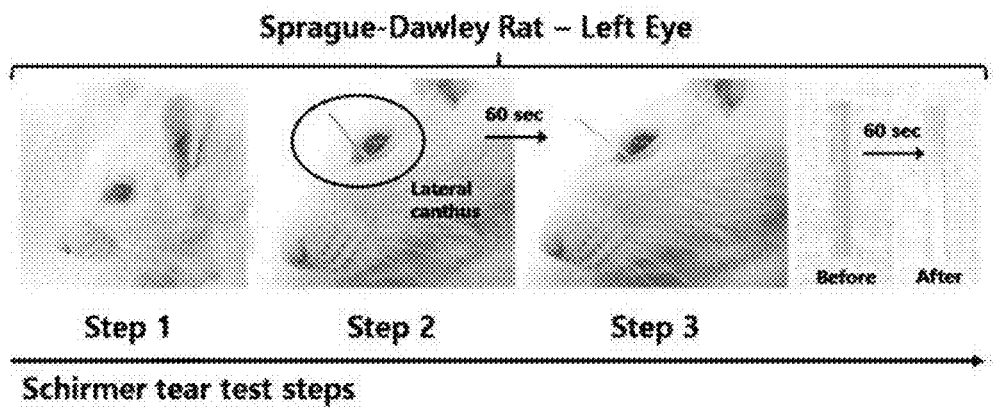

FIG. 8 is a photograph showing a procedure of measuring the amount of tear secretion of a rat model using cobalt chloride paper.

Figure 9:
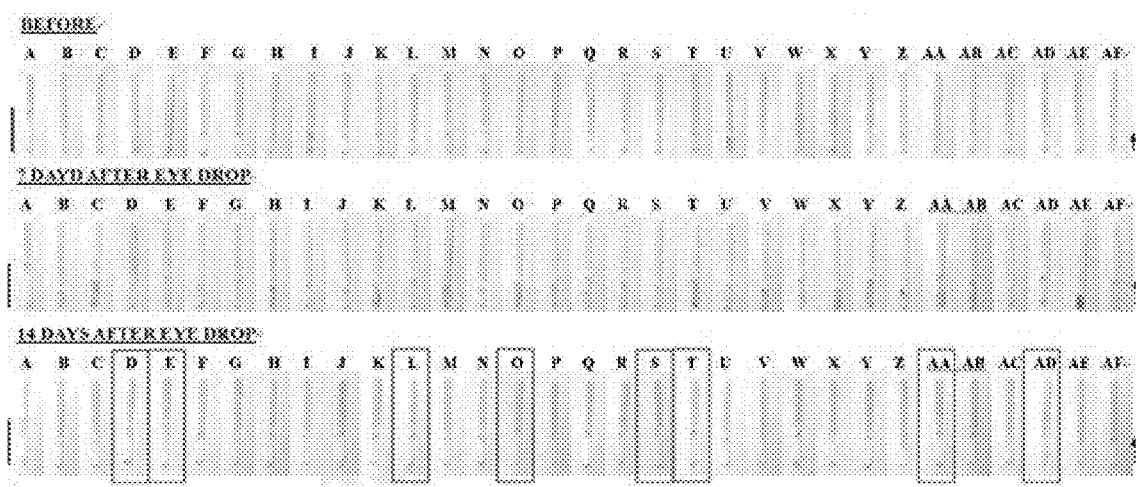

FIG. 9 is a photograph showing the results of measuring the amount of tear secretion of a rat model whose eyes have been administered with YDE-001 to YDE-028 using cobalt chloride paper.

FIG. 10 is a diagram showing the changes in the amount of tear secretion of a rat model whose eyes have been administered with YDE-001 to YDE-028.

Figure 11:
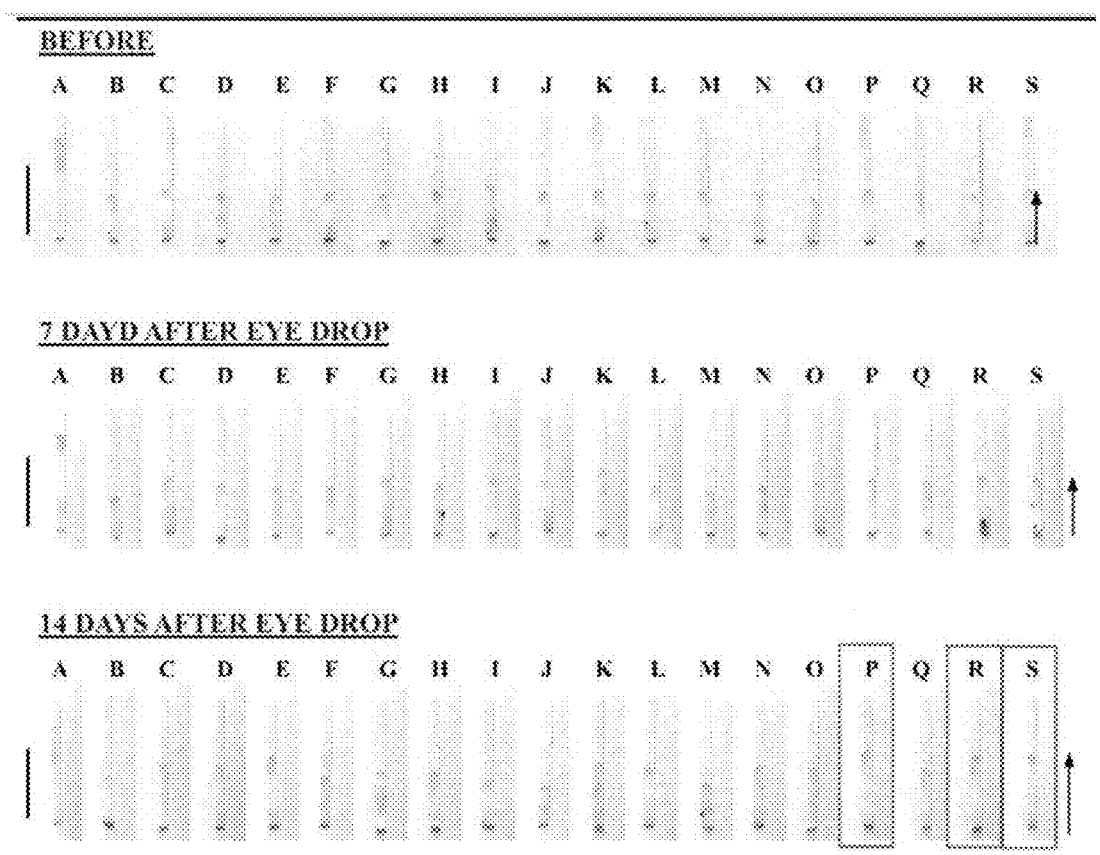

FIG. 11 is a photograph showing the results of measuring the amount of tear secretion of a rat model whose eyes have been administered with YDE-029 to YDE-043 using cobalt chloride paper.

Figures 12, 13:
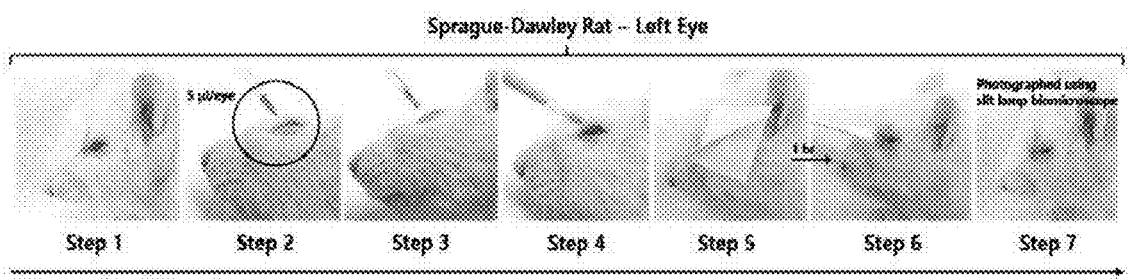

FIG. 12 is a diagram showing the changes in the amount of tear secretion of a rat model whose eyes have been administered with YDE-029 to YDE-043.

FIG. 13 is a photograph showing a procedure of administering a fluorescent substance to the eyes of a rat model for confirming damage to the cornea thereof.

Figure 14:
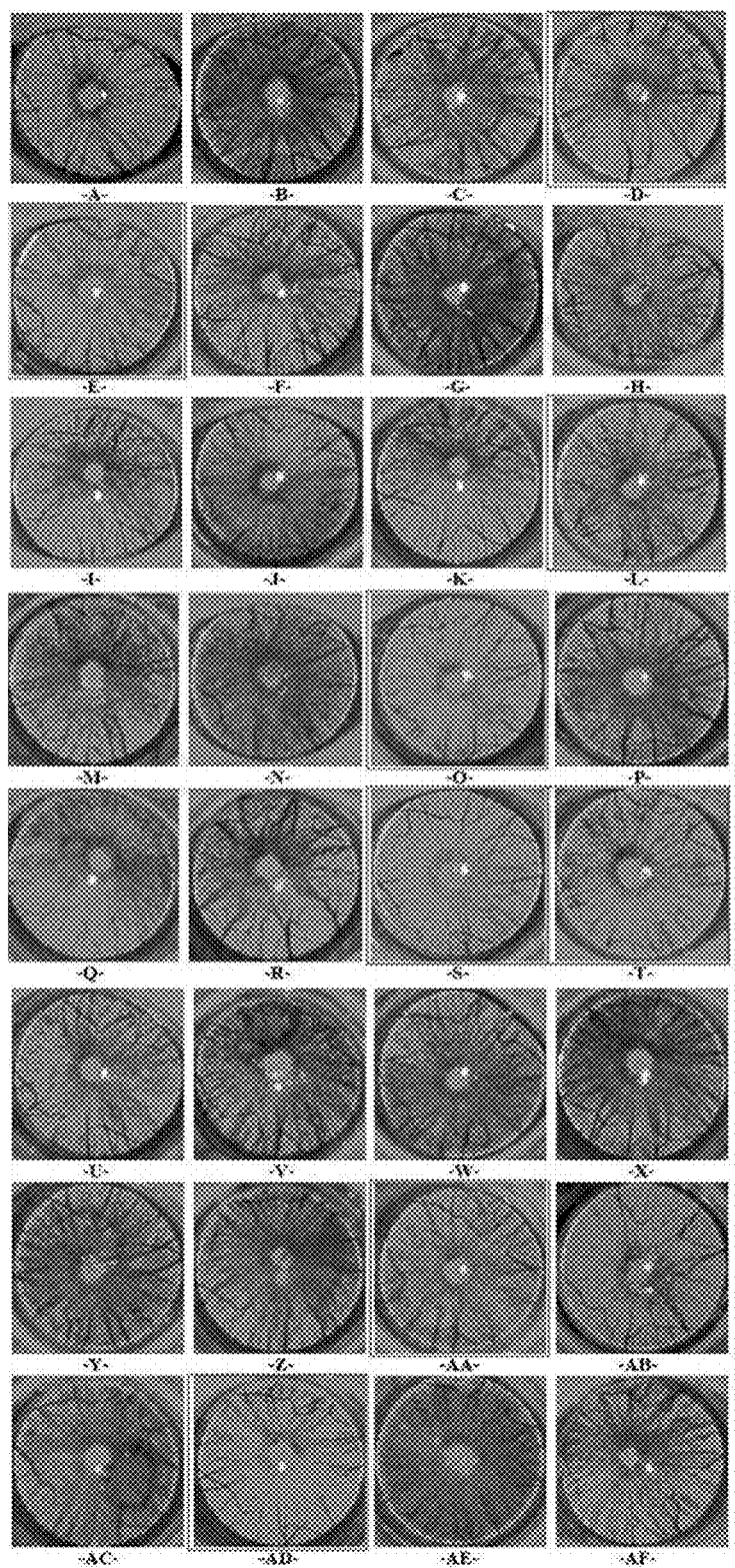

FIG. 14 is a photograph showing the results of measuring damage to the cornea of a rat model whose eyes have been administered with YDE-001 to YDE-028 using a fluorescent substance.

FIG. 15 is a diagram showing the permeability of a fluorescence dye to confirm the recovery of corneal damage of a rat model whose eyes have been administered with YDE-001 to YDE-028.

Figure 16:
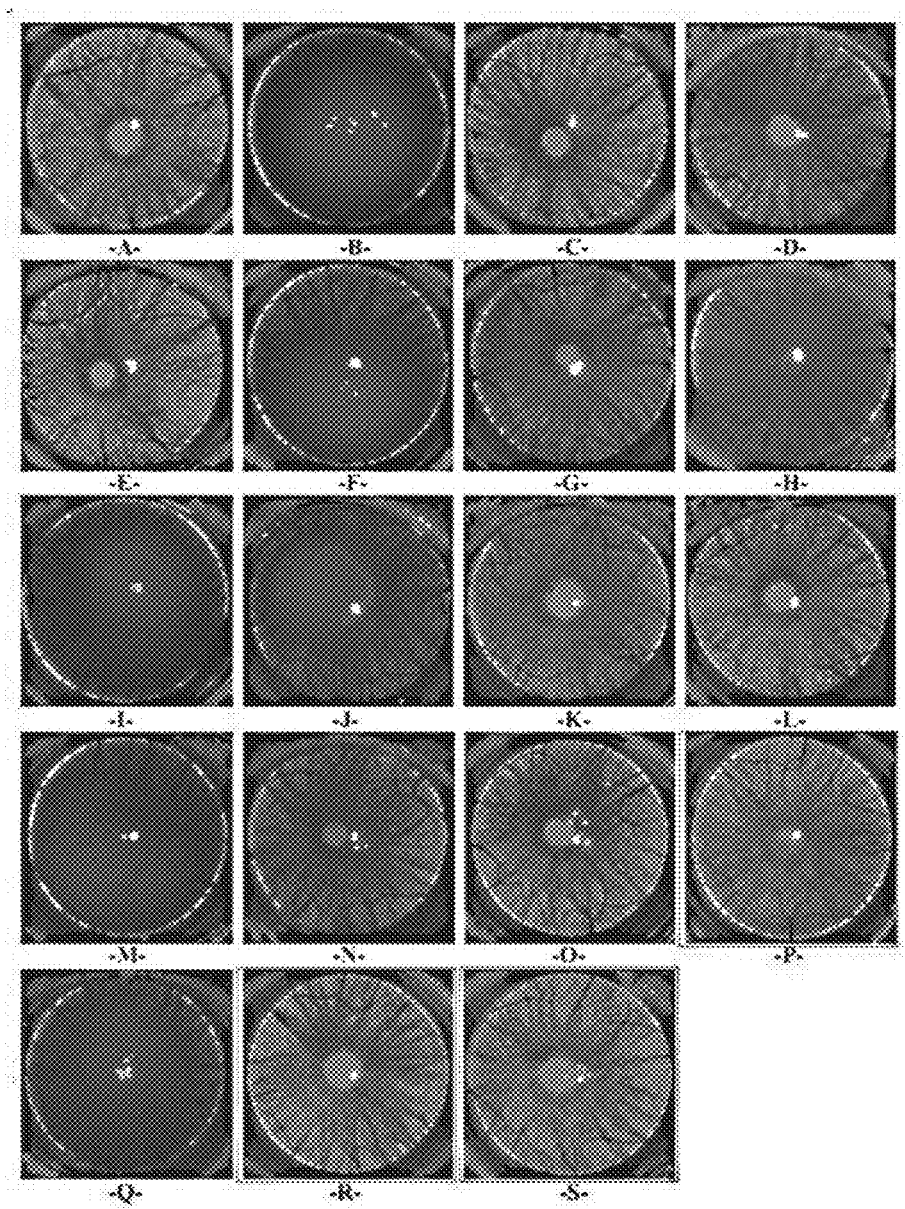

FIG. 16 is a photograph showing the results of measuring damage to the cornea of a rat model whose eyes have been administered with YDE-029 to YDE-043 using a fluorescent substance.

FIG. 17 is a diagram showing the permeability of a fluorescence dye to confirm the recovery of corneal damage of a rat model whose eyes have been administered with YDE-029 to YDE-043.

Figure 18:
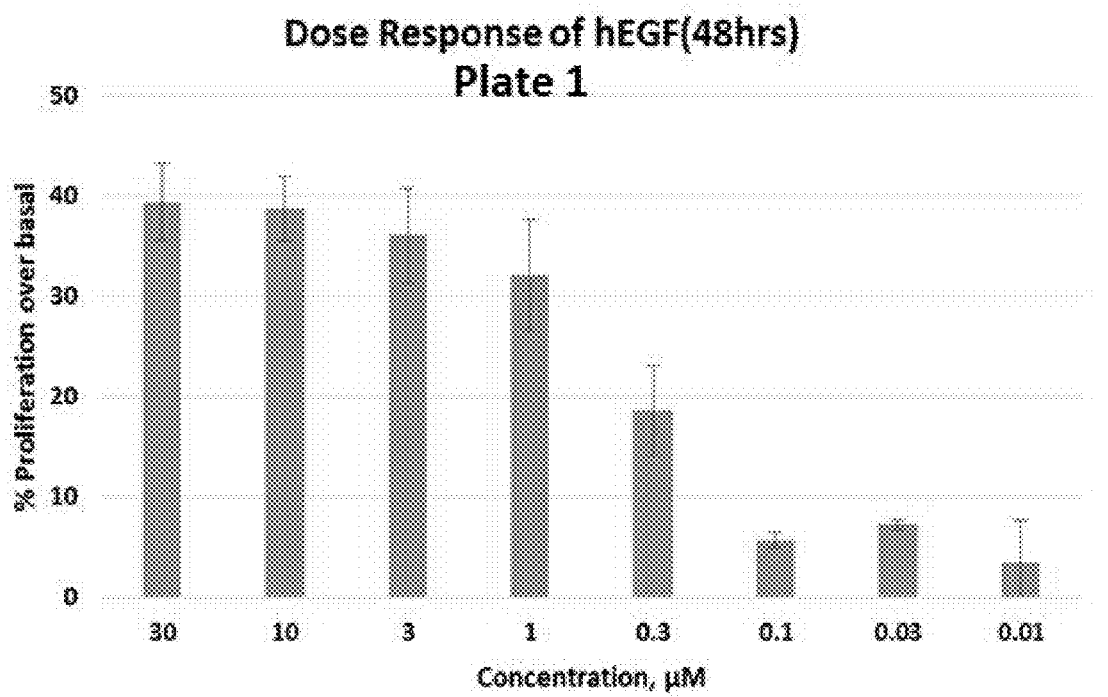

FIG. 18 is a diagram showing the cell growth rate after 48 hours from the treatment of hEGF on human corneal epithelial cells of plate No. 1.

Figure 19:
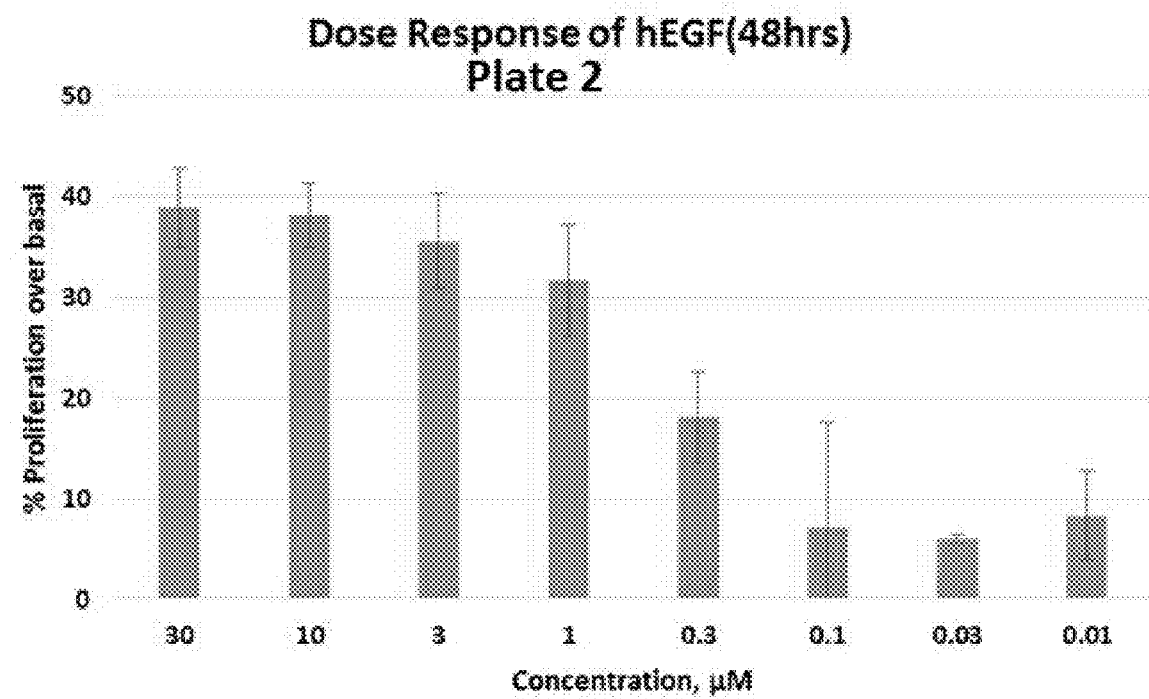

FIG. 19 is a diagram showing the cell growth rate after 48 hours from the treatment of hEGF on human corneal epithelial cells of plate No. 2.

Figure 20:
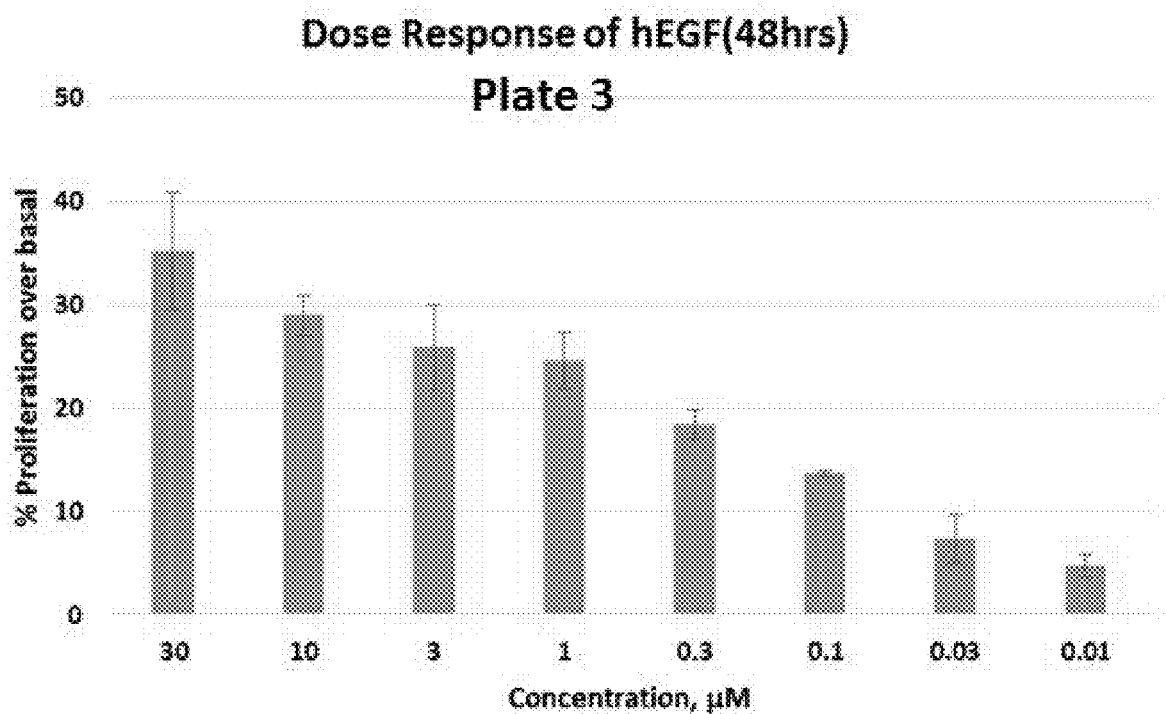

FIG. 20 is a diagram showing the cell growth rate after 48 hours from the treatment of hEGF on human corneal epithelial cells of plate No. 3.

Figure 21:
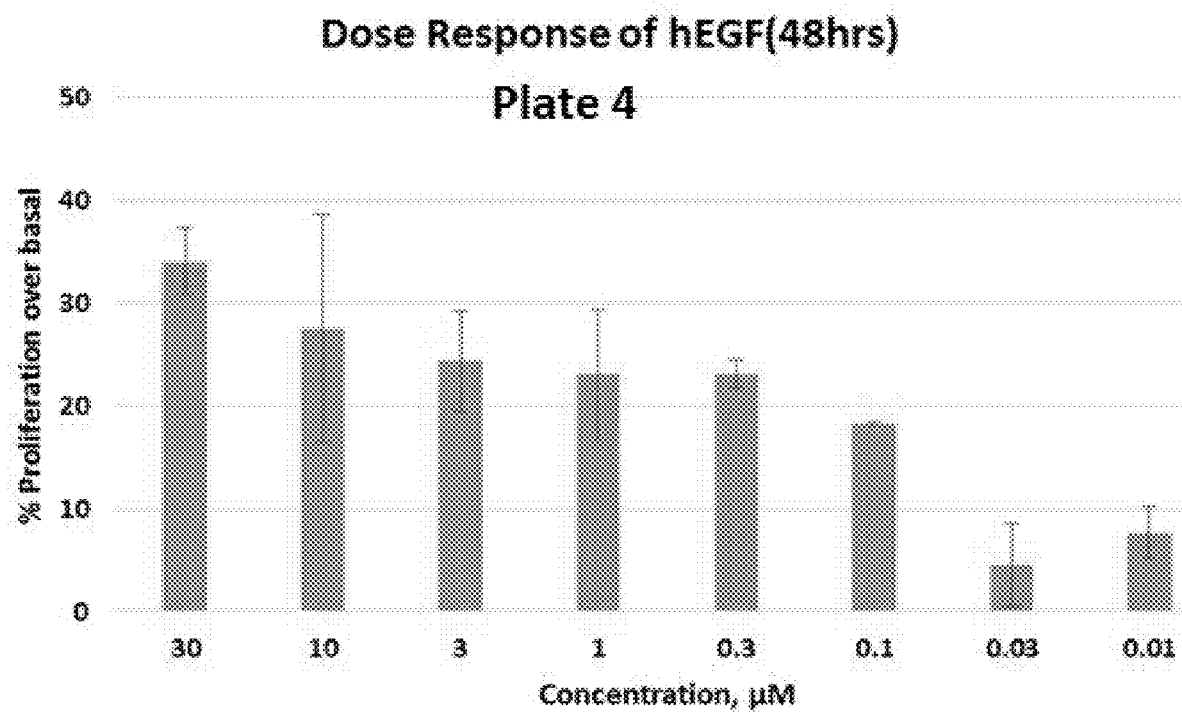

FIG. 21 is a diagram showing the cell growth rate after 48 hours from the treatment of hEGF on human corneal epithelial cells of plate No. 4.

Figure 22:
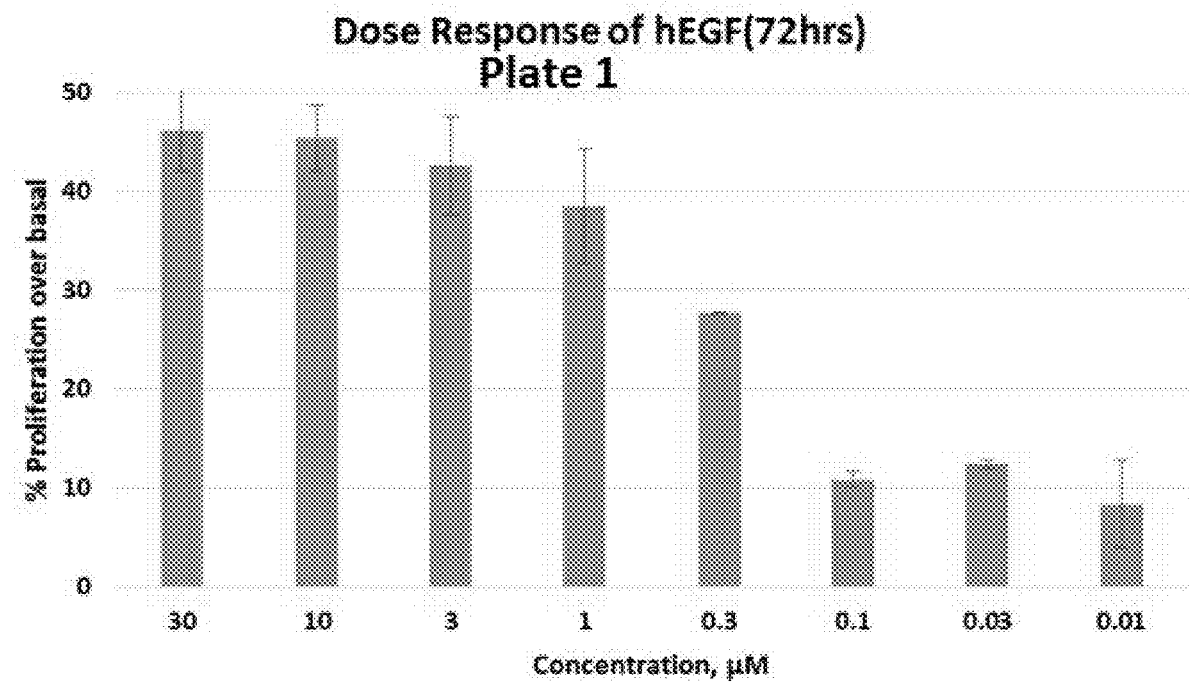

FIG. 22 is a diagram showing the cell growth rate after 72 hours from the treatment of hEGF on human corneal epithelial cells of plate No. 1.

Figure 23:
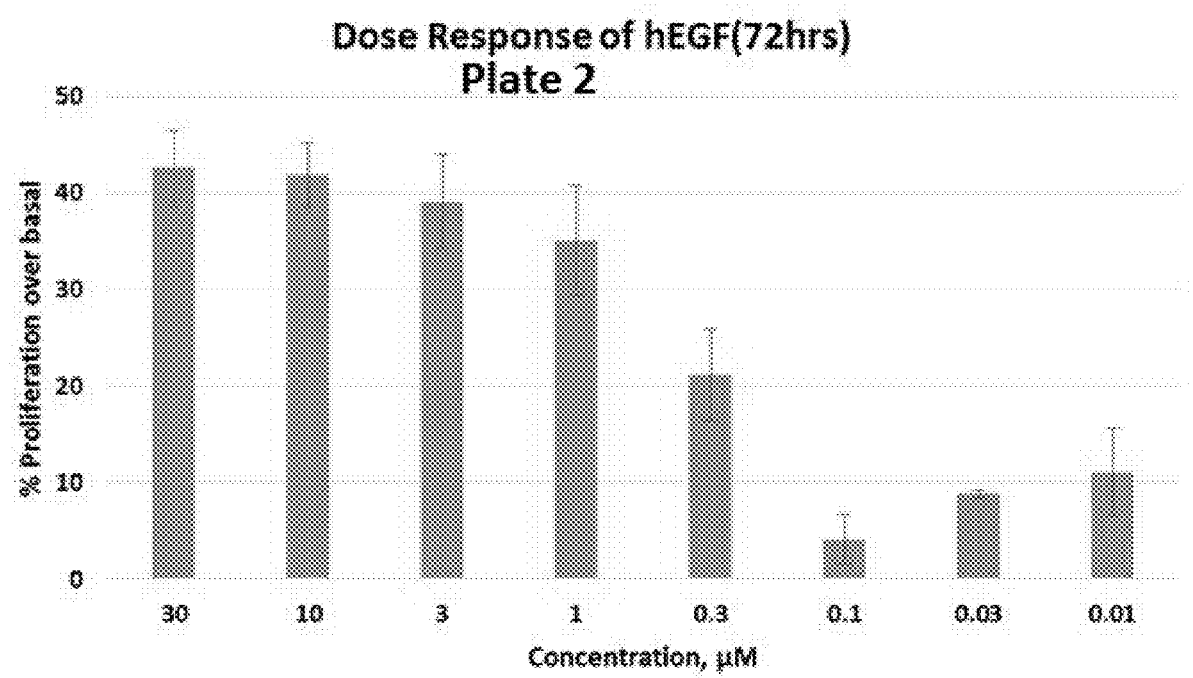

FIG. 23 is a diagram showing the cell growth rate after 72 hours from the treatment of hEGF on human corneal epithelial cells of plate No. 2.

Figure 24:
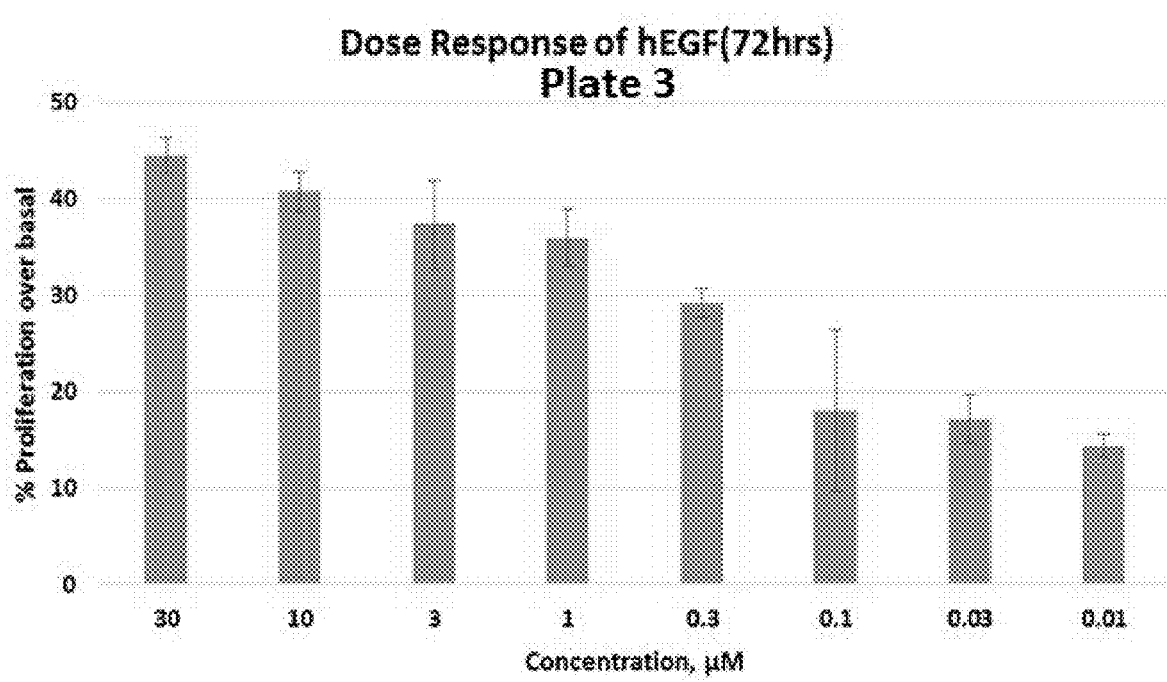

FIG. 24 is a diagram showing the cell growth rate after 72 hours from the treatment of hEGF on human corneal epithelial cells of plate No. 3.

Figure 25:
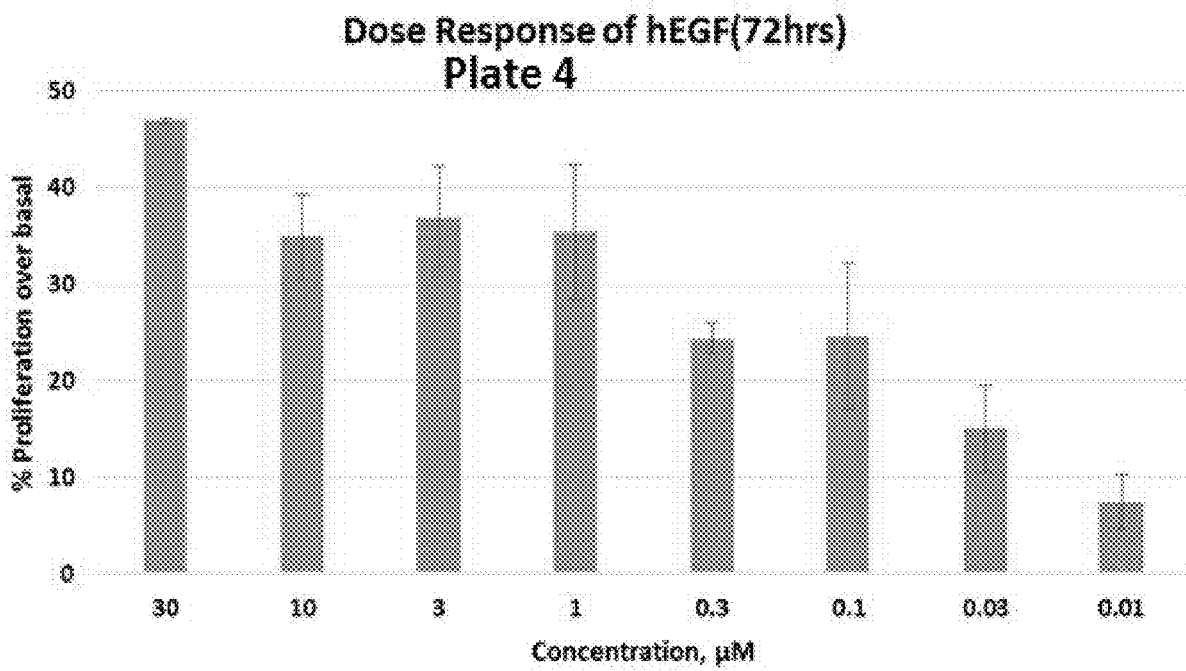

FIG. 25 is a diagram showing the cell growth rate after 72 hours from the treatment of hEGF on human corneal epithelial cells of plate No. 4.

Figure 26:
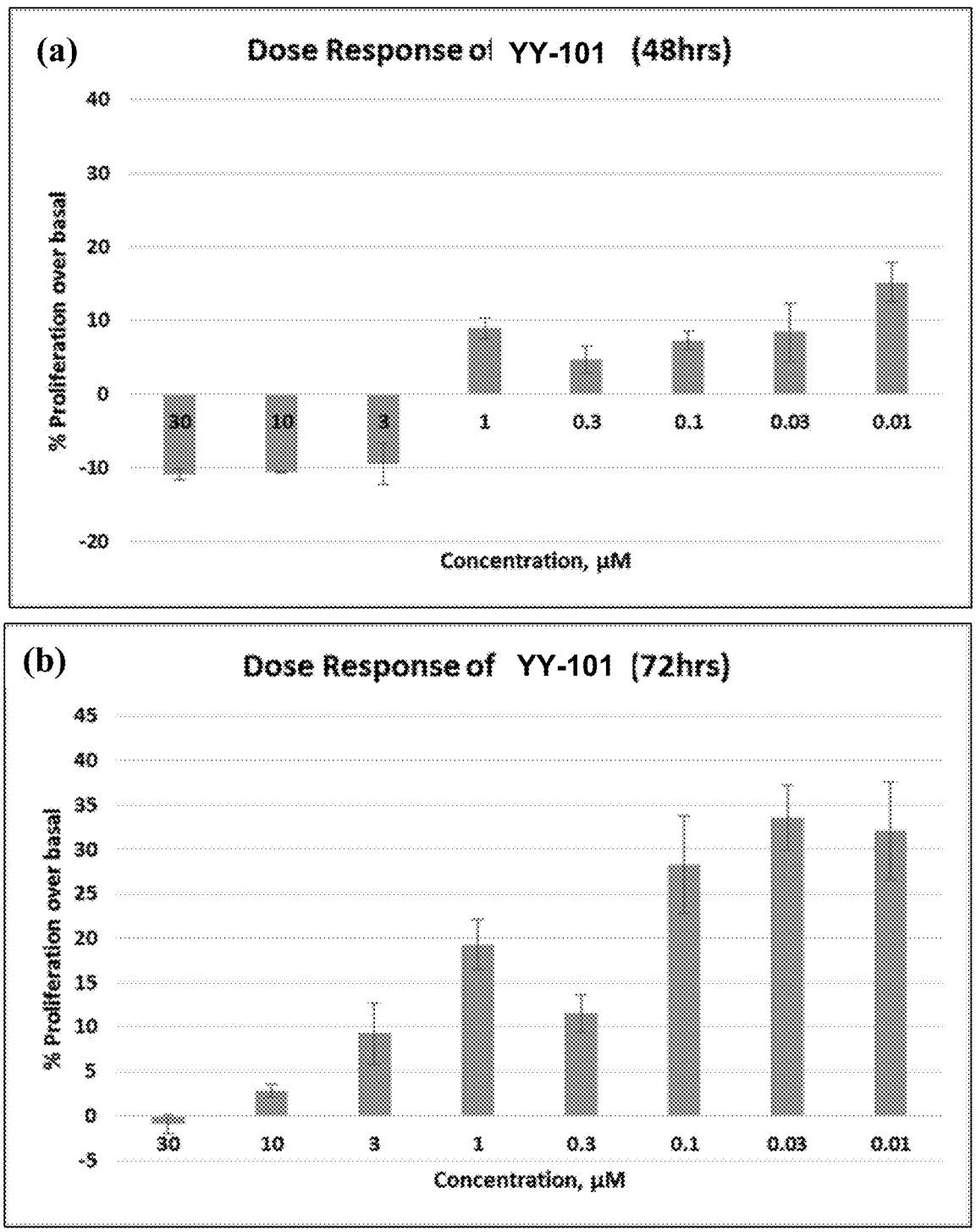

FIG. 26 is a diagram showing the cell growth rate after (a) 48 hours or (b) 72 hours from the treatment of YY-101 on human corneal epithelial cells.

Figure 27:
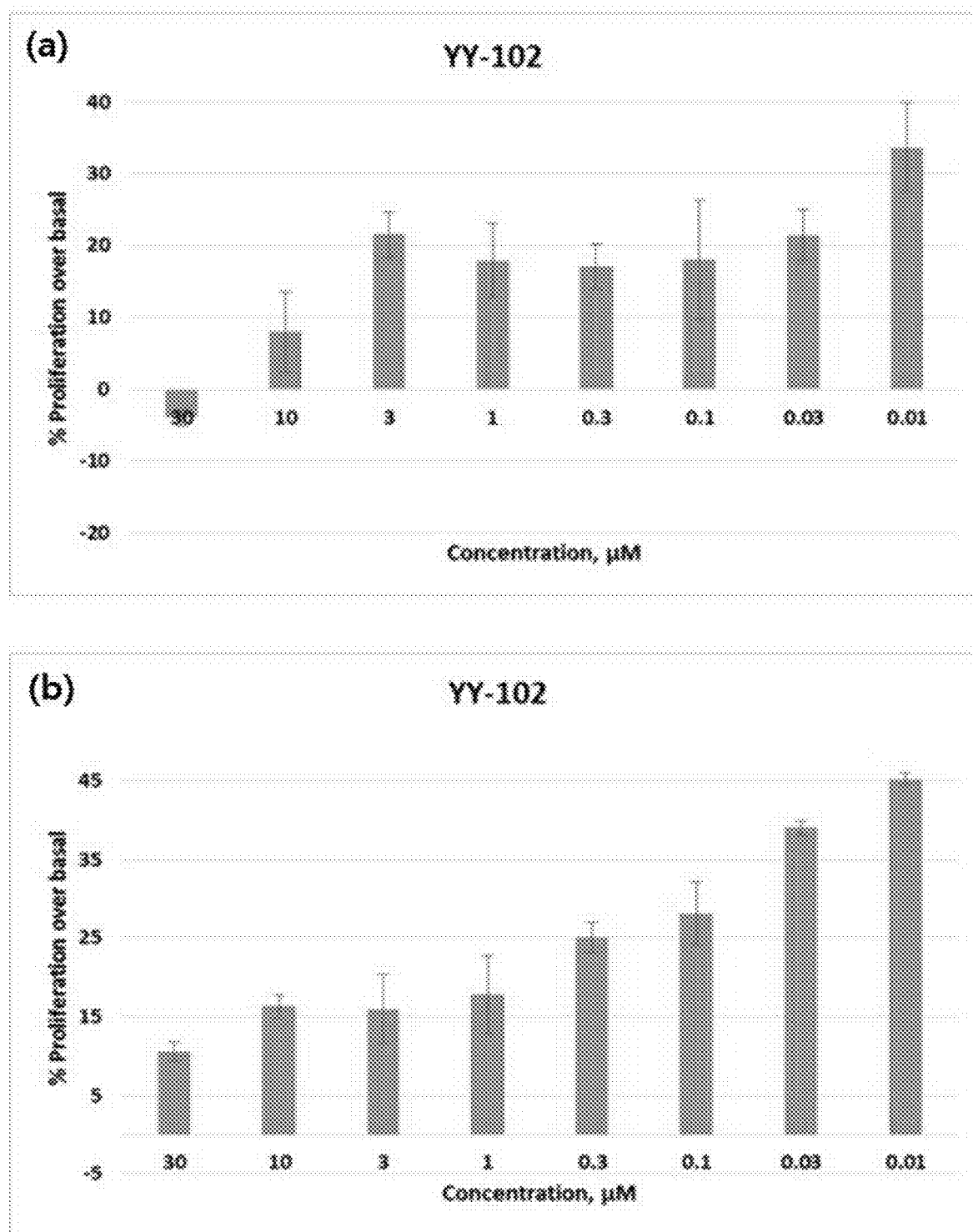

FIG. 27 is a diagram showing the cell growth rate after (a) 48 hours or (b) 72 hours from the treatment of YY-102 on human corneal epithelial cells.

Figure 28:
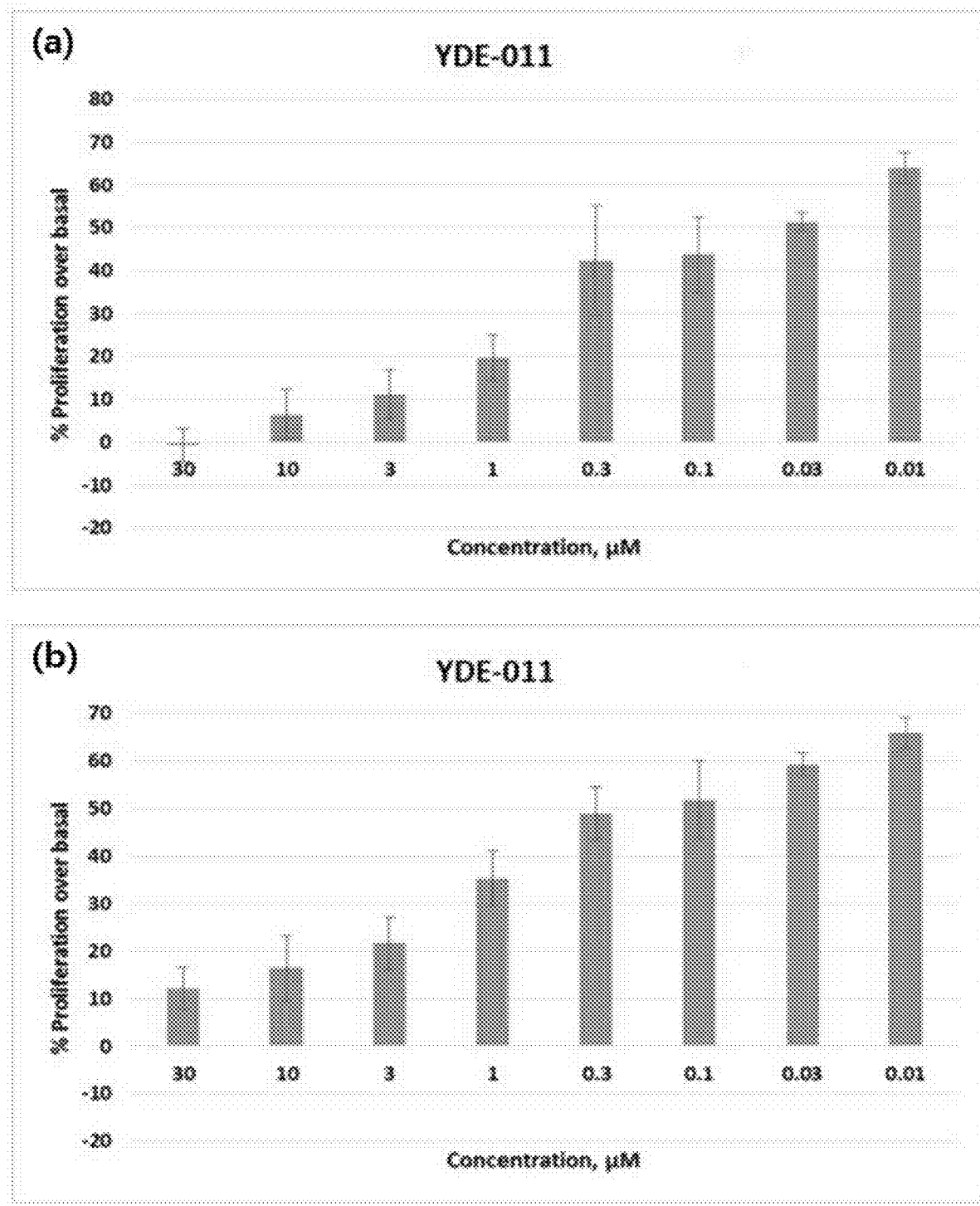

FIG. 28 is a diagram showing the cell growth rate after (a) 48 hours or (b) 72 hours from the treatment of YDE-011 on human corneal epithelial cells.

Figure 29:
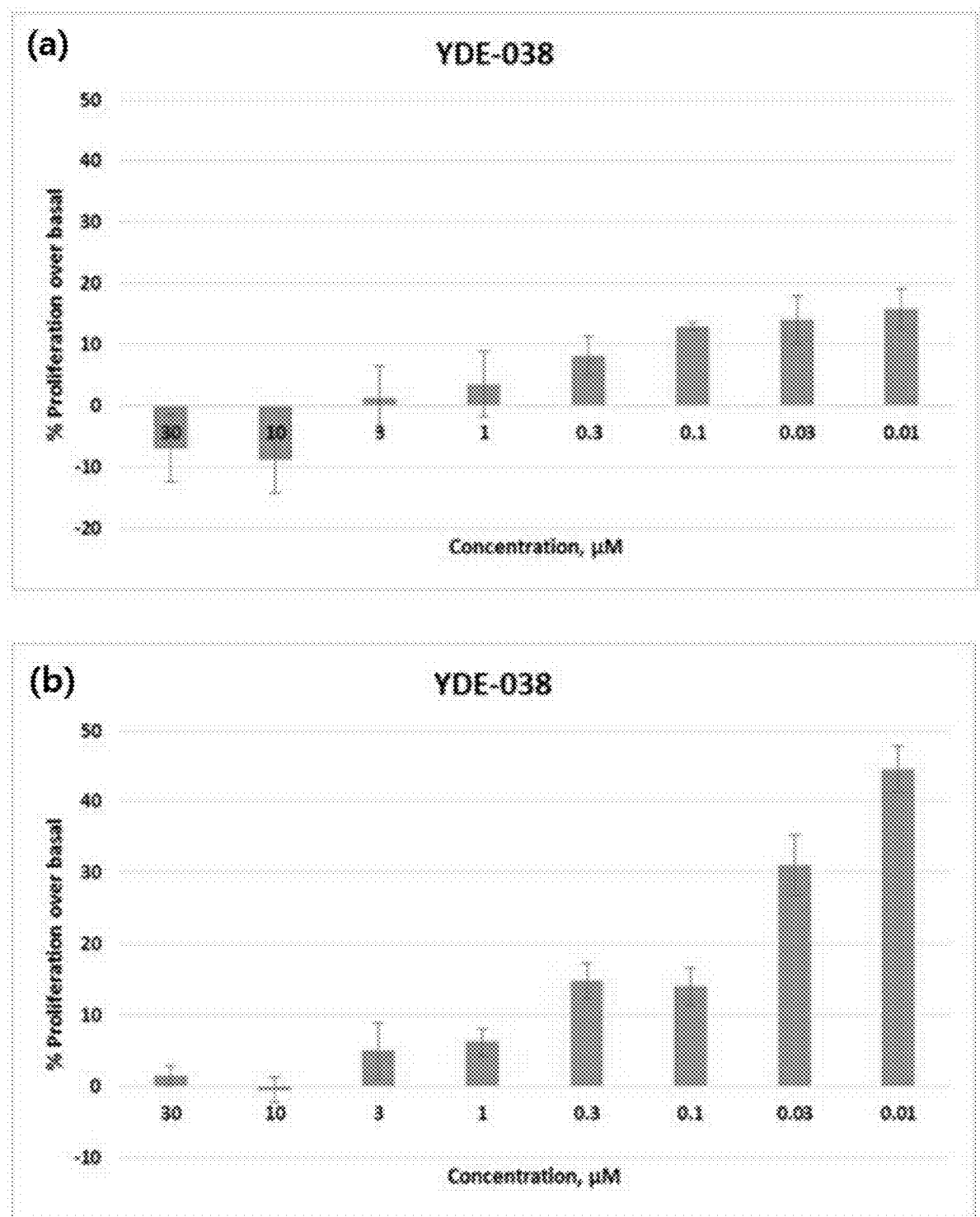

FIG. 29 is a diagram showing the cell growth rate after (a) 48 hours or (b) 72 hours from the treatment of YDE-038 on human corneal epithelial cells.

Figure 30:
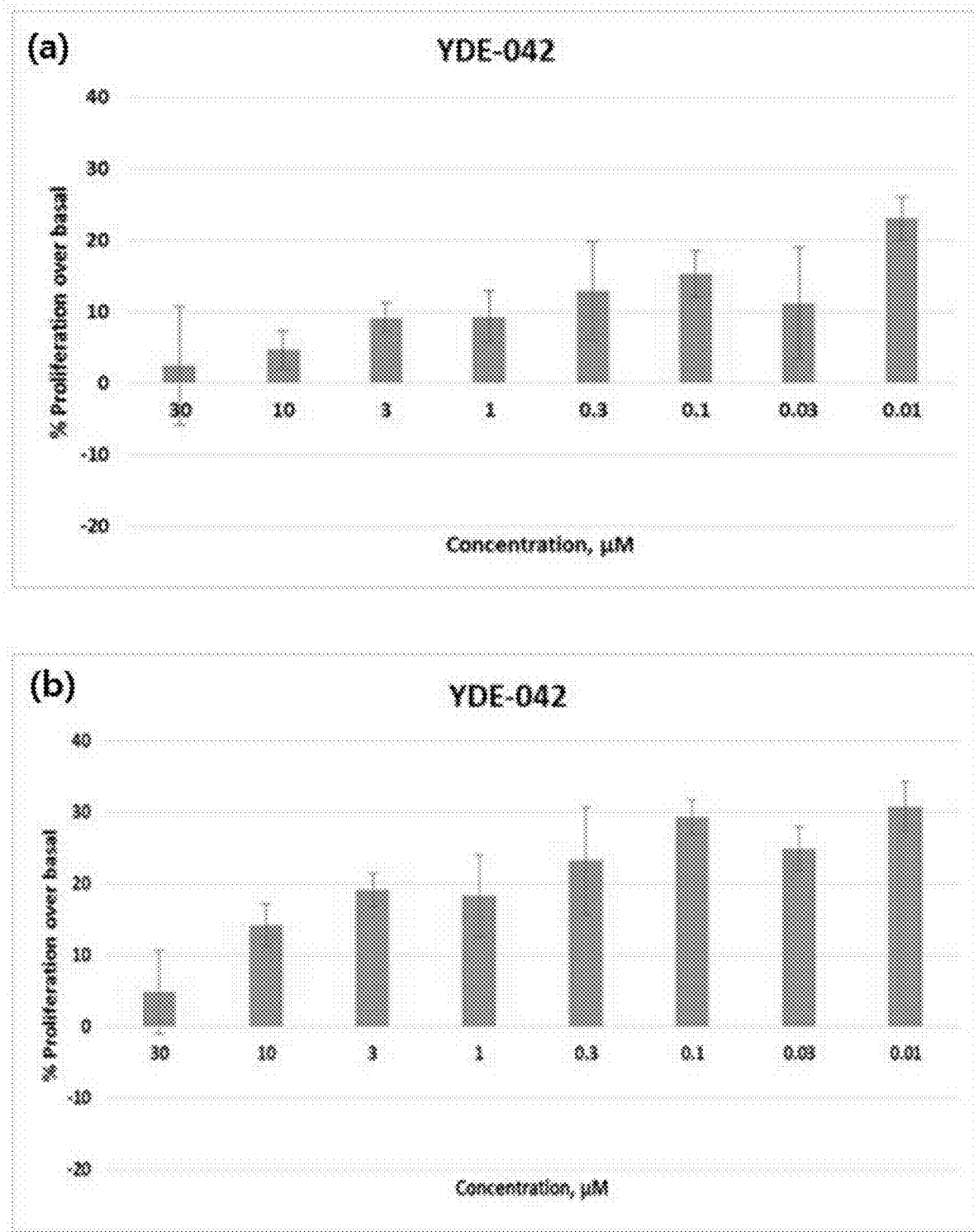

FIG. 30 is a diagram showing the cell growth rate after (a) 48 hours or (b) 72 hours from the treatment of YDE-042 on human corneal epithelial cells.

Figure 31:
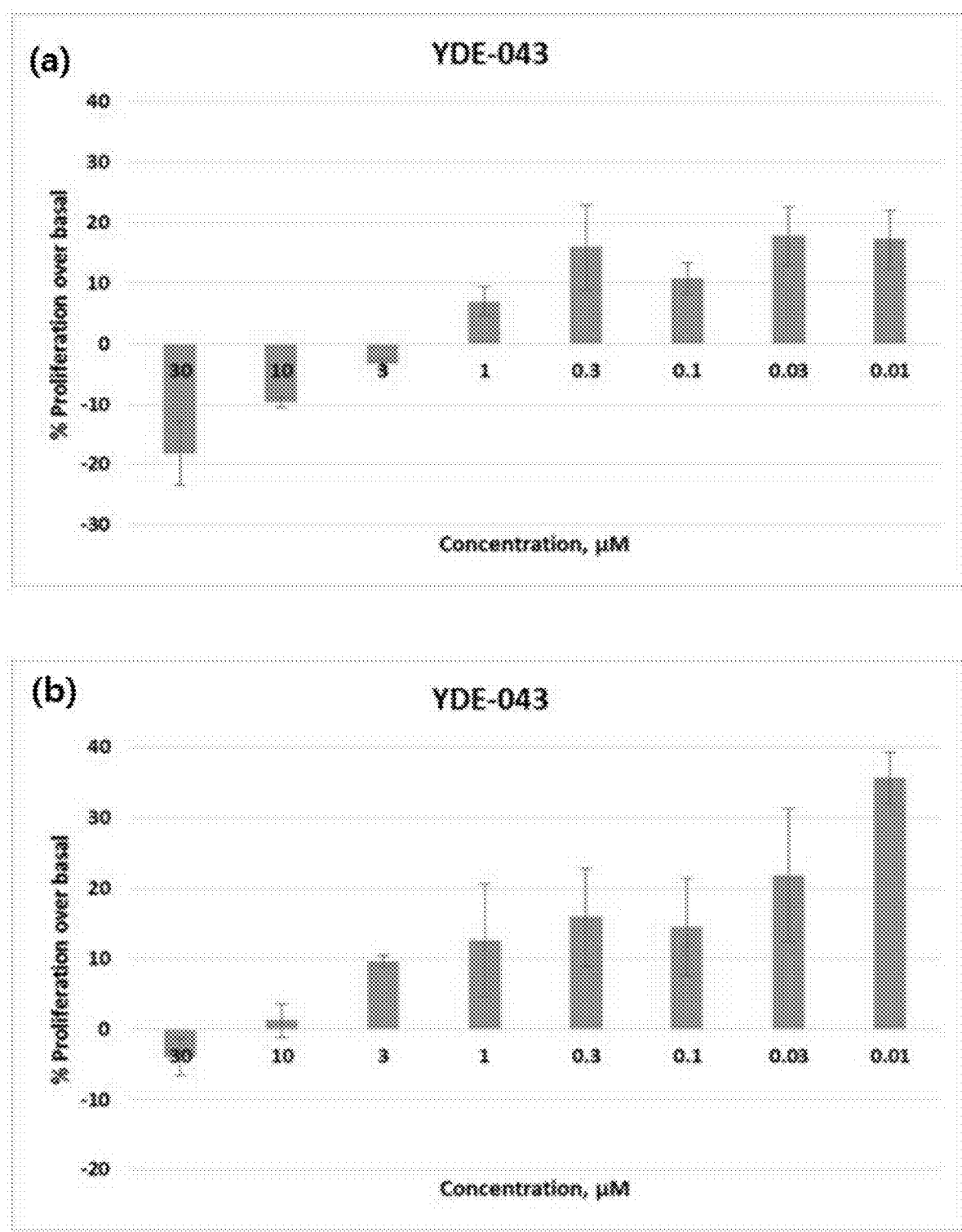

FIG. 31 is a diagram showing the cell growth rate after (a) 48 hours or (b) 72 hours from the treatment of YDE-043 on human corneal epithelial cells.

Figure 32:
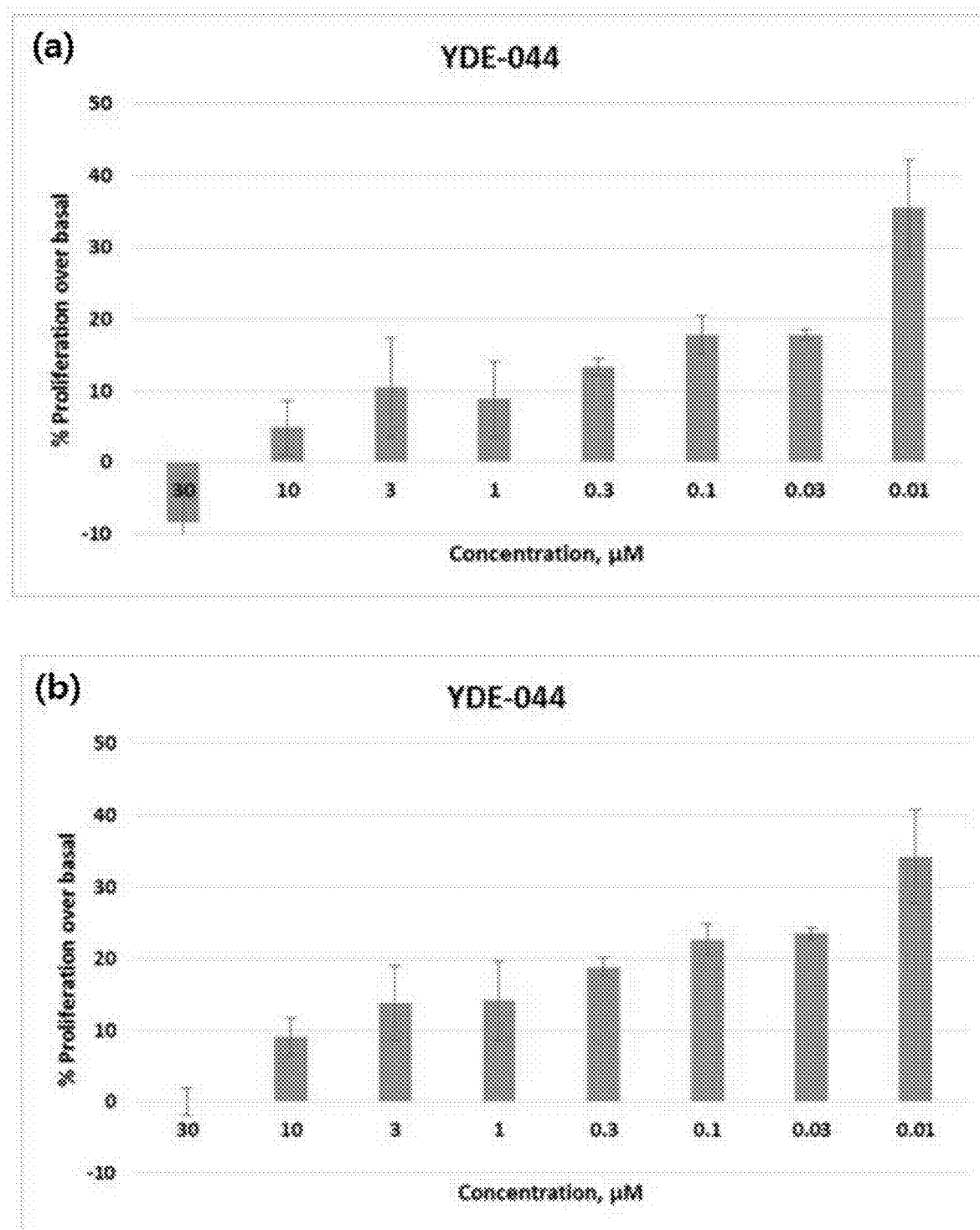

FIG. 32 is a diagram showing the cell growth rate after (a) 48 hours or (b) 72 hours from the treatment of YDE-044 on human corneal epithelial cells.

Figure 33:
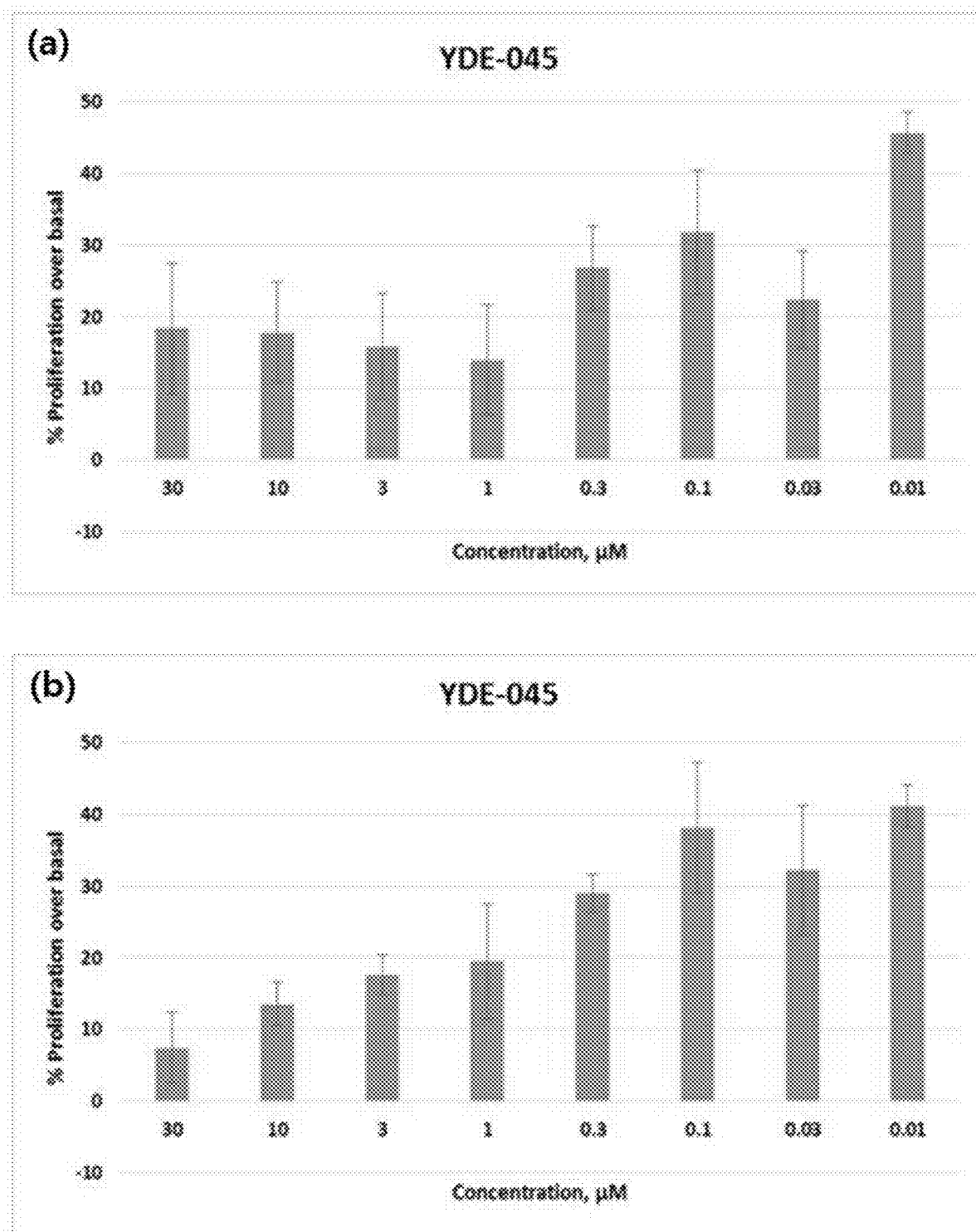

FIG. 33 is a diagram showing the cell growth rate after (a) 48 hours or (b) 72 hours from the treatment of YDE-045 on human corneal epithelial cells.

Figure 34:
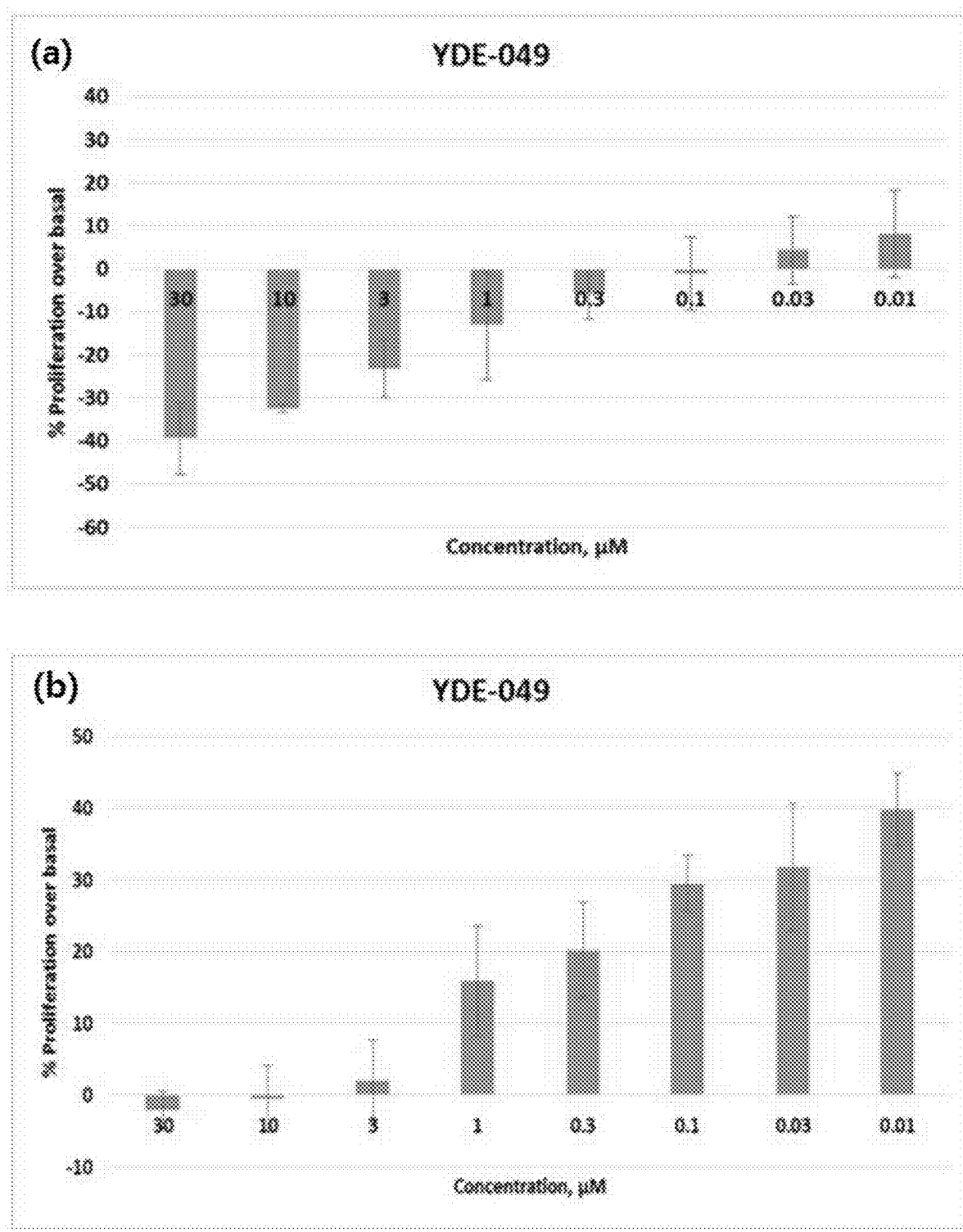

FIG. 34 is a diagram showing the cell growth rate after (a) 48 hours or (b) 72 hours from the treatment of YDE-049 on human corneal epithelial cells.

Figure 35:
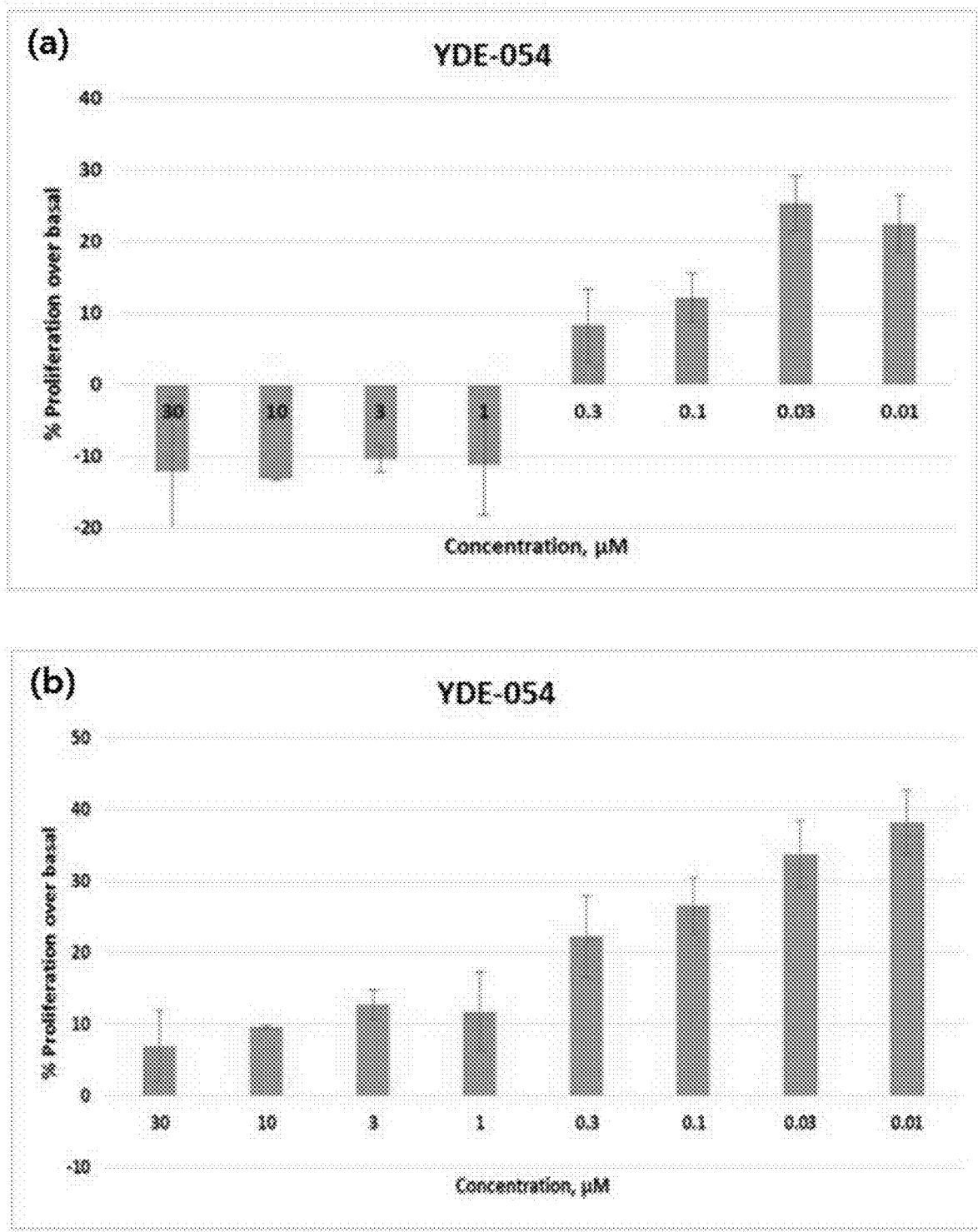

FIG. 35 is a diagram showing the cell growth rate after (a) 48 hours or (b) 72 hours from the treatment of YDE-054 on human corneal epithelial cells.

Figure 36:
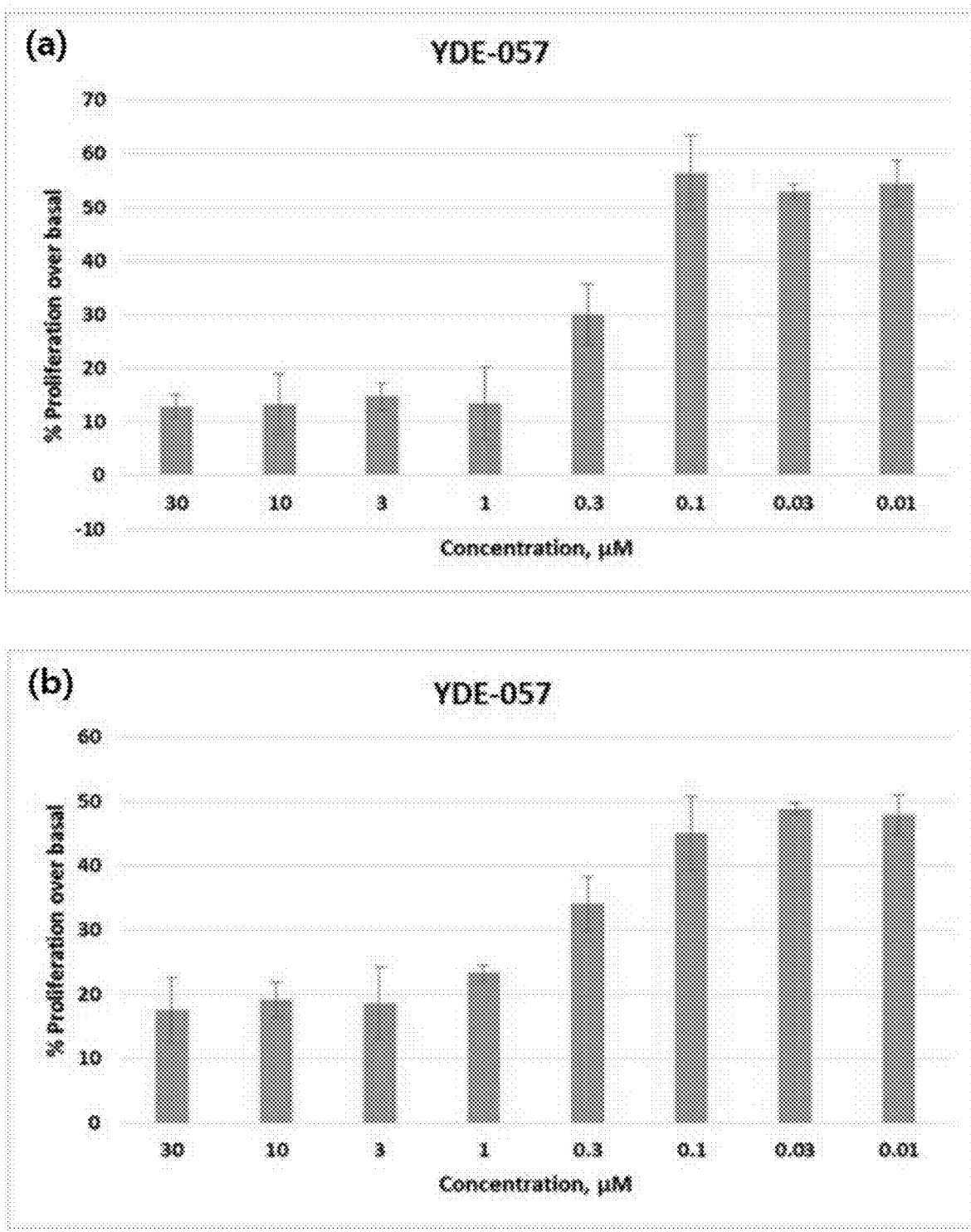

FIG. 36 is a diagram showing the cell growth rate after (a) 48 hours or (b) 72 hours from the treatment of YDE-057 on human corneal epithelial cells.

FIG. 37 is a diagram showing the cell growth rate after (a) 48 hours or (b) 72 hours from the treatment of YDE-058 on human corneal epithelial cells.

Figure 38:
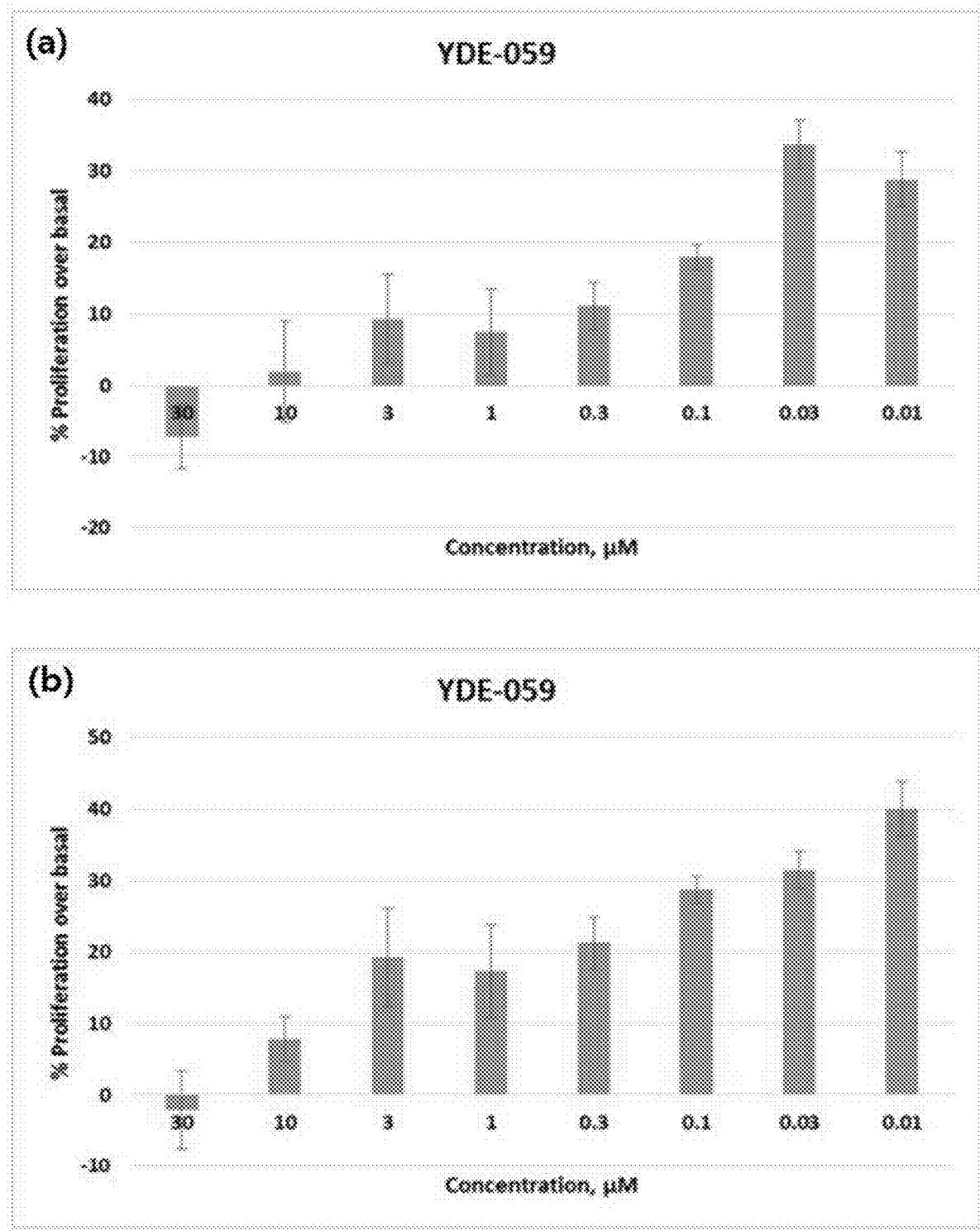

FIG. 38 is a diagram showing the cell growth rate after (a) 48 hours or (b) 72 hours from the treatment of YDE-059 on human corneal epithelial cells.

Figure 39:
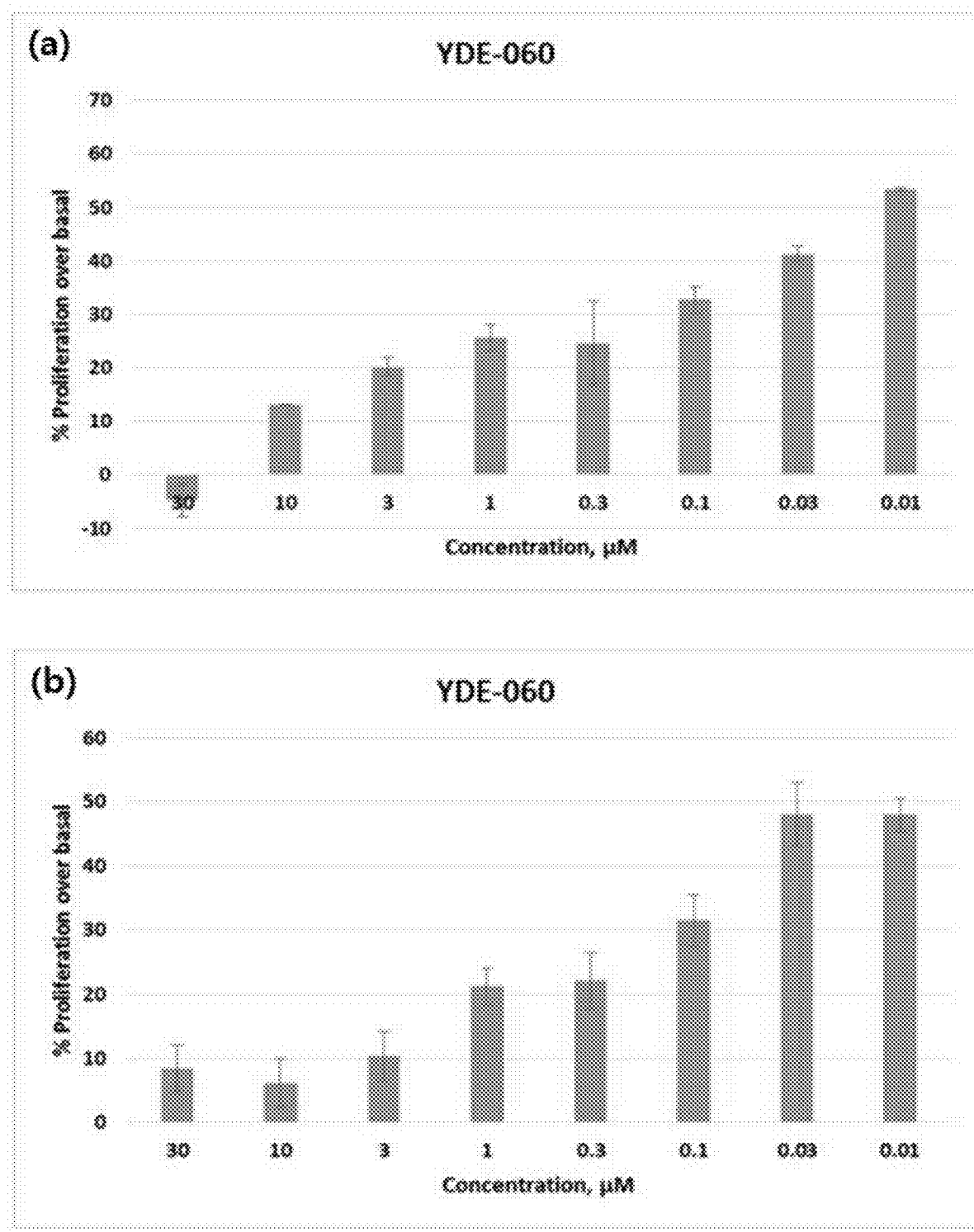

FIG. 39 is a diagram showing the cell growth rate after (a) 48 hours or (b) 72 hours from the treatment of YDE-060 on human corneal epithelial cells.

Figure 40:
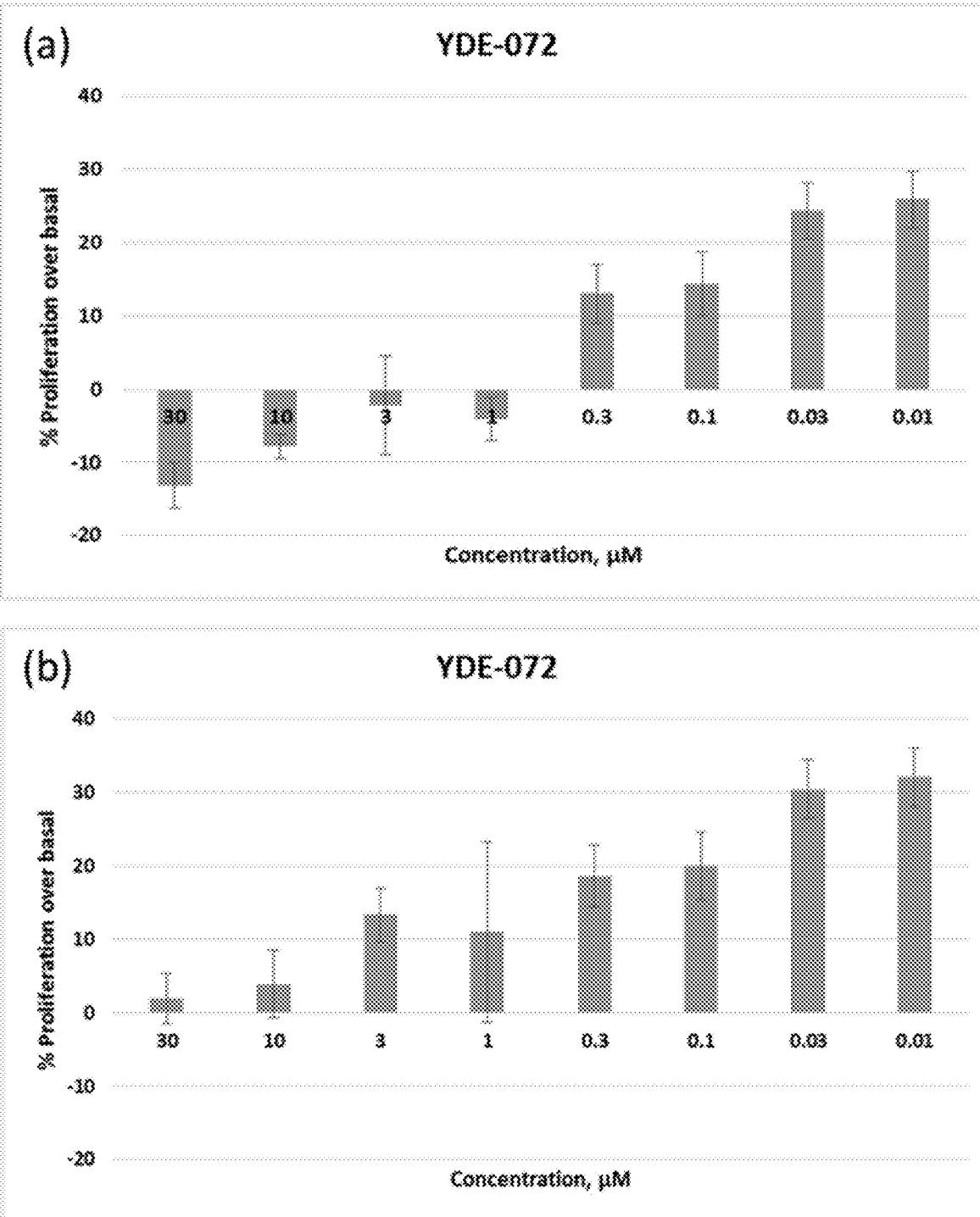

FIG. 40 is a diagram showing the cell growth rate after (a) 48 hours or (b) 72 hours from the treatment of YDE-072 on human corneal epithelial cells.

Figure 41:
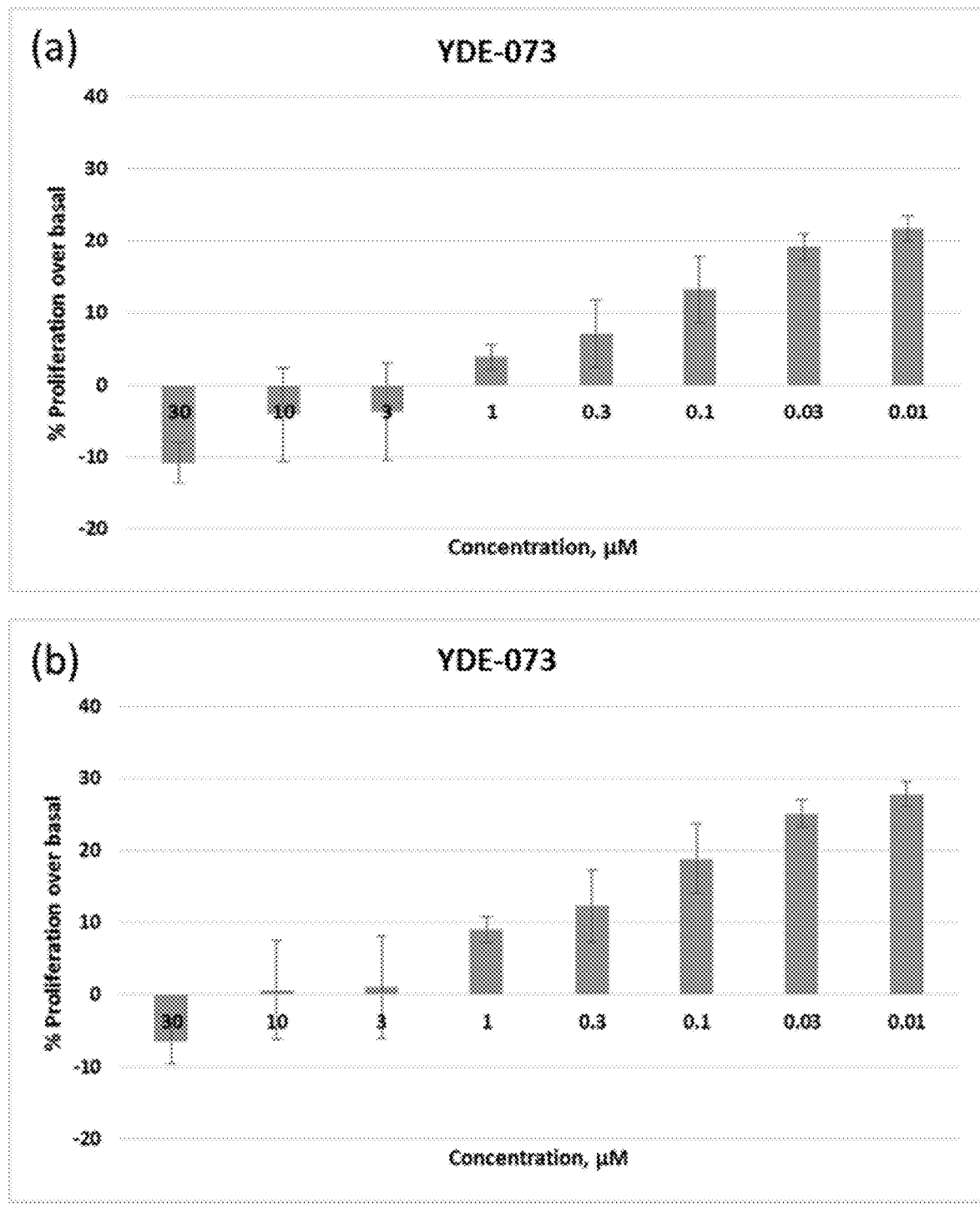

FIG. 41 is a diagram showing the cell growth rate after (a) 48 hours or (b) 72 hours from the treatment of YDE-073 on human corneal epithelial cells.

Figure 42:
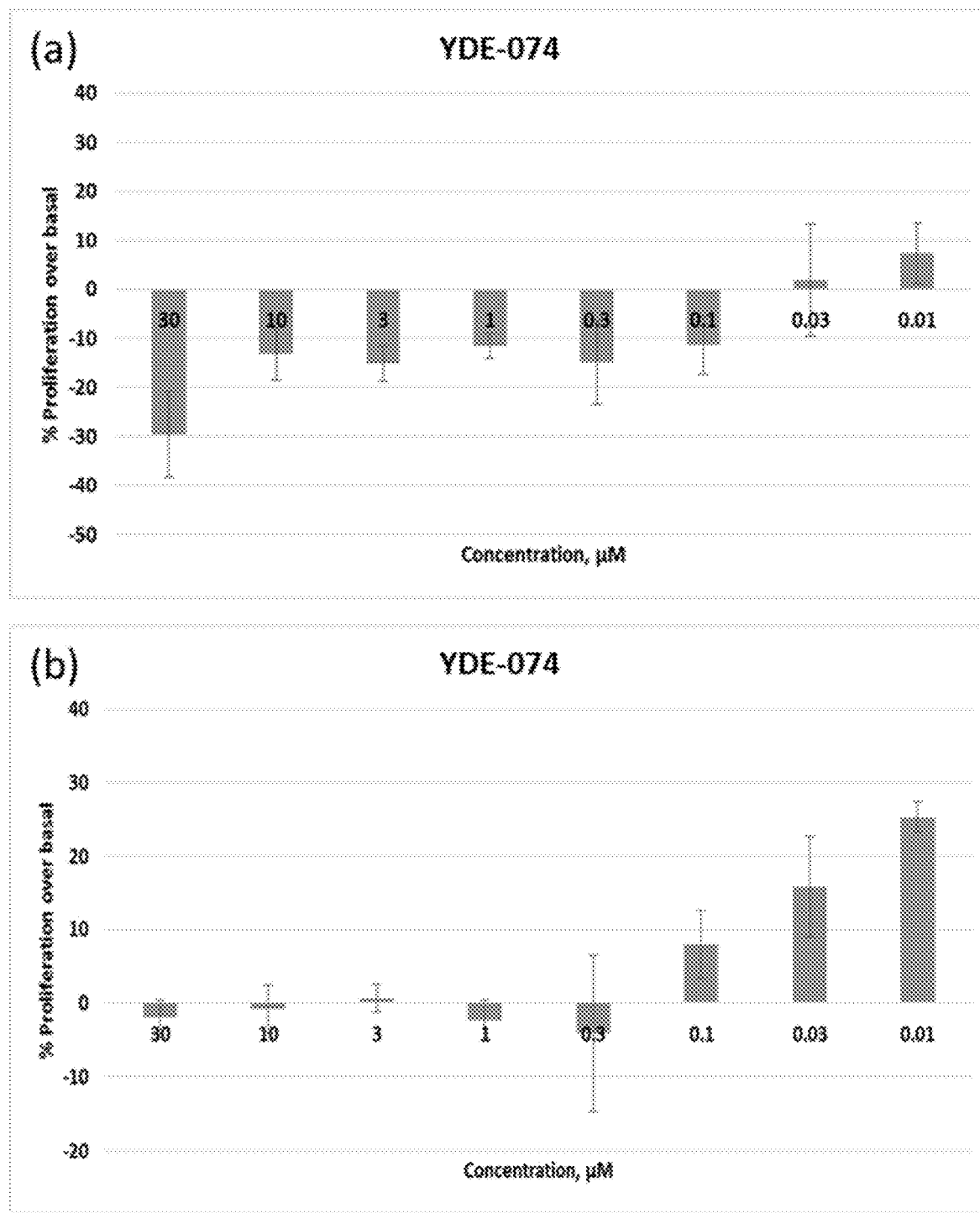

FIG. 42 is a diagram showing the cell growth rate after (a) 48 hours or (b) 72 hours from the treatment of YDE-074 on human corneal epithelial cells.

Figure 43:
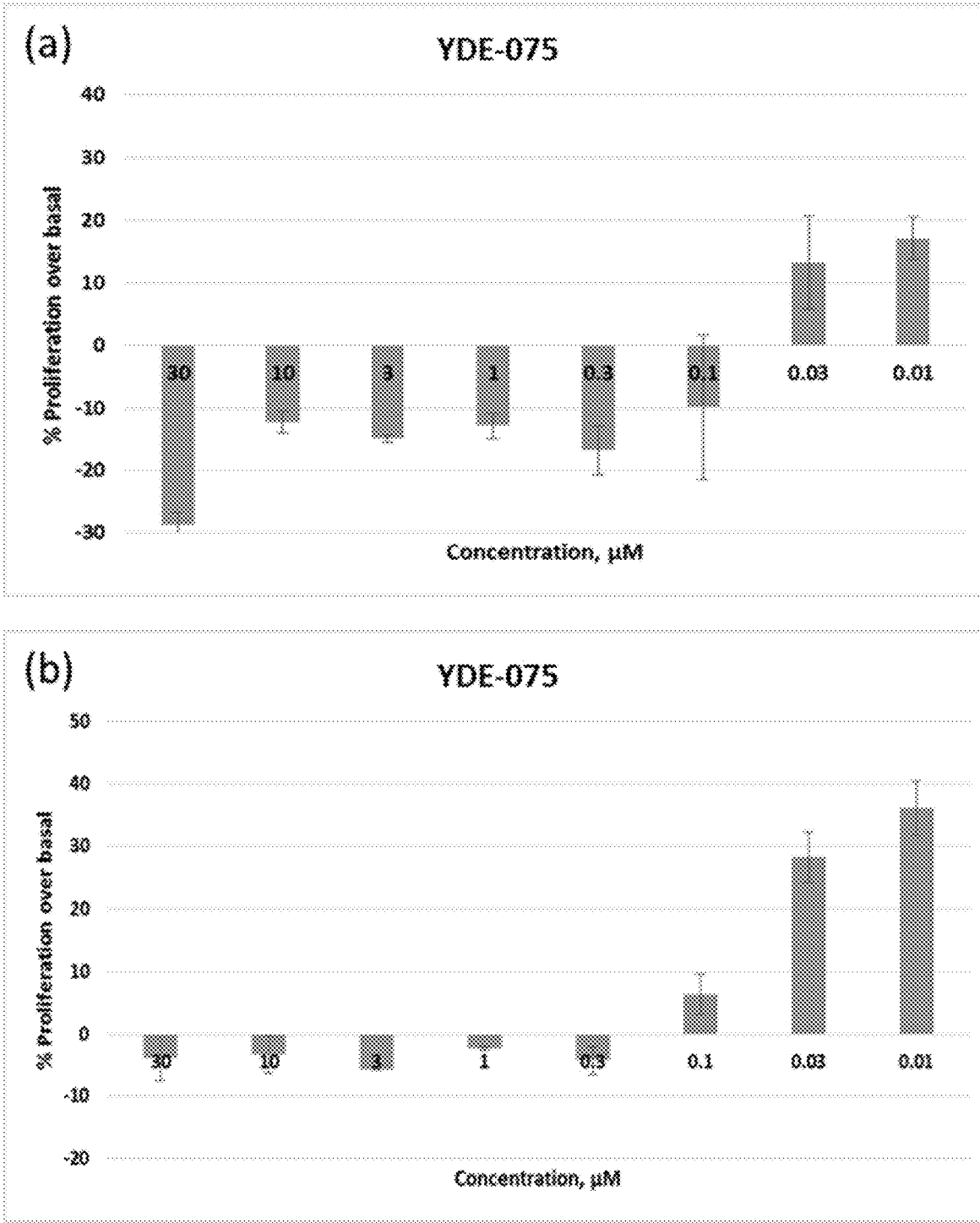

FIG. 43 is a diagram showing the cell growth rate after (a) 48 hours or (b) 72 hours from the treatment of YDE-075 on human corneal epithelial cells.

Figure 44:
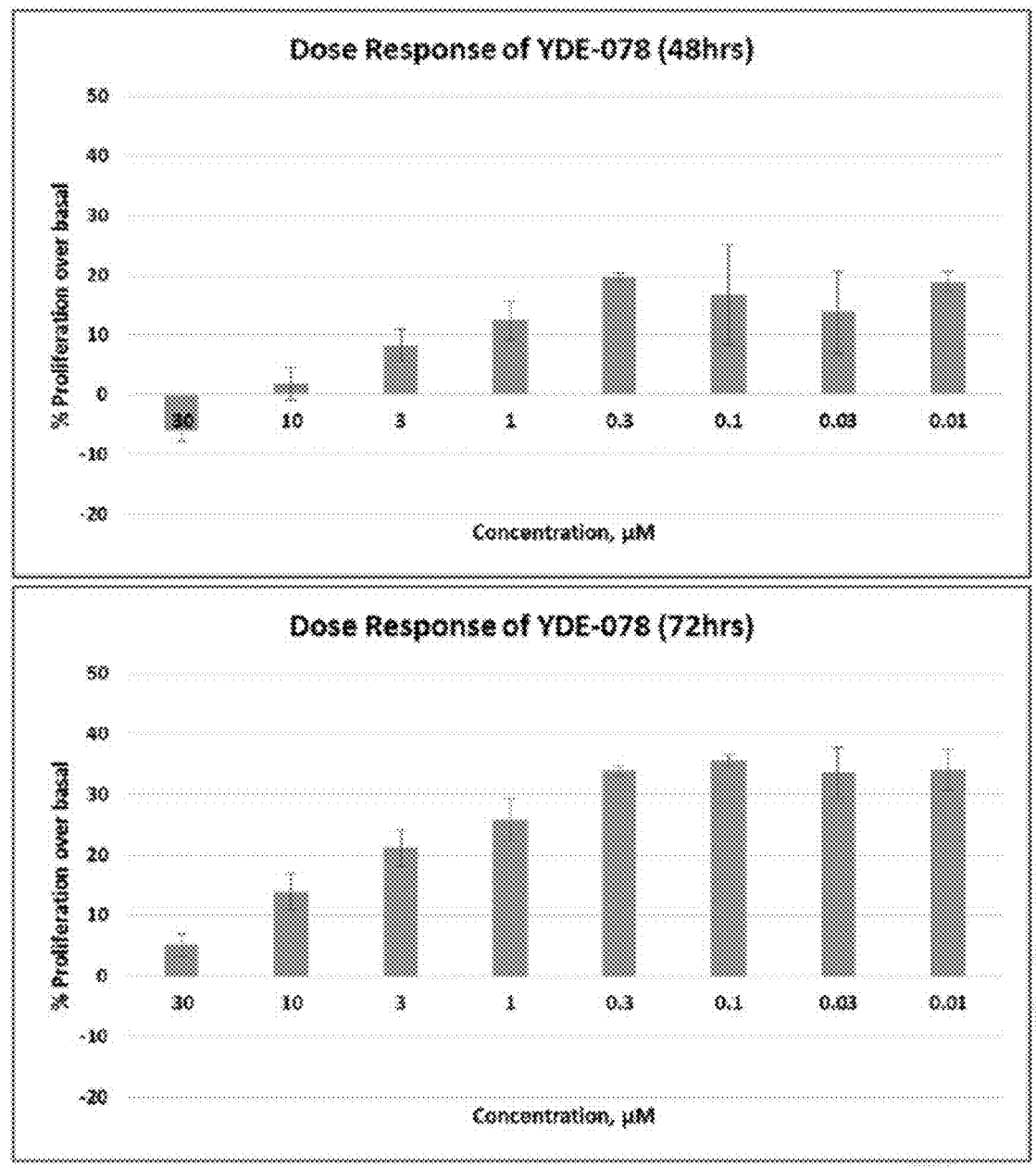

FIG. 44 is a diagram showing the cell growth rate after 48 hours and 72 hours from the treatment of YDE-078 on human corneal epithelial cells.

Figure 45:
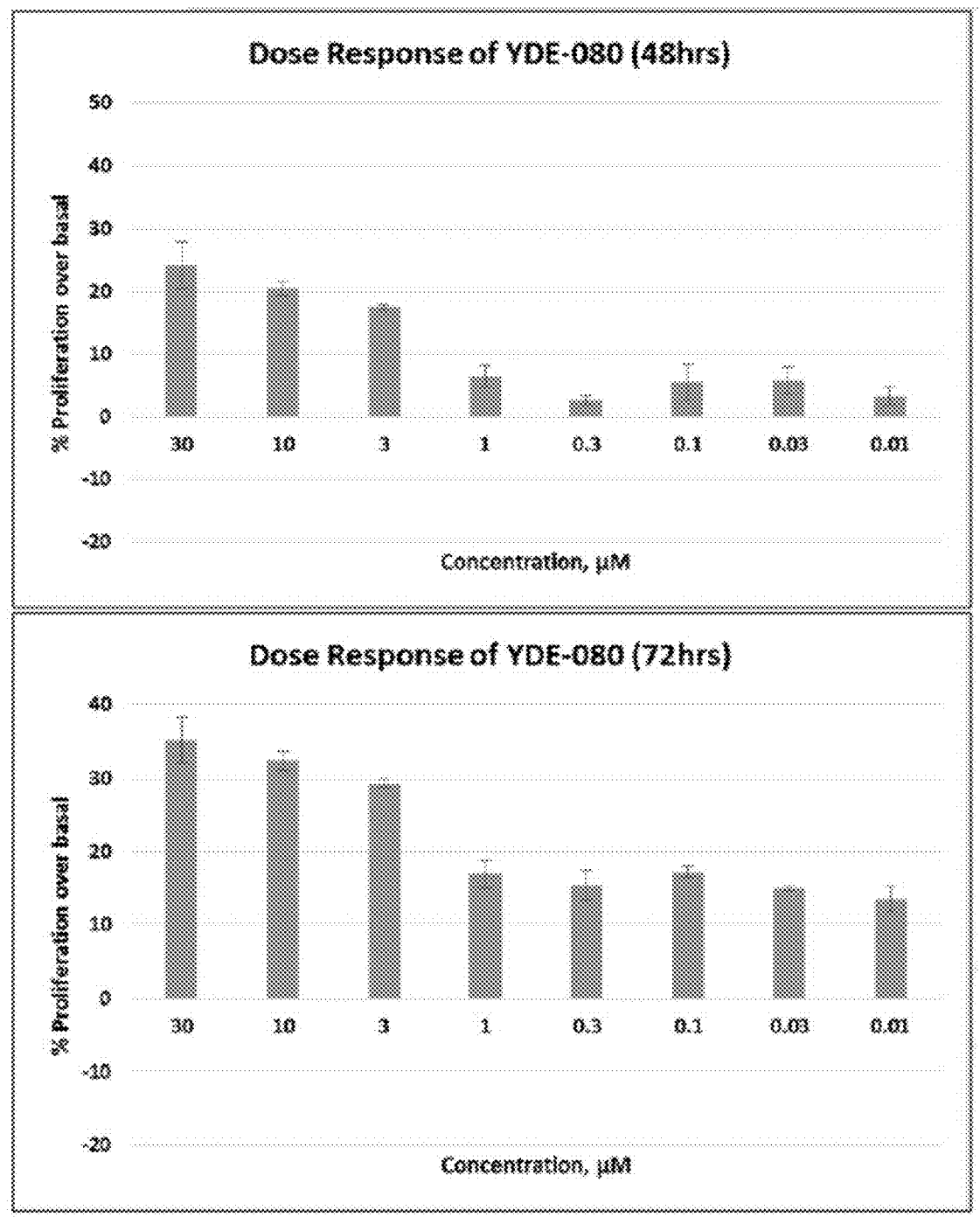

FIG. 45 is a diagram showing the cell growth rate after 48 hours and 72 hours from the treatment of YDE-080 on human corneal epithelial cells.

Figure 46:
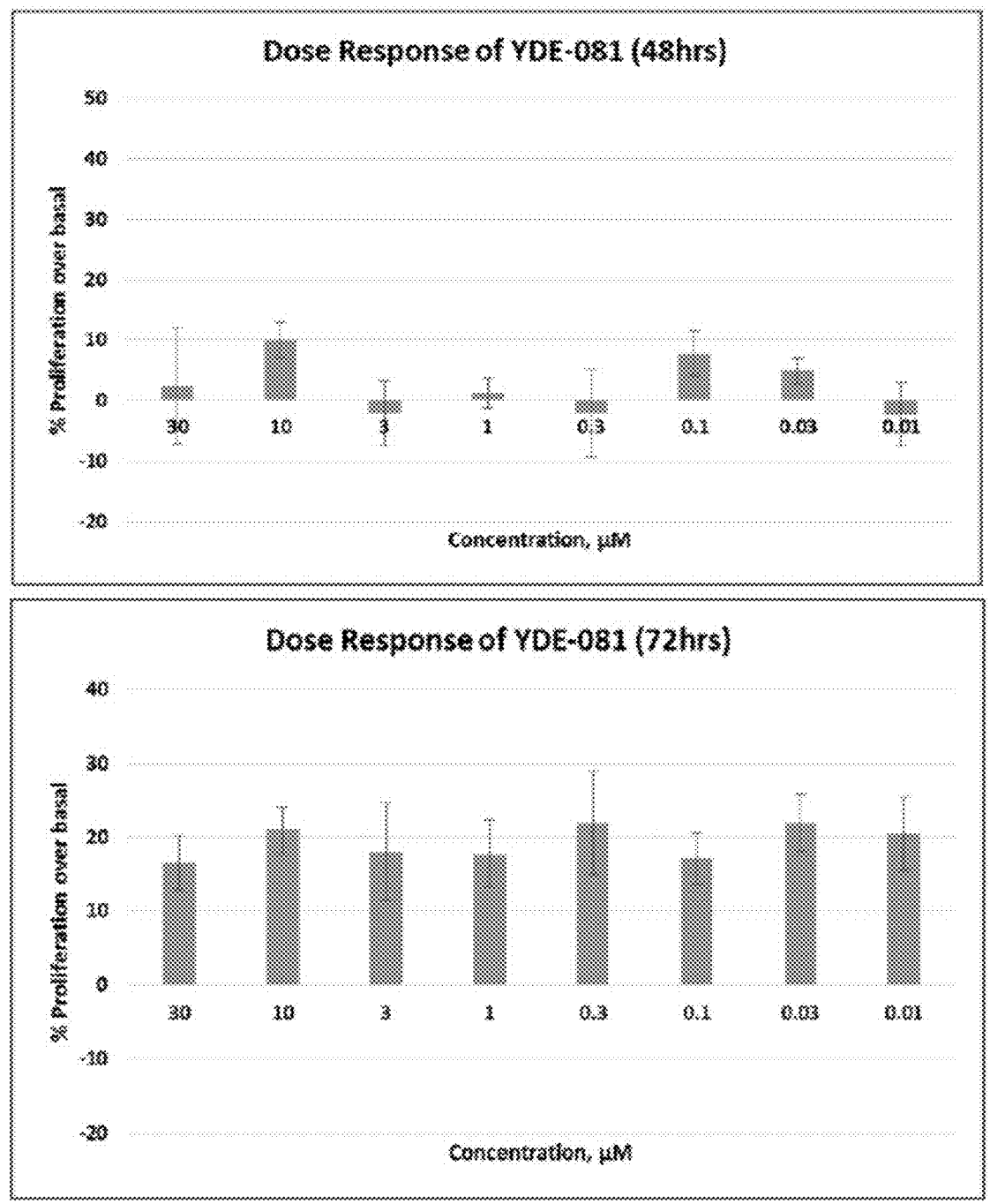

FIG. 46 is a diagram showing the cell growth rate after 48 hours and 72 hours from the treatment of YDE-081 on human corneal epithelial cells.

Figure 47:
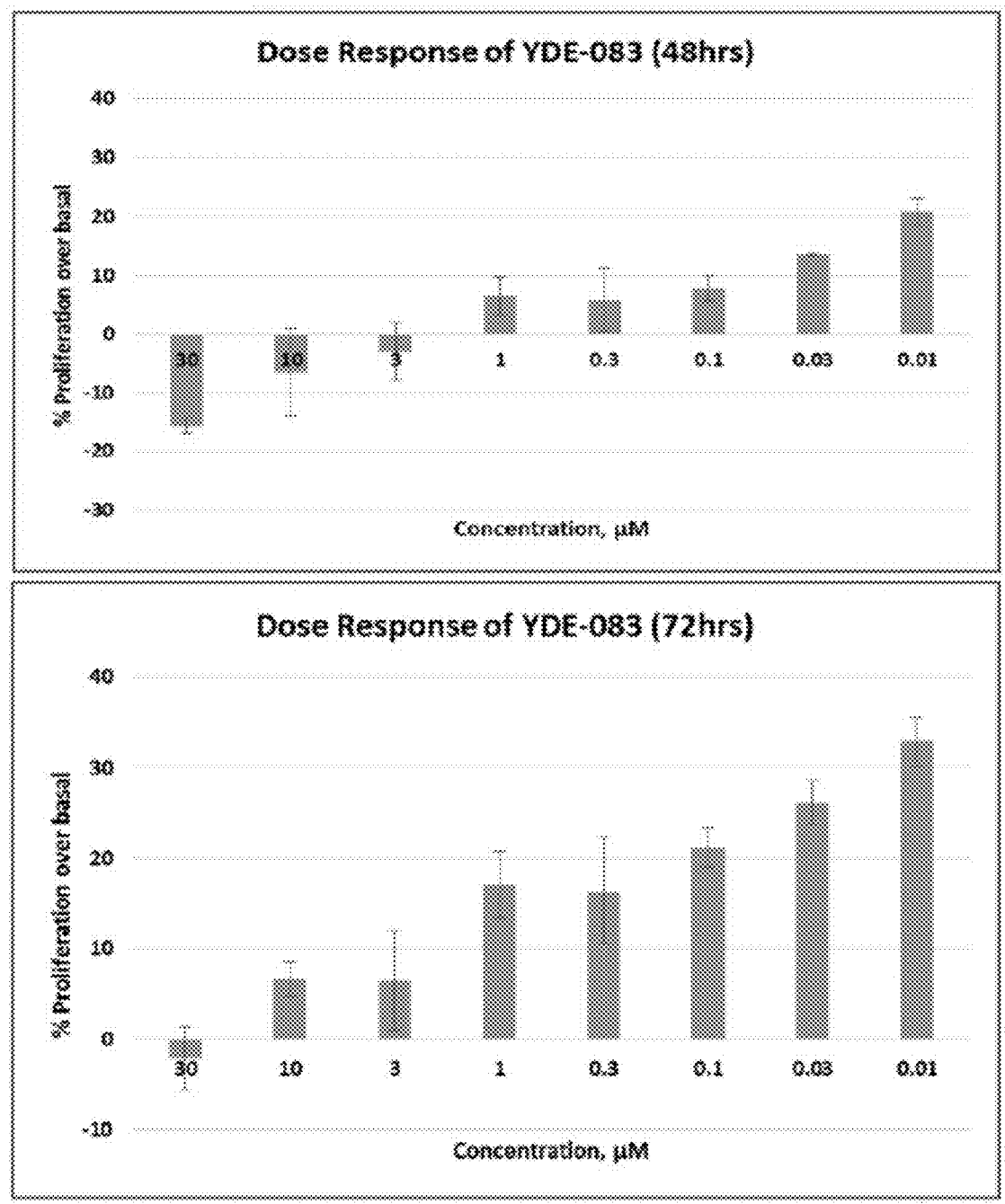

FIG. 47 is a diagram showing the cell growth rate after 48 hours and 72 hours from the treatment of YDE-083 on human corneal epithelial cells.

Figure 48:
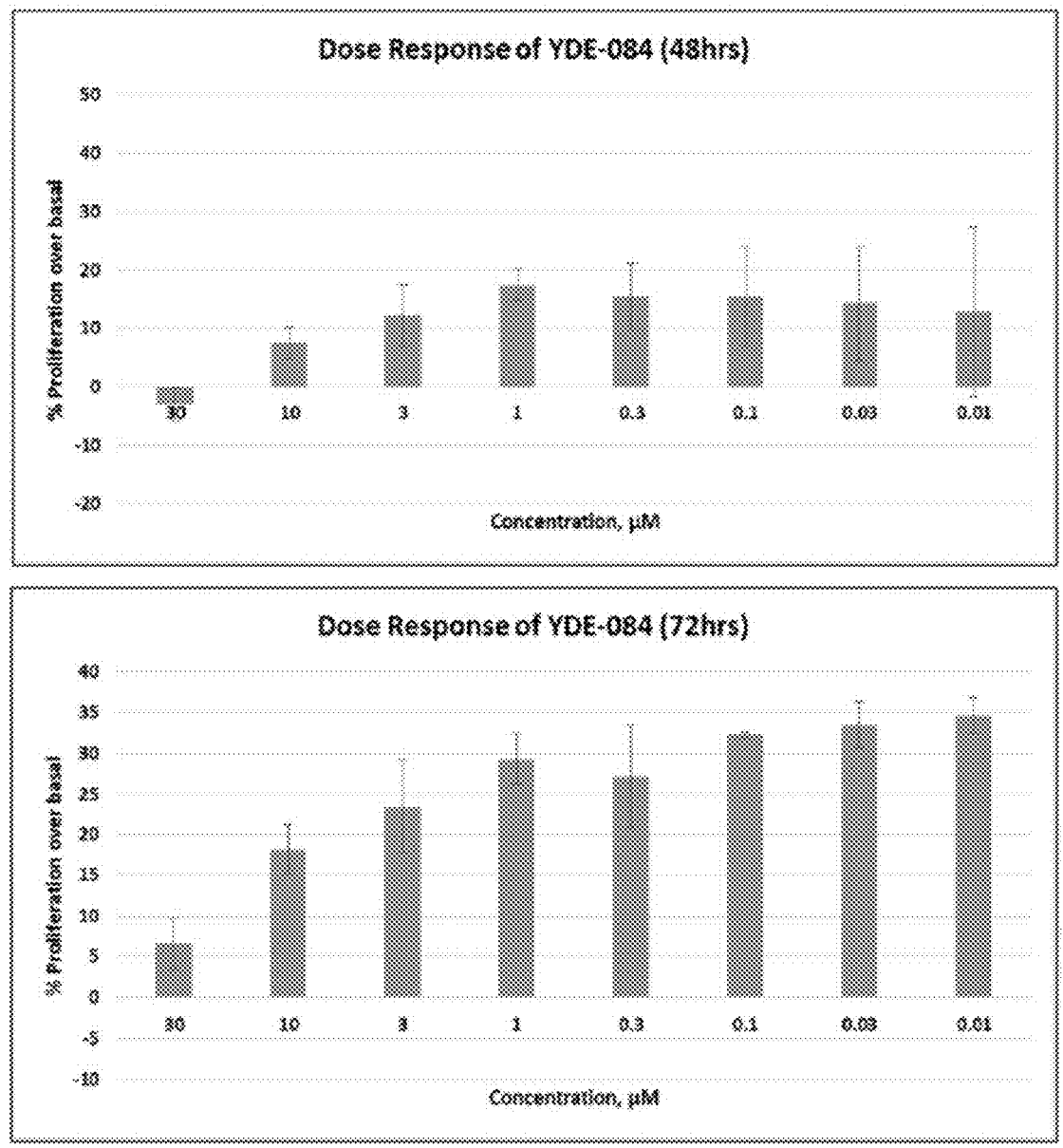

FIG. 48 is a diagram showing the cell growth rate after 48 hours and 72 hours from the treatment of YDE-084 on human corneal epithelial cells.

Figure 49:
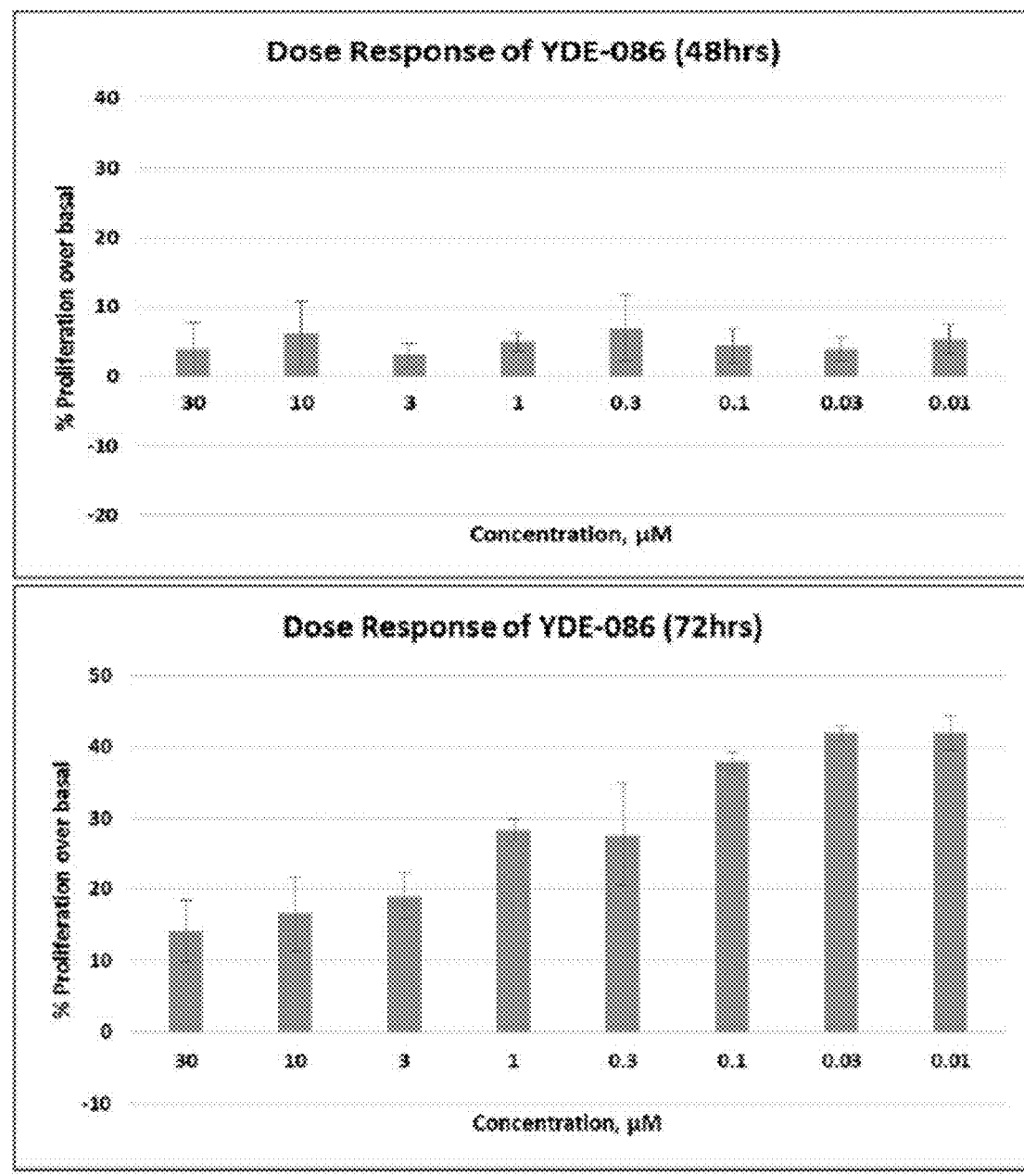

FIG. 49 is a diagram showing the cell growth rate after 48 hours and 72 hours from the treatment of YDE-086 on human corneal epithelial cells.

Figure 50:
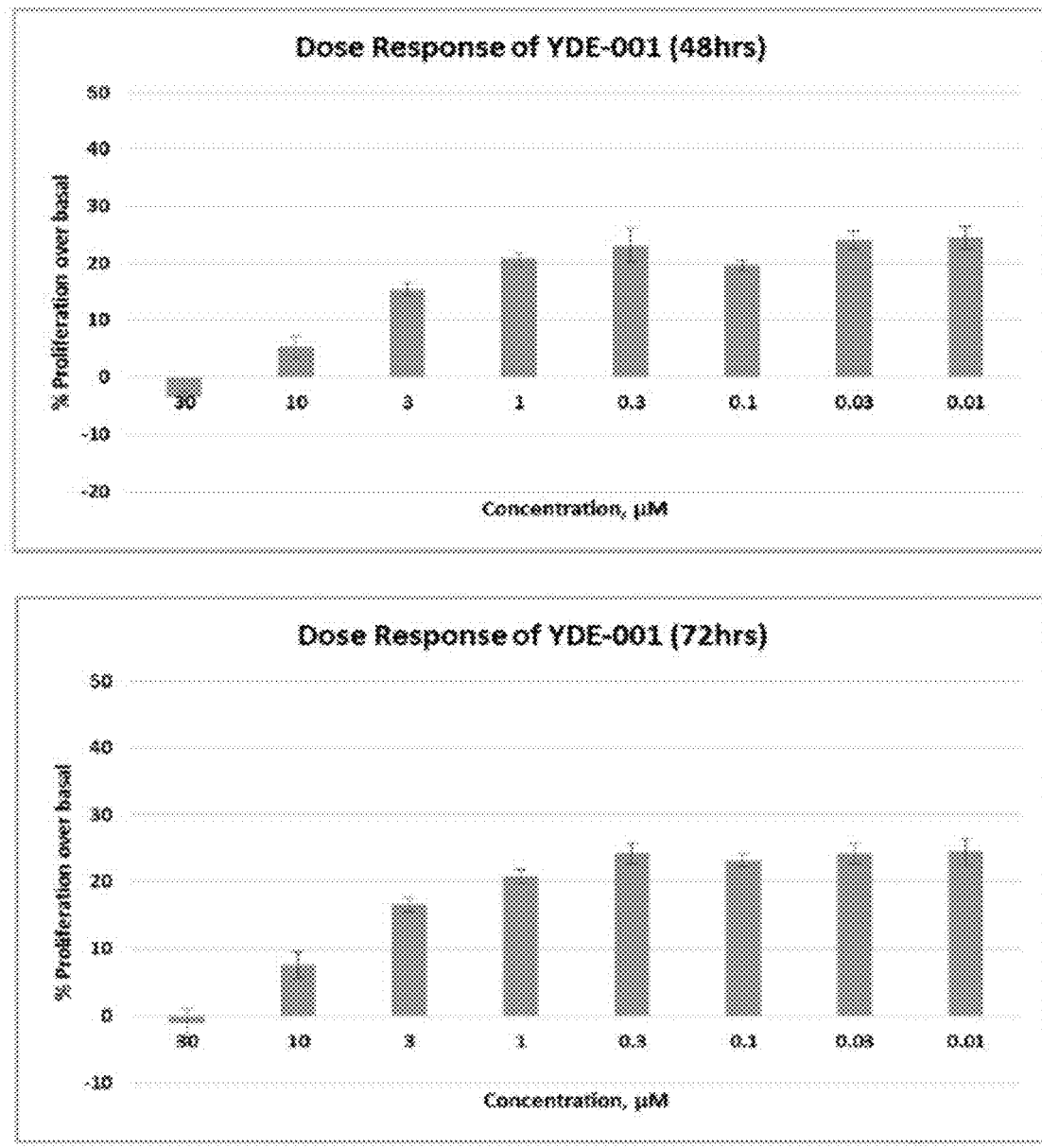

FIG. 50 is a diagram showing the cell growth rate after 48 hours and 72 hours from the treatment of YDE-001 on human corneal epithelial cells.

Figure 51:
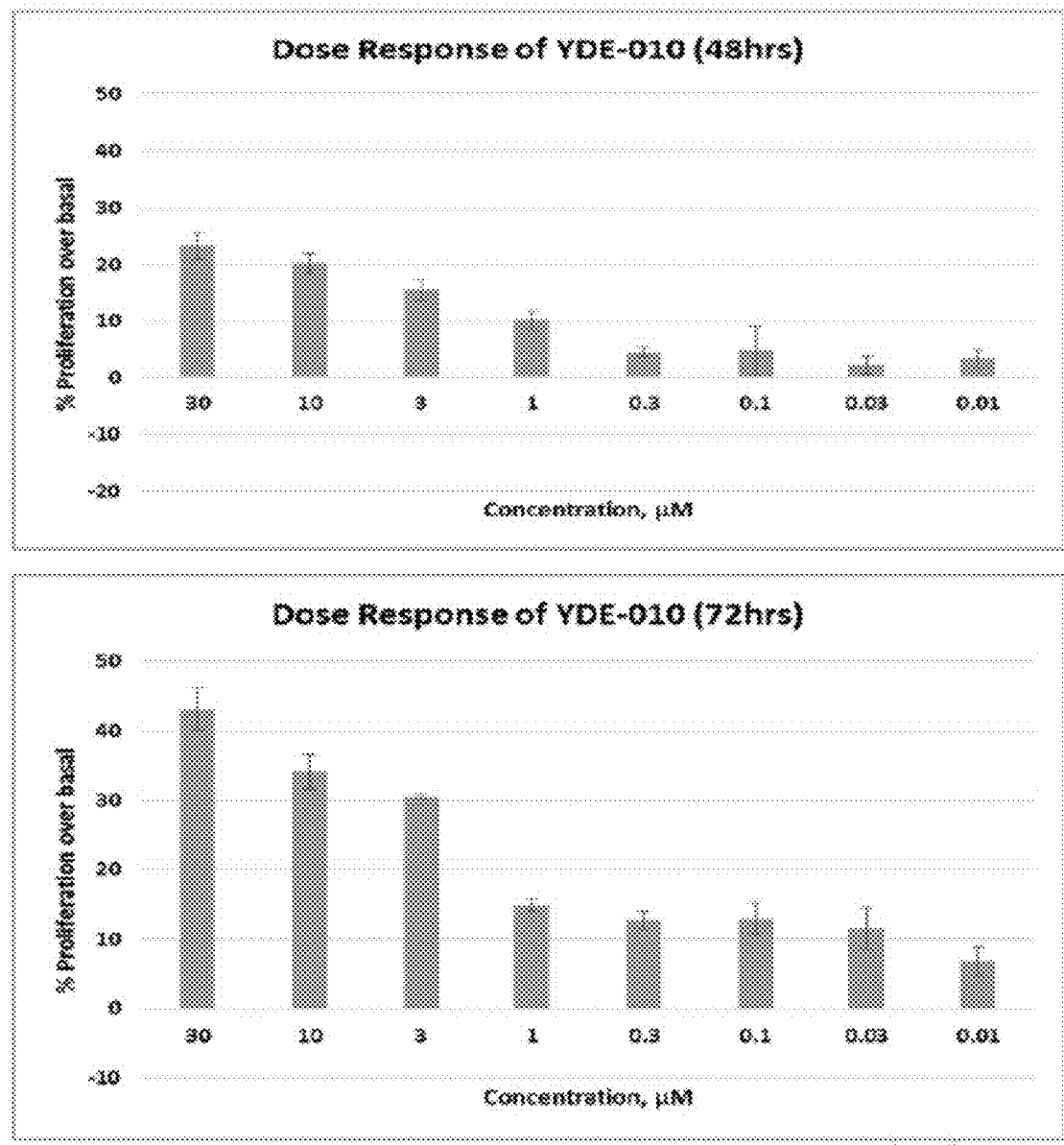

FIG. 51 is a diagram showing the cell growth rate after 48 hours and 72 hours from the treatment of YDE-010 on human corneal epithelial cells.

Figure 52:
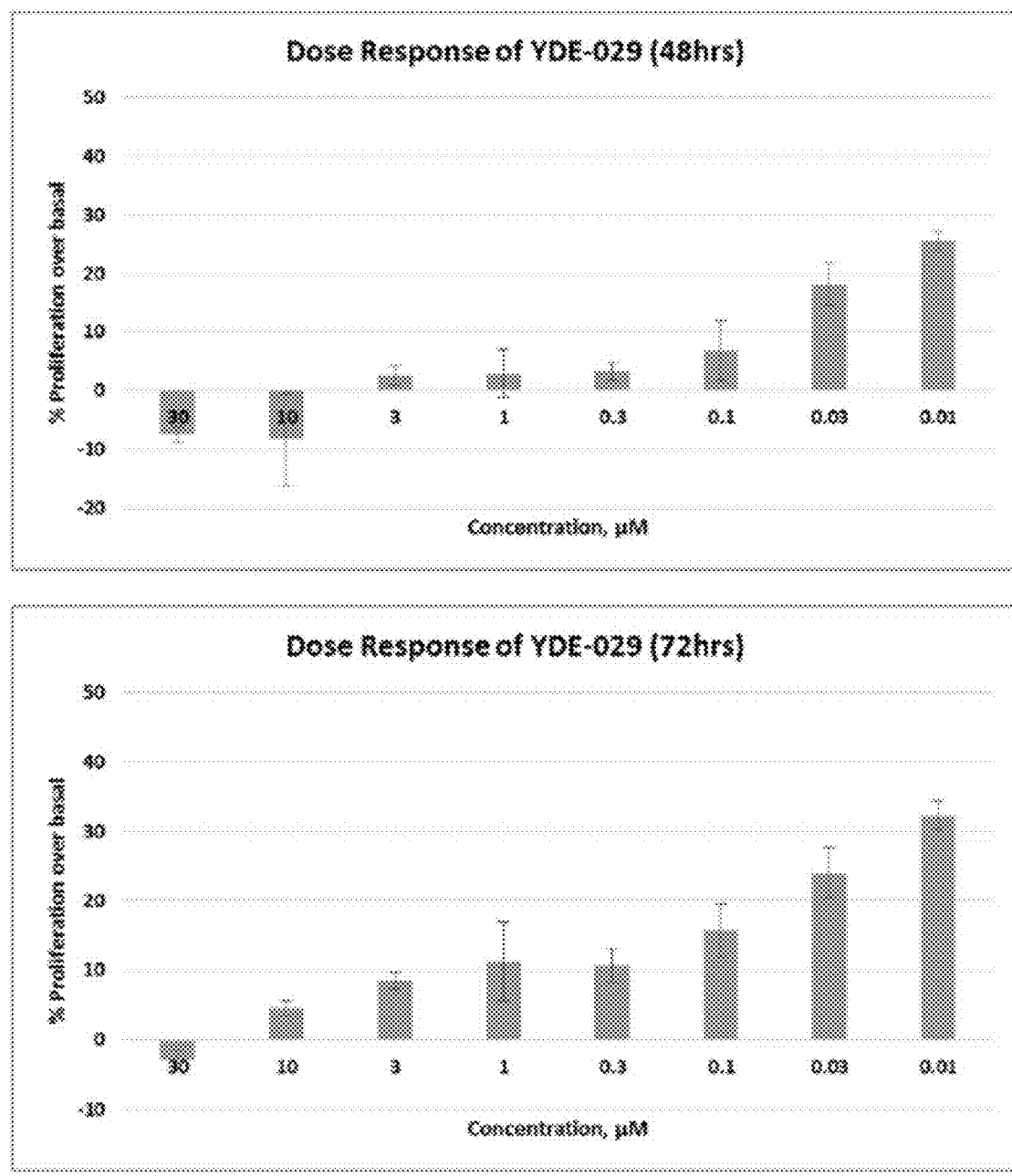

FIG. 52 is a diagram showing the cell growth rate after 48 hours and 72 hours from the treatment of YDE-029 on human corneal epithelial cells.

Figure 53:
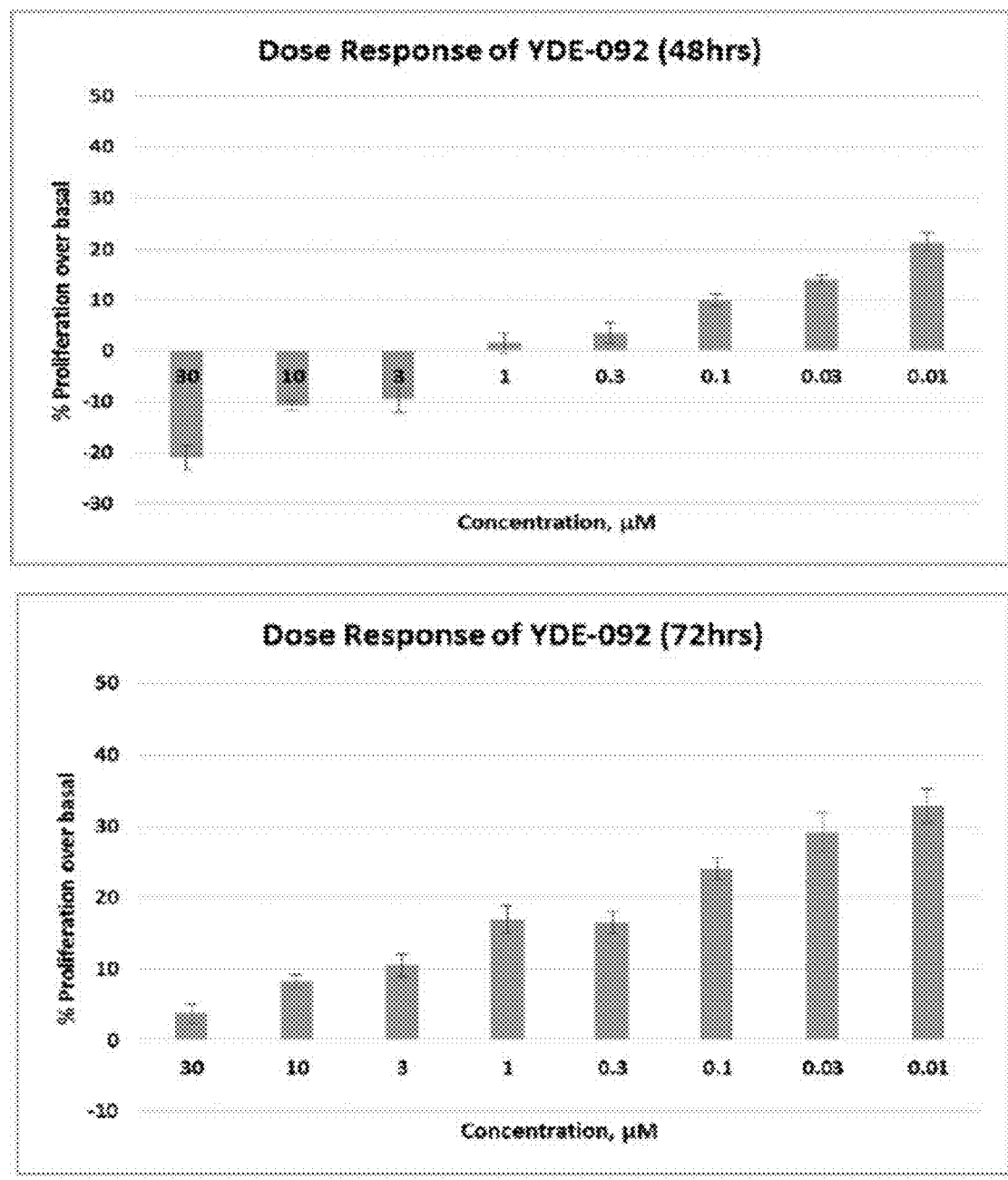

FIG. 53 is a diagram showing the cell growth rate after 48 hours and 72 hours from the treatment of YDE-092 on human corneal epithelial cells.

Figure 54:
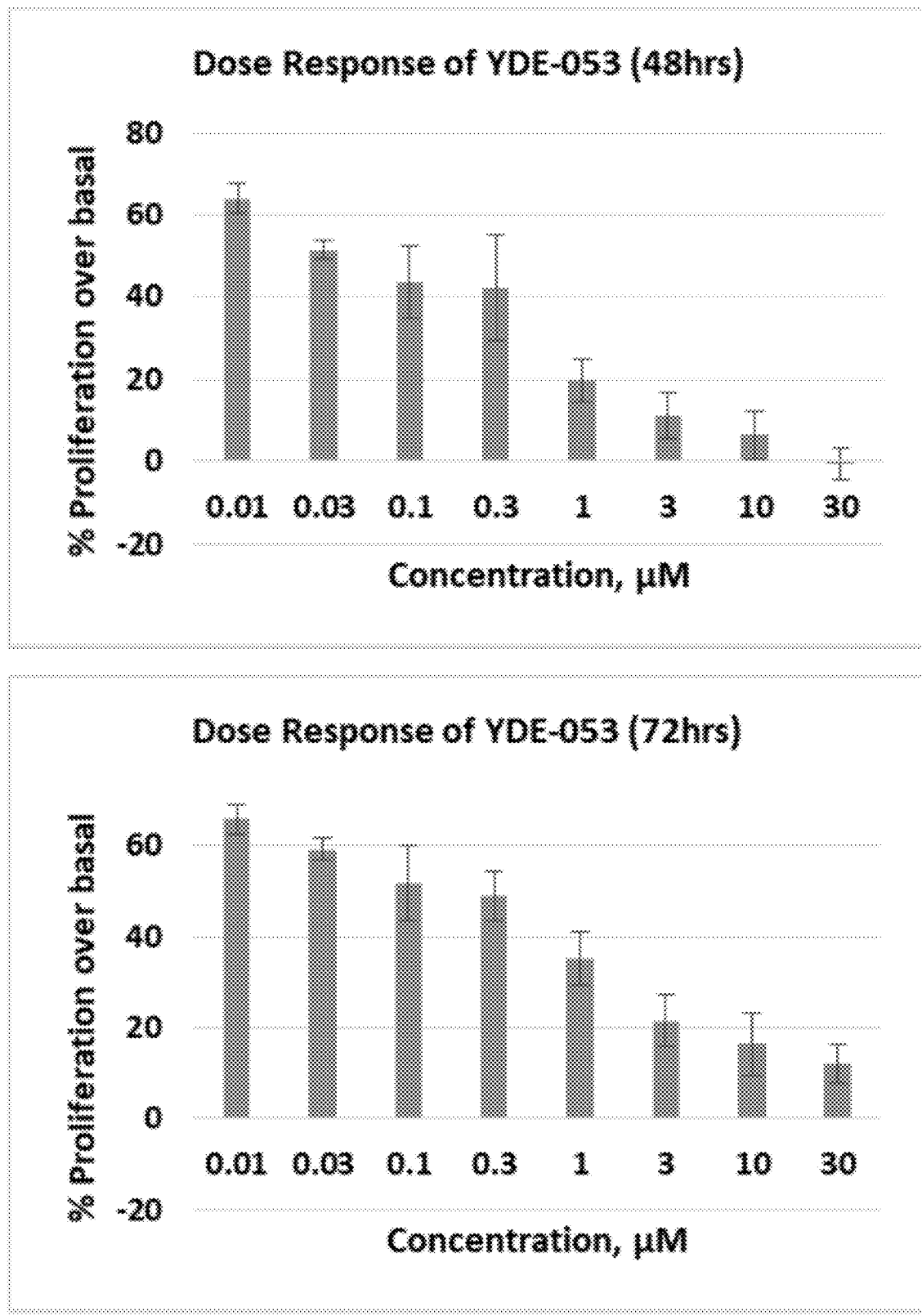

FIG. 54 is a diagram showing the cell growth rate after 48 hours and 72 hours from the treatment of YDE-053 on human corneal epithelial cells.

Figure 55:
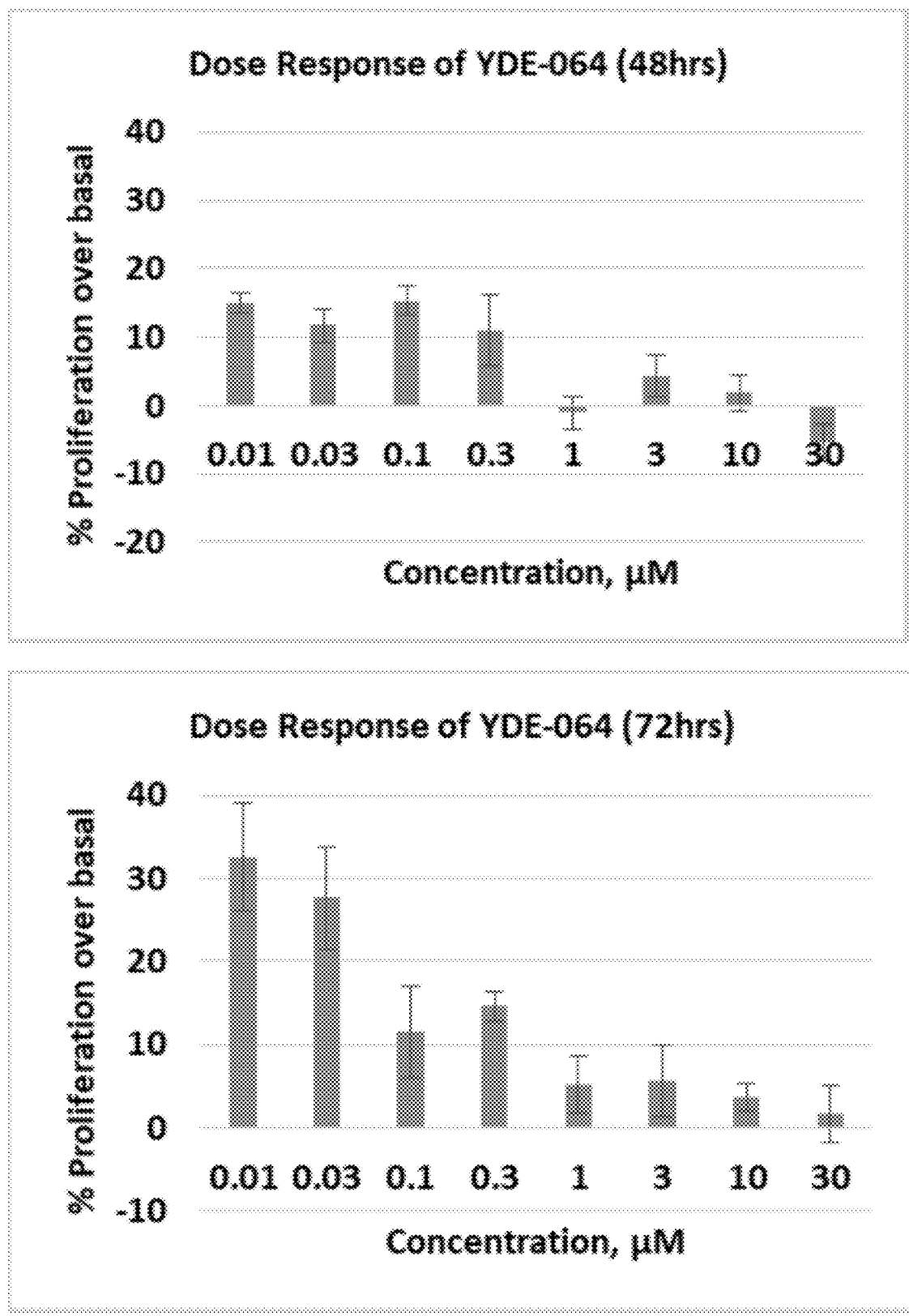

FIG. 55 is a diagram showing the cell growth rate after 48 hours and 72 hours from the treatment of YDE-064 on human corneal epithelial cells.

Figure 56:
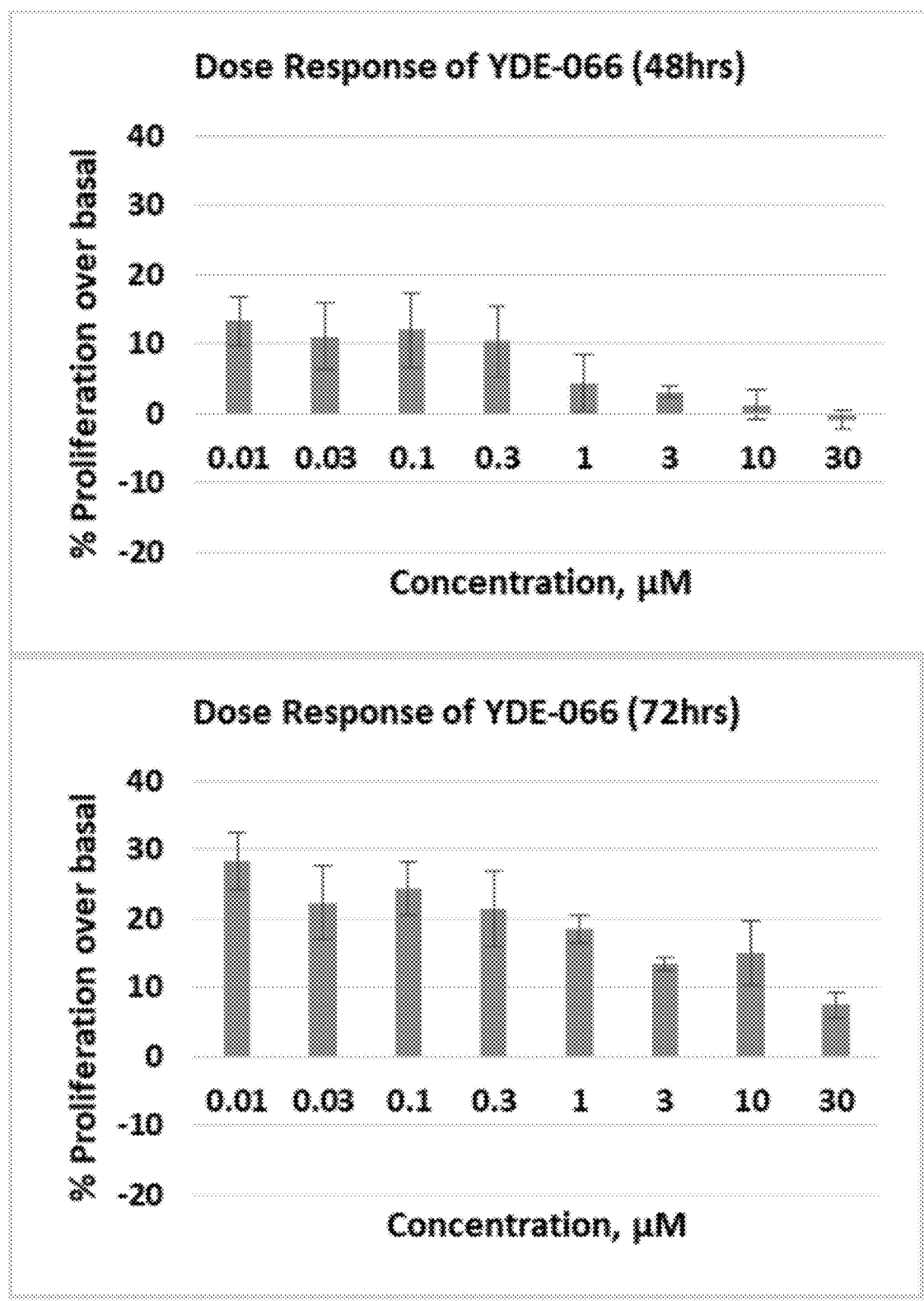

FIG. 56 is a diagram showing the cell growth rate after 48 hours and 72 hours from the treatment of YDE-066 on human corneal epithelial cells.

Figure 57:
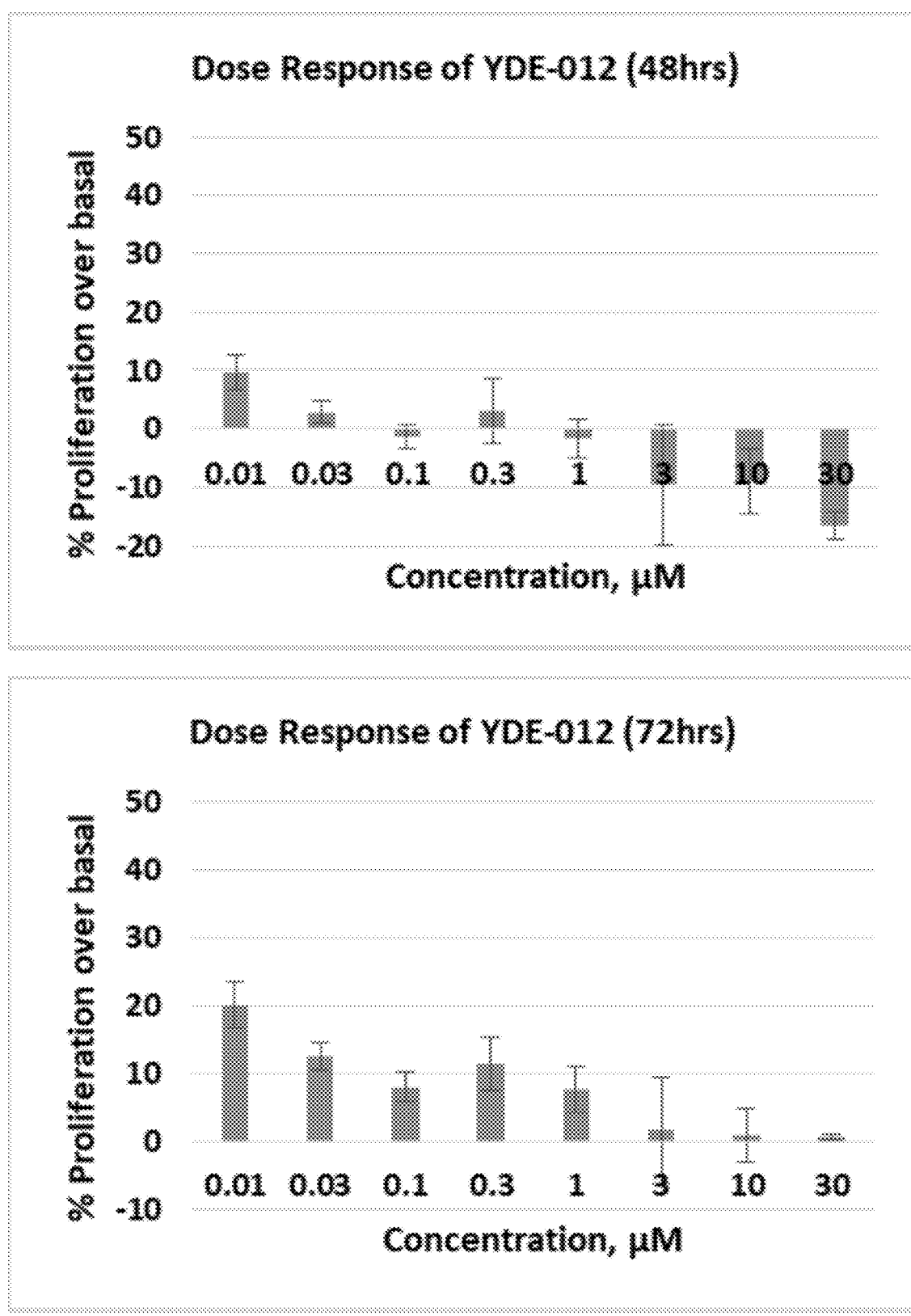

FIG. 57 is a diagram showing the cell growth rate after 48 hours and 72 hours from the treatment of YDE-012 on human corneal epithelial cells.

Figure 58:
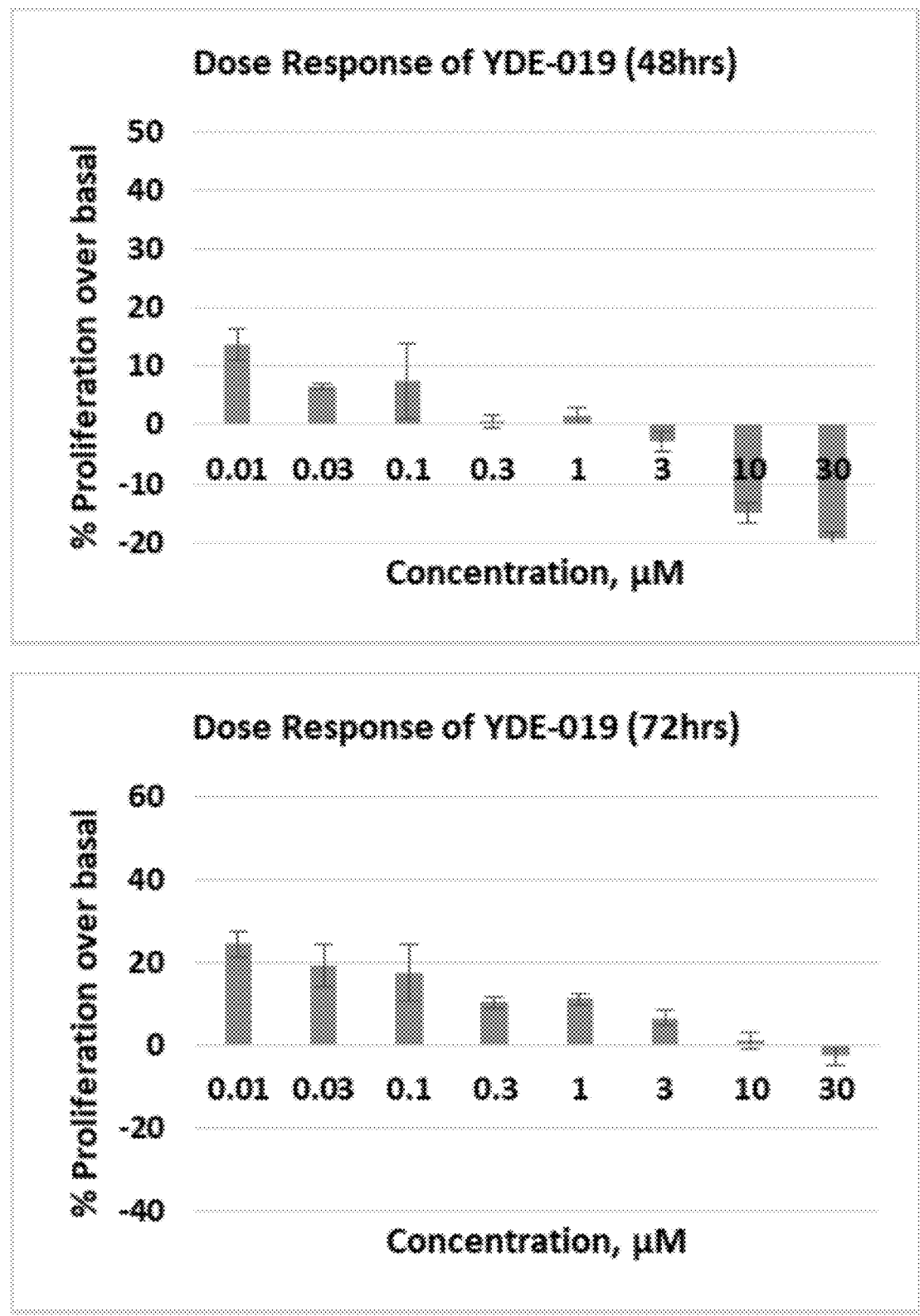

FIG. 58 is a diagram showing the cell growth rate after 48 hours and 72 hours from the treatment of YDE-019 on human corneal epithelial cells.

Figure 59:
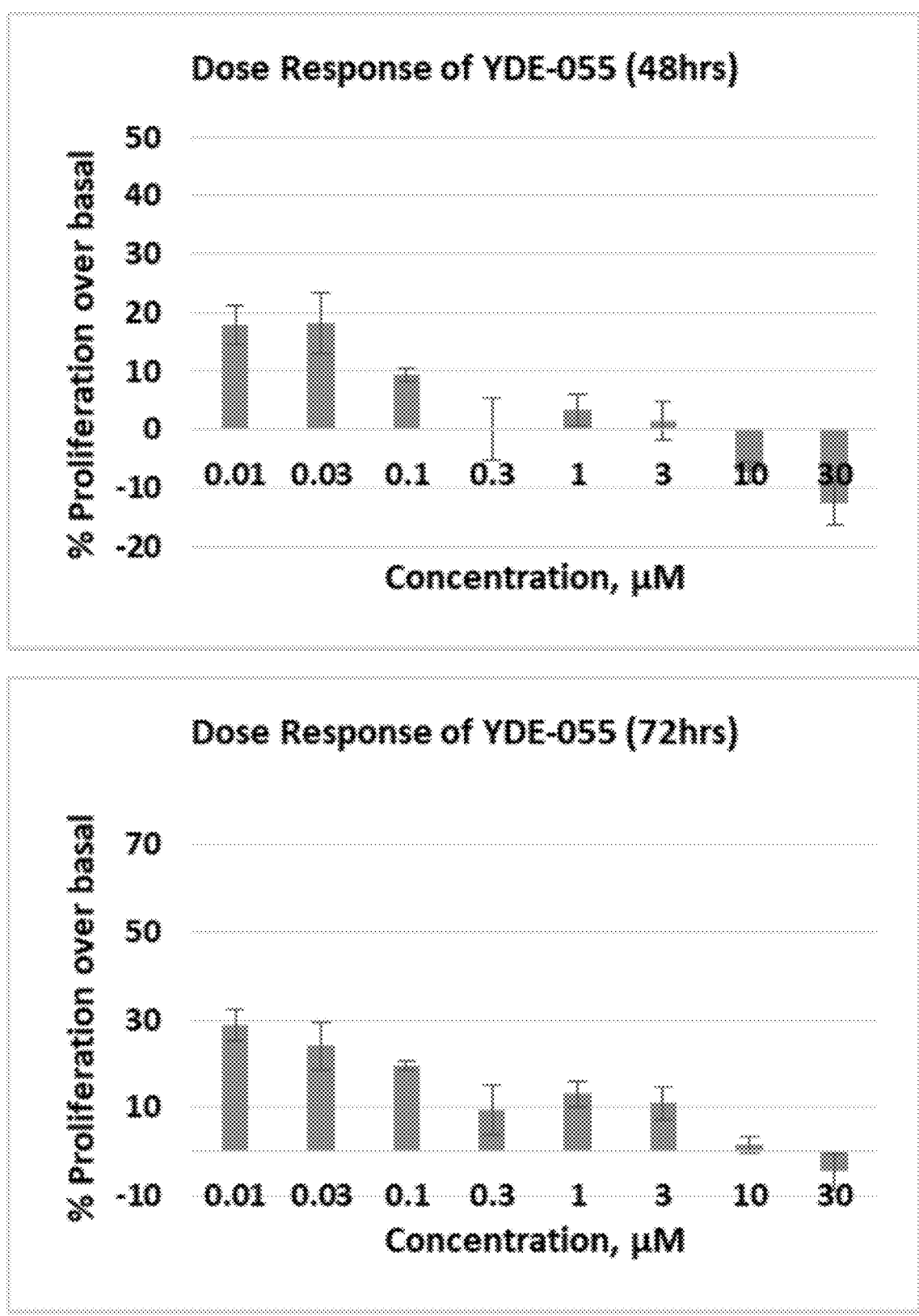

FIG. 59 is a diagram showing the cell growth rate after 48 hours and 72 hours from the treatment of YDE-055 on human corneal epithelial cells.

Figure 60:
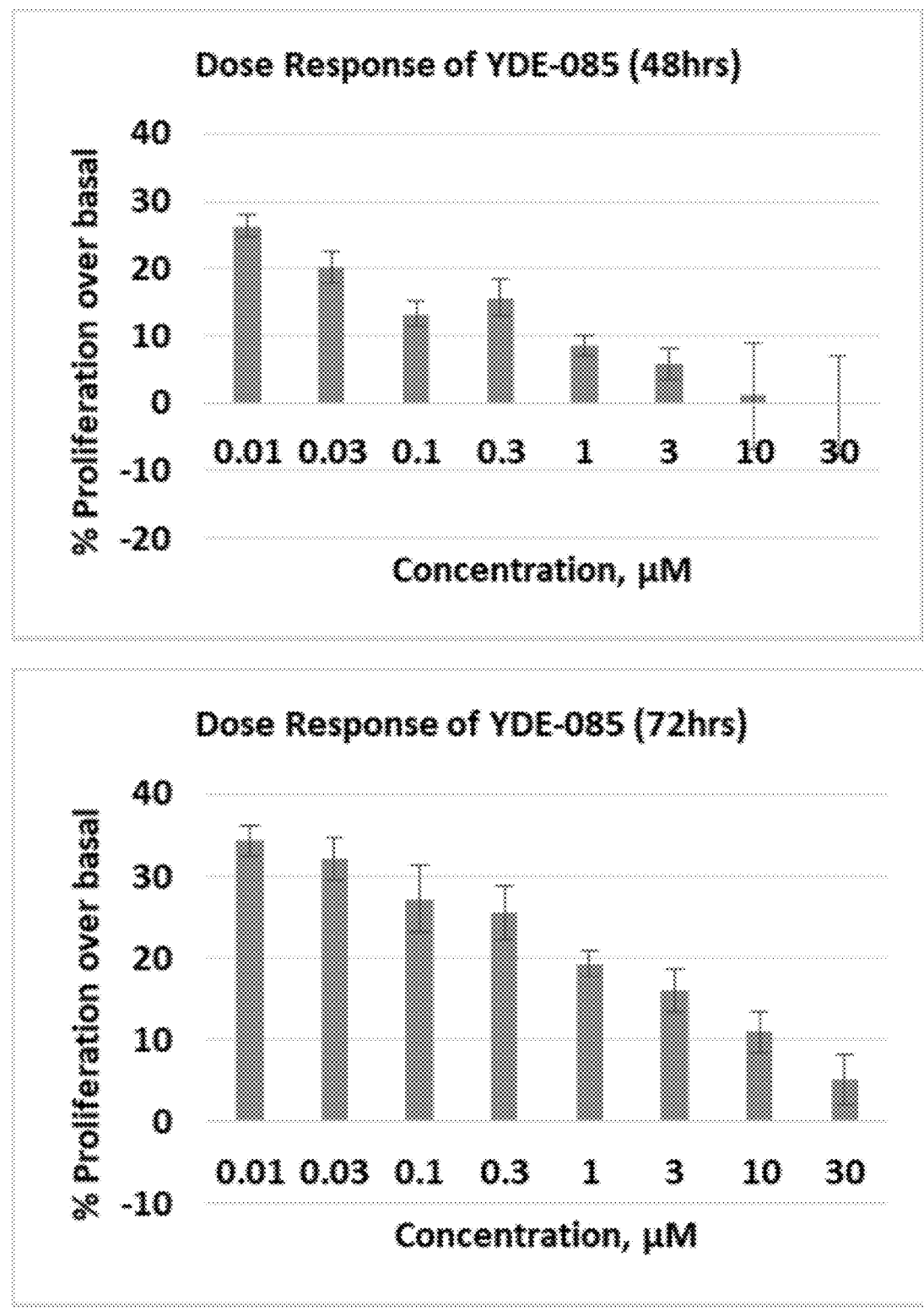

FIG. 60 is a diagram showing the cell growth rate after 48 hours and 72 hours from the treatment of YDE-085 on human corneal epithelial cells.

Figure 61:
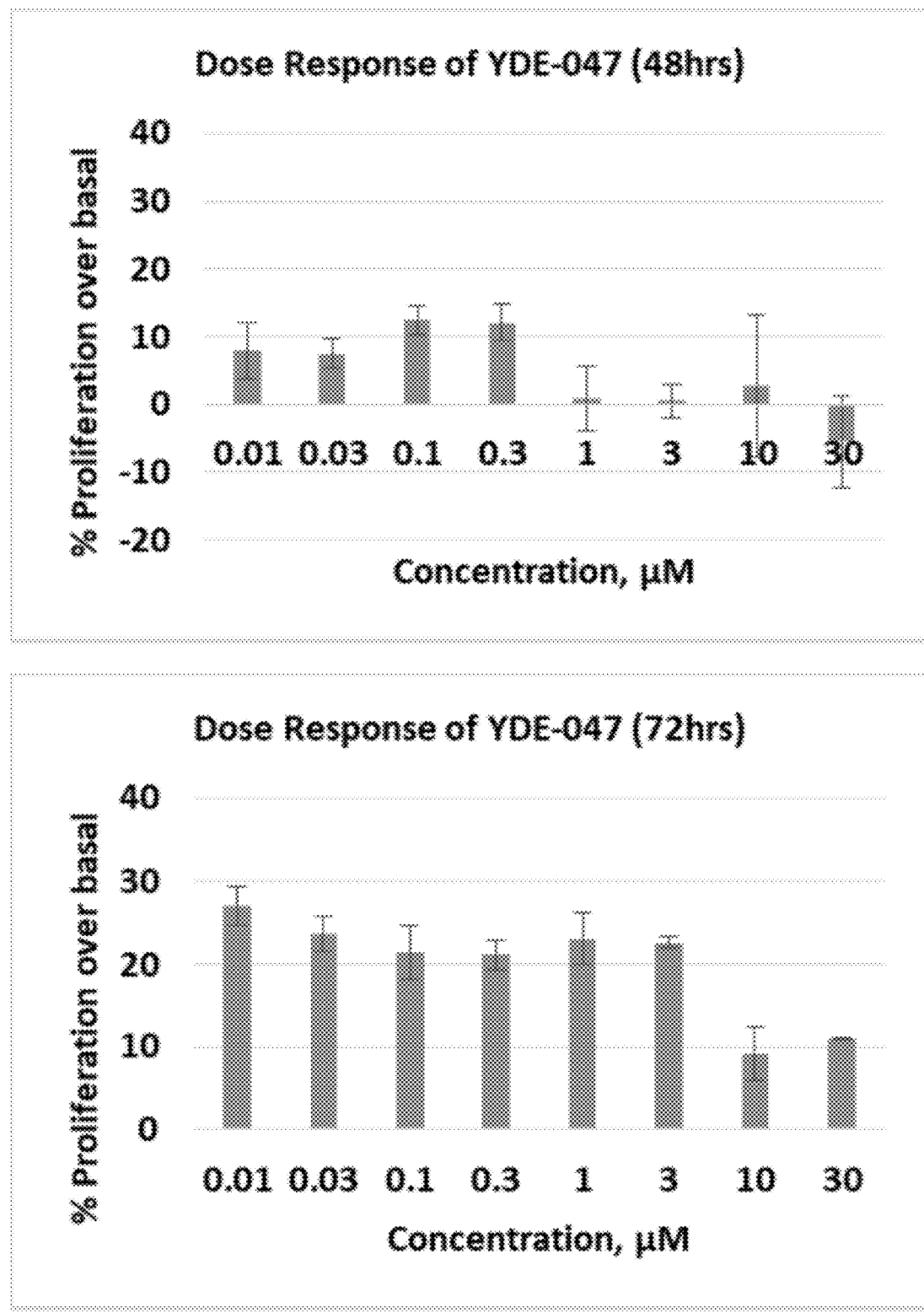

FIG. 61 is a diagram showing the cell growth rate after 48 hours and 72 hours from the treatment of YDE-047 on human corneal epithelial cells.

Figure 62:
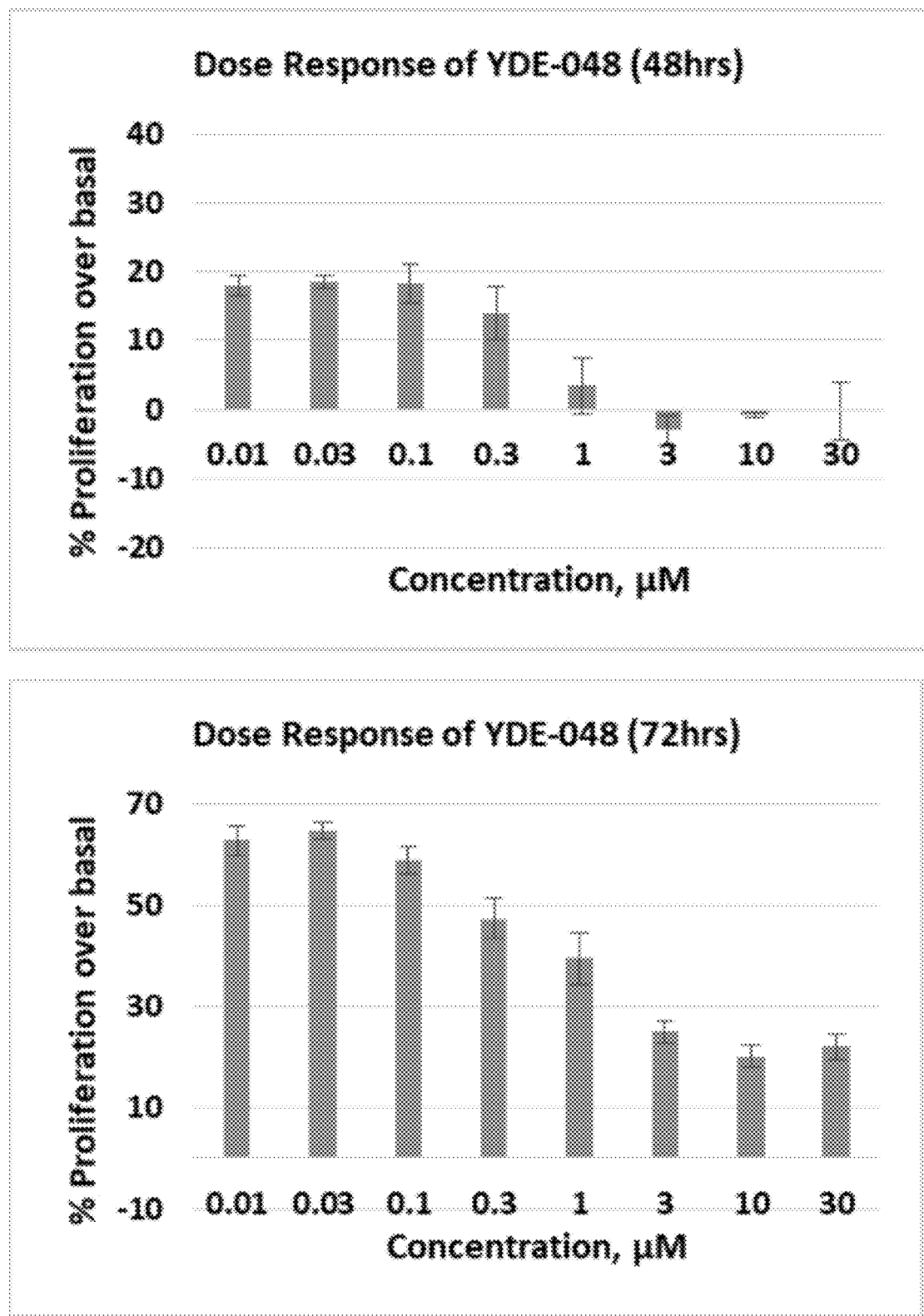

FIG. 62 is a diagram showing the cell growth rate after 48 hours and 72 hours from the treatment of YDE-048 on human corneal epithelial cells.

Figure 63:
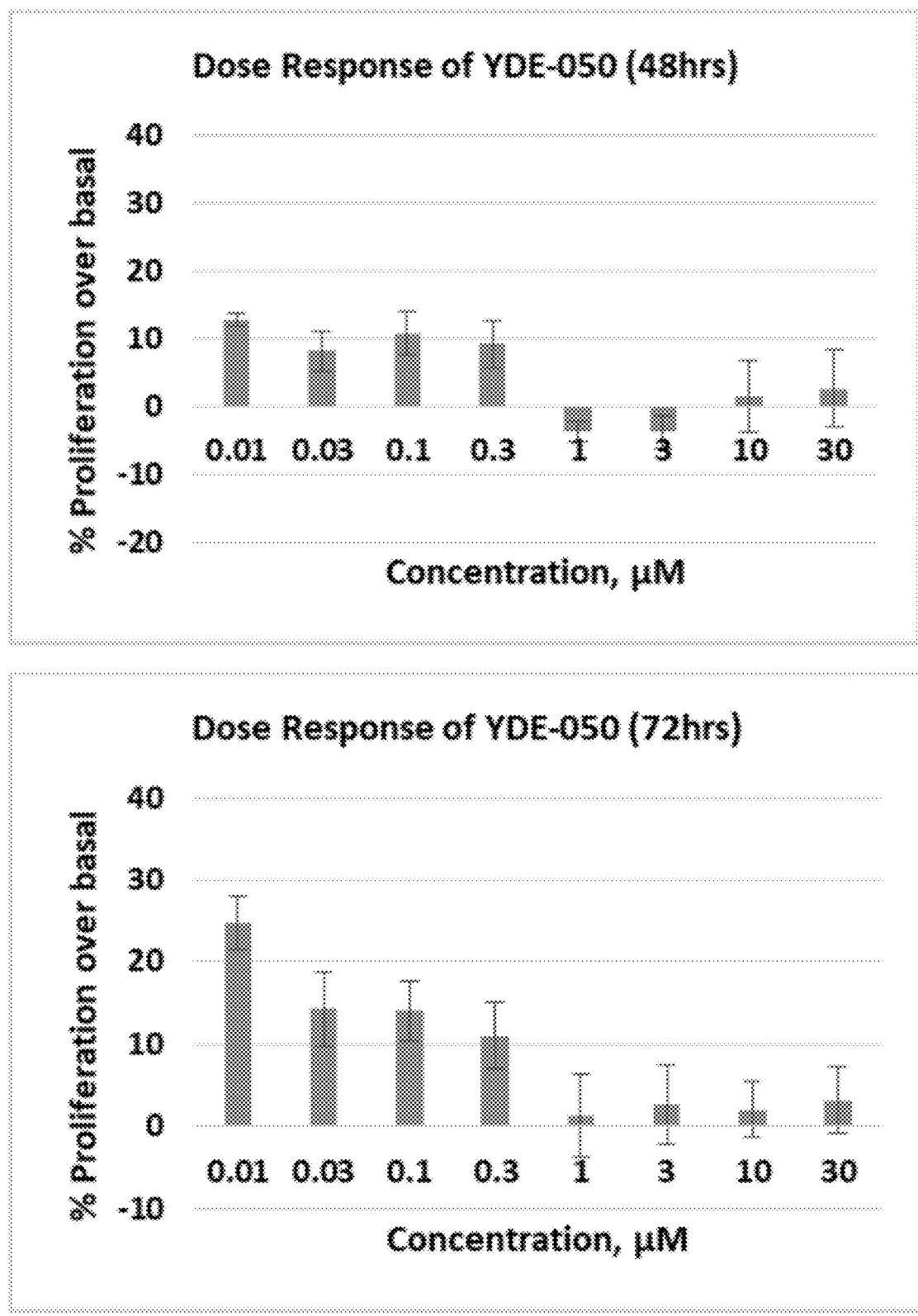

FIG. 63 is a diagram showing the cell growth rate after 48 hours and 72 hours from the treatment of YDE-050 on human corneal epithelial cells.

Figure 64:
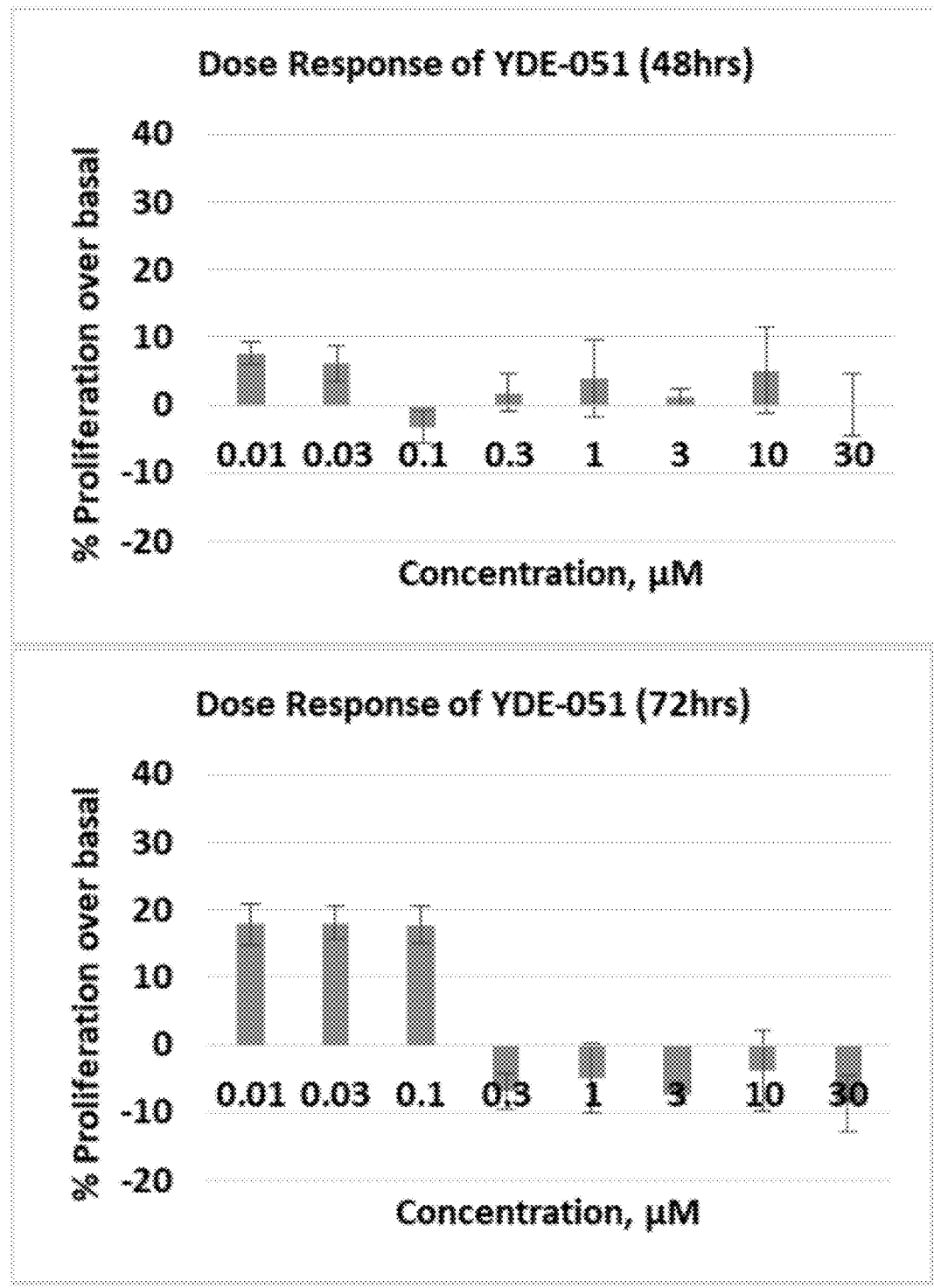

FIG. 64 is a diagram showing the cell growth rate after 48 hours and 72 hours from the treatment of YDE-051 on human corneal epithelial cells.

Figure 65:
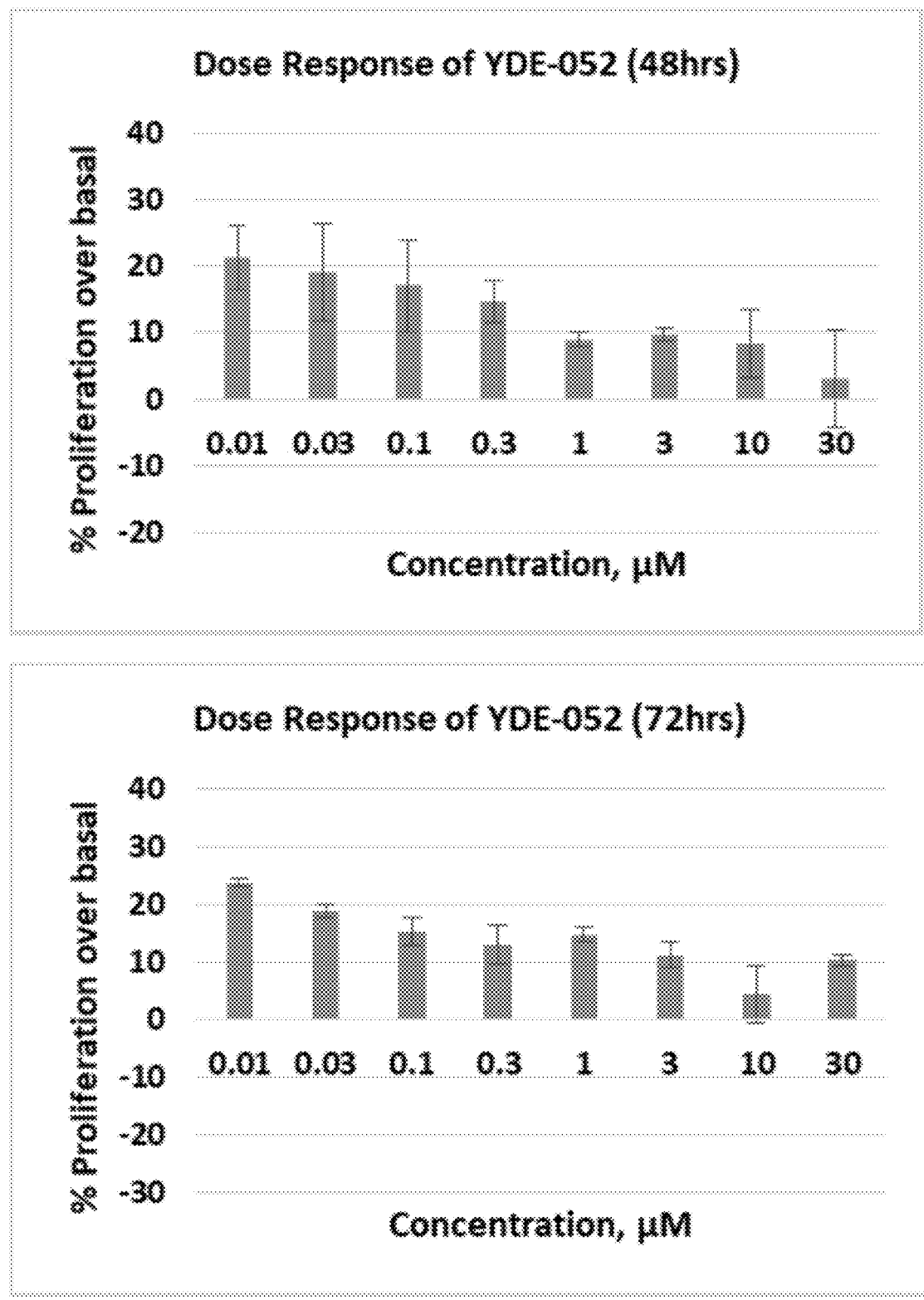

FIG. 65 is a diagram showing the cell growth rate after 48 hours and 72 hours from the treatment of YDE-052 on human corneal epithelial cells.

Figure 66:
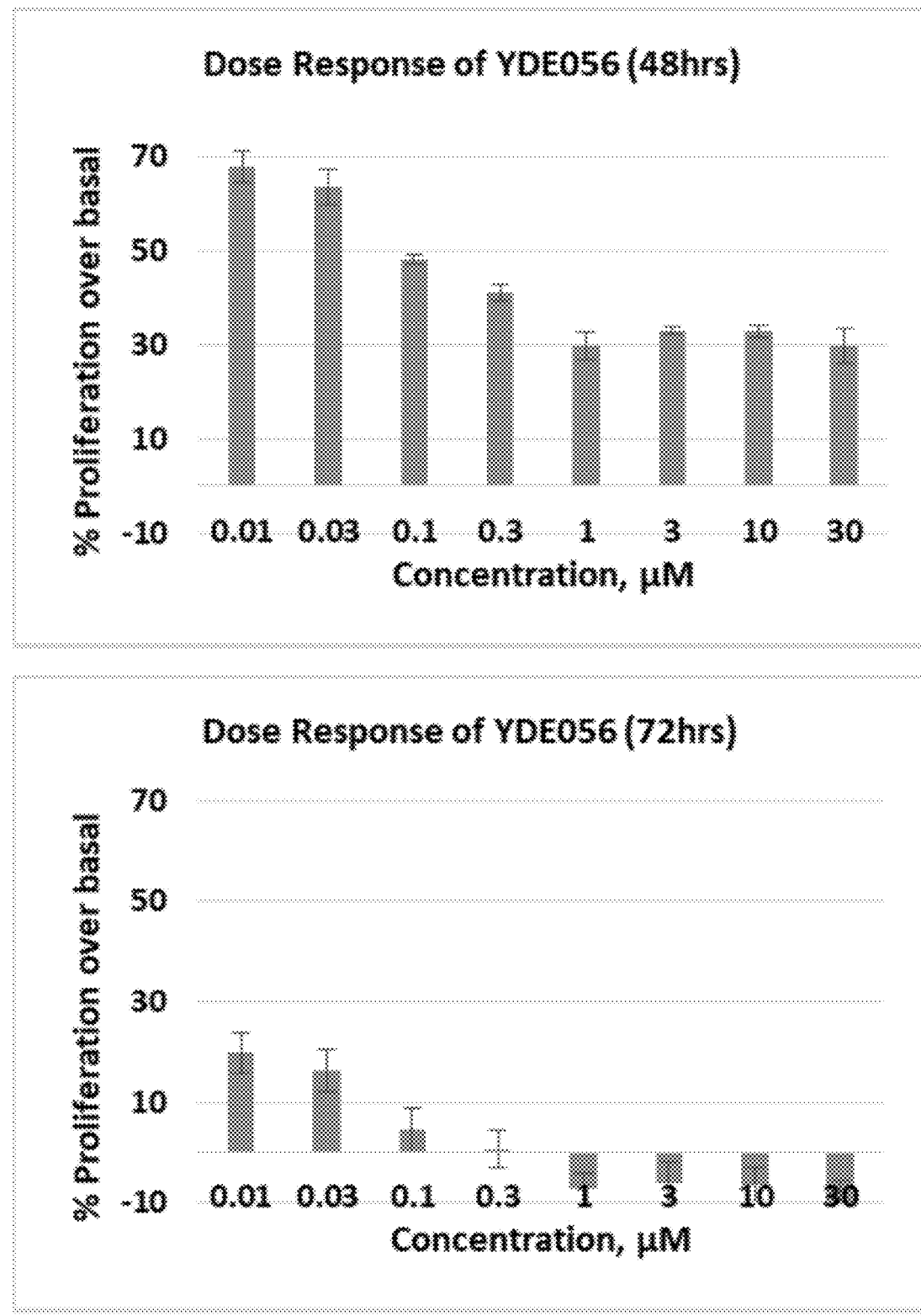

FIG. 66 is a diagram showing the cell growth rate after 48 hours and 72 hours from the treatment of YDE-056 on human corneal epithelial cells.

Figure 67:
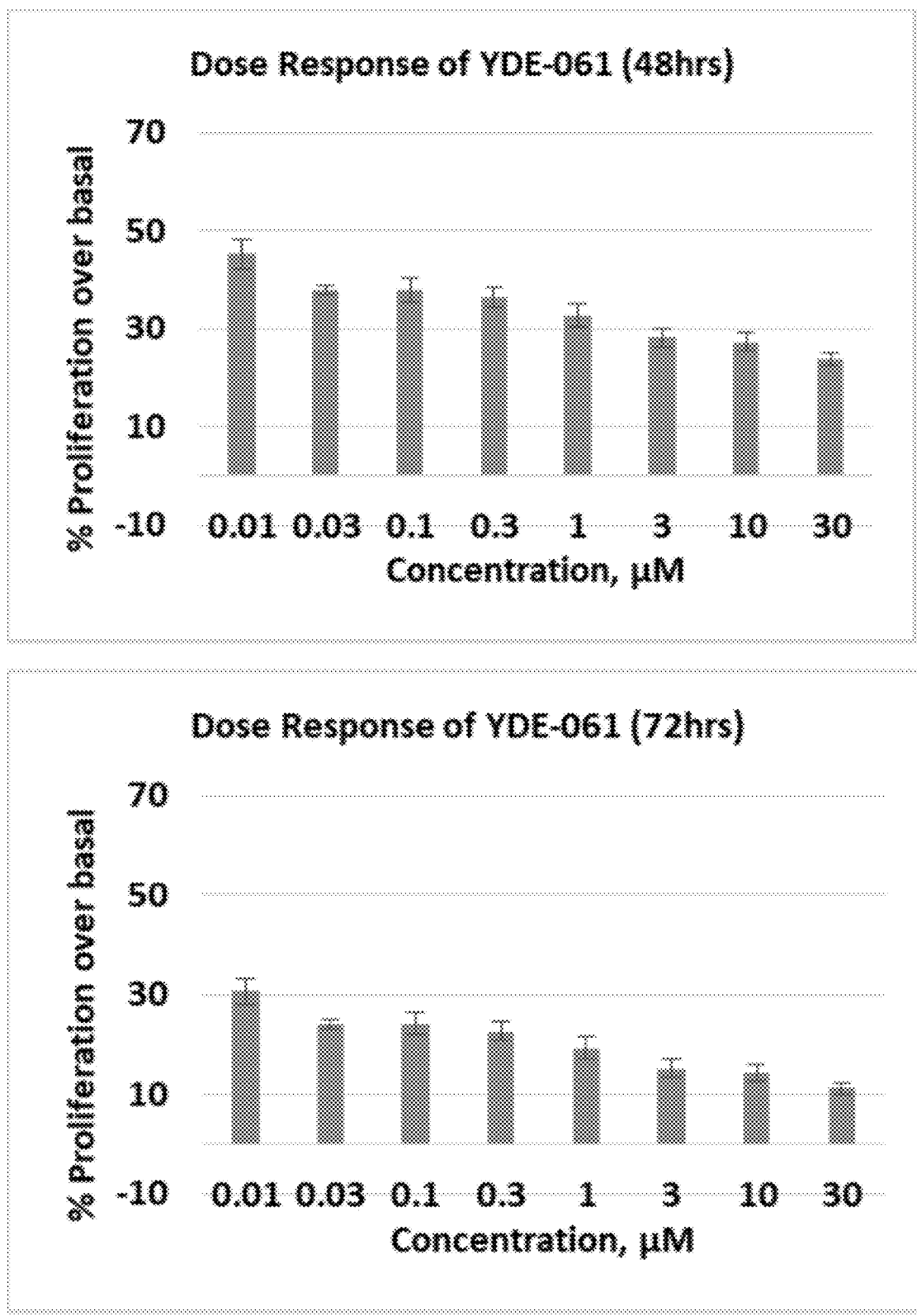

FIG. 67 is a diagram showing the cell growth rate after 48 hours and 72 hours from the treatment of YDE-061 on human corneal epithelial cells.

FIG. 68 is a diagram showing the cell growth rate after 48 hours and 72 hours from the treatment of YDE-062 on human corneal epithelial cells.

DETAILED DESCRIPTION OF THE INVENTION

The present invention is based on the surprising discovery of therapeutic agents for treating eye diseases such as dry eye syndrome. The effectiveness of the agents has been demonstrated by synthesizing these peptides, administering them to the eyes of rats with dry eye syndrome, and confirming the eye protection effect through the Schirmer test and the fluorescent dye deposition test.

When the novel peptide of the present invention is administered to the eye, it increases the amount of tear secretion and promotes recovery of the damaged cornea. Hence, they can be advantageously used as therapeutic agents for treating eye diseases.

Definitions

According to the convention used in the art, "

" in the formulae herein is used to indicate that a moiety or substituent "R" is attached to a backbone structure.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group.

The term "alkenyl", as used herein, refers to an aliphatic group containing at least one carbon-carbon double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, an alkenyl group may be substituted by one or more alkyl, carbocyclyl, aryl, heterocyclyl, or heteroaryl groups is contemplated. Exemplary alkenyl groups include, but are not limited to, vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing one or more hydrogens on one or more carbons of the hydrocarbon backbone.

Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a guanidino, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like. In some embodiments, exemplary typical substituents include halo, haloalkyl, oxo, —CN, —$NO_2$, =N—OH, —$N_3$, —R, —OR, —SR, —N(R)$_2$, —N(R)$_3$+, =NR, —NHC(=O)R, —C(=O)R, —C(=O)N(R)$_2$, —S(=O)$_2$R, —OS(=O)$_2$OR, —S(=O)$_2$OR, —S(=O)$_2$N(R)$_2$, —S(=O)R, —OP(=O)(OR)$_2$, -(alkylene)-C(=O)R, —C(=S)R, —C(=O)OR, -(alkylene)-C(=O)OR, —C(=S)OR, —C(=O)SR, —C(=S)SR, -(alkylene)-C(=O)N(R)$_2$, —C(=S)N(R)$_2$, and —C(—NR)N(R)$_2$, where R is independently H, alkyl, aryl, arylalkyl, heteroaryl, heteroarylalkyl, cycloalkyl, (cycloalkyl)alkyl, heterocycloalkyl, or (heterocycloalkyl)alkyl, but it is not limited thereto.

The term "$C_x$-$C_y$" when used in conjunction with a chemical moiety, such as, acyl, acyloxy, alkyl, alkenyl, alkynyl, or alkoxy is meant to include groups that contain from x to y carbons in the chain. For example, the term "$C_x$-$C_y$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_2$-$C_y$alkenyl" and "$C_2$-$C_y$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS-.

The term "alkynyl", as used herein, refers to an aliphatic group containing at least one carbon-carbon triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated. Exemplary alkynyl groups include acetylenic (—C≡CH) and propargyl (—$CH_2$C≡CH).

"Alkylene" refers to an unsaturated hydrocarbon group that may be branched, straight, or cyclic (or may have a combination of branched, straight, or cyclic moeities) and has two valencies derived by a removal of two hydrogen atoms from the same carbon atom or two different carbon atoms of a parent alkene. For example, an alkenylene group may have 1 to 20 carbon atoms, 1 to 10 carbon atoms, or 1 to 6 carbon atoms. Examples of a typical alkenylene group include 1,2-ethylene (—CH=CH—), but it is not limited thereto.

"Alkenylene" refers to an unsaturated hydrocarbon group that may be branched, straight, or cyclic (or may have a combination of branched, straight, or cyclic moeities) and has two valencies derived by a removal of two hydrogen atoms from the same carbon atom or two different carbon atoms of a parent alkene. For example, an alkenylene group may have 1 to 20 carbon atoms, 1 to 10 carbon atoms, or 1 to 6 carbon atoms. Examples of a typical alkenylene group include 1,2-ethylene (—CH=CH—), but it is not limited thereto.

"Alkynylene" refers to an unsaturated hydrocarbon group that is branched, straight, or cyclic (or may have a combination of branched, straight, or cyclic moeities) and has two valencies derived by a removal of two hydrogen atoms from the same carbon atom or two different carbon atoms of a parent alkyne. For example, an alkynylene group may have 1 to 20 carbon atoms, 1 to 10 carbon atoms, or 1 to 6 carbon atoms. Examples of a typical alkynylene radical include acetylenylene (—C≡C—), propargylene (—$CH_2$C≡C—), and 4-pentynylene (—$CH_2CH_2CH_2$C≡C—), but it is not limited thereto.

The term "amide", as used herein, refers to a group

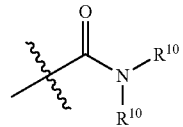

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

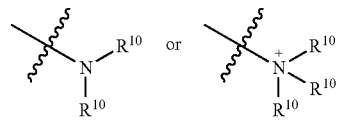

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "arylalkyl", as used herein, refers to an alkyl group substituted with an aryl group. Exemplary arylalkyl groups include benzyl, 2-phenylethan-1-yl, naphthylmethyl, 2-naphthylethan-1-yl, naphthobenzyl, 2-naphthophenylethan-1-yl, and the like, each of which may be substituted or unsubstituted.

The term "arylalkenyl", as used herein, refers to an alkenyl group substituted with an aryl group.

The term "arylalkynyl", as used herein, refers to an alkynyl group substituted with an aryl group.

The term "aryl" as used herein include substituted or unsubstituted single-ring aromatic groups in which each atom of the ring is carbon. Preferably the ring is a 5- to 14-membered ring, more preferably a 6-10-membered ring, and more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

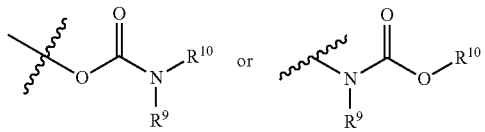

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds. Non-limiting examples of a monocyclic cycloalkyl include cyclopropyl, cyclobutyl, cyclopentyl, and cyclohexyl (each of which may be substituted or unsubstituted).

The term "(cycloalkyl)alkyl", as used herein, refers to an alkyl group substituted with a cycloalkyl group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

"Haloalkyl" is an alkyl group in which at least one of the hydrogen atoms of the alkyl group as defined above is replaced by a halogen atom. Examples of a suitable haloalkyl group include, but are not limited to, —CF$_3$, —CHF$_2$, —CFH$_2$, and —CH$_2$CF$_3$.

The term "heteroalkyl", as used herein, refers to a saturated or unsaturated chain of carbon atoms, wherein at least one carbon atoms is replaced by a heteroatom, wherein no two heteroatoms are adjacent.

The term "heteroaryl" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, benzofuran, thiophene, imidazole, indole, isoindole, oxazole, thiazole, pyrazole, pyridine, pyrazine, pyridazine, and pyrimidine, and the like.

The term "heteroarylalkyl" refers to an alkyl group substituted with a heteroaryl group.

The term "heteroatom" as used herein means an atom of any element other than carbon or hydrogen. Preferred heteroatoms are nitrogen, oxygen, and sulfur.

The terms "heterocycloalkyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocycloalkyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocycloalkyl groups include, for example, piperidine, piperazine, pyrrolidine, morpholine, lactones, lactams, and the like.

The term "(heterocycloalkyl)alkyl", as used herein, refers to an alkyl group substituted with a heterocycloalkyl group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

In certain embodiments, exemplary typical substituents include halo, haloalkyl, oxo, —CN, —NO$_2$, =N—OH, —N$_3$, —R, —OR, —SR, —N(R)$_2$, —N(R)$_3$+, =NR, —NHC(=O)R, —C(=O)R, —C(=O)N(R)$_2$, —S(=O)$_2$R, —OS(=O)$_2$OR, —S(=O)$_2$OR, —S(=O)$_2$N(R)$_2$, —S(=O)R, —OP(=O)(OR)$_2$, -(alkylene)-C(=O)R, —C(=S)R, —C(=O)OR, -(alkylene)-C(=O)OR, —C(=S)OR, —C(=O)SR, —C(=S)SR, -(alkylene)-C(=O)N(R)$_2$, —C(=S)N(R)$_2$, and —C(=NR)N(R)$_2$, where R is independently H, alkyl, aryl, arylalkyl, heteroaryl, heteroarylalkyl, cycloalkyl, (cycloalkyl)alkyl, heterocycloalkyl, or (heterocycloalkyl)alkyl, but it is not limited thereto.

The term "sulfate" is art-recognized and refers to the group —OSO$_3$H, or a pharmaceutically acceptable salt thereof.

The term "sulfonamide" is art-recognized and refers to the group represented by the general formulae

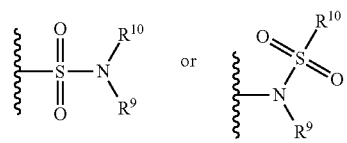

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

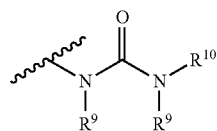

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Silyloxy" refers to the group —O—SiR$_3$, wherein each R independently is a optionally substituted hydrocarbyl. Non-limiting examples of silyloxy include —O—Si(CH$_3$)$_3$, —O—Si(CH$_3$)$_2$tBu, —O—Si(tBu)$_2$CH$_3$, —O—Si(tBu)$_3$, —O—Si(CH$_3$)$_2$Ph, —O—Si(Ph)$_2$CH$_3$, and —O—Si(Ph)$_3$.

The term "optionally substituted" refers to a particular moiety (e.g., an optionally substituted aryl group) of the compound of Formula I that optionally has one, two, or more substituents.

The term "ester thereof" refers to any ester of a compound wherein any —COOH functional group of the molecule is modified to be a —COOR functional group or any —OH functional group of the molecule is modified to be a —OC(═O)R. Here, the R moiety of the ester may be any carbon-containing group that forms a stable ester moiety, which includes, but is not limited to, alkyl, alkenyl, alkynyl, cycloalkyl, cycloalkylalkyl, aryl, arylalkyl, heterocyclyl, heterocyclylalkyl, and substituted derivatives thereof. Examples of the ester may also include an ester such as those described above of a "tautomeric enol" as described below.

COMPOUNDS OF THE INVENTION

In certain embodiments, the invention provides a compound represented by Formula (I):

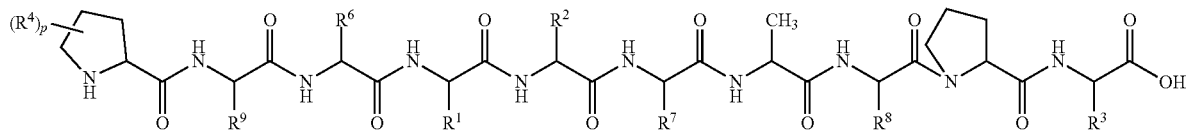

(I)

or a pharmaceutically acceptable salt thereof; wherein:

R$^1$, R$^2$, and R$^3$ are each independently H or substituted or unsubstituted alkyl, alkoxy, haloalkyl, alkenyl, alkynyl, aryl, arylalkyl, arylalkenyl, arylalkynyl, heteroalkyl, cycloalkyl, heterocycloalkyl, heteroaryl, or heteroarylalkyl;

R$^4$, independently for each occurrence, is selected from substituted or unsubstituted alkyl, aryl, arylalkyl, heterocycloalkyl, oxo, —OR$^b$, —CH$_2$OR$^b$, halo, hydroxyl, and hydroxyalkyl;

R$^b$ is substituted or unsubstituted alkyl, aryl, arylalkyl, or heterocycloalkyl;

p is 0, 1, or 2;

R$^6$ is hydrogen or substituted or unsubstituted alkyl; and

R$^7$, R$^8$, and R$^9$ are each independently hydrogen or alkyl;

wherein the compound is not:

(SEQ ID NO: 101)

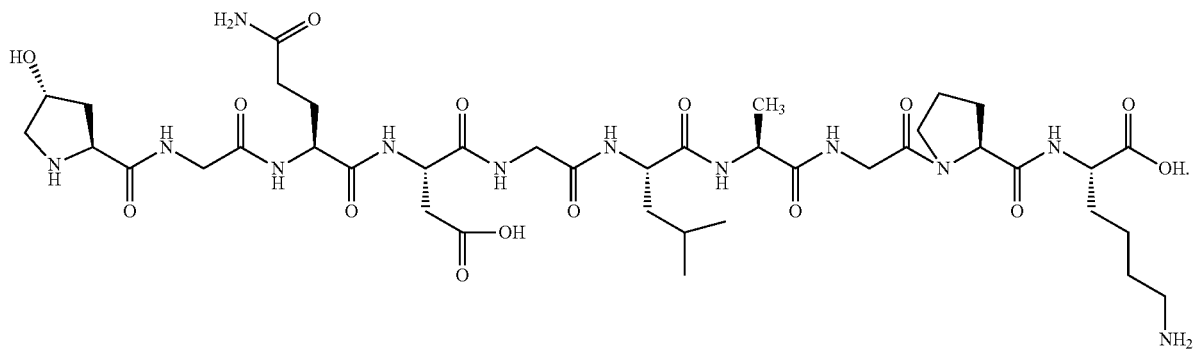

In certain embodiments:

R$^1$, R$^2$, and R$^3$ are each independently H or substituted or unsubstituted alkyl, arylalkyl, or heteroarylalkyl;

R$^4$, independently for each occurrence, is selected from substituted or unsubstituted alkyl, oxo, hydroxyl, —OR$^b$, hydroxyalkyl, —CH$_2$OR$^b$, and halo;

R$^b$ is substituted or unsubstituted alkyl, aryl, arylalkyl, or heterocycloalkyl;

R$^6$ is hydrogen or substituted or unsubstituted alkyl; and

R$^7$, R$^8$, and R$^9$ are each independently hydrogen or alkyl.

In some embodiments, where indicated, alkyl, alkoxy, haloalkyl, alkenyl, alkynyl, aryl, arylalkyl, arylalkenyl, arylalkynyl, heteroalkyl, cycloalkyl, heterocycloalkyl, or heteroaryl is unsubstituted or is substituted with one or more substituents selected from halo, haloalkyl, oxo, —CN, —NO₂, =N—OH, —N₃, —Rᵃ, —ORᵃ, —SRᵃ, —N(Rᵃ)₂, —N(Rᵃ)₃⁺, =NRᵃ, —NHC(=O)Rᶜ, —C(=O)Rᶜ, —C(=O)N(Rᵃ)₂, —S(=O)₂Rᶜ, —OS(=O)₂ORᵃ, —S(=O)₂ORᵃ, —S(=O)₂N(Rᵃ)₂, —S(=O)Rᶜ, —OP(=O)(ORᵃ)₂, -(alkylene)-C(=O)Rᶜ, —C(=S)Rᶜ, —C(=O)ORᵃ, -(alkylene)-C(=O)ORᵃ, —C(=S)ORᵃ, —C(=O)SRᵃ, —C(=S)SRᵃ, -(alkylene)-C(=O)N(Rᵃ)₂, —C(=S)N(Rᵃ)₂, and —C(=NRᵃ)N(Rᵃ)₂;

Rᵃ, independently for each occurrence, is hydrogen, or substituted or unsubstituted alkyl, aryl, arylalkyl, heteroaryl, heteroarylalkyl, cycloalkyl, (cycloalkyl)alkyl, heterocycloalkyl, or (heterocycloalkyl)alkyl; and Rᶜ, independently for each occurrence, is substituted or unsubstituted alkyl, aryl, arylalkyl, heteroaryl, heteroarylalkyl, cycloalkyl, (cycloalkyl)alkyl, heterocycloalkyl, or (heterocycloalkyl)alkyl.

In more particular embodiments, where indicated, alkyl, alkoxy, haloalkyl, alkenyl, alkynyl, aryl, arylalkyl, arylalkenyl, arylalkynyl, heteroalkyl, cycloalkyl, heterocycloalkyl, or heteroaryl is unsubstituted or is substituted with one or more substituents selected from halo, haloalkyl, oxo, —Rᵃ, —ORᵃ, —N(Rᵃ)₂, —N(Rᵃ)₃⁺, —NHC(=O)Rᶜ, —C(=O)Rᶜ, —C(=O)N(Rᵃ)₂, —C(=O)ORᵃ, -(alkylene)-C(=O)ORᵃ, and -(alkylene)-C(=O)N(Rᵃ)₂;

Rₐ, independently for each occurrence, is hydrogen, or substituted or unsubstituted alkyl, aryl, arylalkyl, heteroaryl, heteroarylalkyl, cycloalkyl, (cycloalkyl)alkyl, heterocycloalkyl, or (heterocycloalkyl)alkyl; and Rᶜ, independently for each occurrence, is substituted or unsubstituted alkyl, aryl, arylalkyl, heterocyclyl, heterocyclylalkyl, cycloalkyl, or (cycloalkyl)alkyl.

In certain such embodiments, Rᶜa, independently for each occurrence, is hydrogen, alkyl, aryl, arylalkyl, heteroaryl, heteroarylalkyl, heterocycloalkyl, or (heterocycloalkyl)alkyl; and Rᶜ, alkyl, aryl, arylalkyl, heterocyclyl, or heterocyclylalkyl.

In certain embodiments, the compound has the structure of formula (I-10L):

In certain embodiments, R¹ is substituted or unsubstituted alkyl, arylalkyl, or heteroarylalkyl. More specifically, R¹ may be selected from substituted or unsubstituted alkyl,

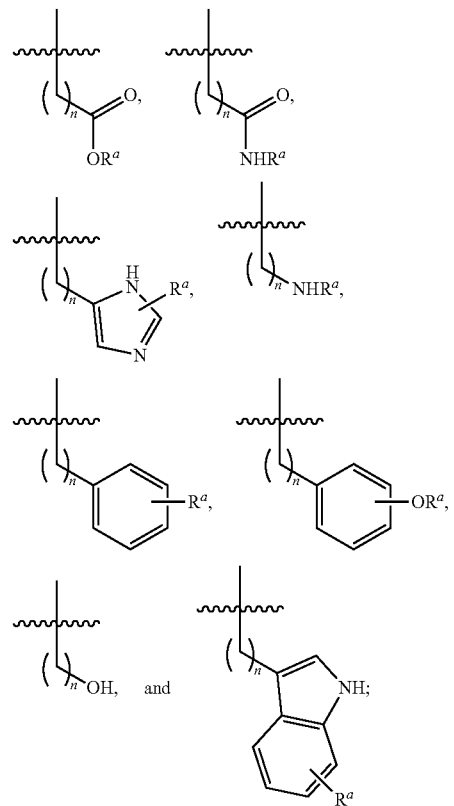

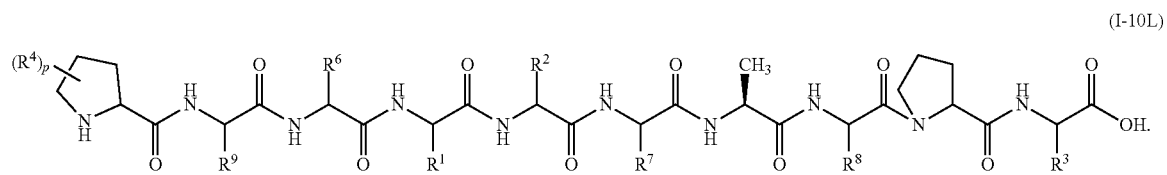

(I-10L)

Alternatively, the compound may have the structure of formula (I-10D):

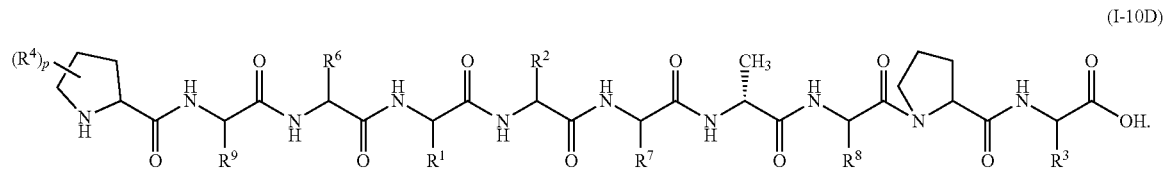

(I-10D)

$R^a$ is hydrogen or alkyl; and
n is an integer from 1 to 10, preferably 1-5, more preferably 1-3.
Exemplary $R^1$ groups include
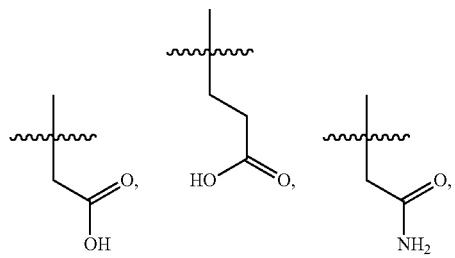
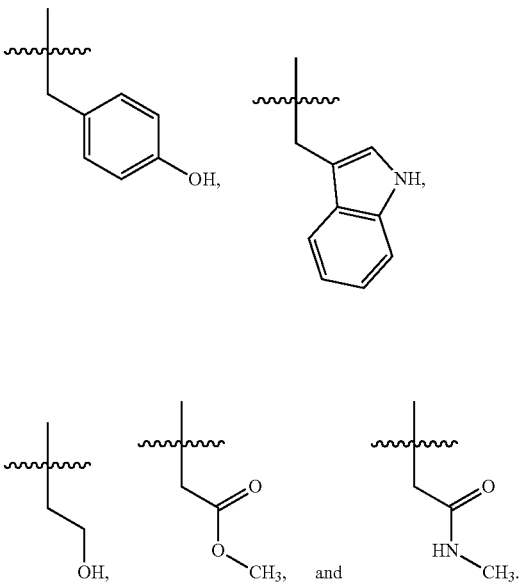
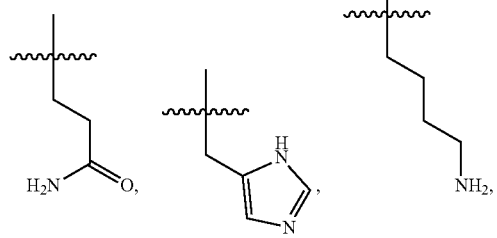
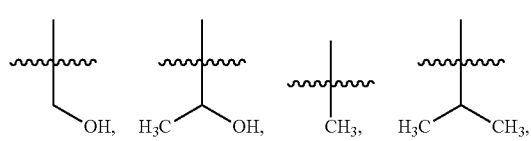
In some preferred embodiments, $R^1$ is
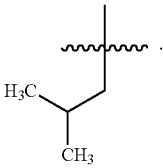
In alternative preferred embodiments, $R^1$ is
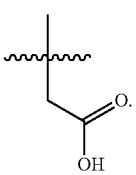
In certain embodiments, the compound has the structure of formula (I-1L):
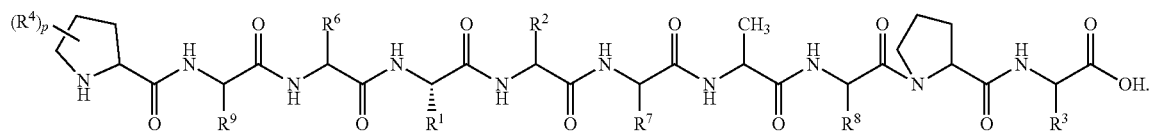
(I-1L)

Alternatively, the compound may have the structure of formula (I-1D)

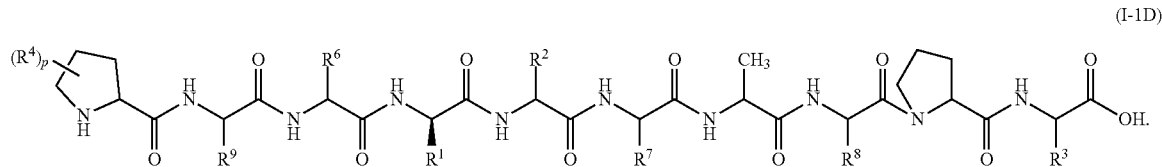

(I-1D)

In certain embodiments, $R^2$ is H or substituted or unsubstituted alkyl, arylalkyl, or heteroarylalkyl. In some such embodiments, $R^2$ is selected from hydrogen, substituted or unsubstituted alkyl,

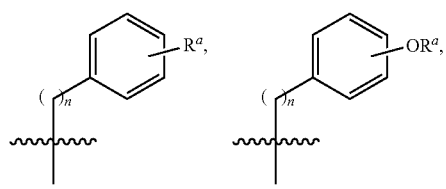

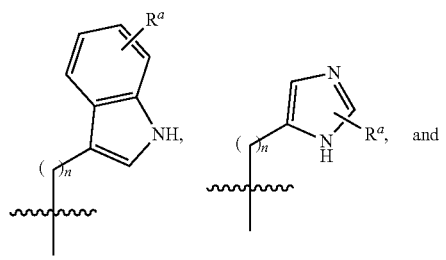

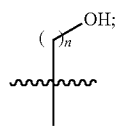

$R^a$ is hydrogen or alkyl; and
n is an integer from 1 to 10, preferably 1-5, more preferably 1-3.

Exemplary $R^2$ groups include

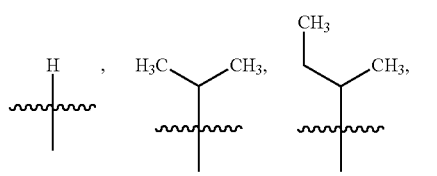

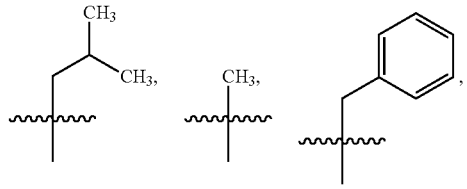

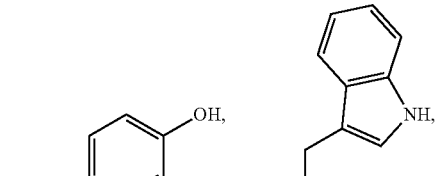

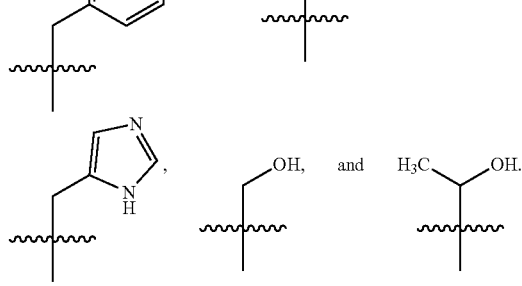

Preferably, $R^2$ is hydrogen.
In certain embodiments, the compound has the structure of formula (I-2L):

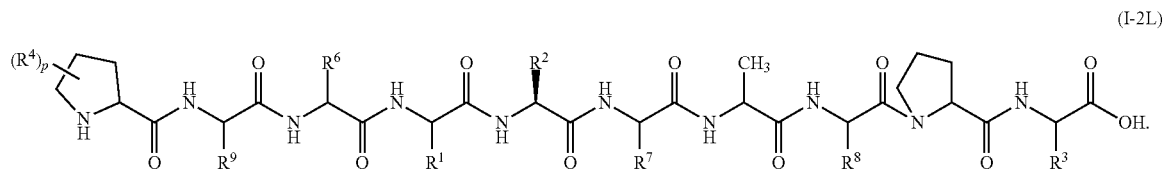

(I-2L)

Alternatively, the compound may have the structure of formula (I-2D):

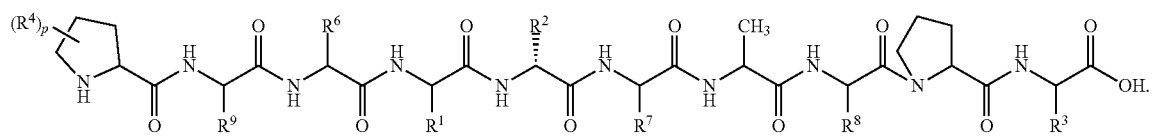

In certain embodiments, $R^3$ is substituted or unsubstituted alkyl or arylalkyl. In some such embodiments, $R^3$ is selected from substituted or unsubstituted alkyl,

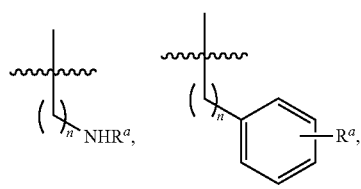

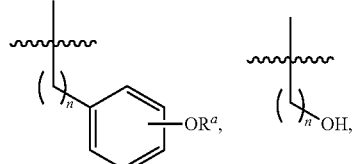

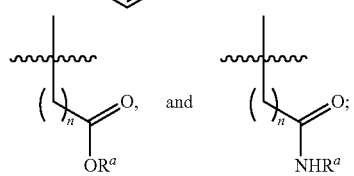

$R^a$ is hydrogen or alkyl; and
n is an integer from 1 to 10, preferably 1-5, more preferably 1-3.

Exemplary $R^3$ groups include

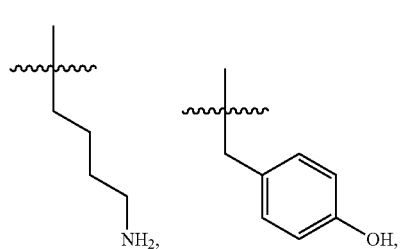

-continued

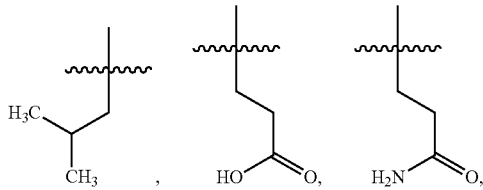

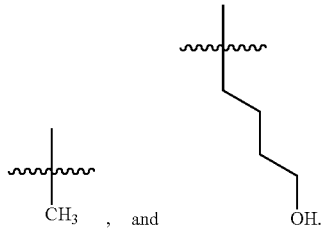

Preferably, $R^3$ is

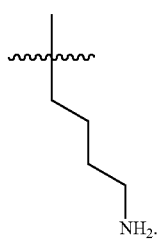

In certain embodiments, the compound has the structure of formula (I-3L):

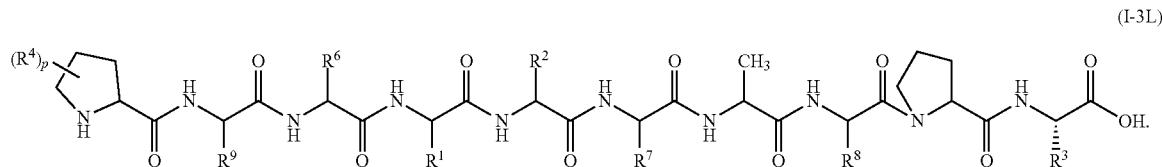

(I-3L)

Alternatively, the compound may have the structure of formula (I-3D):

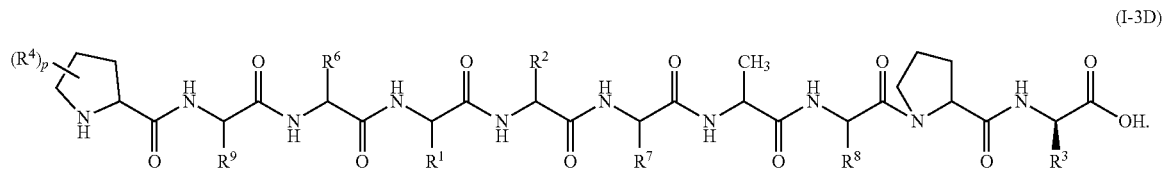

(I-3D)

In certain embodiments, p is 1 or 2; and $R^4$, independently for each occurrence, is selected from substituted or unsubstituted alkyl, —$OR^b$, —$CH_2OR^b$, halo, hydroxyl, and hydroxyalkyl.

In certain embodiments, p is 1 or 2; and $R^4$, independently for each occurrence, is selected from —$CH_3$, halo, hydroxyl, and hydroxyalkyl.

In certain preferred embodiments, $R^4$ is hydroxyl. In alternative preferred embodiments, $R^4$ is —$CH_3$.

In any of the disclosed embodiments, p may be 1.

In certain embodiments, the compound has the structure of formula (I-4Lg):

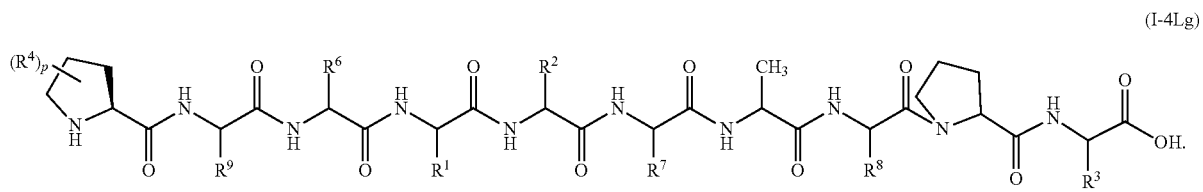

(I-4Lg)

In certain embodiments, the compound has the structure of formula (I-4La):

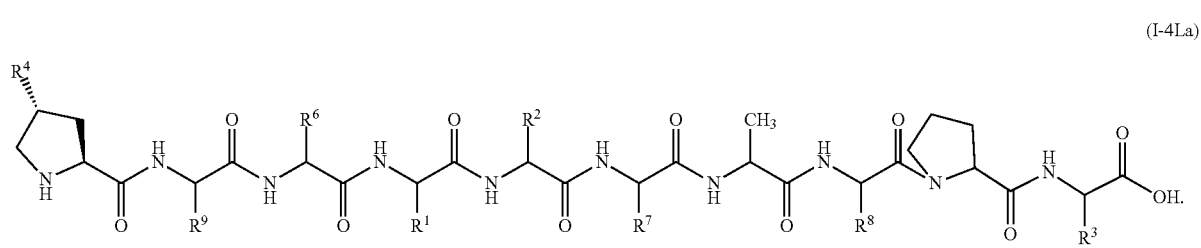

(I-4La)

In certain embodiments, the compound has the structure of formula (I-4Lb):
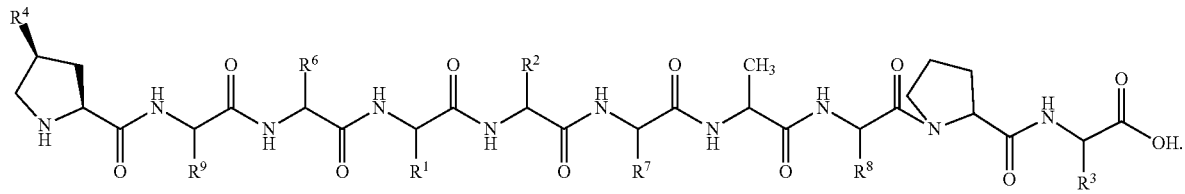
(I-4Lb)
In certain embodiments, the compound has the structure of formula (I-4Lc):
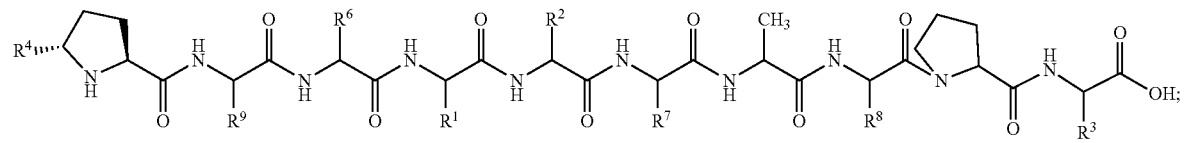
(I-4Lc)
provided that $R^4$ is not hydroxyl.
In certain embodiments, the compound has the structure of formula (I-4Dg):
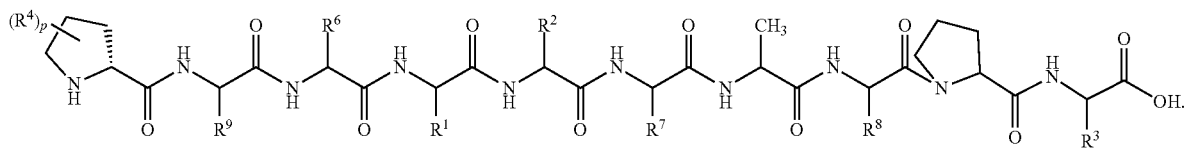
(I-4Dg)
In certain embodiments, the compound has the structure of formula (I-4 Da):
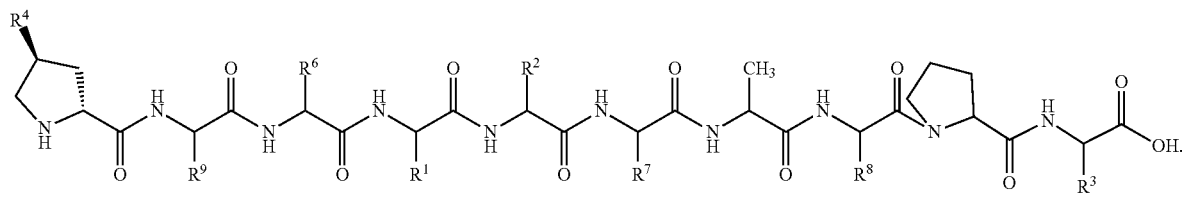
(I-4Da)

In certain embodiments, the compound has the structure of formula (I-4Db):
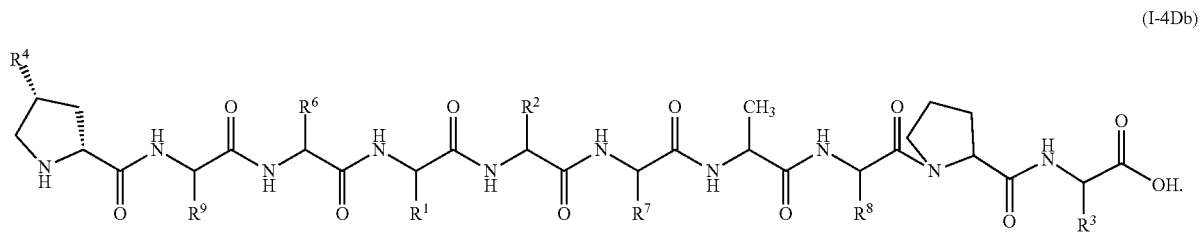
(I-4Db)
In certain embodiments, the compound has the structure of formula (I-4Dc):
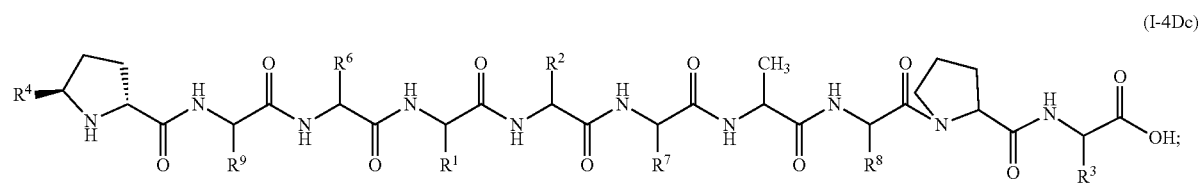
(I-4Dc)
provided that R⁴ is not hydroxyl.
In certain embodiments, R⁴ is oxo.
In certain embodiments, the compound has the structure of formula (I-4Ld):
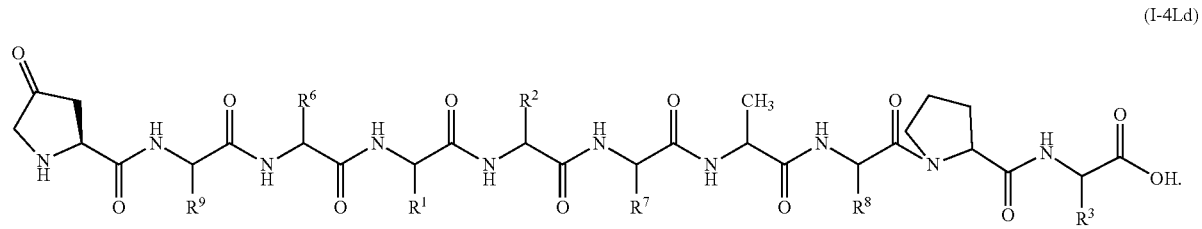
(I-4Ld)
In certain embodiments, the compound has the structure of formula (I-4Le):
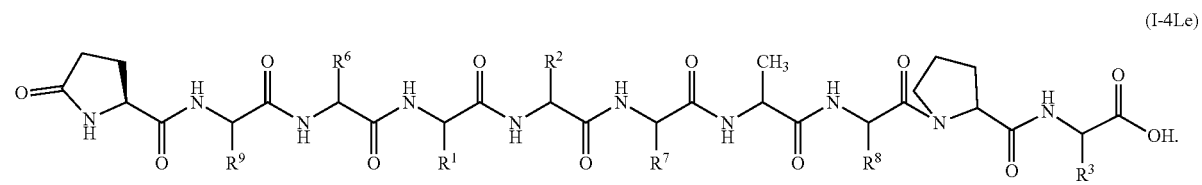
(I-4Le)

In certain embodiments, the compound has the structure of formula (I-4Dd):

(I-4Dd)

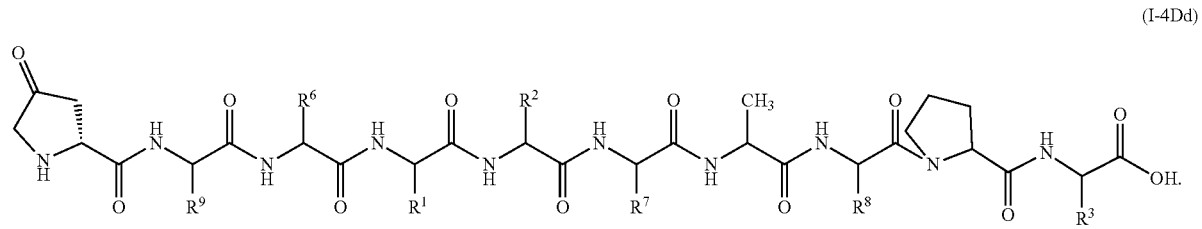

In certain embodiments, the compound has the structure of formula (I-4De):

(I-4De)

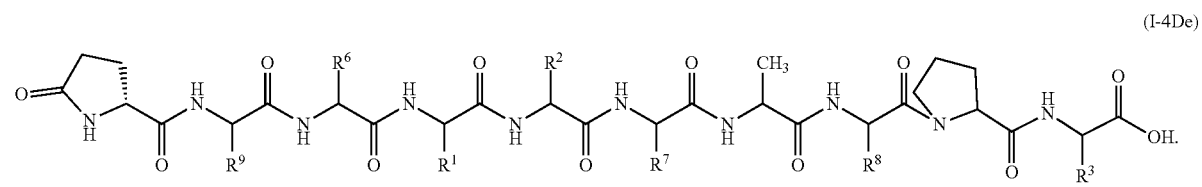

In certain embodiments, $R^6$ is hydrogen or alkyl, wherein the alkyl is optionally substituted with one occurrence of —C(=O)NH$_2$. In certain embodiments, wherein $R^6$ is alkyl optionally substituted with one occurrence of —C(=O)NH$_2$. For example, $R^6$ may be —CH$_3$. Alternatively, $R^6$ may be

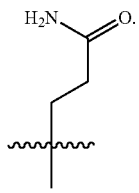 [SMILES: *CCC(N)=O]

In certain embodiments, the compound has the structure of formula (I-6L):

(I-6L)

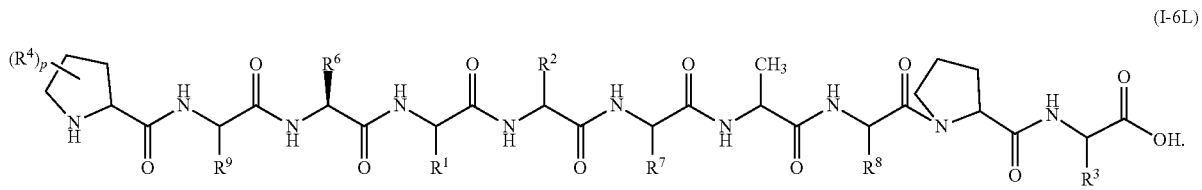

Alternatively, the compound may have the structure of formula (I-6D):

(I-6D)

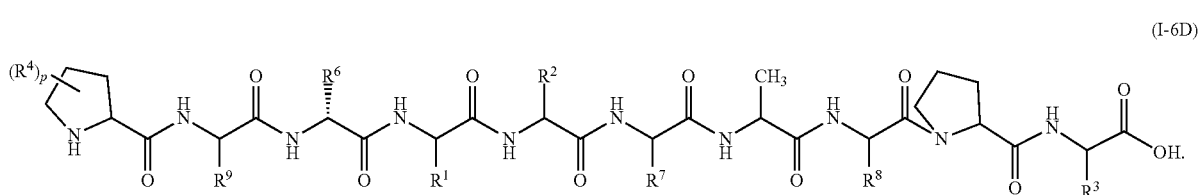

In certain embodiments, $R^7$ is $(C_1-C_{10})$alkyl, preferably

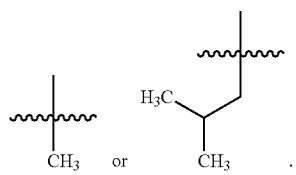

In certain embodiments, the compound has the structure of formula (I-7L):

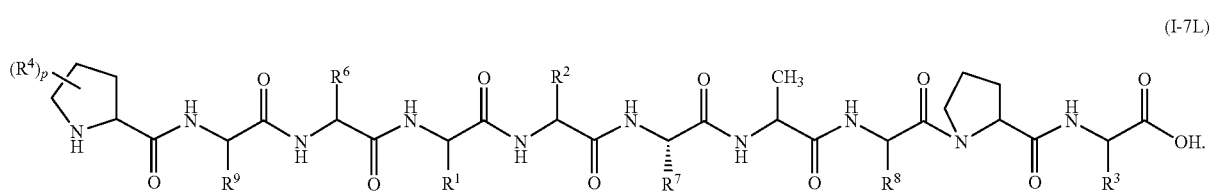

(I-7L)

Alternatively, the compound may have the structure of formula (I-7D):

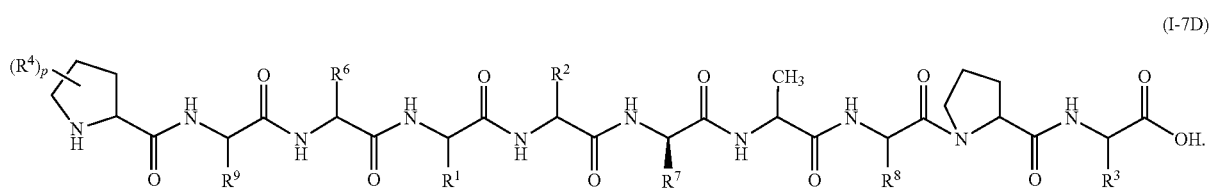

(I-7D)

In certain embodiments, the compound has the structure of formula (I-11L):

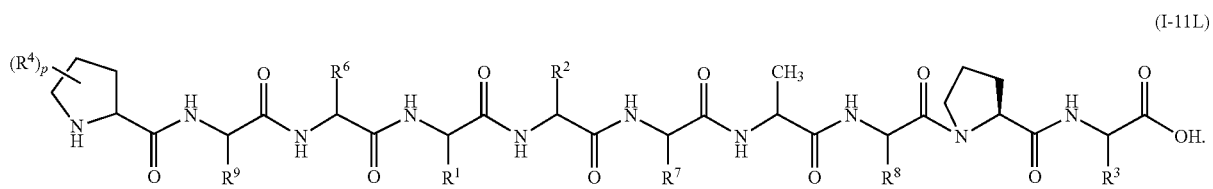

(I-11L)

Alternatively, the compound may have the structure of formula (I-11D):

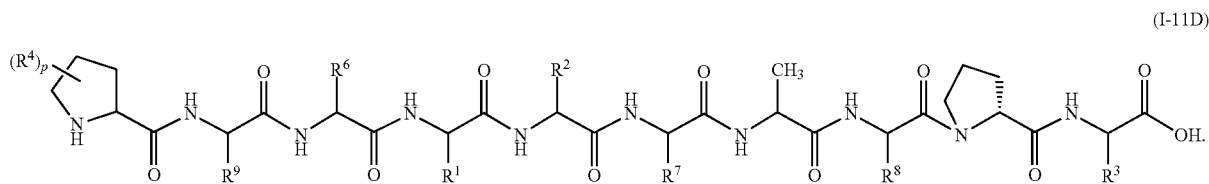

(I-11D)

In certain preferred embodiments, $R^8$ is —$CH_3$ or —H, most preferably —H.

In certain preferred embodiments, $R^9$ is —$CH_3$ or —H, most preferably —H.

In some preferred embodiments, the compound comprises at least one D-amino acid residue. In certain such embodiments, the compound comprises at least two, at least three, at least four, at least five, at least six, at least seven, or at least eight D-amino acid residues.

In certain embodiments, the compound is selected from the following:
(SEQ ID NO: 1)
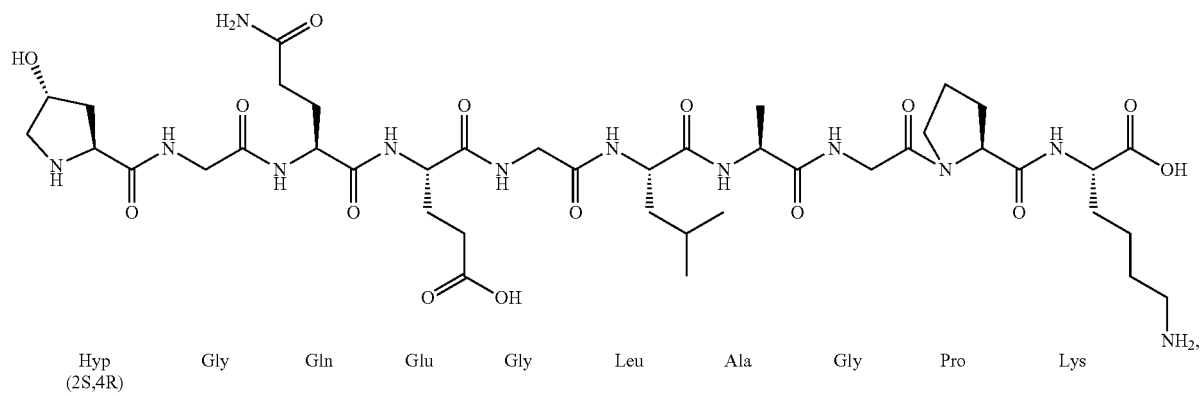
| Hyp (2S,4R) | Gly | Gln | Glu | Gly | Leu | Ala | Gly | Pro | Lys |
(SEQ ID NO: 2)
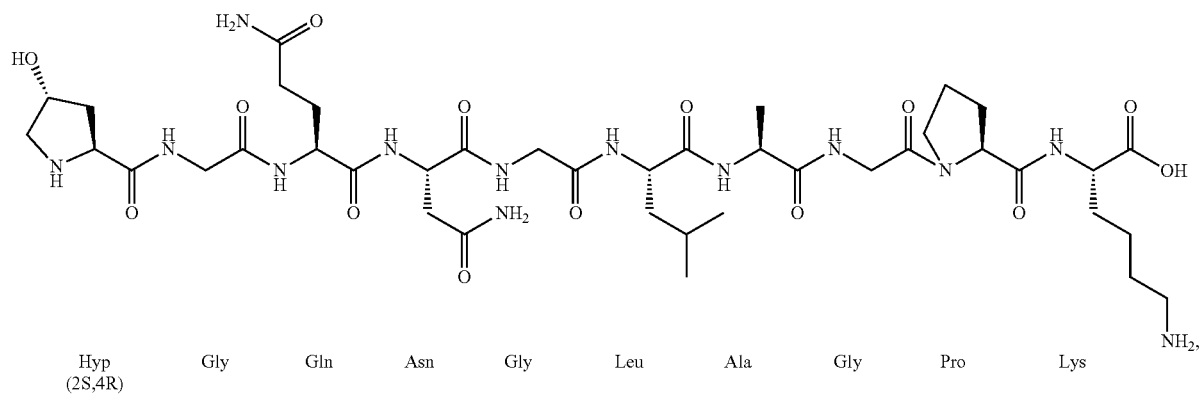
| Hyp (2S,4R) | Gly | Gln | Asn | Gly | Leu | Ala | Gly | Pro | Lys |
(SEQ ID NO: 3)
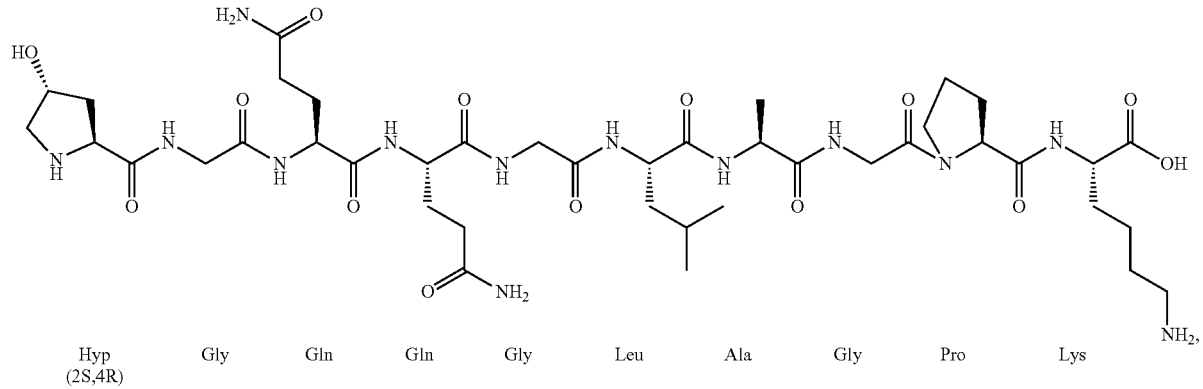
| Hyp (2S,4R) | Gly | Gln | Gln | Gly | Leu | Ala | Gly | Pro | Lys |

(SEQ ID NO: 4)
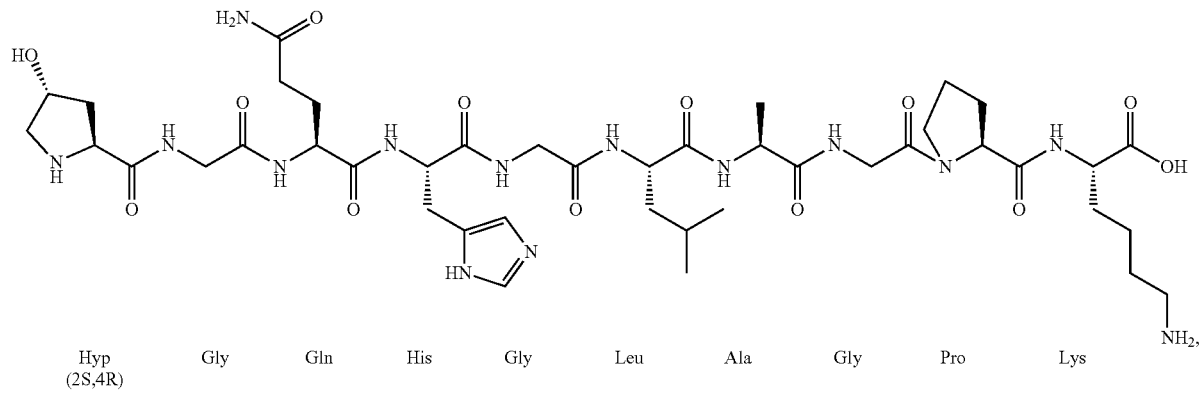
Hyp (2S,4R) — Gly — Gln — His — Gly — Leu — Ala — Gly — Pro — Lys
(SEQ ID NO: 5)
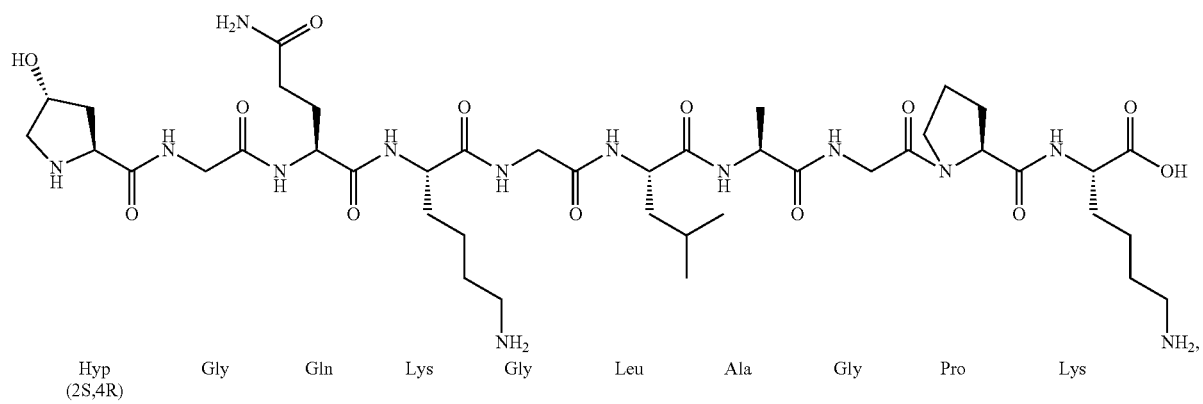
Hyp (2S,4R) — Gly — Gln — Lys — Gly — Leu — Ala — Gly — Pro — Lys
(SEQ ID NO: 6)
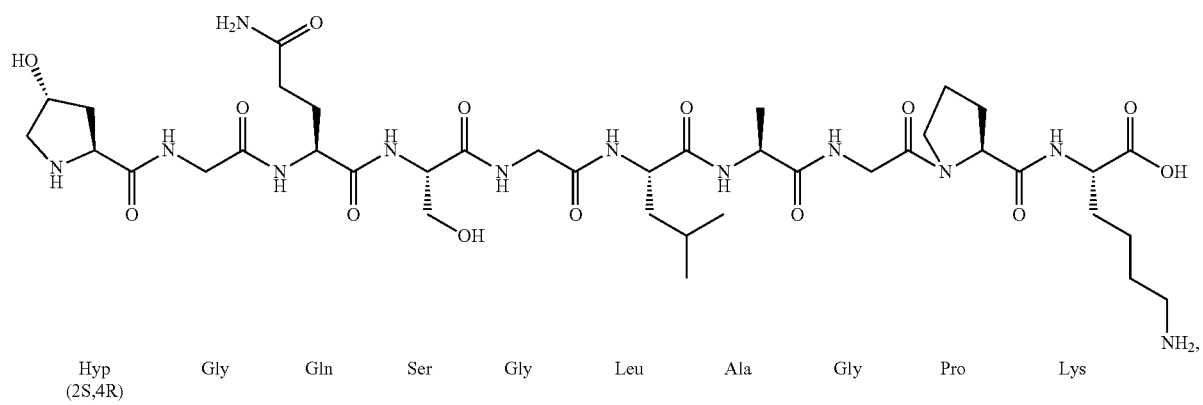
Hyp (2S,4R) — Gly — Gln — Ser — Gly — Leu — Ala — Gly — Pro — Lys -continued
(SEQ ID NO: 7)
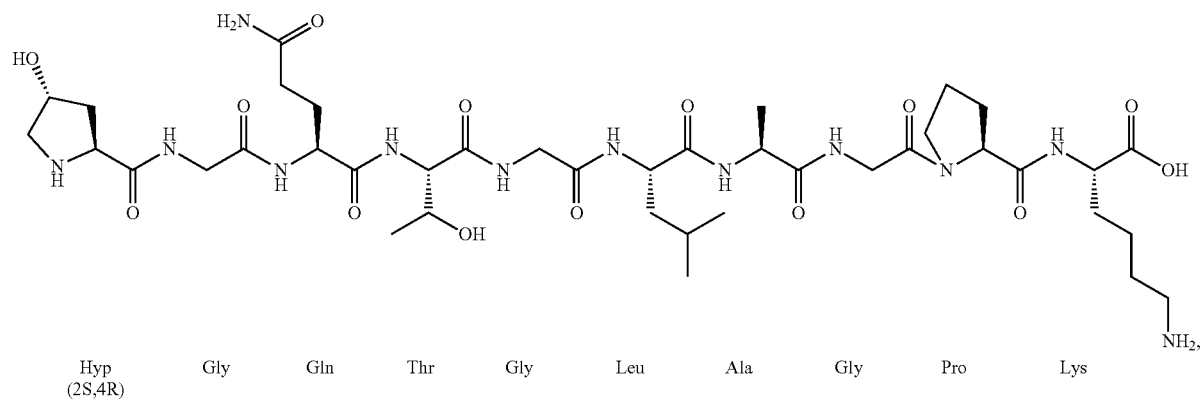
Hyp (2S,4R) — Gly — Gln — Thr — Gly — Leu — Ala — Gly — Pro — Lys
(SEQ ID NO: 8)
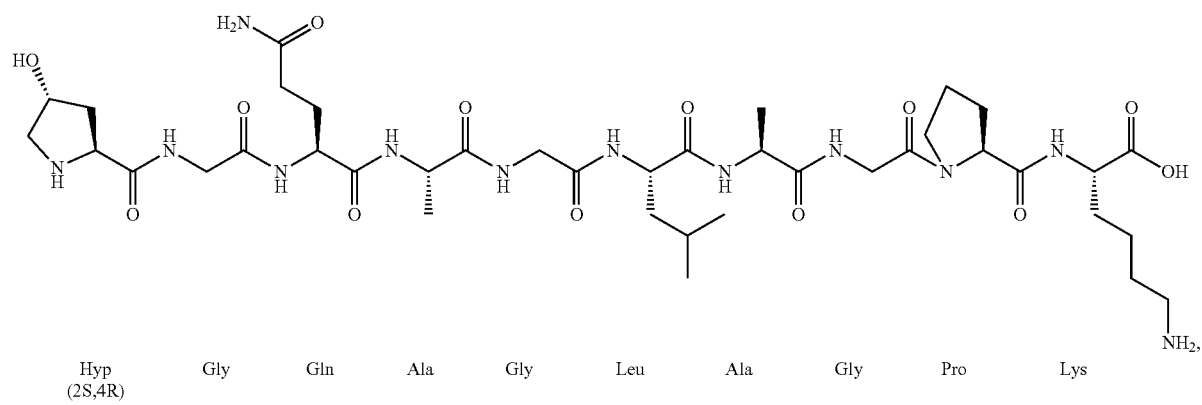
Hyp (2S,4R) — Gly — Gln — Ala — Gly — Leu — Ala — Gly — Pro — Lys
(SEQ ID NO: 9)
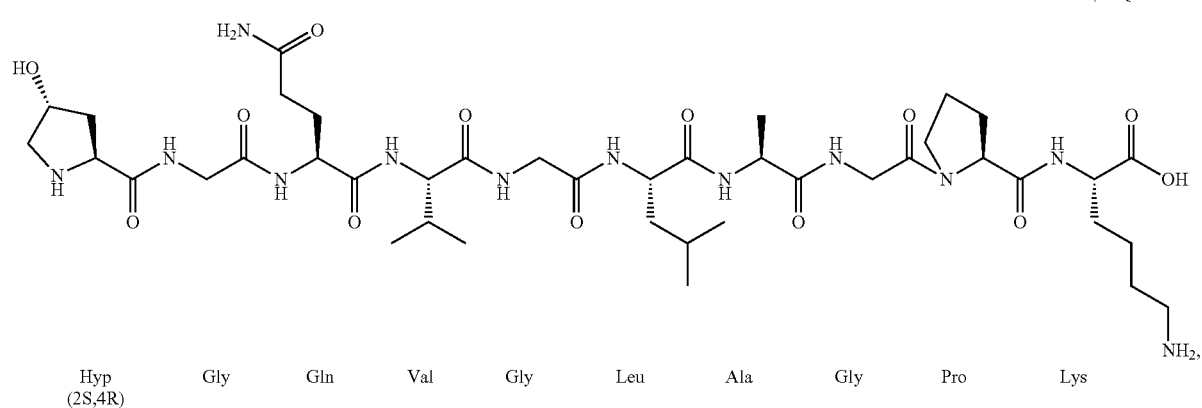
Hyp (2S,4R) — Gly — Gln — Val — Gly — Leu — Ala — Gly — Pro — Lys (SEQ ID NO: 10)
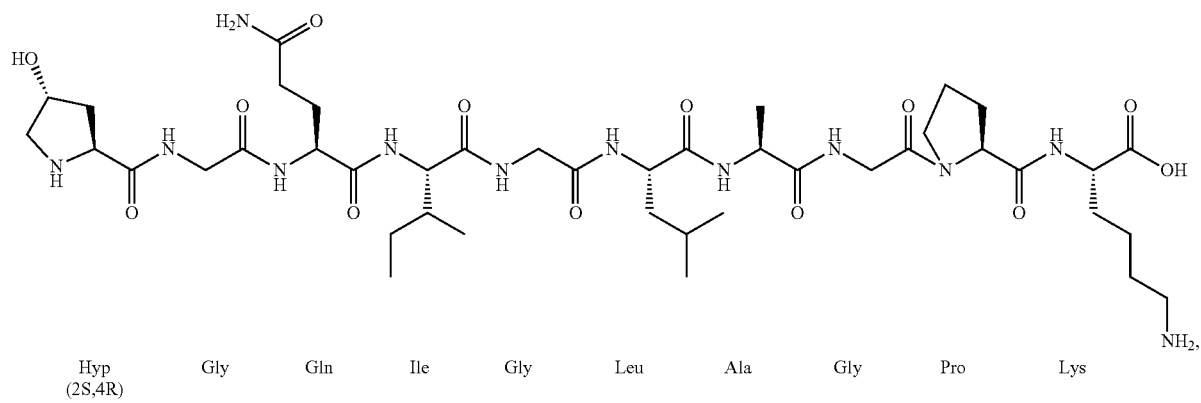
Hyp (2S,4R) — Gly — Gln — Ile — Gly — Leu — Ala — Gly — Pro — Lys
(SEQ ID NO: 11)
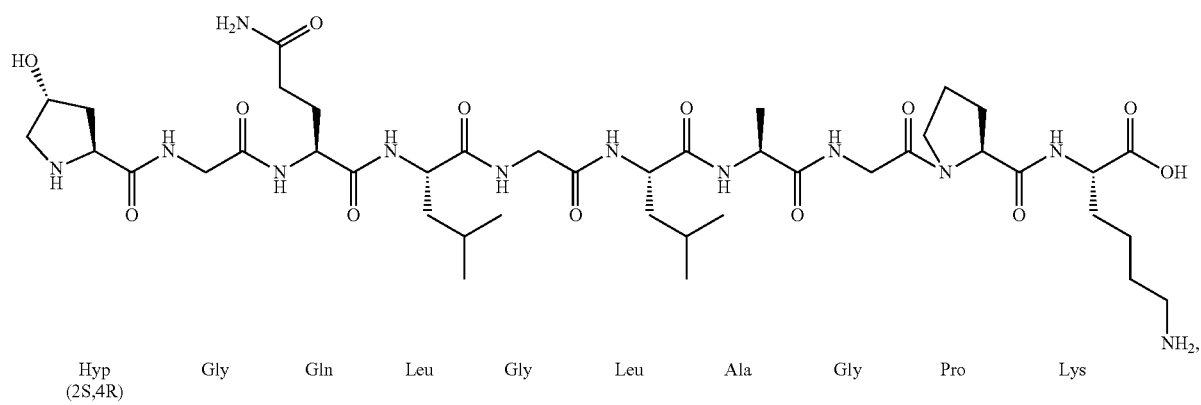
Hyp (2S,4R) — Gly — Gln — Leu — Gly — Leu — Ala — Gly — Pro — Lys
(SEQ ID NO: 12)
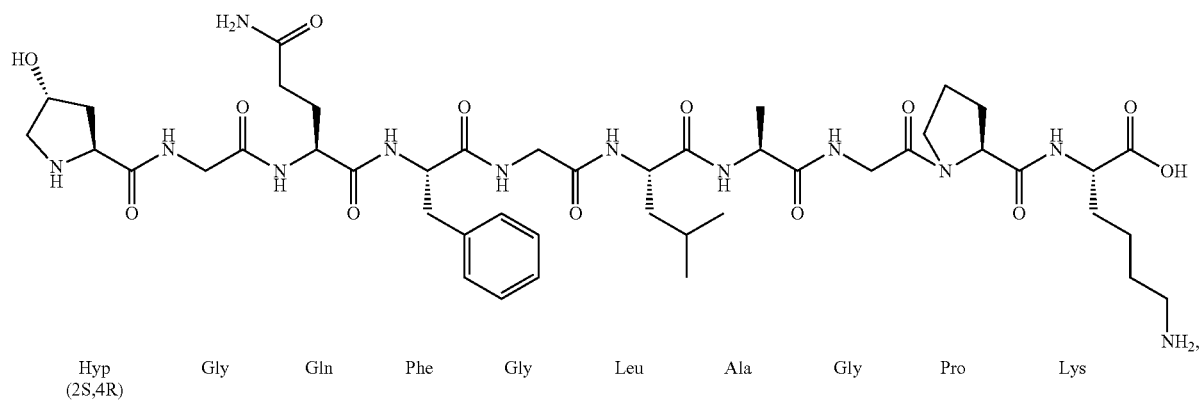
Hyp (2S,4R) — Gly — Gln — Phe — Gly — Leu — Ala — Gly — Pro — Lys (SEQ ID NO: 13)
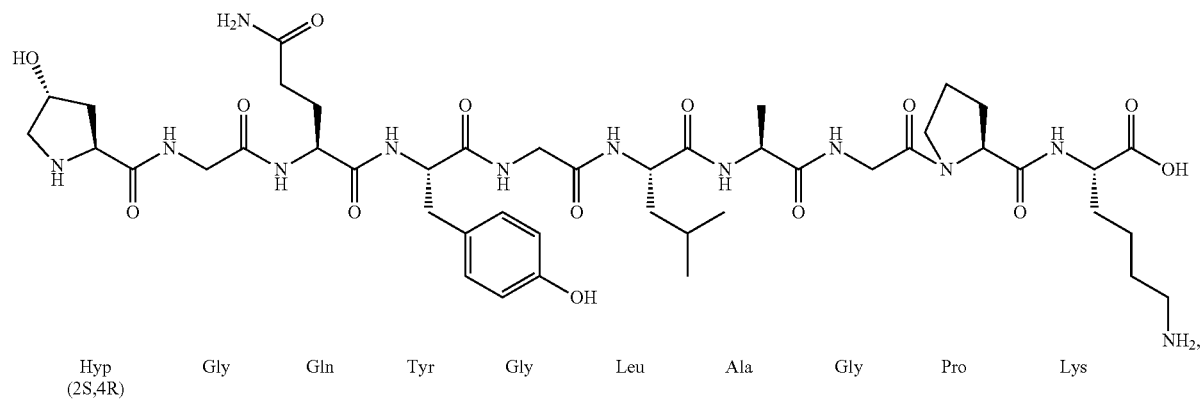
| Hyp (2S,4R) | Gly | Gln | Tyr | Gly | Leu | Ala | Gly | Pro | Lys |
(SEQ ID NO: 14)
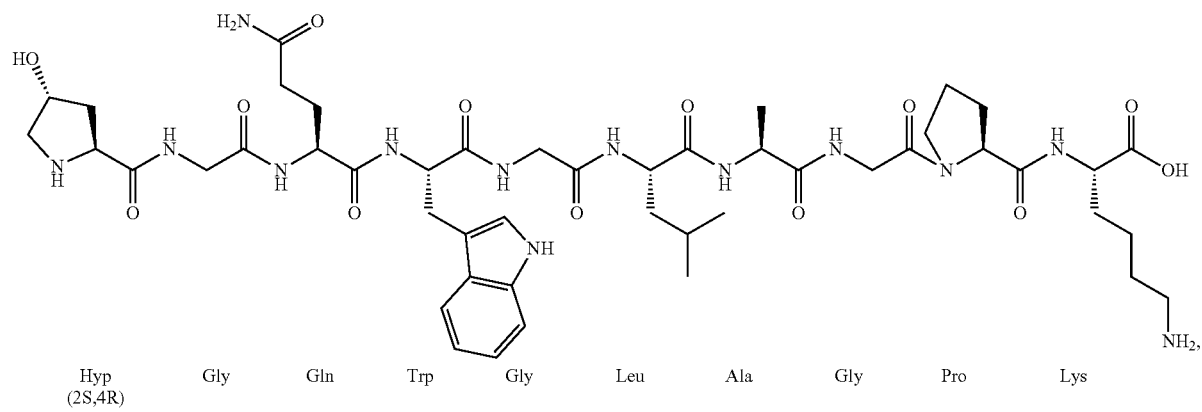
| Hyp (2S,4R) | Gly | Gln | Trp | Gly | Leu | Ala | Gly | Pro | Lys |
(SEQ ID NO: 15)
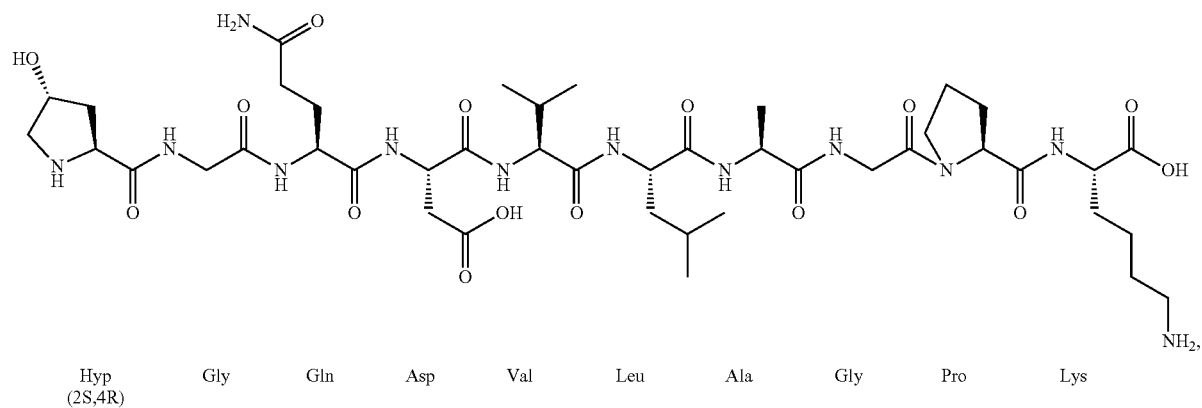
| Hyp (2S,4R) | Gly | Gln | Asp | Val | Leu | Ala | Gly | Pro | Lys |

(SEQ ID NO: 16)
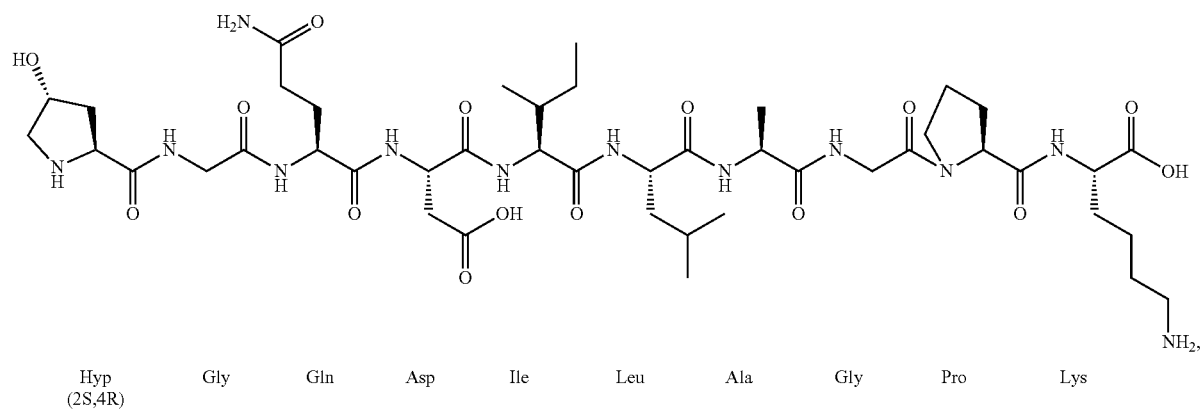
| Hyp (2S,4R) | Gly | Gln | Asp | Ile | Leu | Ala | Gly | Pro | Lys |
(SEQ ID NO: 17)
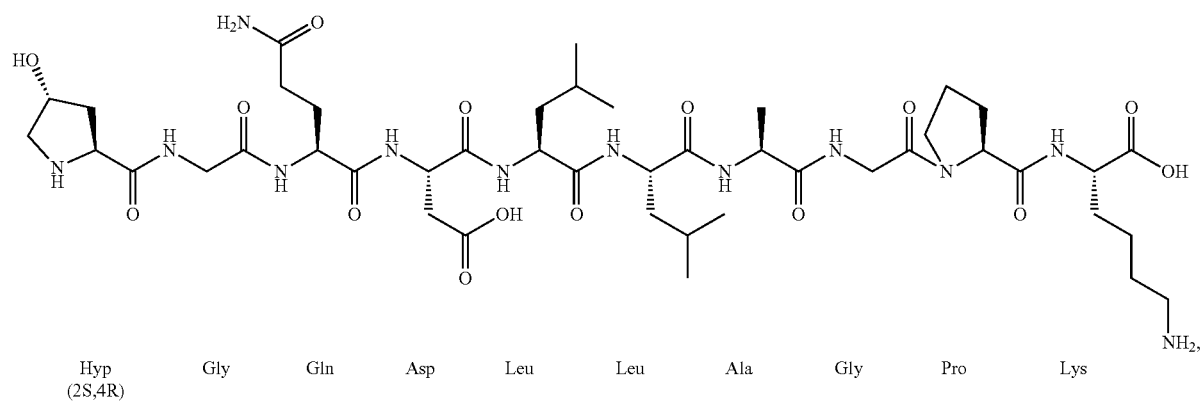
| Hyp (2S,4R) | Gly | Gln | Asp | Leu | Leu | Ala | Gly | Pro | Lys |
(SEQ ID NO: 18)
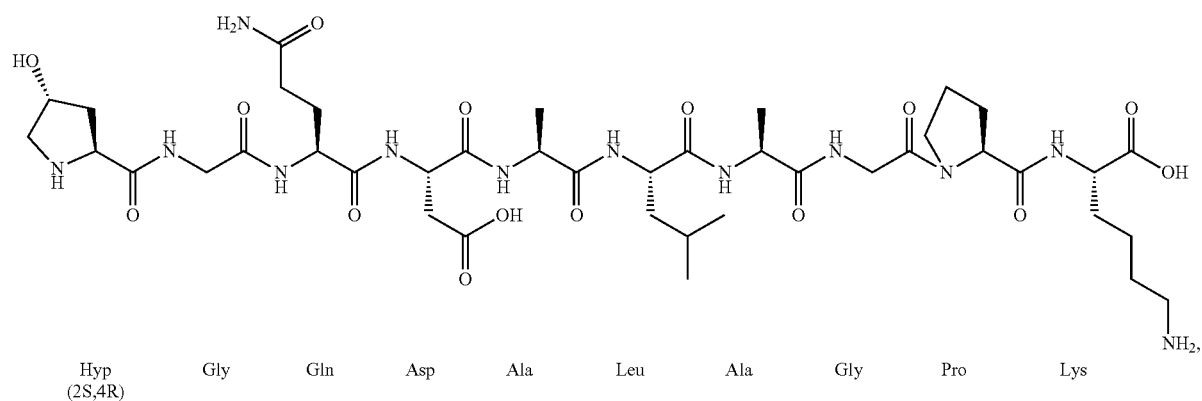
| Hyp (2S,4R) | Gly | Gln | Asp | Ala | Leu | Ala | Gly | Pro | Lys |

(SEQ ID NO: 19)
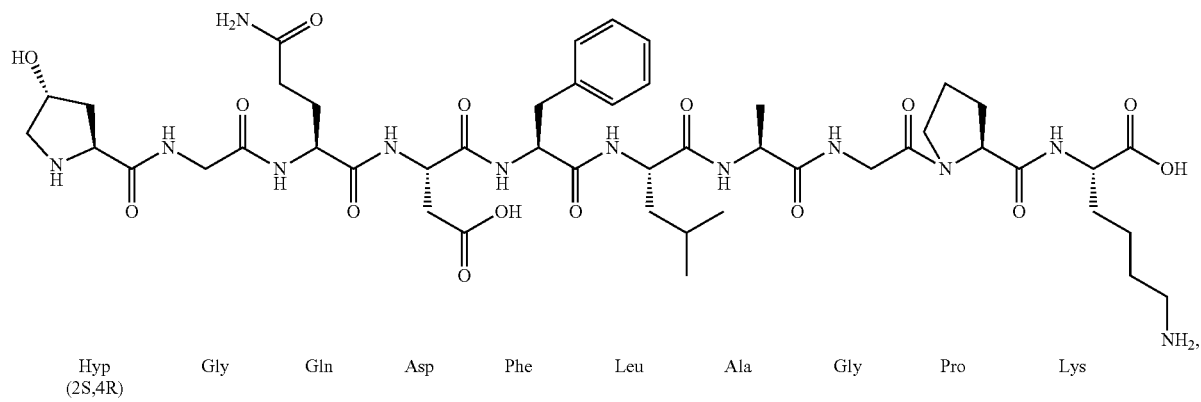
| Hyp (2S,4R) | Gly | Gln | Asp | Phe | Leu | Ala | Gly | Pro | Lys |
(SEQ ID NO: 20)
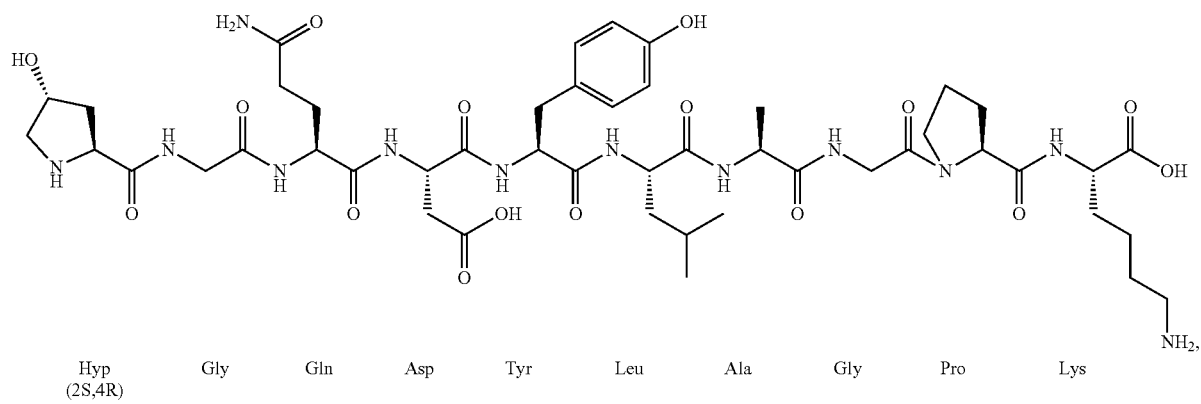
| Hyp (2S,4R) | Gly | Gln | Asp | Tyr | Leu | Ala | Gly | Pro | Lys |
(SEQ ID NO: 21)
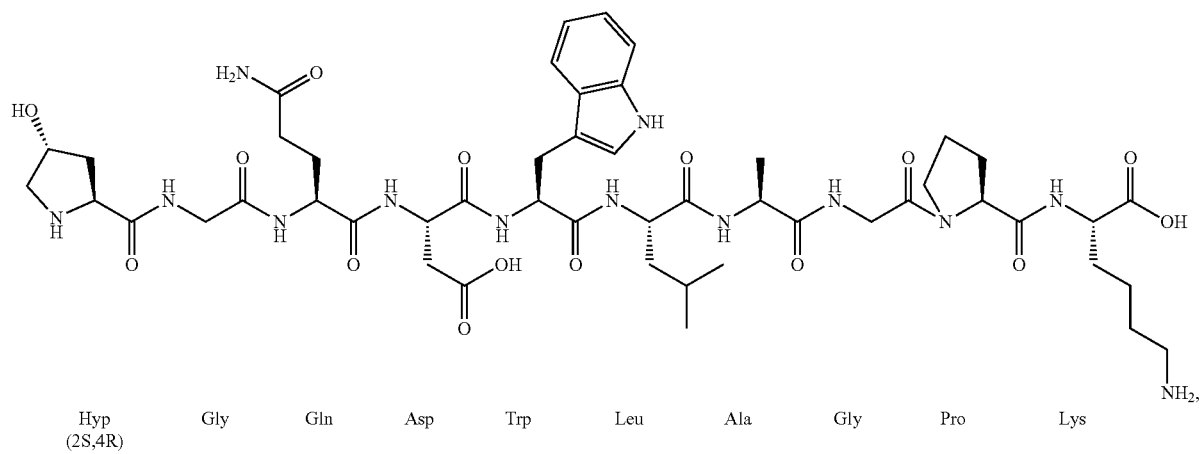
| Hyp (2S,4R) | Gly | Gln | Asp | Trp | Leu | Ala | Gly | Pro | Lys |

(SEQ ID NO: 22)
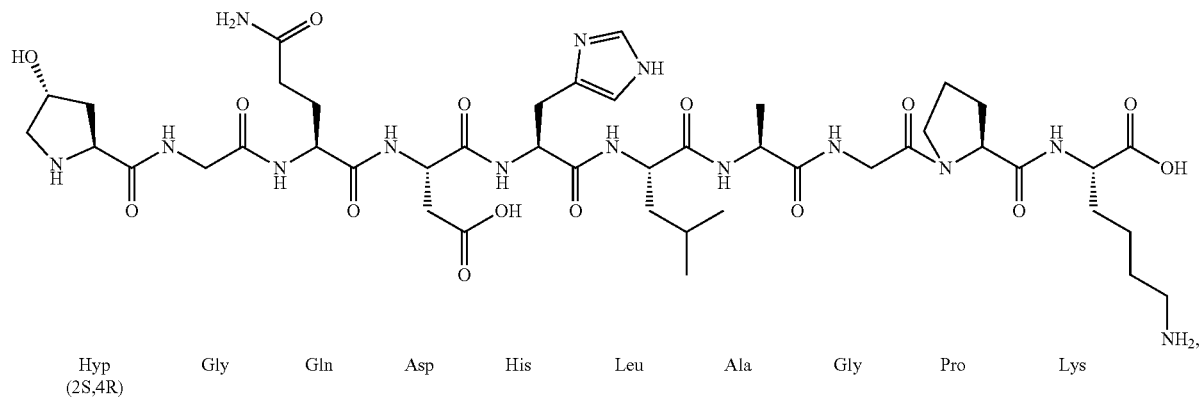
| Hyp (2S,4R) | Gly | Gln | Asp | His | Leu | Ala | Gly | Pro | Lys |
(SEQ ID NO: 23)
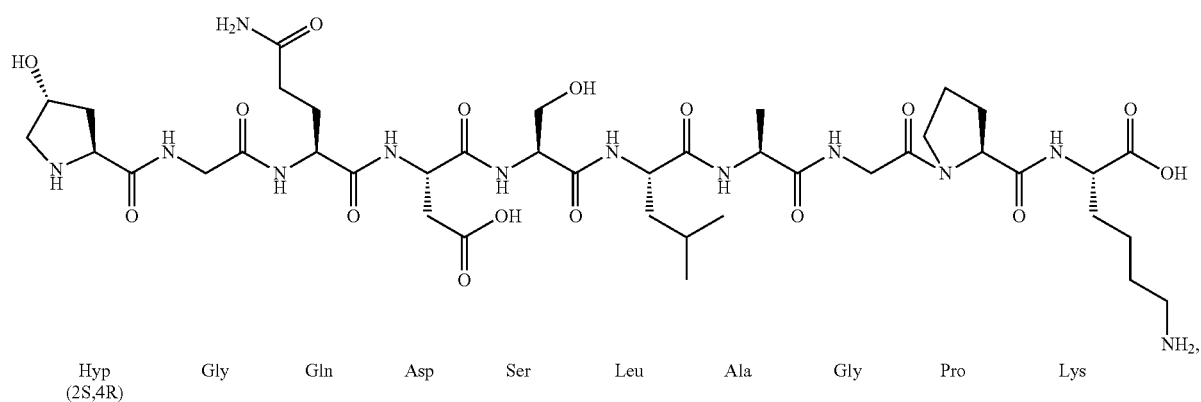
| Hyp (2S,4R) | Gly | Gln | Asp | Ser | Leu | Ala | Gly | Pro | Lys |
(SEQ ID NO: 24)
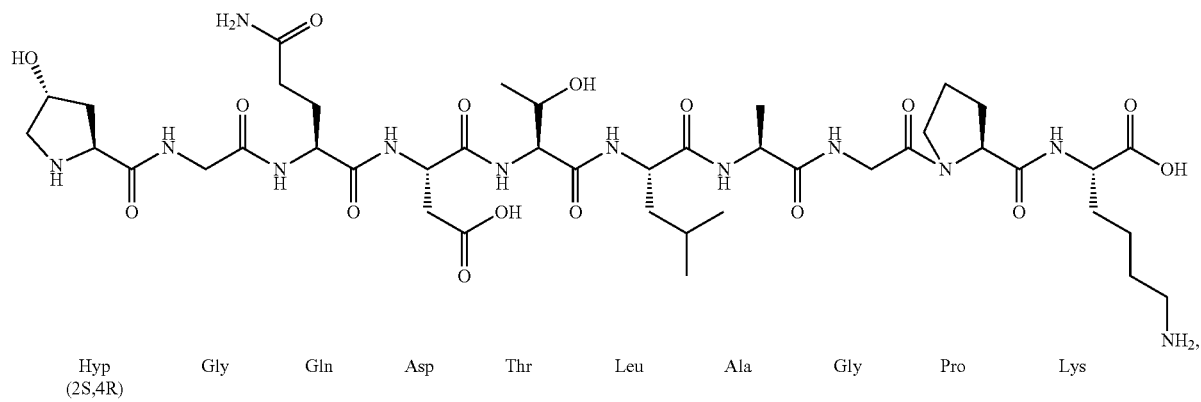
| Hyp (2S,4R) | Gly | Gln | Asp | Thr | Leu | Ala | Gly | Pro | Lys |

(SEQ ID NO: 26)
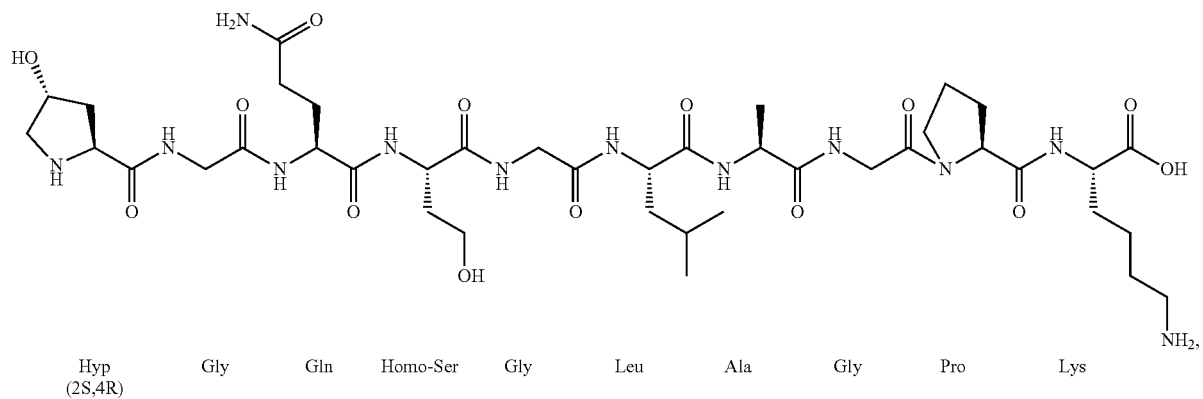
| Hyp (2S,4R) | Gly | Gln | Homo-Ser | Gly | Leu | Ala | Gly | Pro | Lys |
(SEQ ID NO: 27)
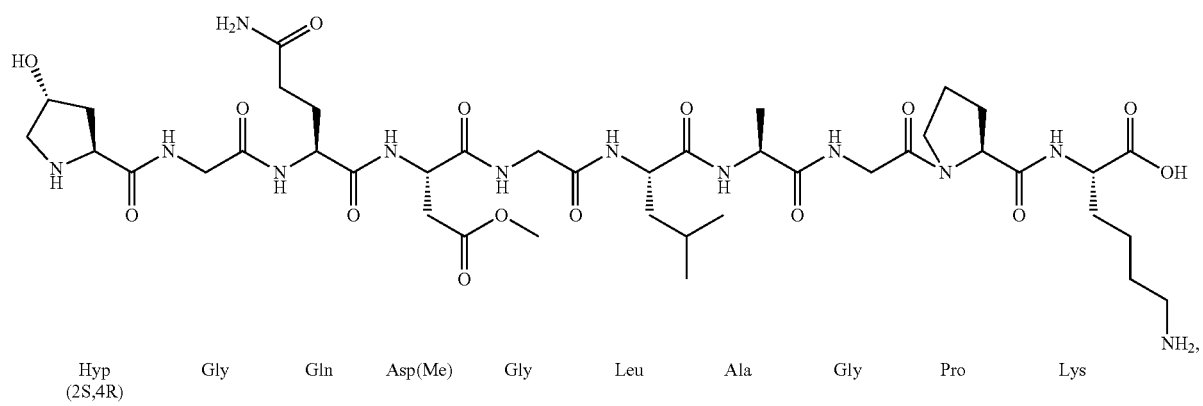
| Hyp (2S,4R) | Gly | Gln | Asp(Me) | Gly | Leu | Ala | Gly | Pro | Lys |
(SEQ ID NO: 28)
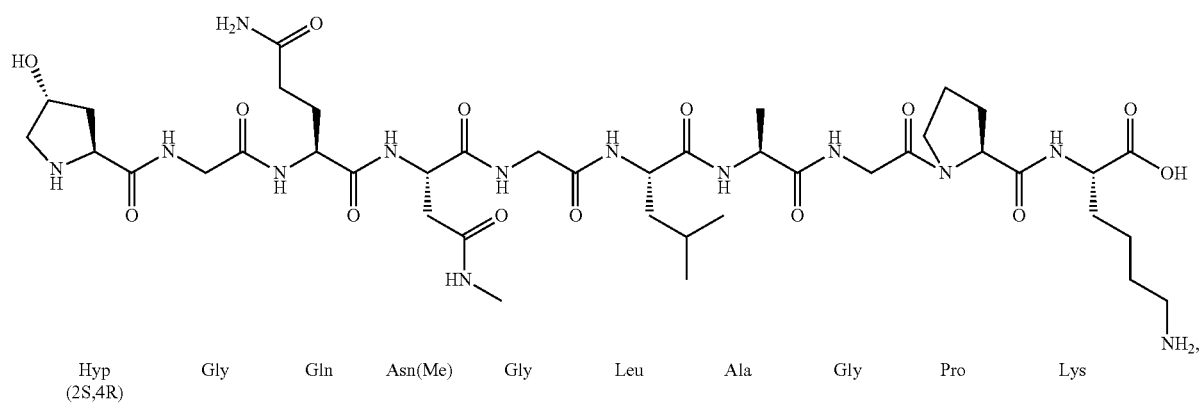
| Hyp (2S,4R) | Gly | Gln | Asn(Me) | Gly | Leu | Ala | Gly | Pro | Lys |
(SEQ ID NO: 29)
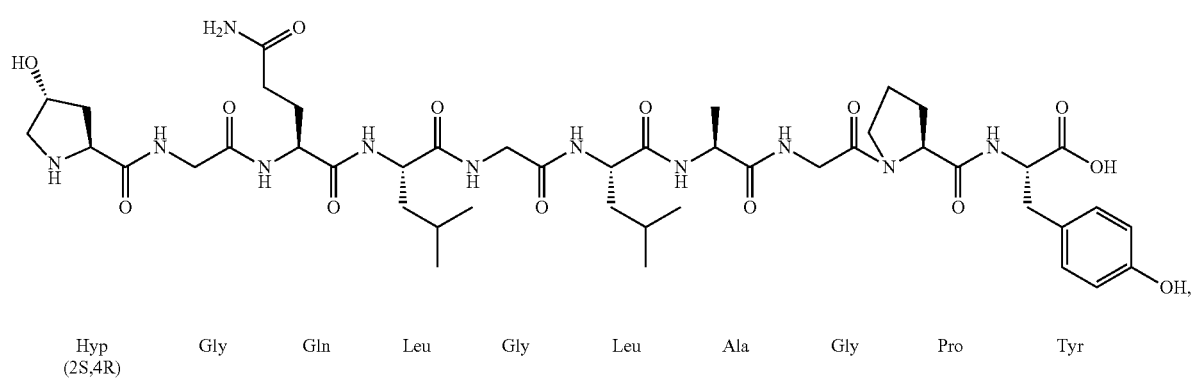
| Hyp (2S,4R) | Gly | Gln | Leu | Gly | Leu | Ala | Gly | Pro | Tyr |

(SEQ ID NO: 30)
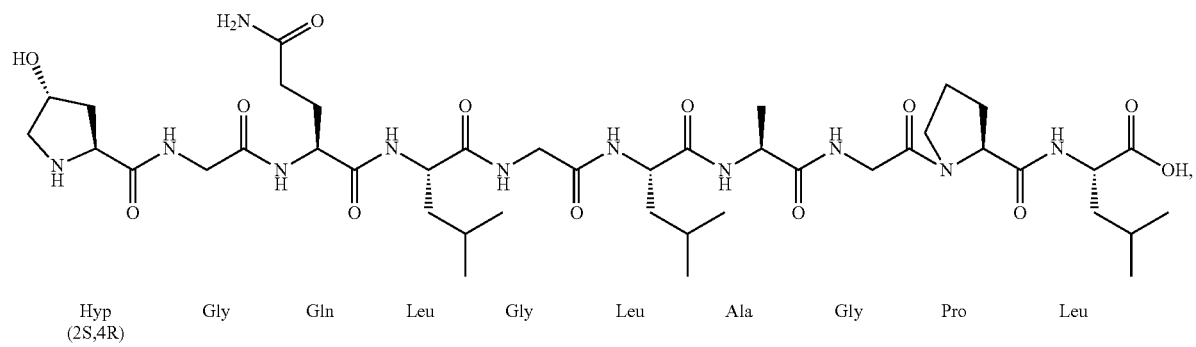
| Hyp (2S,4R) | Gly | Gln | Leu | Gly | Leu | Ala | Gly | Pro | Leu |
(SEQ ID NO: 31)
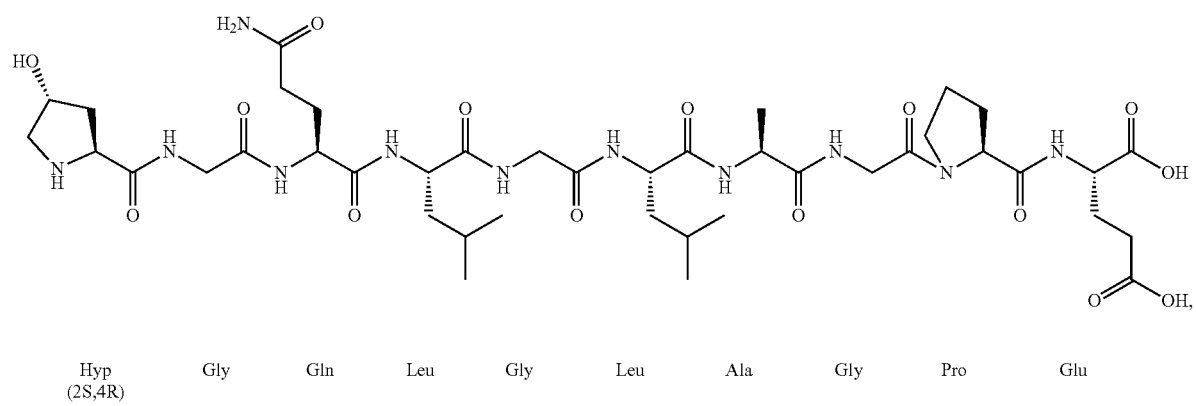
| Hyp (2S,4R) | Gly | Gln | Leu | Gly | Leu | Ala | Gly | Pro | Glu |
(SEQ ID NO: 32)
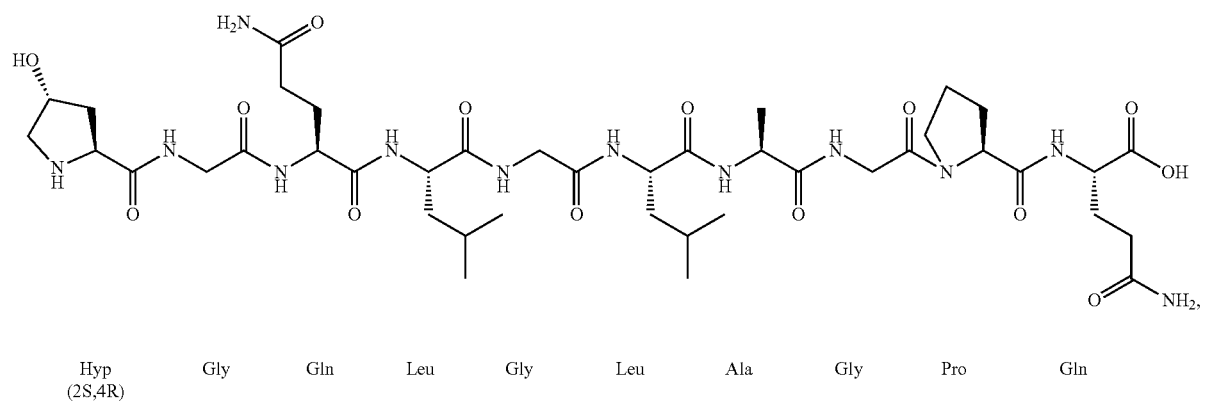
| Hyp (2S,4R) | Gly | Gln | Leu | Gly | Leu | Ala | Gly | Pro | Gln |
(SEQ ID NO: 33)
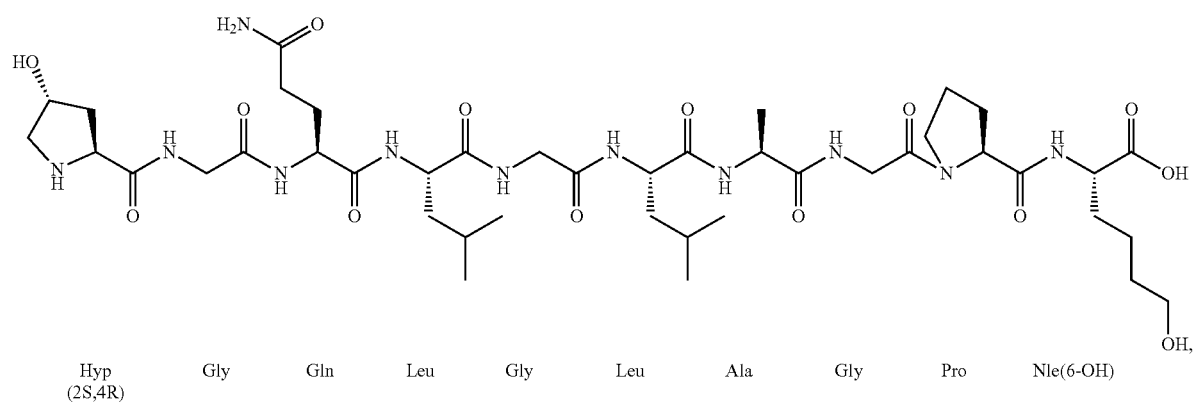
| Hyp (2S,4R) | Gly | Gln | Leu | Gly | Leu | Ala | Gly | Pro | Nle(6-OH) |

(SEQ ID NO: 34)
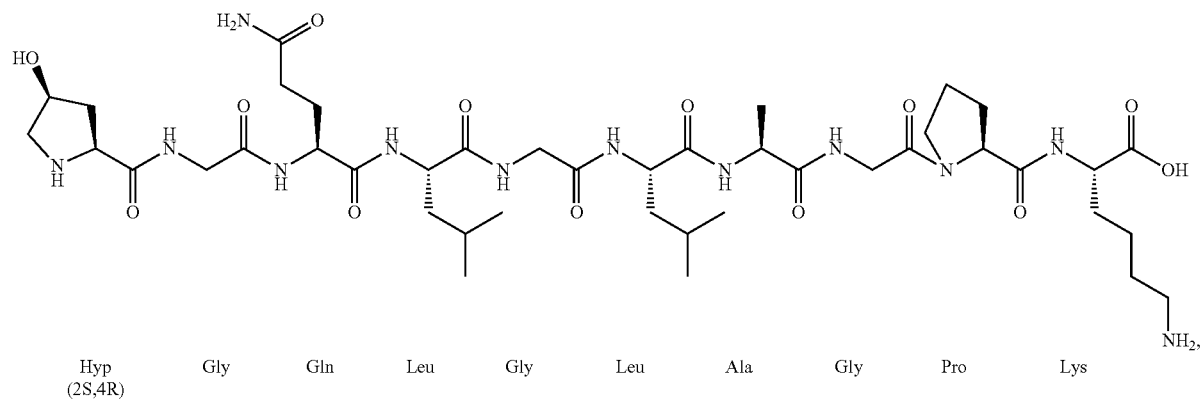
Hyp (2S,4R) — Gly — Gln — Leu — Gly — Leu — Ala — Gly — Pro — Lys
(SEQ ID NO: 35)
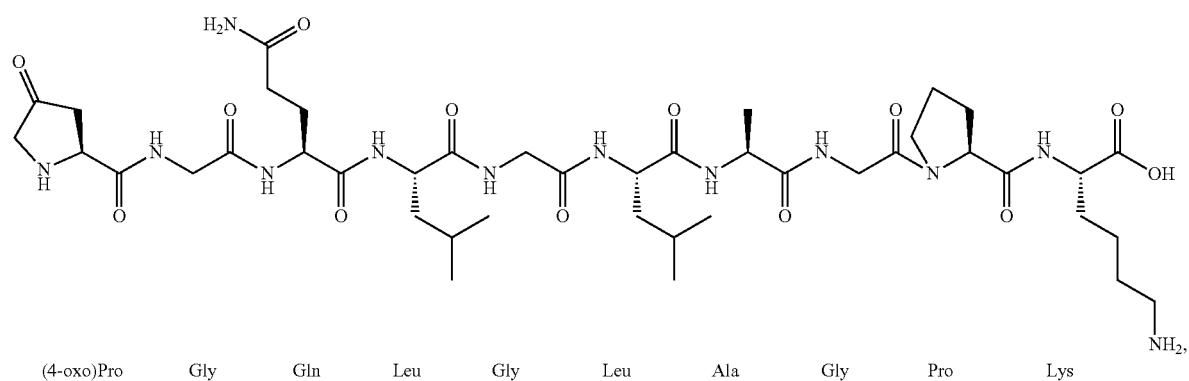
(4-oxo)Pro — Gly — Gln — Leu — Gly — Leu — Ala — Gly — Pro — Lys
(SEQ ID NO: 36)
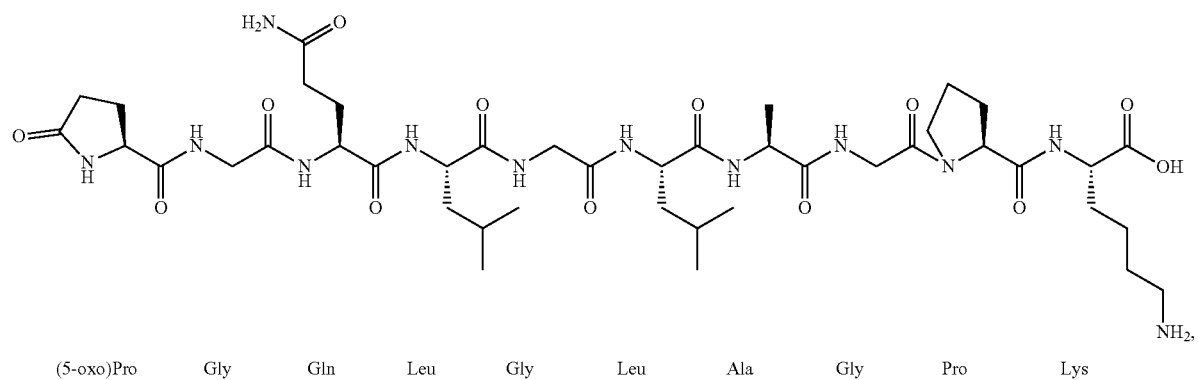
(5-oxo)Pro — Gly — Gln — Leu — Gly — Leu — Ala — Gly — Pro — Lys
(SEQ ID NO: 37)
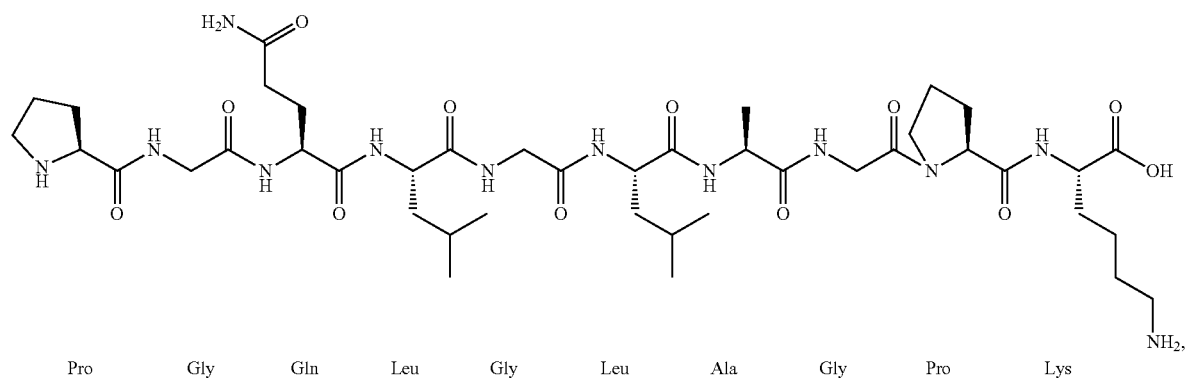
Pro — Gly — Gln — Leu — Gly — Leu — Ala — Gly — Pro — Lys (SEQ ID NO: 38)
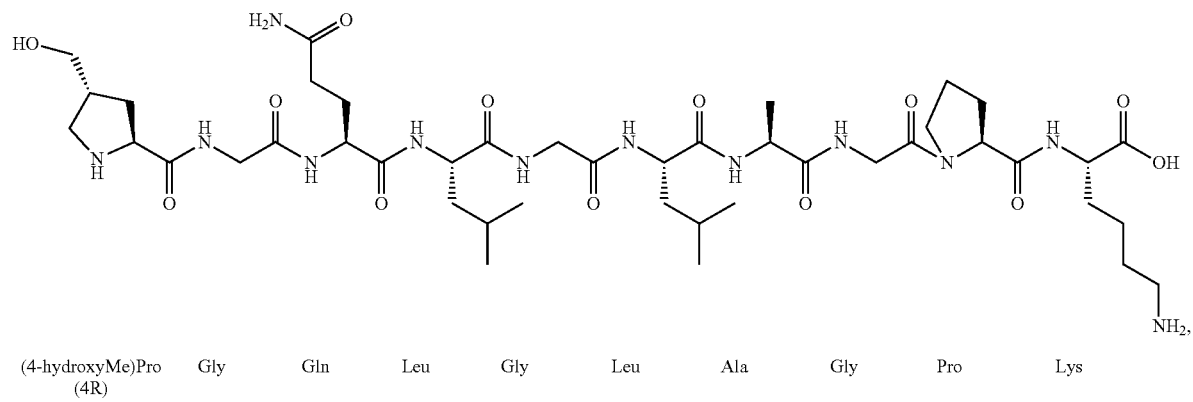
(4-hydroxyMe)Pro (4R)    Gly    Gln    Leu    Gly    Leu    Ala    Gly    Pro    Lys
(SEQ ID NO: 39)
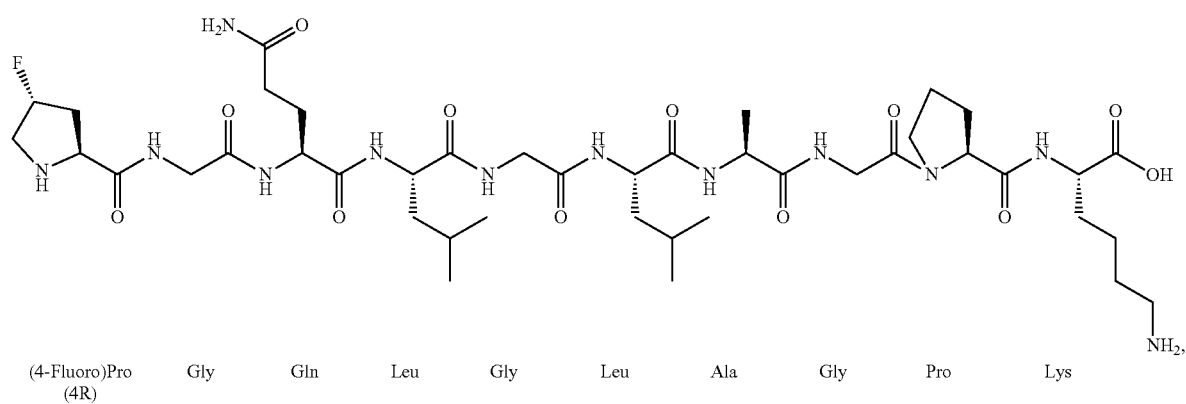
(4-Fluoro)Pro (4R)    Gly    Gln    Leu    Gly    Leu    Ala    Gly    Pro    Lys
(SEQ ID NO: 40)
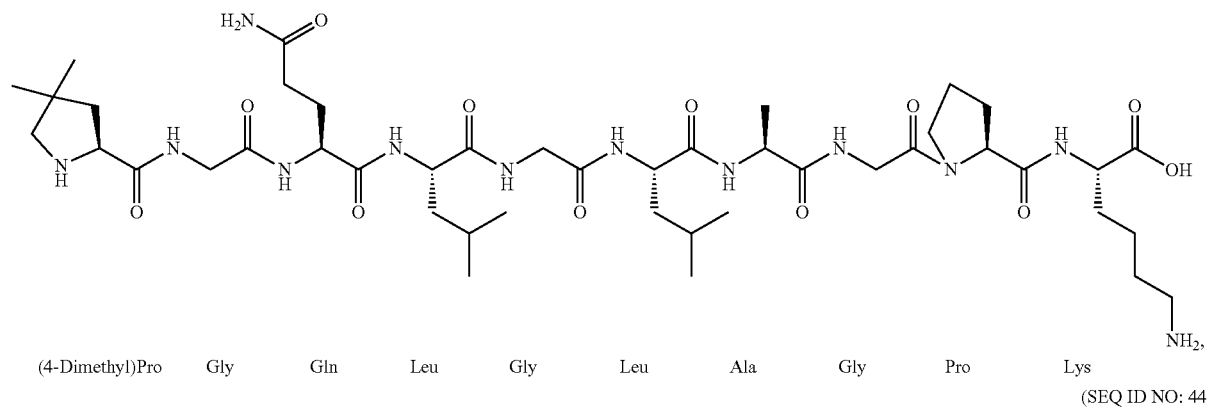
(4-Dimethyl)Pro    Gly    Gln    Leu    Gly    Leu    Ala    Gly    Pro    Lys
(SEQ ID NO: 44)
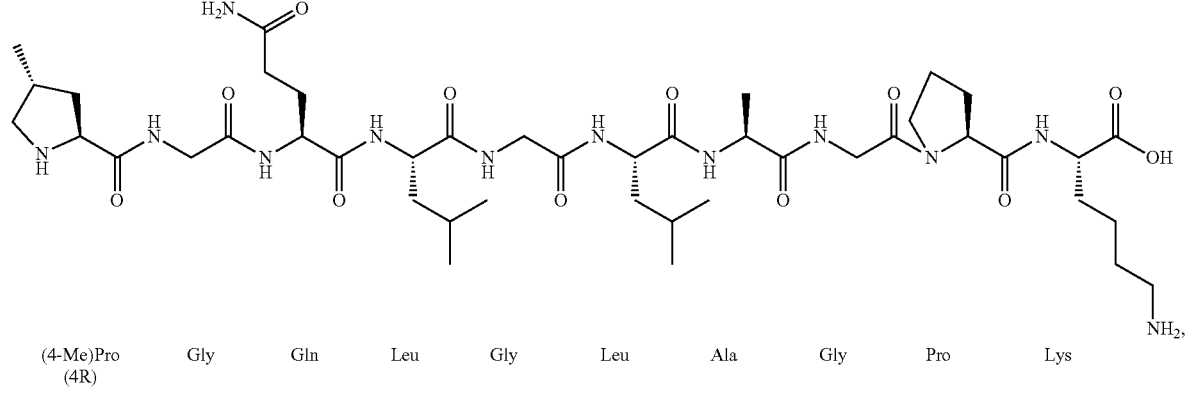
(4-Me)Pro (4R)    Gly    Gln    Leu    Gly    Leu    Ala    Gly    Pro    Lys (SEQ ID NO: 45)
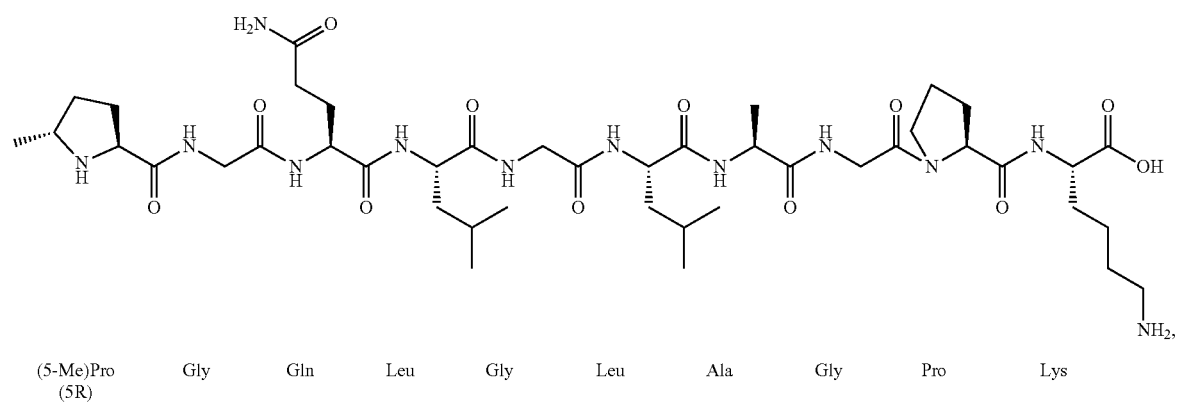
(5-Me)Pro  Gly  Gln  Leu  Gly  Leu  Ala  Gly  Pro  Lys
(5R)
(SEQ ID NO: 48)
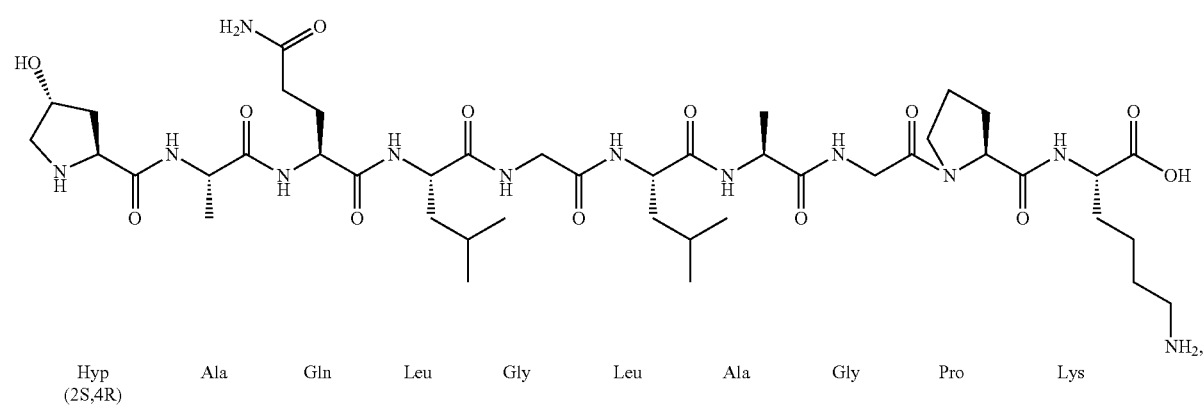
Hyp   Ala  Gln  Leu  Gly  Leu  Ala  Gly  Pro  Lys
(2S,4R)
(SEQ ID NO: 49)
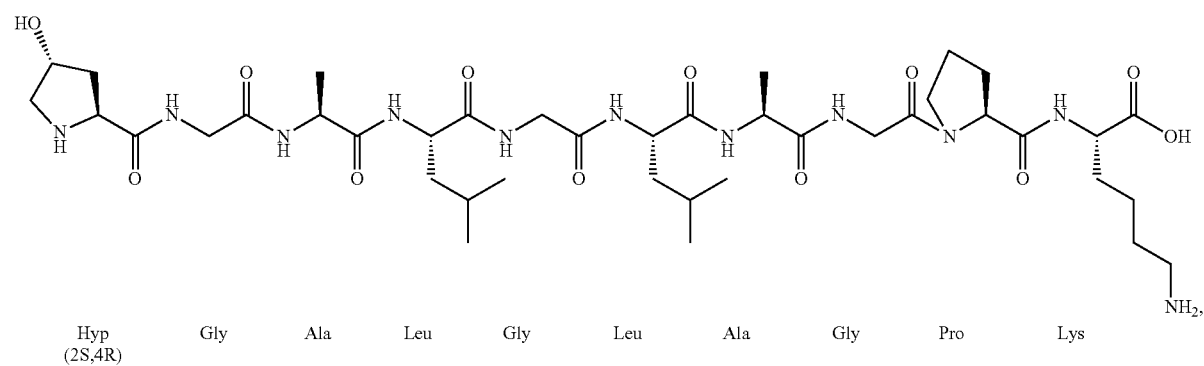
Hyp   Gly  Ala  Leu  Gly  Leu  Ala  Gly  Pro  Lys
(2S,4R)
(SEQ ID NO: 8)
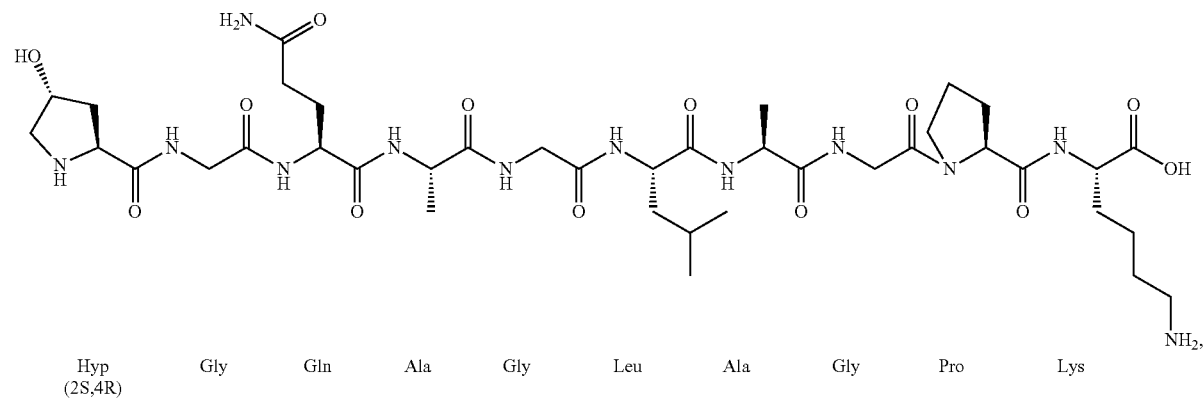
Hyp   Gly  Gln  Ala  Gly  Leu  Ala  Gly  Pro  Lys
(2S,4R)

(SEQ ID NO: 51)
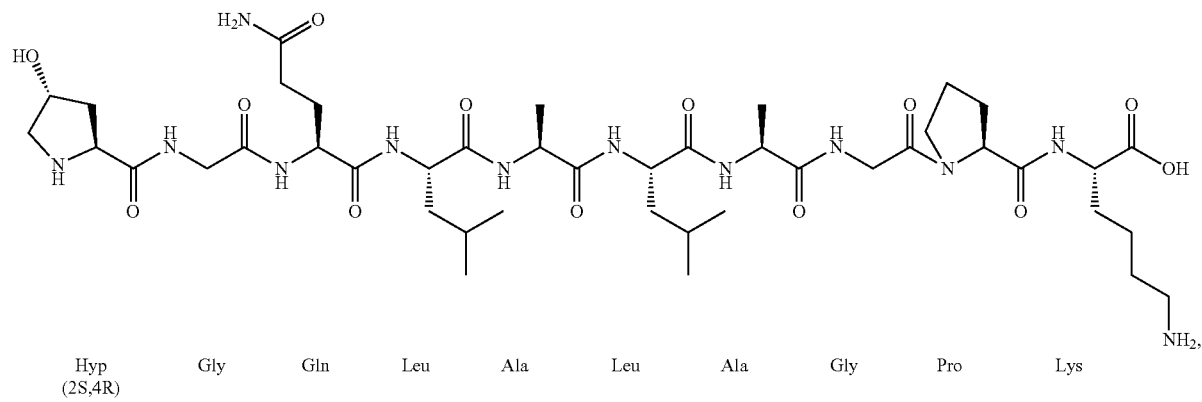
| Hyp (2S,4R) | Gly | Gln | Leu | Ala | Leu | Ala | Gly | Pro | Lys |
(SEQ ID NO: 52)
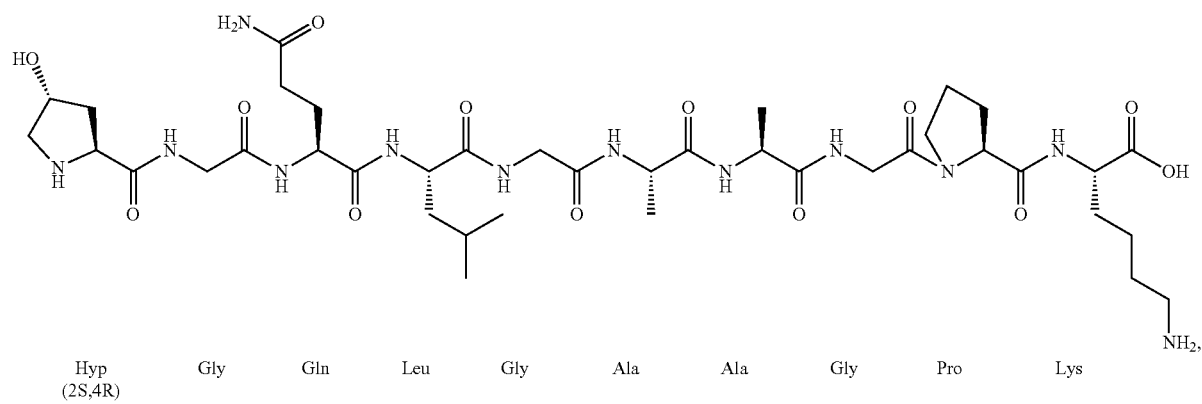
| Hyp (2S,4R) | Gly | Gln | Leu | Gly | Ala | Ala | Gly | Pro | Lys |
(SEQ ID NO: 54)
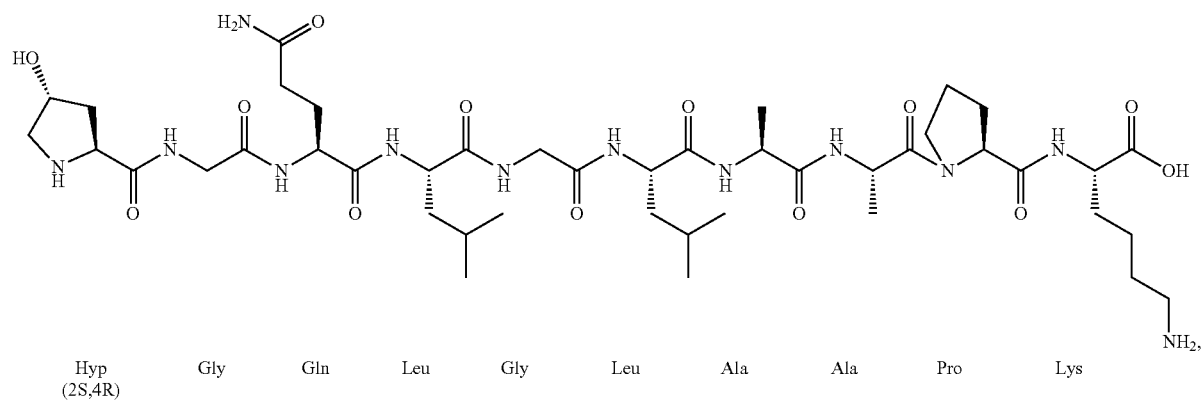
| Hyp (2S,4R) | Gly | Gln | Leu | Gly | Leu | Ala | Ala | Pro | Lys |

(SEQ ID NO: 56)
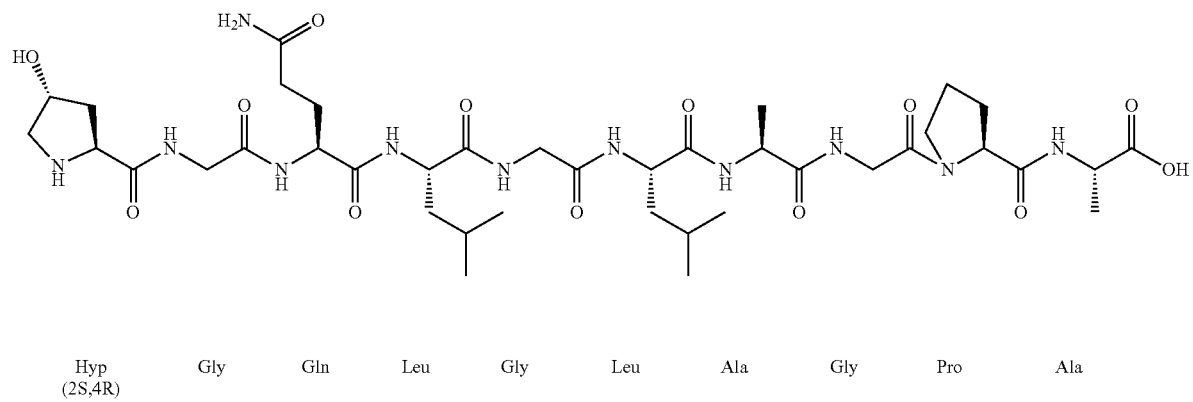
| Hyp (2S,4R) | Gly | Gln | Leu | Gly | Leu | Ala | Gly | Pro | Ala |
(SEQ ID NO: 57)
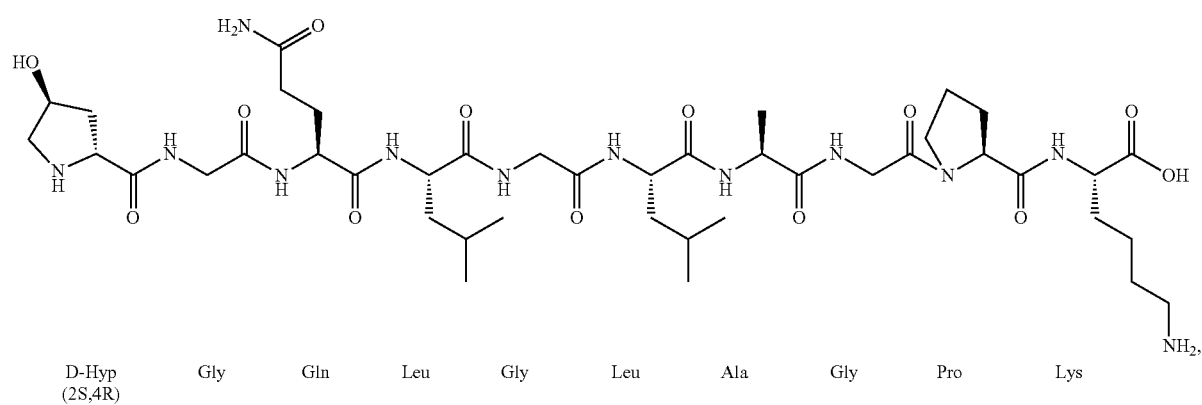
| D-Hyp (2S,4R) | Gly | Gln | Leu | Gly | Leu | Ala | Gly | Pro | Lys |
(SEQ ID NO: 58)
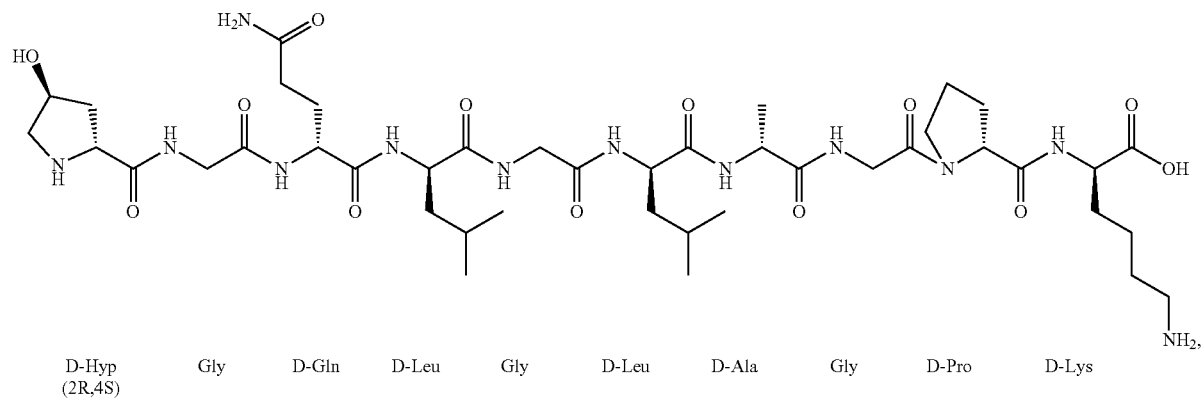
| D-Hyp (2R,4S) | Gly | D-Gln | D-Leu | Gly | D-Leu | D-Ala | Gly | D-Pro | D-Lys |

(SEQ ID NO: 60)
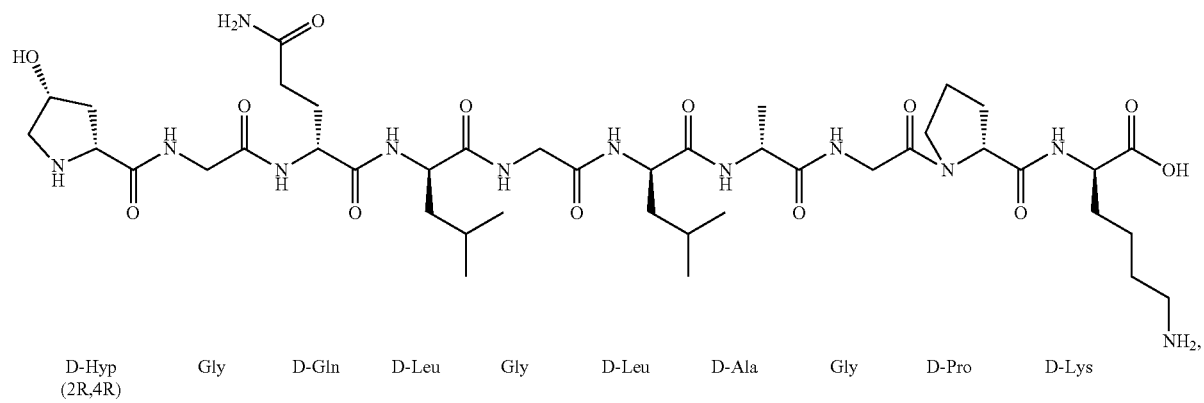
| D-Hyp (2R,4R) | Gly | D-Gln | D-Leu | Gly | D-Leu | D-Ala | Gly | D-Pro | D-Lys |
(SEQ ID NO: 72)
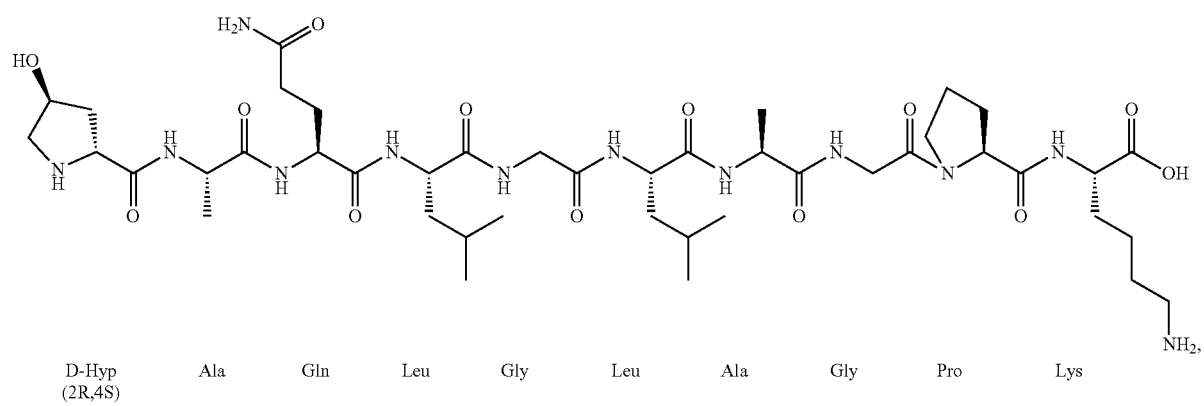
| D-Hyp (2R,4S) | Ala | Gln | Leu | Gly | Leu | Ala | Gly | Pro | Lys |
(SEQ ID NO: 73)
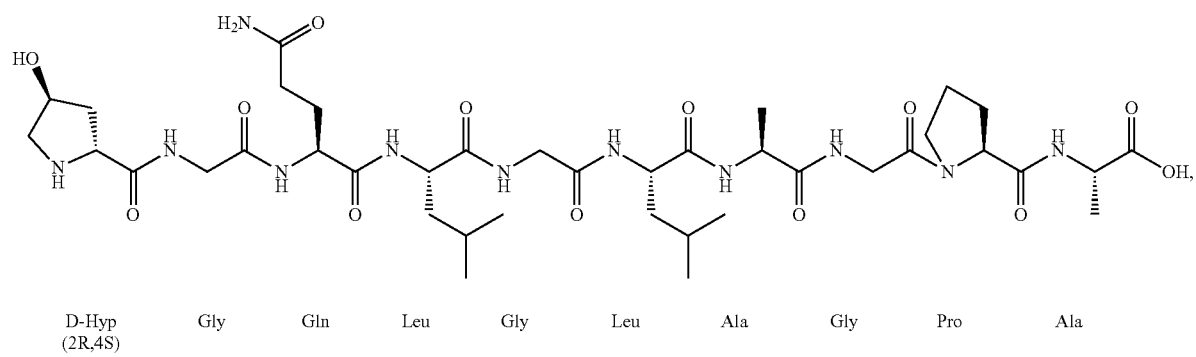
| D-Hyp (2R,4S) | Gly | Gln | Leu | Gly | Leu | Ala | Gly | Pro | Ala |
(SEQ ID NO: 74)
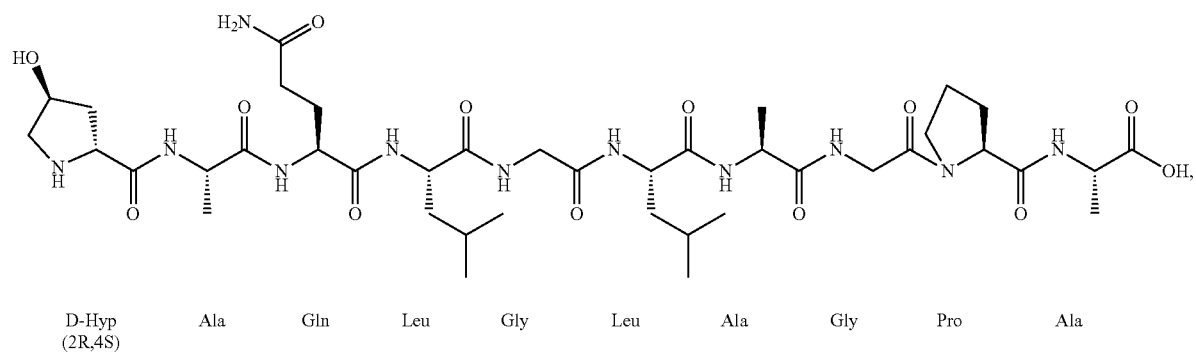
| D-Hyp (2R,4S) | Ala | Gln | Leu | Gly | Leu | Ala | Gly | Pro | Ala |

(SEQ ID NO: 78)

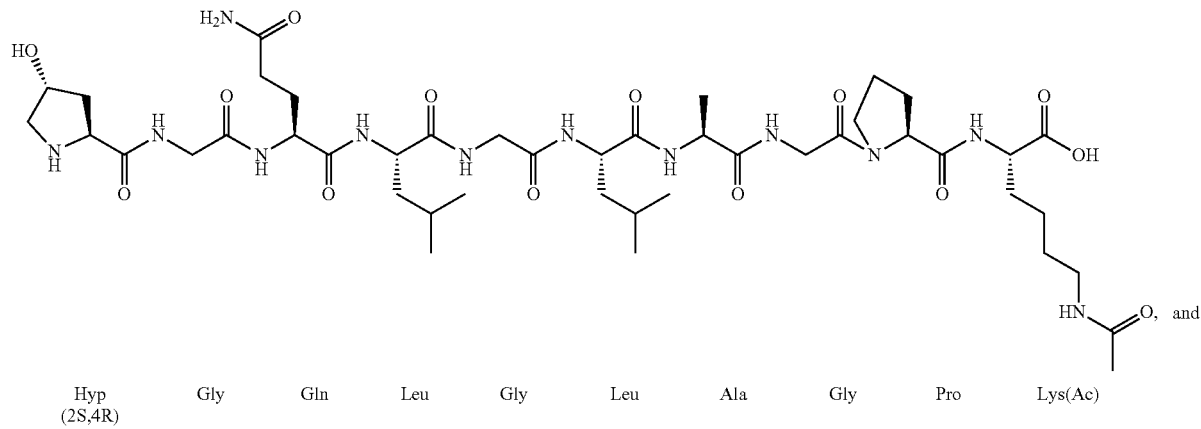

Hyp(2S,4R)  Gly  Gln  Leu  Gly  Leu  Ala  Gly  Pro  Lys(Ac)

(SEQ ID NO: 80)

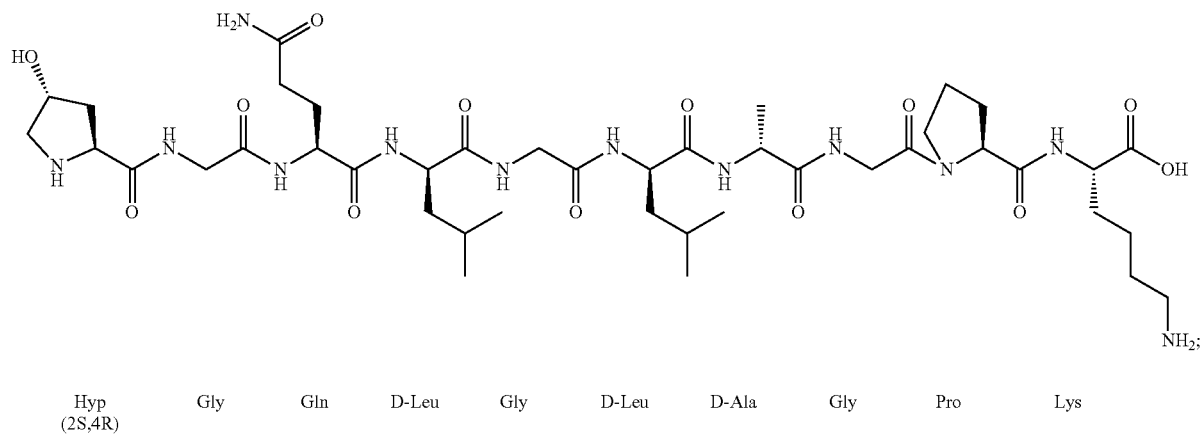

Hyp(2S,4R)  Gly  Gln  D-Leu  Gly  D-Leu  D-Ala  Gly  Pro  Lys or a pharmaceutically acceptable salt thereof.

In certain embodiments, the compound of the invention is a peptide having an amino acid sequence represented by HyP-Gly-Gln-Xaa-Gly-Leu-Ala-Gly-Pro-Lys (SEQ ID NO: 108);

or a pharmaceutically acceptable salt and/or stereoisomer thereof;

wherein Xaa is selected from Glu, Asn, Gln, His, Lys, Ser, Thr, Ala, Val, Ile, Leu, Phe, Tyr, Trp, homo-Ser, Asp(Me), and Asn(Me); and at least one amino acid residue in the peptide is a D-amino acid residue.

In certain such embodiments, at least two, at least three, at least four, at least five, at least six, or at least seven amino acid residues in the peptide are D-amino acid residues.

The peptide may be a variant of a collagen type II α1-derived peptide. The collagen type II α1 may be isolated from the extracellular matrix derived from animal chondrocytes.

The term "peptide" used in the present invention refers to a compound in which two or more amino acids are linked by a peptide bond. Further, it is classified into dipeptide, tripeptide, tetrapeptide, and the like according to the number of constituent amino acids. An oligopeptide has about 10 or fewer peptide bonds, and a polypeptide has a plurality of peptide bonds. In addition, a peptide in the present invention includes a mutated peptide in which its amino acid residue is substituted.

The term "HyP" used in the present invention refers to an amino acid called hydroxyproline, in which a hydroxyl group (—OH) is bonded to the carbon atom at the 4-position of proline. HyP has a structure of $C_5H_9NO_3$ and may be depicted as follows:

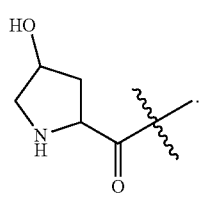

HyP may include all isomers. In addition, HyP may be an isomer represented by the stereochemistry of "2S,4R" unless otherwise specified.

The term "homo-Ser" used in the present invention is called homoserine and refers to an α-amino acid having a hydroxyl group in the side chain. Homo-Ser is an intermediate present in the biosynthesis of threonine and methionine in microorganisms and plants. Homo-Ser may be depicted as follows:

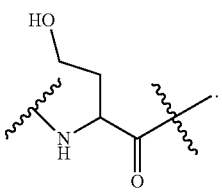 [SMILES: *NC(CCO)C(*)=O]

The term "Asp(Me)" used in the present invention indicates an amino acid in which the hydrogen atom of the hydroxyl group (OH) bonded to the carbon atom at the 4-position of aspartic acid is substituted by a methyl group (CH₃). Asp(Me) may be depicted as follows:

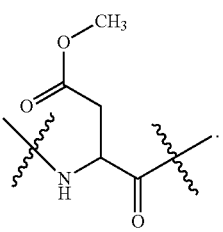 [SMILES: *NC(CC(=O)OC)C(*)=O]

The term "Asn(Me)" used in the present invention indicates an amino acid in which the hydrogen atom of the amine group (NH₂) bonded to the carbon atom at the 4-position of asparagine is substituted by a methyl group (CH₃). Asn(Me) may be depicted as follows:

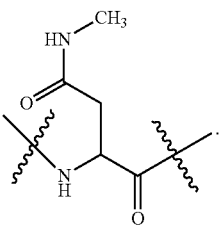 [SMILES: *NC(CC(=O)NC)C(*)=O]

The term "(N-Me)Gly" used in the present invention indicates an amino acid in which the hydrogen atom of the amine group (NH₂) bonded to the carbon atom at the 2-position of glycine is replaced by a methyl group (CH₃). (N-Me)Gly may be depicted as follows:

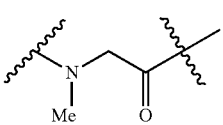

In certain embodiments, the compound is a peptide having an amino acid sequence represented by HyP-Gly-Gln-Asp-Xaa-Leu-Ala-Gly-Pro-Lys (SEQ ID NO: 109);

or a pharmaceutically acceptable salt and/or stereoisomer thereof;

wherein Xaa is selected from Val, Ile, Leu, Ala, Phe, Tyr, Trp, Ser, Thr, and (N-Me)Gly; and at least one amino acid residue in the peptide is a D-amino acid residue.

In certain such embodiments, at least two, at least three, at least four, at least five, at least six, or at least seven amino acid residues in the peptide are D-amino acid residues.

In certain embodiments, the compound is a peptide having an amino acid sequence represented by HyP-Gly-Gln-Leu-Gly-Leu-Ala-Gly-Pro-Xaa (SEQ ID NO: 110);

or a pharmaceutically acceptable salt and/or stereoisomer thereof;

wherein Xaa is selected from Tyr, Leu, Glu, Gln, Ala, and Nle(6-OH); and at least one amino acid residue in the peptide is a D-amino acid residue.

In certain such embodiments, at least two, at least three, at least four, at least five, at least six, or at least seven amino acid residues in the peptide are D-amino acid residues.

In certain embodiments, the compound is a peptide having an amino acid sequence represented by Xaa-Gly-Gln-Leu-Gly-Leu-Ala-Gly-Pro-Lys (SEQ ID NO: 111);

or a pharmaceutically acceptable salt and/or stereoisomer thereof;

wherein Xaa is selected from:

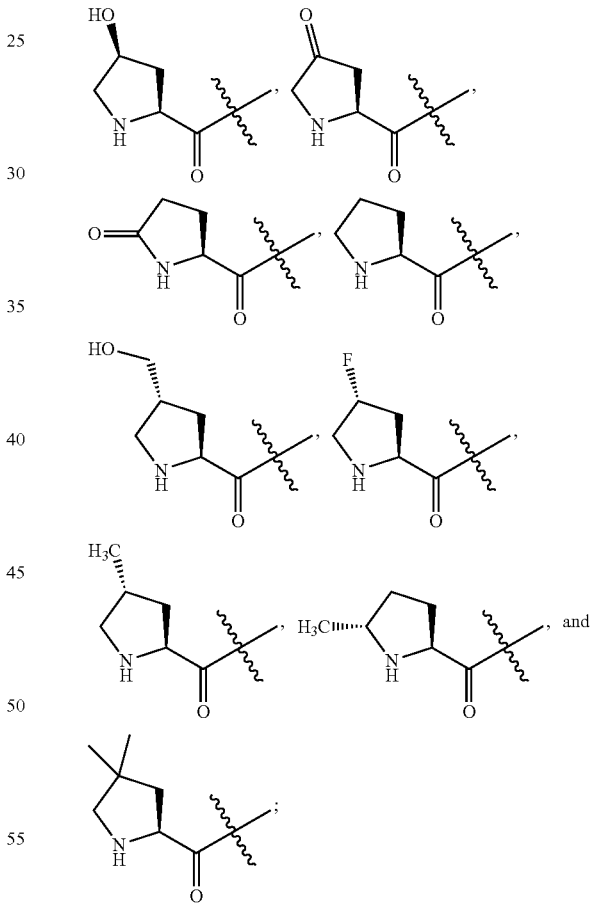

and at least one amino acid residue in the peptide is a D-amino acid residue.

In certain such embodiments, at least two, at least three, at least four, at least five, at least six, or at least seven amino acid residues in the peptide are D-amino acid residues.

In certain embodiments, the invention provides a compound represented by Formula (V):

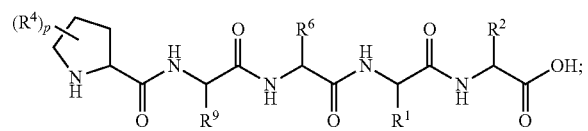

(V)

or a pharmaceutically acceptable salt thereof; wherein:
$R^1$ and $R^2$ are each independently H or substituted or unsubstituted alkyl, alkoxy, haloalkyl, alkenyl, alkynyl, aryl, arylalkyl, arylalkenyl, arylalkynyl, heteroalkyl, cycloalkyl, heterocycloalkyl, heteroaryl, or heteroarylalkyl;
$R^4$, independently for each occurrence, is selected from substituted or unsubstituted alkyl, aryl, arylalkyl, heterocycloalkyl, oxo, —$OR^b$, —$CH_2OR^b$, halo, hydroxyl, and hydroxyalkyl;
$R^b$ is substituted or unsubstituted alkyl, aryl, arylalkyl, or heterocycloalkyl;
p is 0, 1, or 2;
$R^6$ is hydrogen or substituted or unsubstituted alkyl; and
$R^9$ is hydrogen or alkyl.
In certain embodiments:
$R^1$ and $R^2$ are each independently H or substituted or unsubstituted alkyl;
$R^4$ for each occurrence is hydroxyl;
p is 1;
$R^6$ is alkyl optionally substituted with one occurrence of —C(=O)$NH_2$; and
$R^9$ is hydrogen.
In certain embodiments, $R^1$ is substituted or unsubstituted alkyl, such as

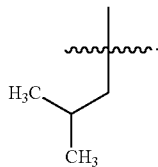

In certain embodiments, the compound has the structure of formula (V-1L)

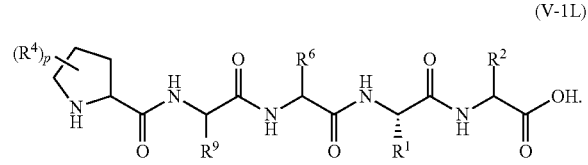

(V-1L)

Alternatively, the compound may have the structure of formula (V-1D)

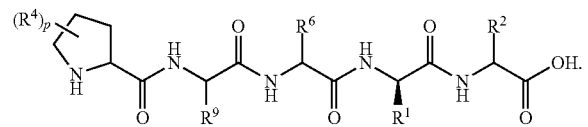

(V-1D)

In certain embodiments, $R^2$ is H.
In certain embodiments, p is 1 and $R^4$ is hydroxyl.
In certain embodiments, the compound has the structure of formula (V-4La):

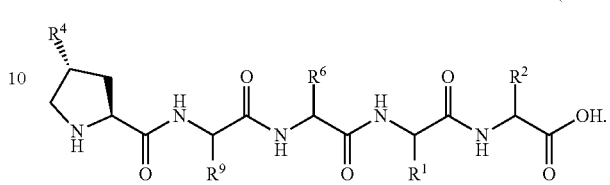

(V-4La)

In certain embodiments, the compound has the structure of formula (V-4Lb):

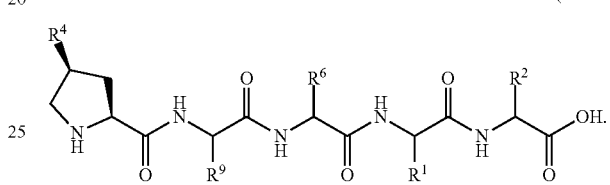

(V-4Lb)

In certain embodiments, the compound has the structure of formula (V-4 Da):

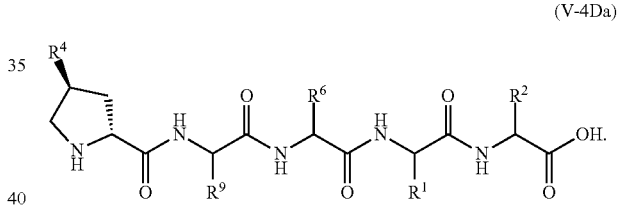

(V-4Da)

In certain embodiments, the compound has the structure of formula (V-4Db):

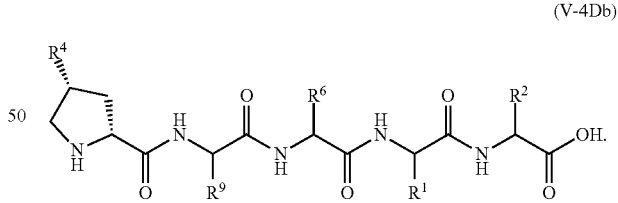

(V-4Db)

In certain embodiments, $R^6$ is alkyl substituted with one occurrence of —C(=O)$NH_2$, such as

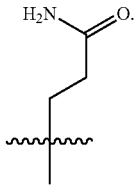 [SMILES: *CCC(N)=O]

In certain embodiments, the compound has the structure of formula (V-6L):

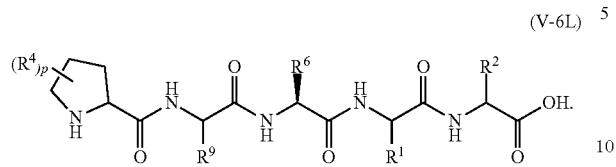
(V-6L)

Alternatively, the compound may have the structure of formula (V-6D):

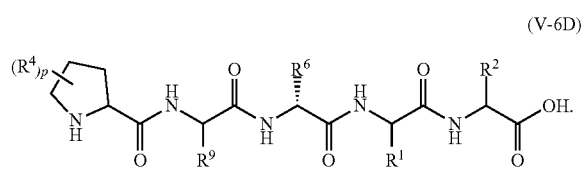
(V-6D)

In certain embodiments, $R^9$ is —H.

In certain embodiments, the compound is selected from the following:

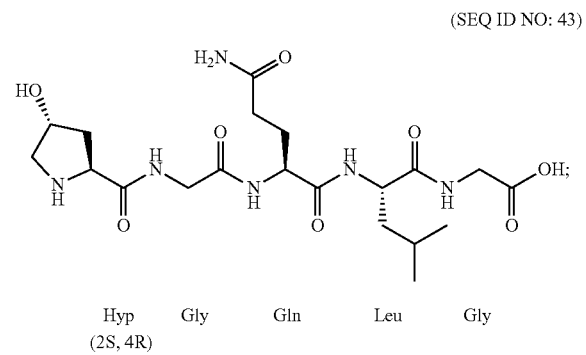
(SEQ ID NO: 43)

Hyp   Gly   Gln   Leu   Gly
(2S, 4R)

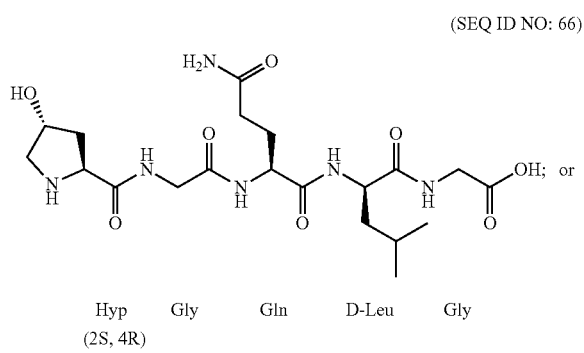
(SEQ ID NO: 66)

Hyp   Gly   Gln   D-Leu   Gly
(2S, 4R)

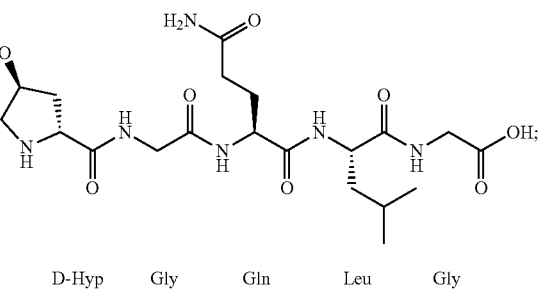
(SEQ ID NO: 75)

D-Hyp   Gly   Gln   Leu   Gly
(2R, 4S)

or a pharmaceutically acceptable salt thereof.

In certain embodiments, the compound is selected from the following:

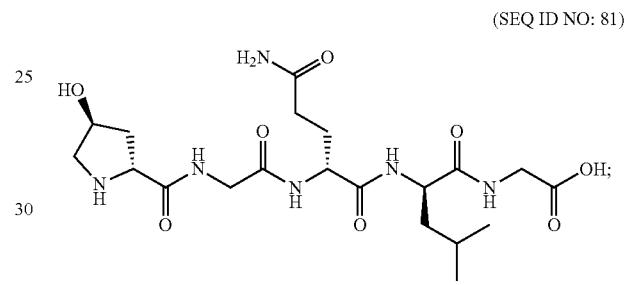
(SEQ ID NO: 81)

D-Hyp   Gly   D-Gln   D-Leu   Gly
(2R,4S)

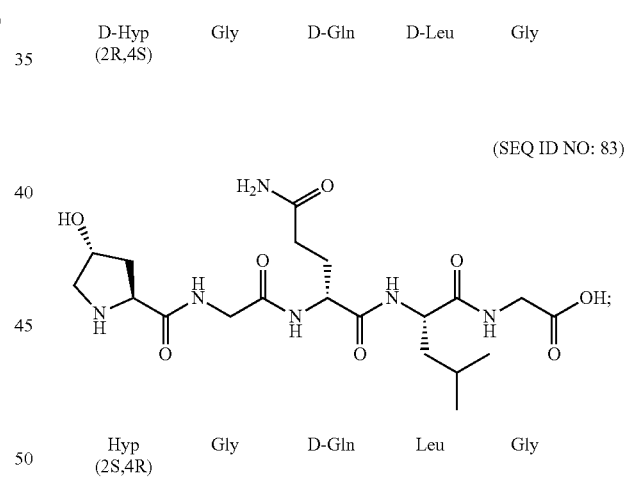
(SEQ ID NO: 83)

Hyp   Gly   D-Gln   Leu   Gly
(2S,4R)

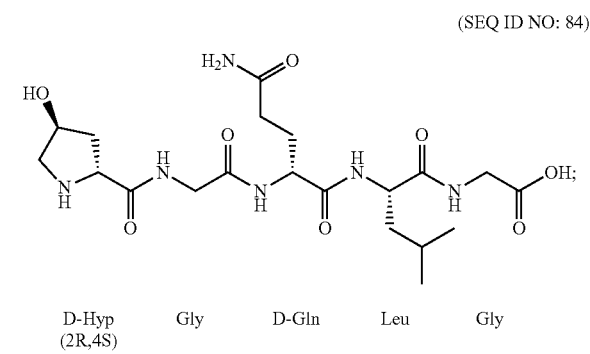
(SEQ ID NO: 84)

D-Hyp   Gly   D-Gln   Leu   Gly
(2R,4S)

-continued

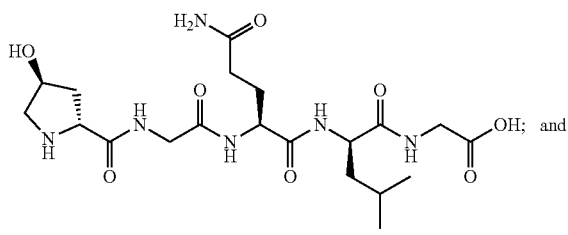

(SEQ ID NO: 85)

D-Hyp   Gly   Gln   D-Leu   Gly
(2R,4S)

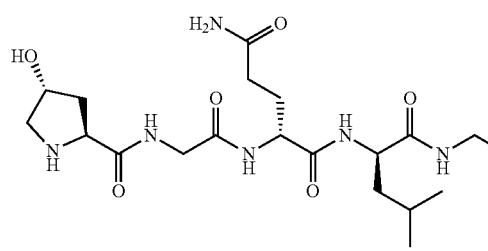

(SEQ ID NO: 86)

Hyp   Gly   D-Gln   D-Leu   Gly
(2S,4R)

or a pharmaceutically acceptable salt thereof.

In certain embodiments, the invention provides a compound represented by Formula (VI):

(VI)

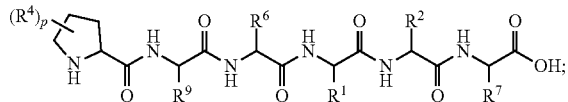

or a pharmaceutically acceptable salt thereof; wherein:

$R^1$ and $R^2$ are each independently H or substituted or unsubstituted alkyl, alkoxy, haloalkyl, alkenyl, alkynyl, aryl, arylalkyl, arylalkenyl, arylalkynyl, heteroalkyl, cycloalkyl, heterocycloalkyl, heteroaryl, or heteroarylalkyl;

$R^4$, independently for each occurrence, is selected from substituted or unsubstituted alkyl, aryl, arylalkyl, heterocycloalkyl, oxo, —$OR^b$, —$CH_2OR^b$, halo, hydroxyl, and hydroxyalkyl;

$R^b$ is substituted or unsubstituted alkyl, aryl, arylalkyl, or heterocycloalkyl;

p is 0, 1, or 2;

$R^6$ is hydrogen or substituted or unsubstituted alkyl;

$R^7$ is hydrogen or alkyl; and $R^9$ is hydrogen or alkyl.

In certain embodiments:

$R^1$ and $R^2$ are each independently H or substituted or unsubstituted alkyl;

$R^4$ for each occurrence is hydroxyl;

p is 1;

$R^6$ is alkyl optionally substituted with one occurrence of —C(=O)$NH_2$; and $R^9$ is hydrogen.

In certain embodiments, $R^1$ is substituted or unsubstituted alkyl, such as

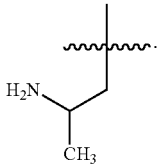

In certain embodiments, the compound has the structure of formula (VI-1L)

(VI-1L)

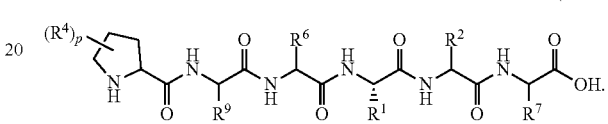

Alternatively, the compound may have the structure of formula (VI-1D)

(VI-1D)

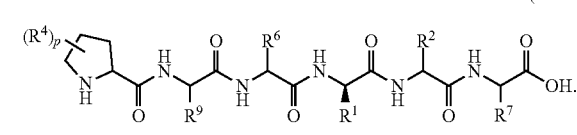

In certain embodiments, $R^2$ is H.

In certain embodiments, p is 1 and $R^4$ is hydroxyl.

In certain embodiments, the compound has the structure of formula (VI-4La):

(VI-4La)

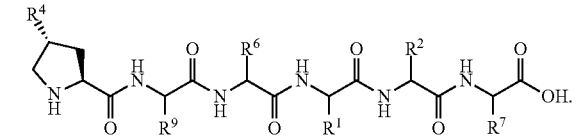

In certain embodiments, the compound has the structure of formula (VI-4Lb):

(VI-4Lb)

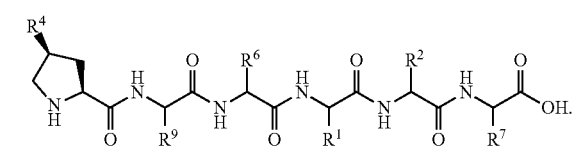

In certain embodiments, the compound has the structure of formula (VI-4 Da):

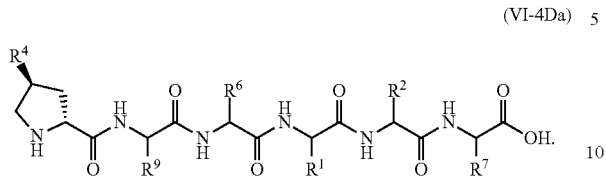
(VI-4Da)

In certain embodiments, the compound has the structure of formula (VI-4Db):

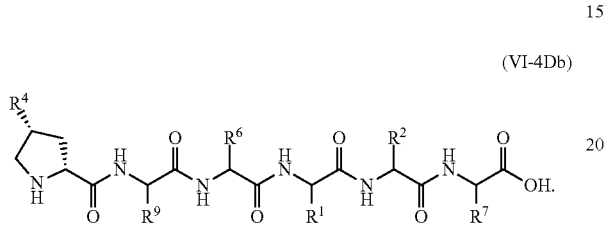
(VI-4Db)

In certain embodiments, $R^6$ is alkyl substituted with one occurrence of —C(=O)NH$_2$, such as

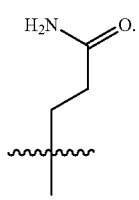 [SMILES: *CCC(N)=O]

In certain embodiments, the compound has the structure of formula (VI-6L):

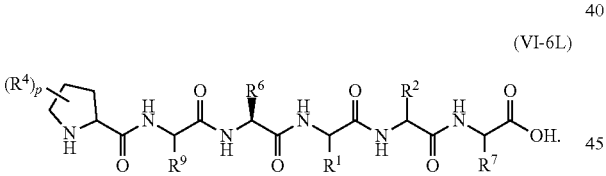
(VI-6L)

Alternatively, the compound may have the structure of formula (VI-6D):

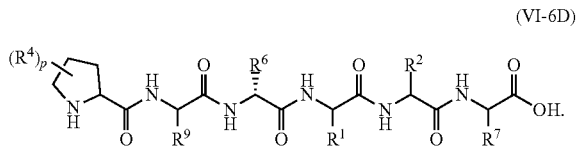
(VI-6D)

In certain embodiments, $R^9$ is —H.

In certain embodiments, $R^7$ is $(C_1$-$C_{10})$alkyl, such as

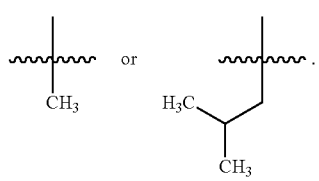

In certain embodiments, the compound has the structure of formula (VI-7L):

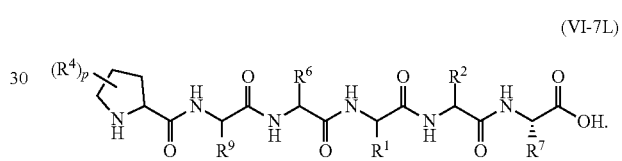
(VI-7L)

Alternatively, the compound may have the structure of formula (VI-7D):

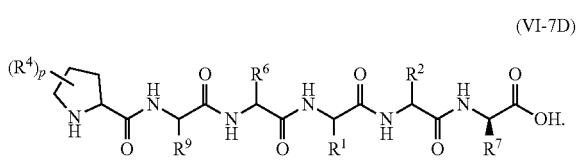
(VI-7D)

In certain embodiments, the compound is selected from the following:

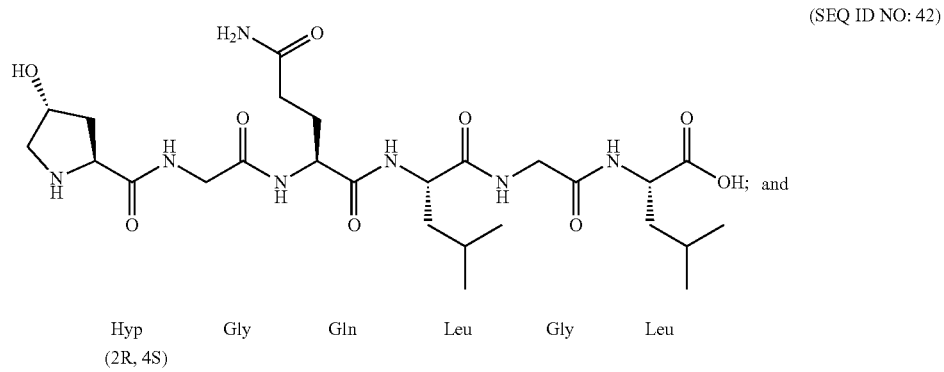
(SEQ ID NO: 42)

Hyp   Gly   Gln   Leu   Gly   Leu
(2R, 4S)

(SEQ ID NO: 64)

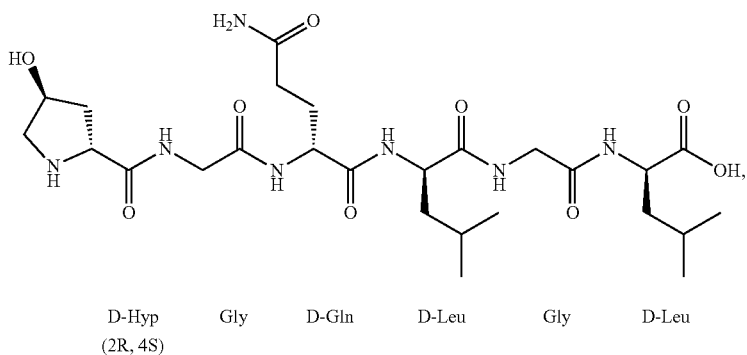

D-Hyp (2R, 4S)    Gly    D-Gln    D-Leu    Gly    D-Leu or a pharmaceutically acceptable salt thereof.

In certain embodiments, the invention provides a compound represented by Formula (VII):

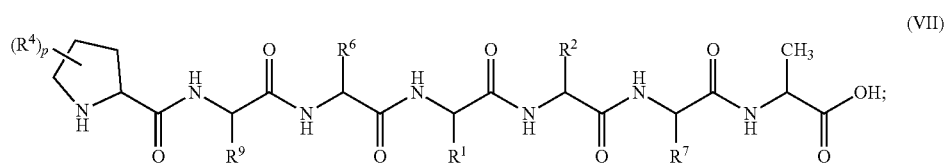

(VII)

or a pharmaceutically acceptable salt thereof; wherein:

$R^1$ and $R^2$ are each independently H or substituted or unsubstituted alkyl, alkoxy, haloalkyl, alkenyl, alkynyl, aryl, arylalkyl, arylalkenyl, arylalkynyl, heteroalkyl, cycloalkyl, heterocycloalkyl, heteroaryl, or heteroarylalkyl;

$R^4$, independently for each occurrence, is selected from substituted or unsubstituted alkyl, aryl, arylalkyl, heterocycloalkyl, oxo, —$OR^b$, —$CH_2OR^b$, halo, hydroxyl, and hydroxyalkyl;

$R^b$ is substituted or unsubstituted alkyl, aryl, arylalkyl, or heterocycloalkyl;

p is 0, 1, or 2;

$R^6$ is hydrogen or substituted or unsubstituted alkyl;

$R^7$ is hydrogen or alkyl; and $R^9$ is hydrogen or alkyl.

In certain embodiments:

$R^1$ and $R^2$ are each independently H or substituted or unsubstituted alkyl;

$R^4$ for each occurrence is hydroxyl;

p is 1;

$R^6$ is alkyl optionally substituted with one occurrence of —C(=O)$NH_2$; and $R^9$ is hydrogen.

In certain embodiments, $R^1$ is substituted or unsubstituted alkyl, such as

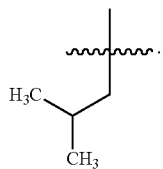 [SMILES: *CC(C)C]

In certain embodiments, the compound has the structure of formula (VII-1L)

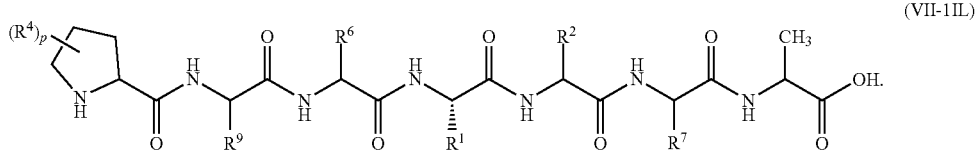

(VII-1L)

Alternatively, the compound may have the structure of formula (VII-1D)

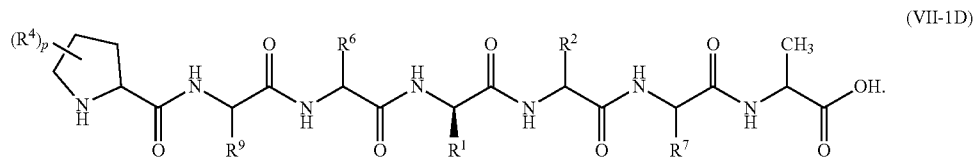

In certain embodiments, R² is H.
In certain embodiments, p is 1 and R⁴ is hydroxyl.
In certain embodiments, the compound has the structure of formula (VII-4La):

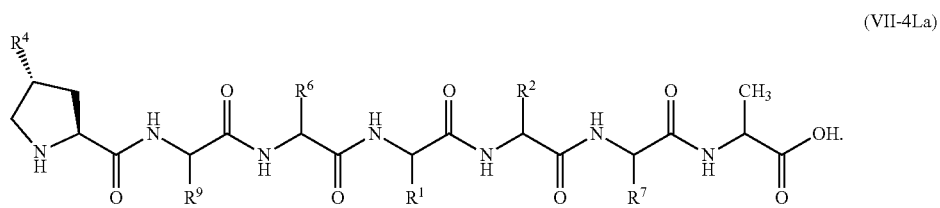

In certain embodiments, the compound has the structure of formula (VII-4Lb):

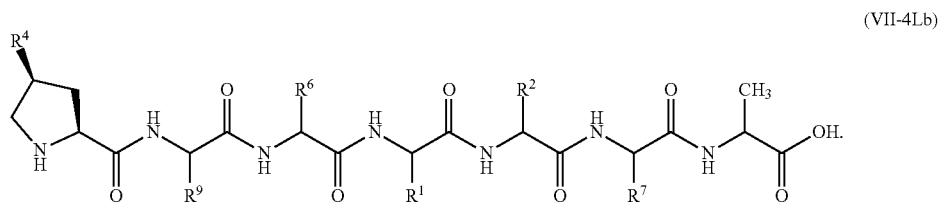

In certain embodiments, the compound has the structure of formula (VII-4 Da):

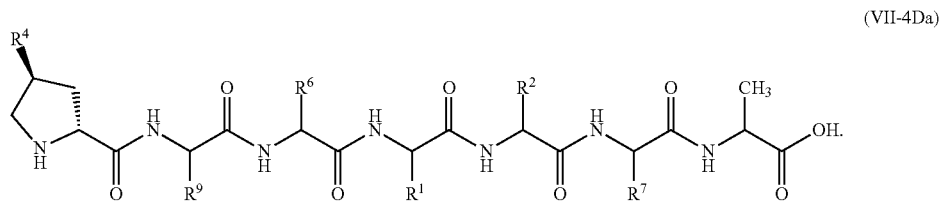

In certain embodiments, the compound has the structure of formula (VII-4Db):

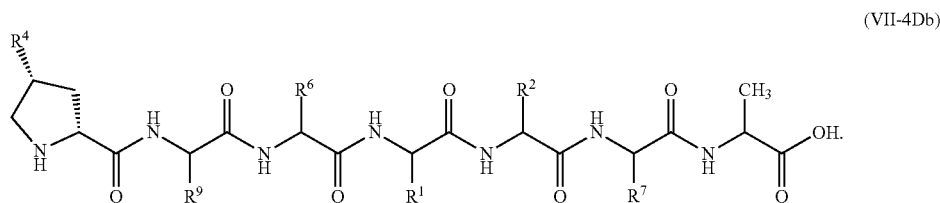

In certain embodiments, $R^6$ is alkyl substituted with one occurrence of —C(=O)NH$_2$, such as

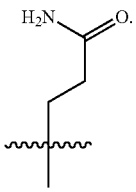 [SMILES: *CCC(N)=O]

In certain embodiments, the compound has the structure of formula (VII-6L):

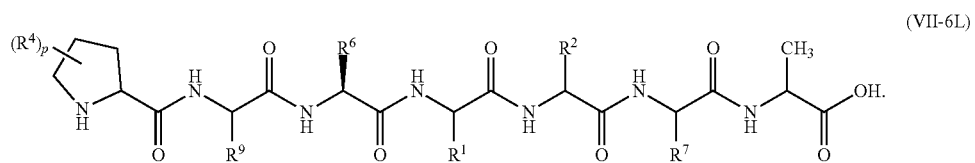

(VII-6L)

Alternatively, the compound may have the structure of formula (VII-6D):

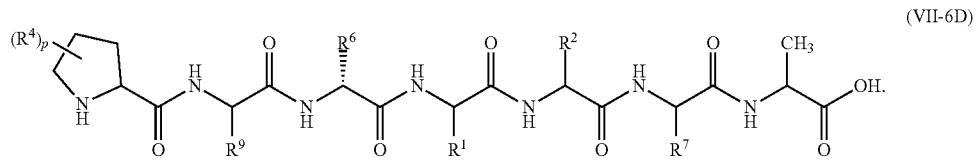

(VII-6D)

In certain embodiments, $R^9$ is —H.
In certain embodiments, $R^7$ is (C$_1$-C$_{10}$)alkyl, such as

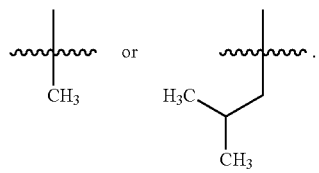

In certain embodiments, the compound has the structure of formula (VII-7L):

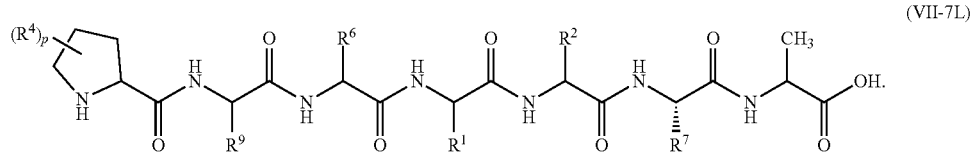

(VII-7L)

Alternatively, the compound may have the structure of formula (VII-7D):

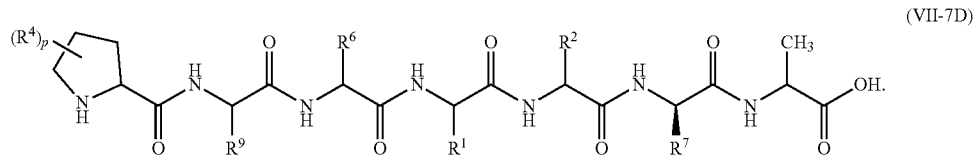

(VII-7D)

In certain embodiments, the compound has the structure of formula (VII-10L):

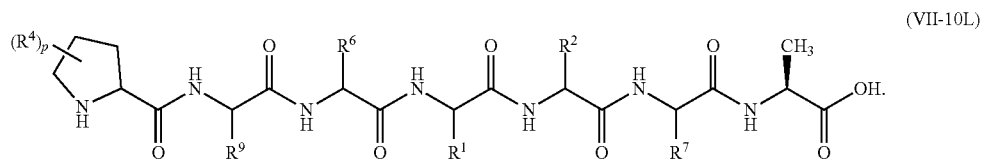

(VII-10L)

Alternatively, the compound may have the structure of formula VII-10D):

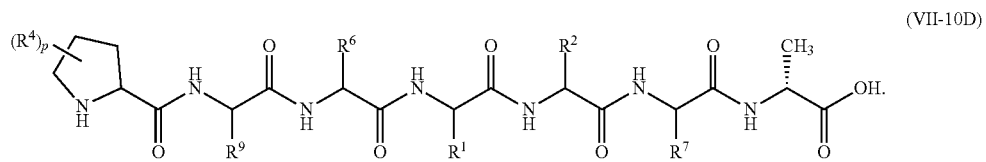

(VII-10D)

In certain embodiments, the compound is:

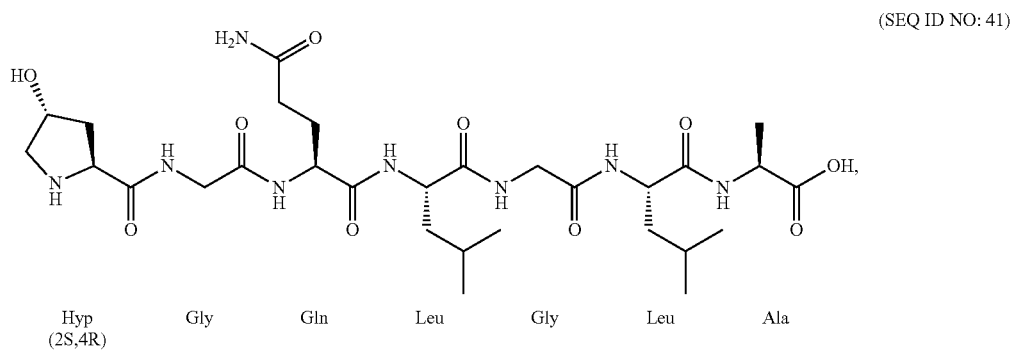 [SMILES: CC(C)C[C@H](NC(=O)CNC(=O)[C@H](CC(C)C)NC(=O)[C@H](CCC(N)=O)NC(=O)CNC(=O)[C@@H]1C[C@@H](O)CN1)C(=O)N[C@@H](C)C(=O)O]

(SEQ ID NO: 41)

or a pharmaceutically acceptable salt thereof.

In certain embodiments, the invention provides a peptide having any one amino acid sequence selected from:

```
                                        (SEQ ID NO: 47)
Ala-Gly-Gln-Leu-Gly-Leu-Ala-Gly-Pro-Lys;

(SEQ ID NO: 117)
Hyp-Gly-Gln-Leu-Gly-Leu-Ala-Gly-Ala-Lys;

(SEQ ID NO: 118)
Hyp-Gly-Gln-Leu-Gly-Leu-Ala;
```

-continued
```
                                       (SEQ ID NO: 119)
HyP-Gly-Gln-Glu-Gly-Leu-Gly;

(SEQ ID NO: 120)
HyP-Gly-Gln-Leu-Gly-Leu;

(SEQ ID NO: 64)
D-HyP(2R, 4S)-Gly-D-Gln-D-Leu-Gly-D-Leu;

(SEQ ID NO: 121)
HyP-Gly-Gln-Leu-Gly,
```

(SEQ ID NO: 122)
HyP-Gly-Gln-<sub>D</sub>-Leu-Gly;
and (SEQ ID NO: 75)
<sub>D</sub>-HyP(2R, 4S)-Gly-Gln-Leu-Gly;

or a pharmaceutically acceptable salt thereof.

The present invention also provides a compound represented by Formula (IX):

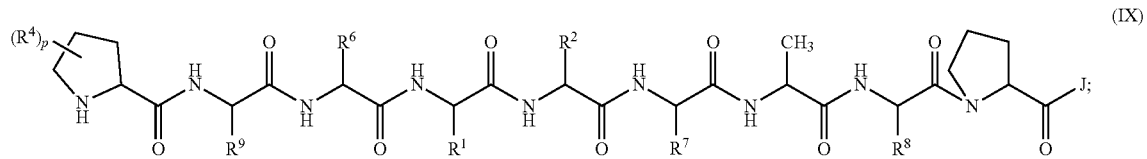

(IX)

or a pharmaceutically acceptable salt thereof;
wherein:
$R^1$ and $R^2$ are each independently H or substituted or unsubstituted alkyl, alkoxy, haloalkyl, alkenyl, alkynyl, aryl, arylalkyl, arylalkenyl, arylalkynyl, heteroalkyl, cycloalkyl, heterocyclyl, or heterocyclylalkyl;

$R^4$, independently for each occurrence, is selected from substituted or unsubstituted alkyl, aryl, arylalkyl, heterocyclyl, oxo, —$OR^b$, —$CH_2OR^b$, halo, hydroxyl, and hydroxyalkyl;

$R^b$ is substituted or unsubstituted alkyl, aryl, arylalkyl, or heterocyclyl;

p is 0, 1, or 2;

$R^6$ is hydrogen or substituted or unsubstituted alkyl;

$R^7$, $R^8$, and $R^9$ are each independently hydrogen or alkyl;

J is OH or —$NR^xR^y$; and $R^x$ and $R^y$ are each independently selected from H, optionally substituted alkyl, optionally substituted alkoxylalkyl, or $R^x$ and $R^y$ taken together with the intervening nitrogen atom form a ring.

Exemplary compounds of Formula (IX) include YDE-100 through YDE-107.

In certain embodiments of the compounds of formula (IX):
$R^1$ and $R^2$ are each independently H or substituted or unsubstituted alkyl;
$R^4$ for each occurrence is hydroxyl;
p is 1;
$R^6$ is alkyl optionally substituted with one occurrence of —C(=O)$NH_2$; and
$R^9$ is hydrogen.

In certain embodiments of the compounds of formula (IX), $R^1$ is substituted or unsubstituted alkyl, for example

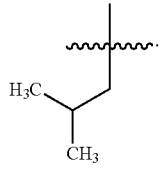

In certain embodiments, the compound has the structure of formula (IX-IL):

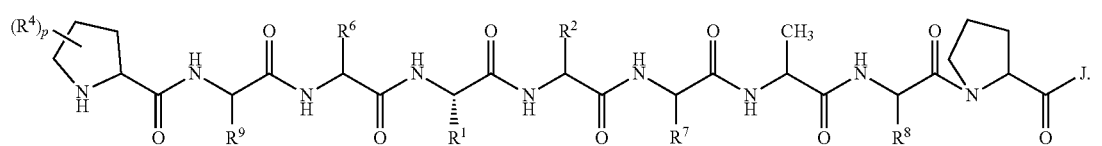

(IX-1L)

Alternatively, in certain embodiments, the compound has the structure of formula (IX-1D):

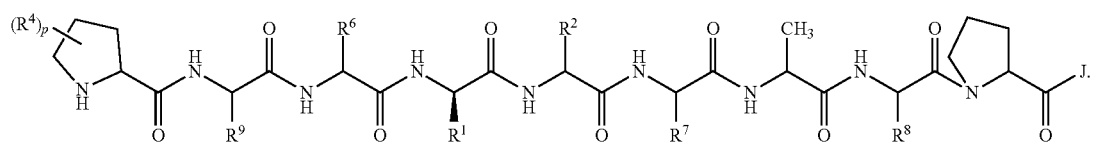

(IX-1D)

In certain embodiments, $R^2$ is H.

In certain embodiments, p is 1 and $R^4$ is hydroxyl. In certain embodiments, the compound has the structure of formula (IX-4La):
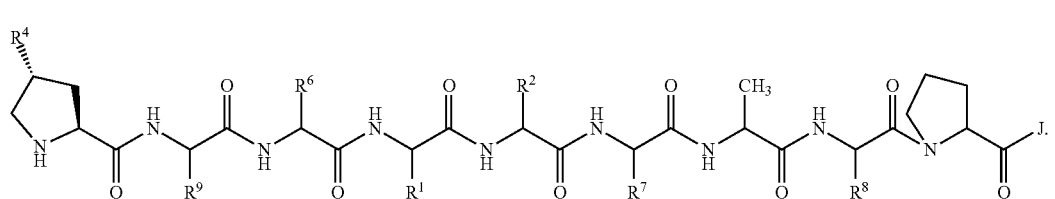
(IX-4La)
In certain embodiments, the compound has the structure of formula (IX-4Lb):
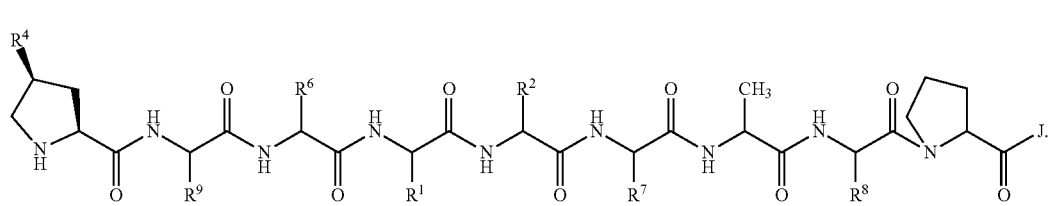
(IX-4Lb)
In certain embodiments, the compound has the structure of formula (IX-4 Da):
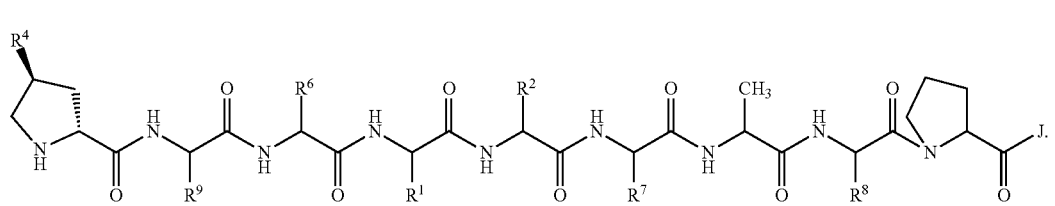
(IX-4Da)
In certain embodiments, the compound has the structure of formula (IX-4Db):
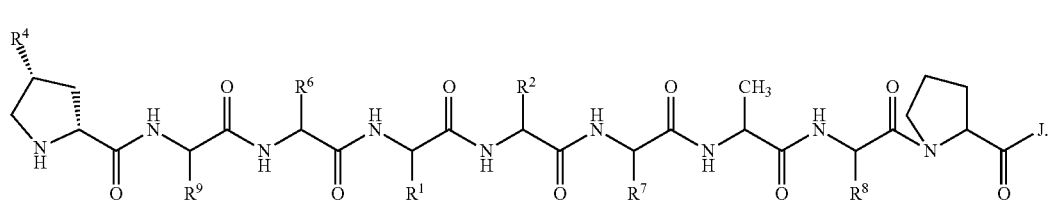
(IX-4Db)

In certain embodiments, $R^6$ is alkyl substituted with one occurrence of —C(=O)NH$_2$, for example, $R^6$ may be

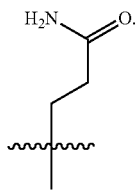 [SMILES: *CCC(N)=O]

In certain embodiments, the compound has the structure of formula (IX-6L):

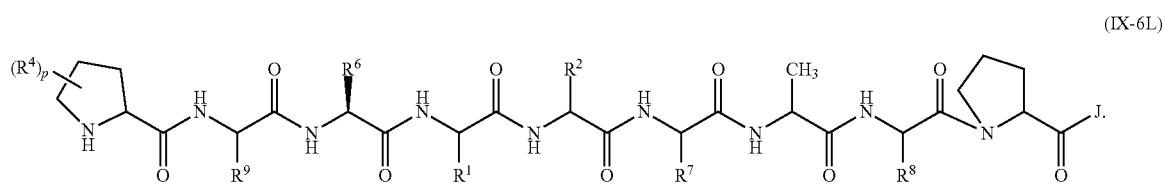

(IX-6L)

In certain embodiments, the compound has the structure of formula (IX-6D):

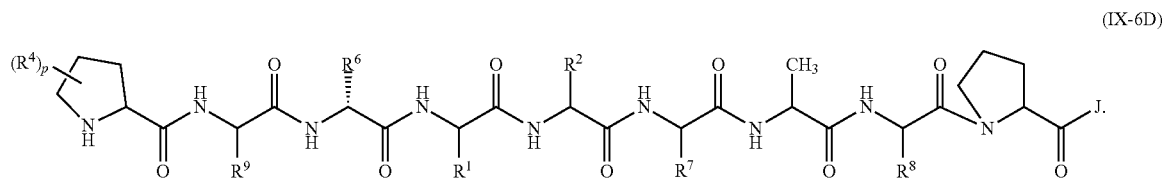

(IX-6D)

In certain embodiments, $R^9$ is —H.
In certain embodiments, $R^7$ is $(C_1-C_{10})$alkyl. For example, $R^7$ may be

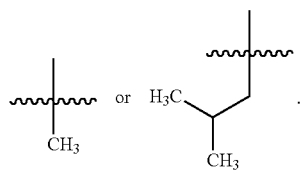

In certain embodiments, the compound has the structure of formula (IX-7L):

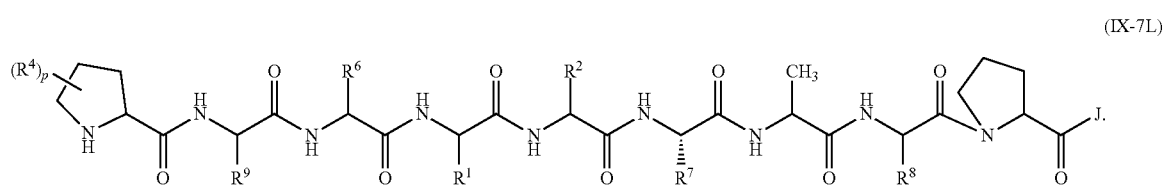

(IX-7L)

In certain embodiments, the compound has the structure of formula (IX-7D):

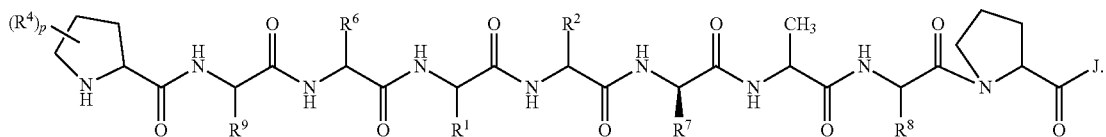
(IX-7D)

In certain embodiments, the compound has the structure of formula (IX-10L):

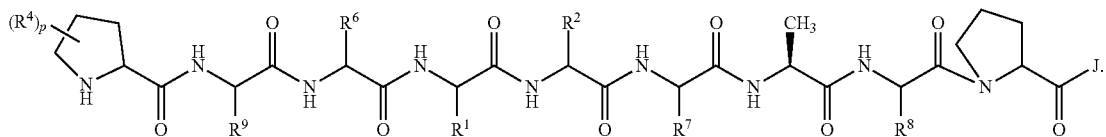
(IX-10L)

In certain embodiments, the compound has the structure of formula (IX-10D):

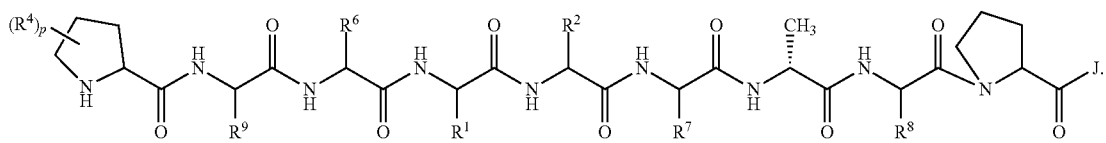

In certain embodiments, the compound has the structure of formula (IX-11L):

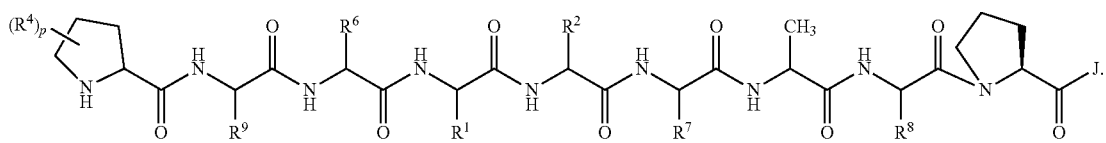
(IX-11L)

In certain embodiments, the compound has the structure of formula (IX-11D):

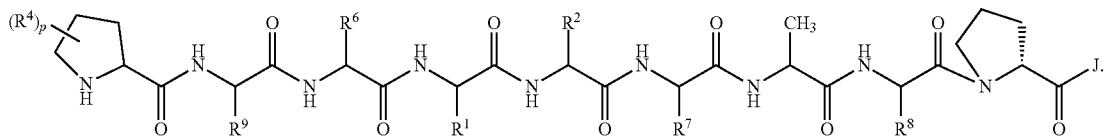
(IX-11D)

In certain embodiments, $R^8$ is —CH$_3$ or —H, preferably —H.

In certain embodiments, J is OH. Alternatively, in other embodiments, J is-NR$^x$R$^y$. In certain such embodiments, $R^x$ and $R^y$ are each independently alkyl. Alternatively, $R^x$ and $R^y$ may be taken together with the intervening nitrogen atom form a ring.

In other embodiments, the present invention also provides a compound compound represented by Formula (X-am):

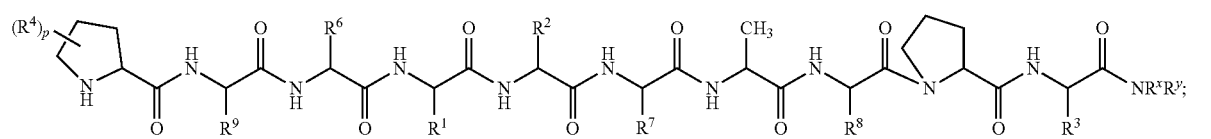

(X-am)

or a pharmaceutically acceptable salt thereof;
wherein:

$R^1$, $R^2$, and $R^3$ are each independently H or substituted or unsubstituted alkyl, alkoxy, haloalkyl, alkenyl, alkynyl, aryl, arylalkyl, arylalkenyl, arylalkynyl, heteroalkyl, cycloalkyl, heterocyclyl, or heterocyclylalkyl;

$R^4$, independently for each occurrence, is selected from substituted or unsubstituted alkyl, aryl, arylalkyl, heterocyclyl, oxo, —OR$^b$, —CH$_2$OR$^b$, halo, hydroxyl, and hydroxyalkyl;

$R^b$ is substituted or unsubstituted alkyl, aryl, arylalkyl, or heterocyclyl;

p is 0, 1, or 2;

$R^6$ is hydrogen or substituted or unsubstituted alkyl;

$R^7$, $R^8$, and $R^9$ are each independently hydrogen or alkyl;

J is OH or —NR$^x$R$^y$; and $R^x$ and $R^y$ are each independently selected from H, optionally substituted alkyl, optionally substituted alkoxylalkyl, or $R^x$ and $R^y$ taken together with the intervening nitrogen atom form a ring.

Exemplary compounds of Formula (X-am) include YDE-93 and YDE-96.

In certain embodiments of the compound of Formula (X-am):

$R^1$, $R^2$, and $R^3$ are each independently H or substituted or unsubstituted alkyl, arylalkyl, or heterocyclylalkyl;

$R^4$, independently for each occurrence, is selected from substituted or unsubstituted alkyl, oxo, hydroxyl, —OR$^b$, hydroxyalkyl, —CH$_2$OR$^b$, and halo;

$R^b$ is substituted or unsubstituted alkyl, aryl, arylalkyl, or heterocyclyl;

$R^6$ is hydrogen or substituted or unsubstituted alkyl; and $R^7$, $R^8$, and $R^9$ are each independently hydrogen or alkyl.

In certain embodiments, where indicated, alkyl, alkoxy, haloalkyl, alkenyl, alkynyl, aryl, arylalkyl, arylalkenyl, arylalkynyl, heteroalkyl, cycloalkyl, heterocyclyl, or heterocyclylalkyl is unsubstituted or is substituted with one or more substituents selected from halo, haloalkyl, oxo, —CN, —NO$_2$, =N—OH, —N$_3$, —R$^a$, —OR$^a$, —SR$^a$, —N(R$^a$)$_2$, —N(R$^a$)$_3$+, =NR$^a$, —NHC(=O)R$^c$, —C(=O)R$^c$, —C(=O)N(R$^a$)$_2$, —S(=O)$_2$R$^c$, —OS(=O)$_2$OR$^a$, —S(=O)$_2$OR$^a$, —S(=O)$_2$N(R$^a$)$_2$, —S(=O)R$^c$, —OP(=O)(OR$^a$)$_2$, -(alkylene)-C(=O)R$^c$, —C(=S)R$^c$, —C(=O)OR$^a$, -(alkylene)-C(=O)OR$^a$, —C(=S)OR$^a$, —C(=O)SR$^a$, —C(=S)SR$^a$, -(alkylene)-C(=O)N(R$^a$)$_2$, —C(=S)N(R$^a$)$_2$, and —C(—NR$^a$)N(R$^a$)$_2$; and $R^a$, independently for each occurrence, is hydrogen, or substituted or unsubstituted alkyl, aryl, arylalkyl, heterocyclyl, heterocyclylalkyl, cycloalkyl, or (cycloalkyl)alkyl; and $R^c$, independently for each occurrence, is substituted or unsubstituted alkyl, aryl, arylalkyl, heterocyclyl, heterocyclylalkyl, cycloalkyl, or (cycloalkyl)alkyl.

In further embodiments, where indicated, alkyl, alkoxy, haloalkyl, alkenyl, alkynyl, aryl, arylalkyl, arylalkenyl, arylalkynyl, heteroalkyl, cycloalkyl, heterocyclyl, or heterocyclylalkyl is unsubstituted or is substituted with one or more substituents selected from halo, haloalkyl, oxo, —R$^a$, —OR$^a$, —N(R$^a$)$_2$, —N(R$^a$)$_3$+, —NHC(=O)R$^c$, —C(=O)R$^c$, —C(=O)N(R$^a$)$_2$, —C(=O)OR$^a$, -(alkylene)-C(=O)OR$^a$, and -(alkylene)-C(=O)N(R$^a$)$_2$; and $R^a$, independently for each occurrence, is hydrogen, or substituted or unsubstituted alkyl, aryl, arylalkyl, heterocyclyl, heterocyclylalkyl, cycloalkyl, or (cycloalkyl)alkyl; and $R^c$, independently for each occurrence, is substituted or unsubstituted alkyl, aryl, arylalkyl, heterocyclyl, heterocyclylalkyl, cycloalkyl, or (cycloalkyl)alkyl.

In still further embodiments, $R^a$, independently for each occurrence, is hydrogen, alkyl, aryl, arylalkyl, heterocyclyl, or heterocyclylalkyl; and $R^c$, independently for each occurrence, is alkyl, aryl, arylalkyl, heterocyclyl, or heterocyclylalkyl.

In certain embodiments, the compound has the structure of formula (X-am-10L):

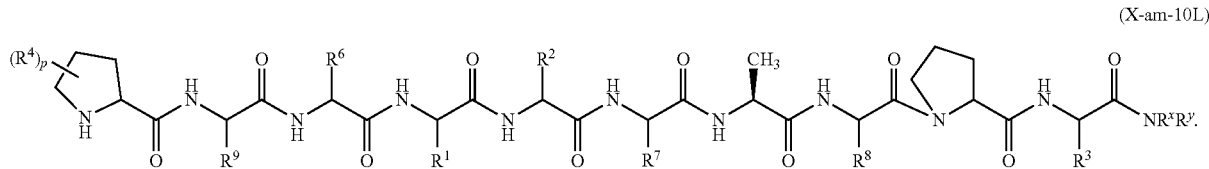

(X-am-10L)

In certain embodiments, the compound has the structure of formula (X-am-10D):

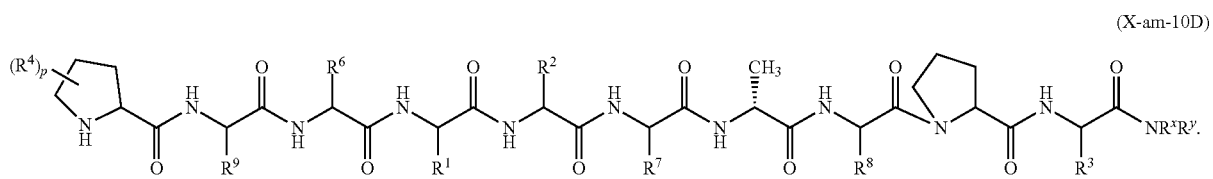

(X-am-10D)

In certain embodiments, $R^1$ is substituted or unsubstituted $(C_2-C_{10})$haloalkyl. Alternatively, $R^1$ may be substituted or unsubstituted alkyl, arylalkyl, or heterocyclylalkyl.

In still further embodiments, $R^1$ is selected from substituted or unsubstituted alkyl,

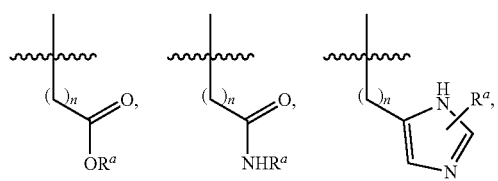

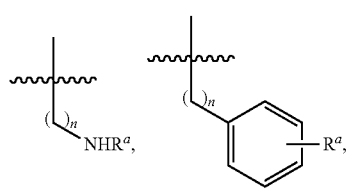

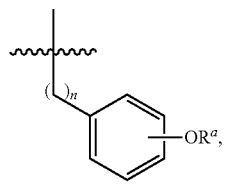

-continued

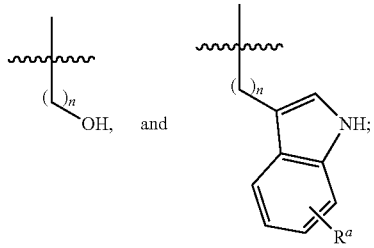

$R^a$ is hydrogen or alkyl; and
n is an integer from 1 to 10, preferably 1-5, more preferably 1-3.

In still further embodiments, $R^1$ is selected from

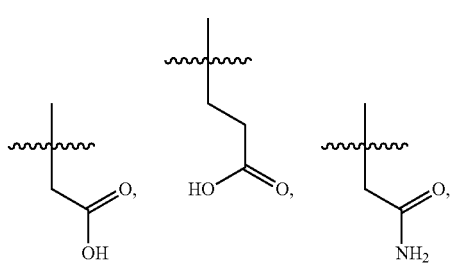

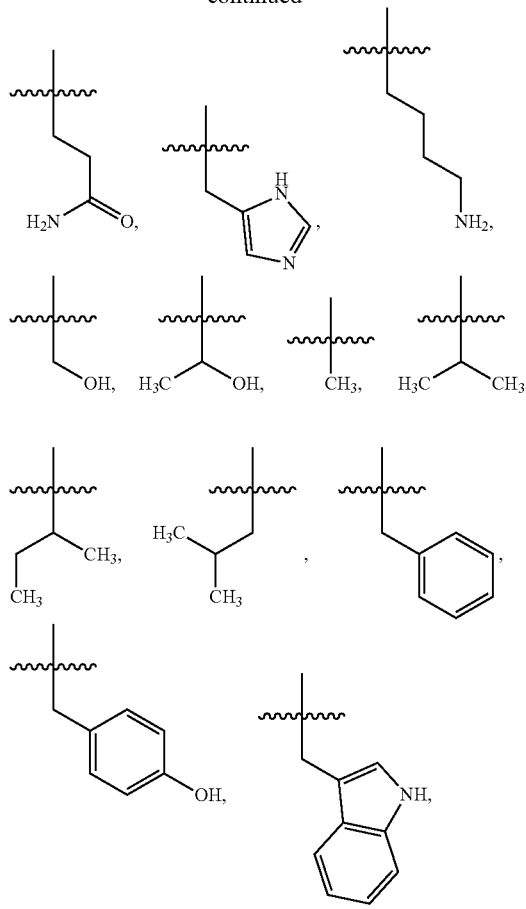
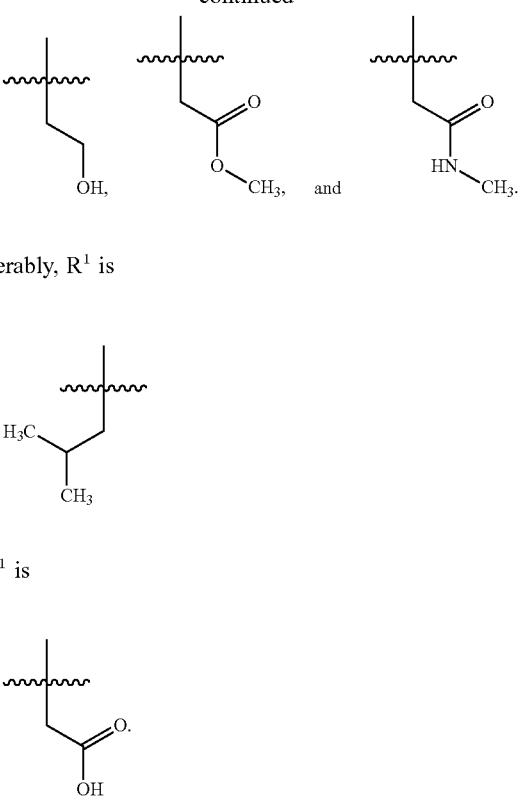
Preferably, $R^1$ is
or $R^1$ is
In certain embodiments, the compound has the structure of formula (X-am-1L):
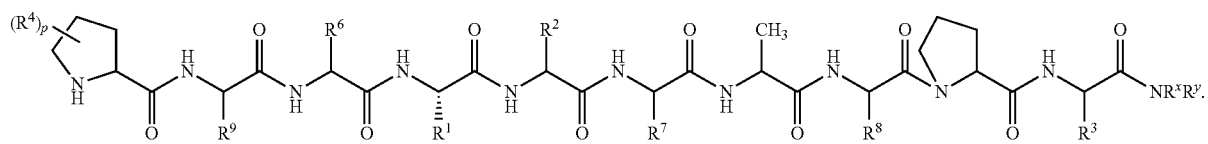
(X-am-1L)
In certain embodiments, the compound has the structure of formula (X-am-1D):
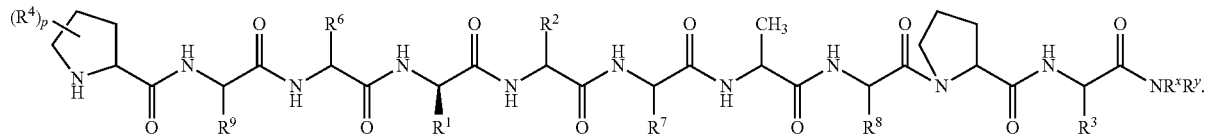
(X-am-1D)

In certain embodiments, R² is substituted or unsubstituted (C₂-C₁₀)haloalkyl. Alternatively, R² may be H or substituted or unsubstituted alkyl, arylalkyl, or heterocyclylalkyl.

In further embodiments, R² is selected from hydrogen, substituted or unsubstituted alkyl,

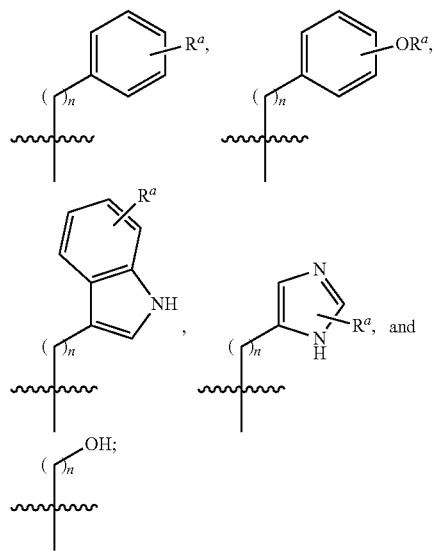

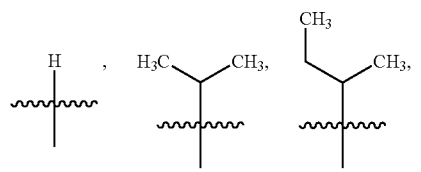

wherein $R^a$ is hydrogen or alkyl; and n is an integer from 1 to 10, preferably 1-5, more preferably 1-3.

In other embodiments, R² may be selected from

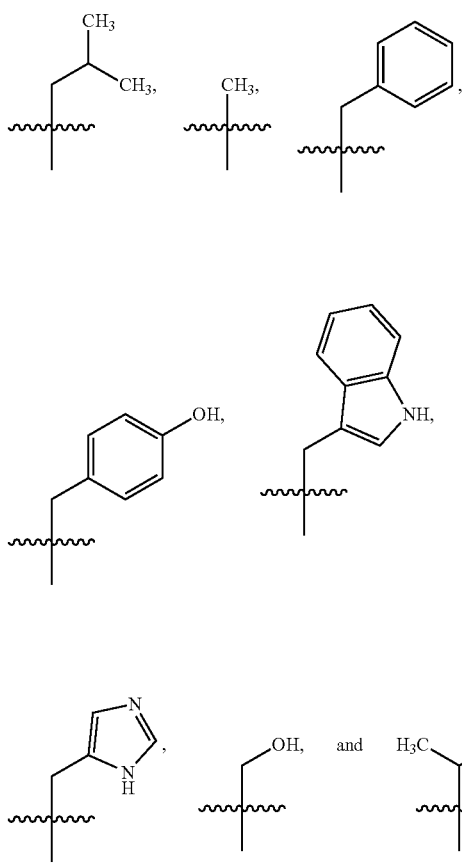

In some preferred embodiments, R² is hydrogen.

In certain embodiments, the compound has the structure of formula (X-am-2L):

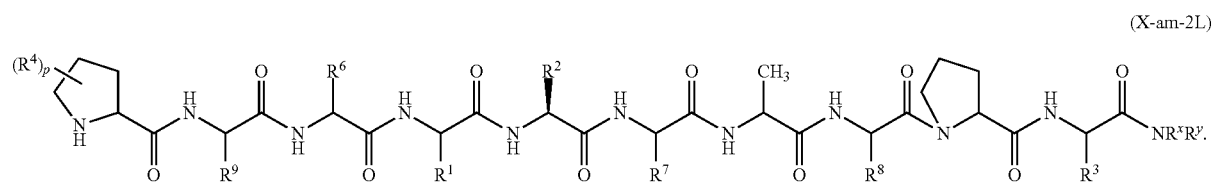

(X-am-2L)

In certain embodiments, the compound has the structure of formula (X-am-2D):

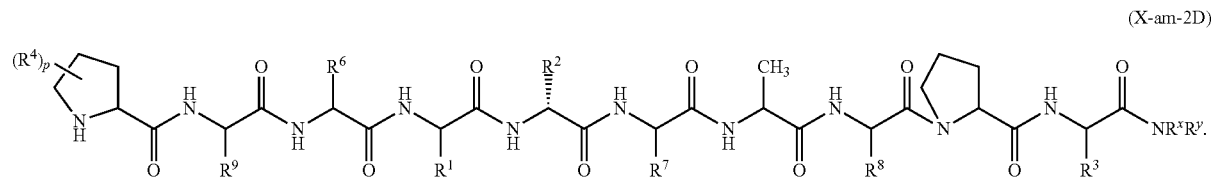

(X-am-2D)

In certain embodiments, $R^3$ is substituted or unsubstituted $(C_2-C_{10})$haloalkyl. Alternatively, $R^3$ may be substituted or unsubstituted alkyl or arylalkyl.

In certain embodiments, $R^3$ is selected from substituted or unsubstituted alkyl,

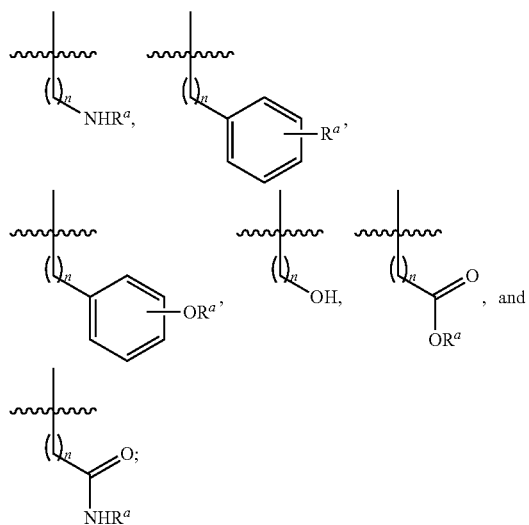

$R^a$ is hydrogen or alkyl; and n is an integer from 1 to 10, preferably 1-5, more preferably 1-3.

In further embodiments, $R^3$ is selected from

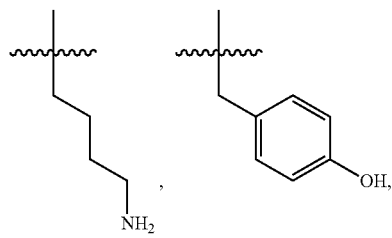

-continued

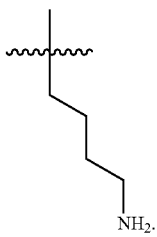

preferably $R^3$ is

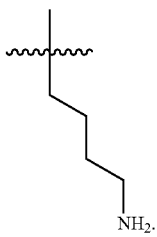

In certain embodiments, the compound has the structure of formula (X-am-3L):

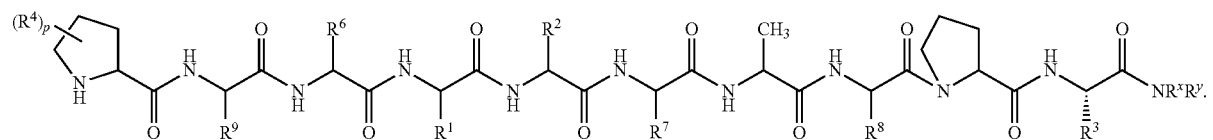
(X-am-3L)

In certain embodiments, the compound has the structure of formula (X-am-3D):

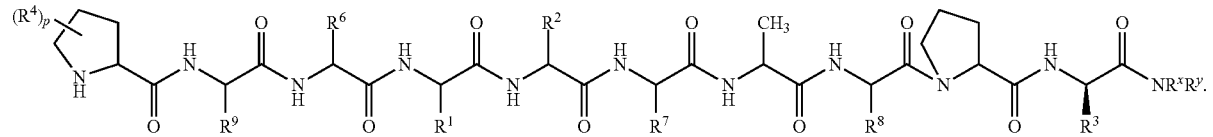
(X-am-3D)

In certain embodiments, p is 1 or 2; and $R^4$, independently for each occurrence, is selected from substituted or unsubstituted alkyl, $-OR^b$, $-CH_2OR^b$, halo, hydroxyl, and hydroxyalkyl.

In further embodiments, p is 1 or 2; and $R^4$, independently for each occurrence, is selected from $-CH_3$, halo, hydroxyl, and hydroxyalkyl. Preferably, $R^4$ is hydroxyl or $R^4$ is $-CH_3$.

In certain embodiments, p is 1.

In certain embodiments, the compound has the structure of formula (X-am-4Lg):

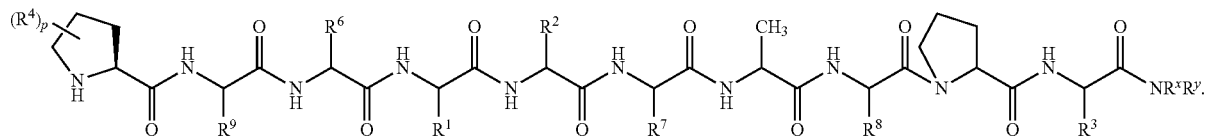

(X-am-4Lg)

In certain embodiments, the compound has the structure of formula (X-am-4La):

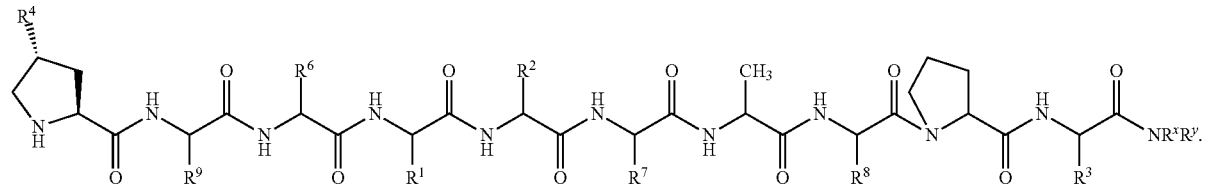

(X-am-4La)

In certain embodiments, the compound has the structure of formula (X-am-4Lb):

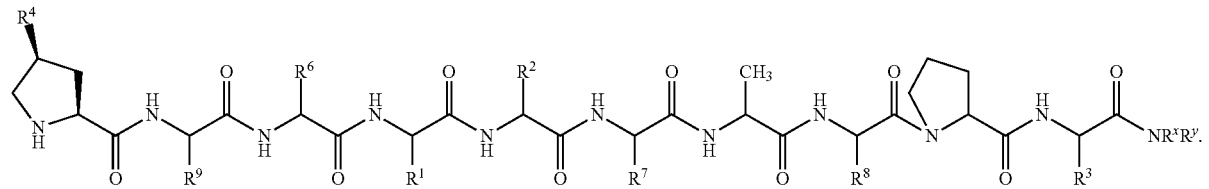

(X-am-4Lb)

In certain embodiments, the compound has the structure of formula (X-am-4Lc):
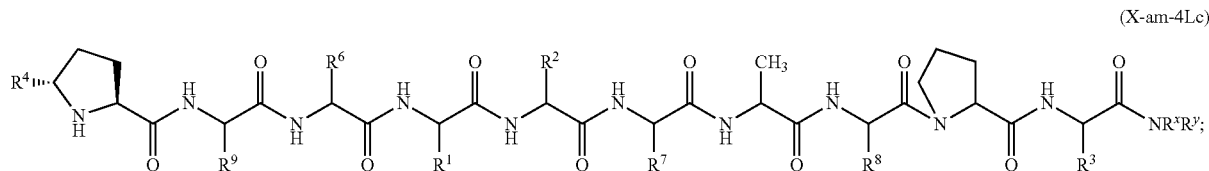
(X-am-4Lc)
provided that R⁴ is not hydroxyl.
In certain embodiments, the compound has the structure of formula (X-am-4Dg):
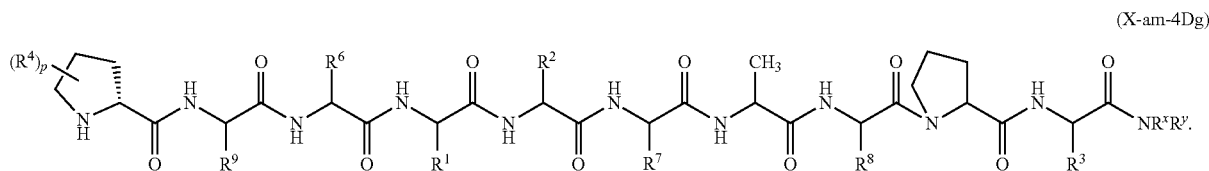
(X-am-4Dg)
In certain embodiments, the compound has the structure of formula (X-am-4 Da):
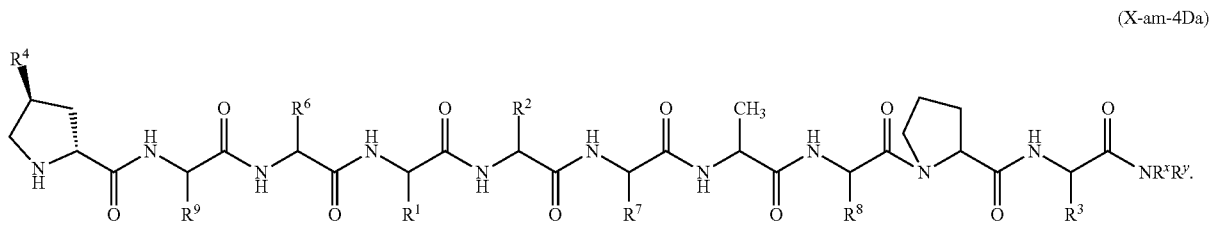
(X-am-4Da)
In certain embodiments, the compound has the structure of formula (X-am-4Db):
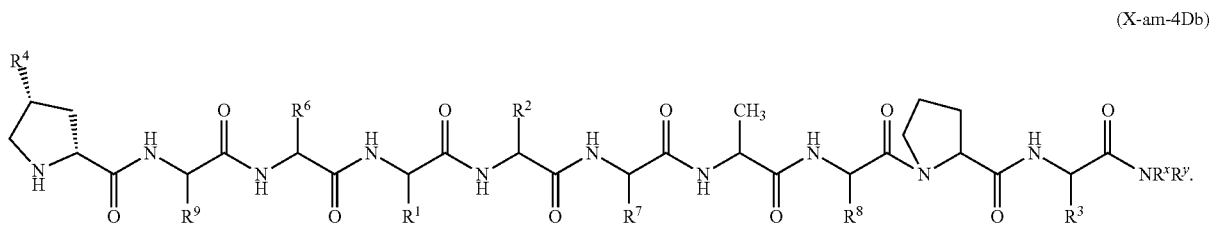
(X-am-4Db)

In certain embodiments, the compound has the structure of formula (X-am-4Dc):

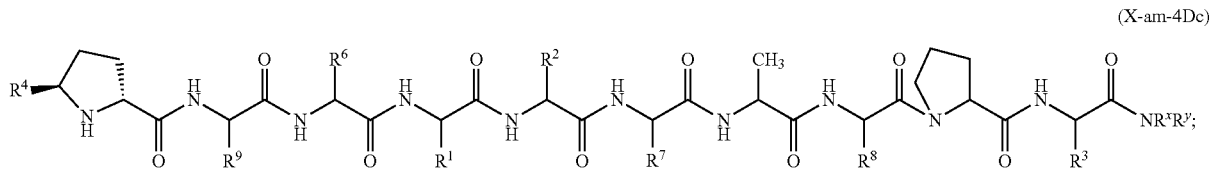
(X-am-4Dc)

provided that R⁴ is not hydroxyl.

In certain embodiments, R⁴ is oxo.

In certain embodiments, the compound has the structure of formula (X-am-4Ld):

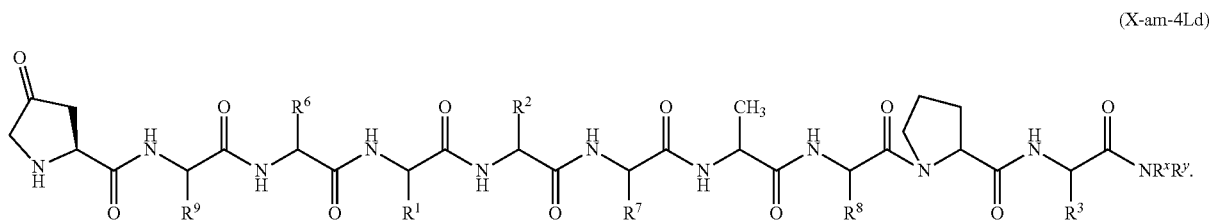
(X-am-4Ld)

In certain embodiments, the compound has the structure of formula (X-am-4Le):

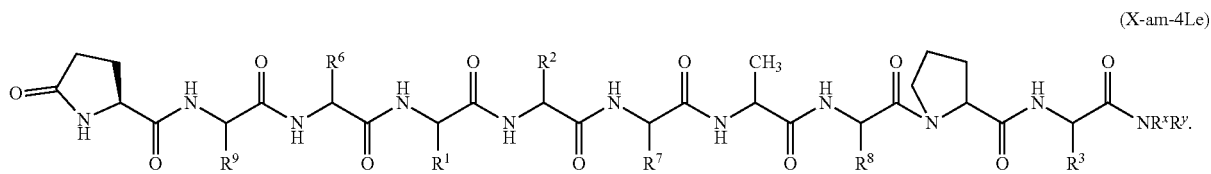
(X-am-4Le)

In certain embodiments, the compound has the structure of formula (X-am-4Dd):

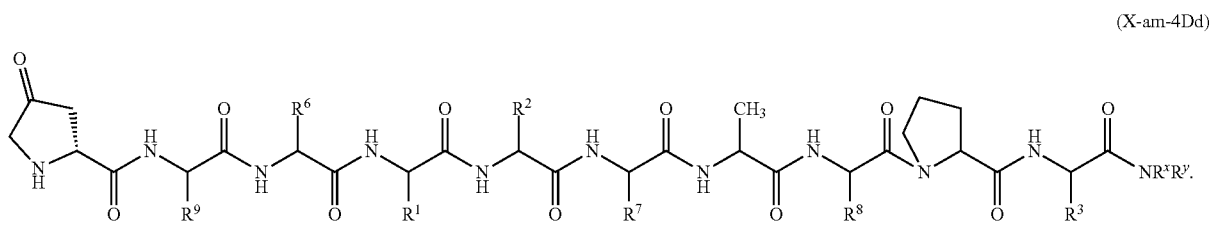
(X-am-4Dd)

In certain embodiments, the compound has the structure of formula (X-am-4De):

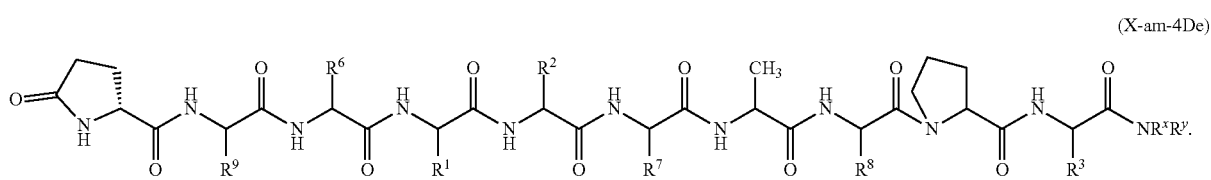
(X-am-4De)

In certain embodiments, R⁶ is hydrogen or alkyl, wherein the alkyl is optionally substituted with one occurrence of —C(=O)NH₂; preferably R⁶ is alkyl optionally substituted with one occurrence of —C(=O)NH₂. For example, R⁶ may be —CH₃ or R⁶ may be

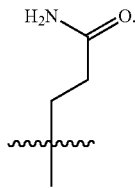 [SMILES: *CCC(N)=O]

In certain embodiments, the compound has the structure of formula (X-am-6L):

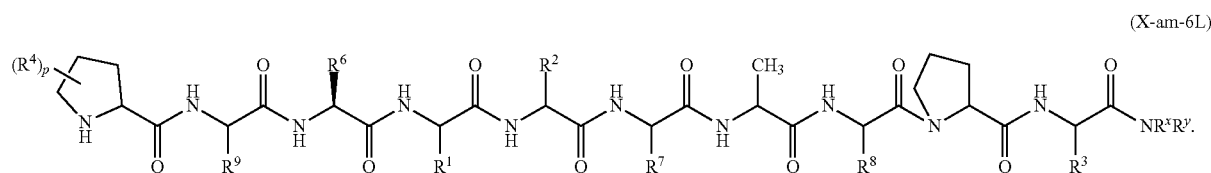

(X-am-6L)

In certain embodiments, the compound has the structure of formula (X-am-6D):

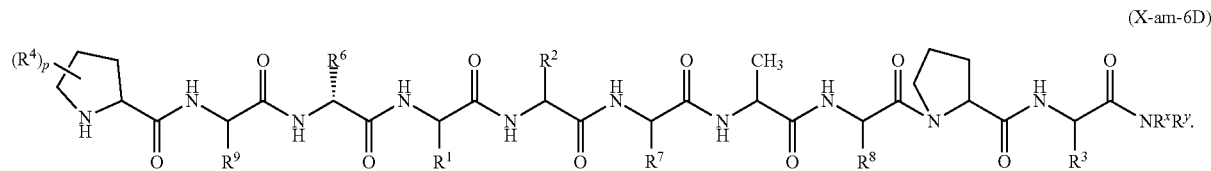

(X-am-6D)

In certain embodiments, R⁷ is (C₁-C₁₀)alkyl. For example, R⁷ may be

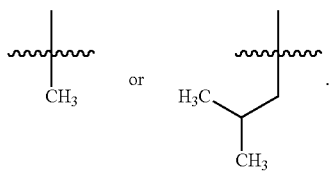

In certain embodiments, the compound has the structure of formula (X-am-7L):

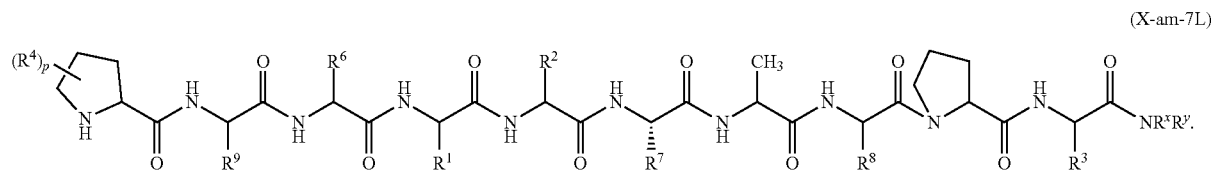

(X-am-7L)

In certain embodiments, the compound has the structure of formula (X-am-7D):

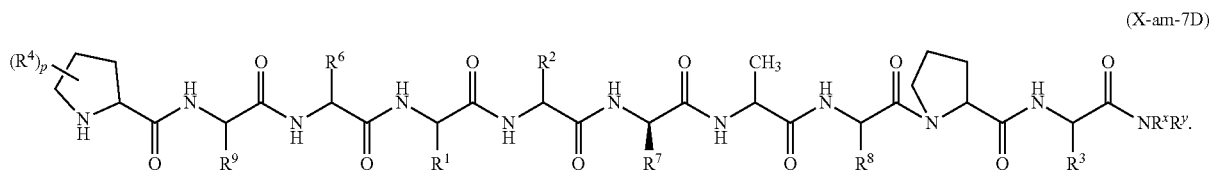
(X-am-7D)

In certain embodiments, the compound has the structure of formula (X-am-11L):

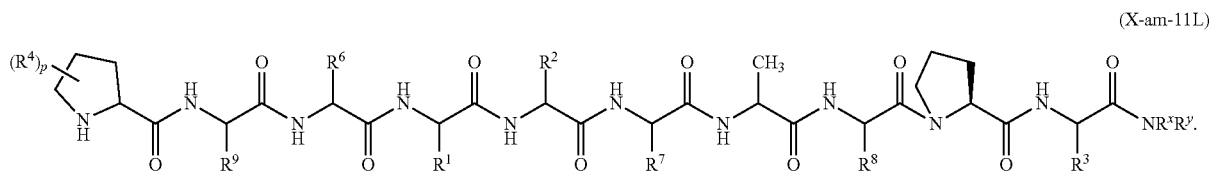
(X-am-11L)

In certain embodiments, the compound has the structure of formula (X-am-11D):

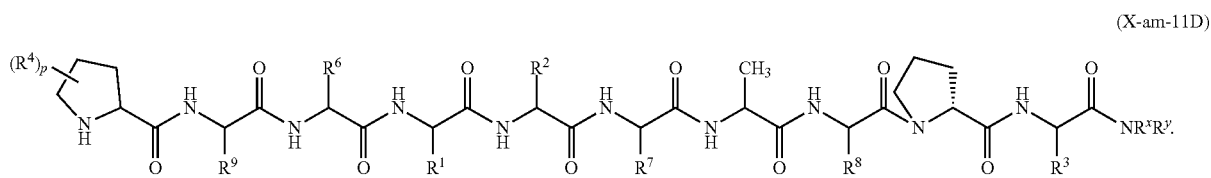
(X-am-11D)

In certain embodiments, $R^8$ is —$CH_3$ or —H, preferably —H.

In certain embodiments, $R^9$ is —$CH_3$ or —H, preferably —H.

In certain embodiments, $R^x$ and $R^y$ are each independently optionally substituted alkyl. In alternative embodiments, $R^x$ and $R^y$ are each independently optionally substituted alkoxylalkyl. In further alternative embodiments, $R^x$ and $R^y$ taken together with the intervening nitrogen atom form a ring.

The invention also provides a compound represented by Formula 8:

[Formula 8]

(SEQ ID NO: 102)

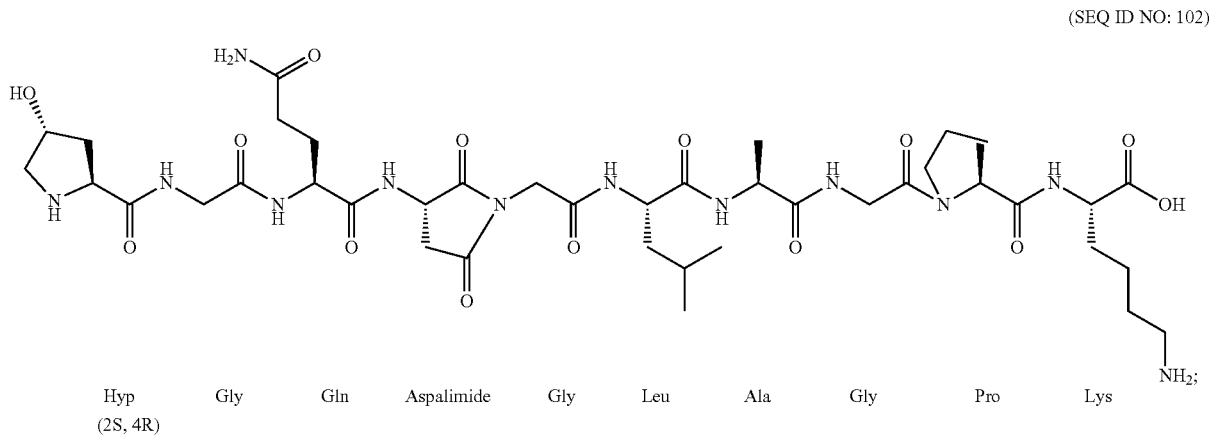

Hyp (2S, 4R) — Gly — Gln — Aspalimide — Gly — Leu — Ala — Gly — Pro — Lys or a compound represented by Formula 10:

[Formula 10]

(SEQ ID NO: 112)

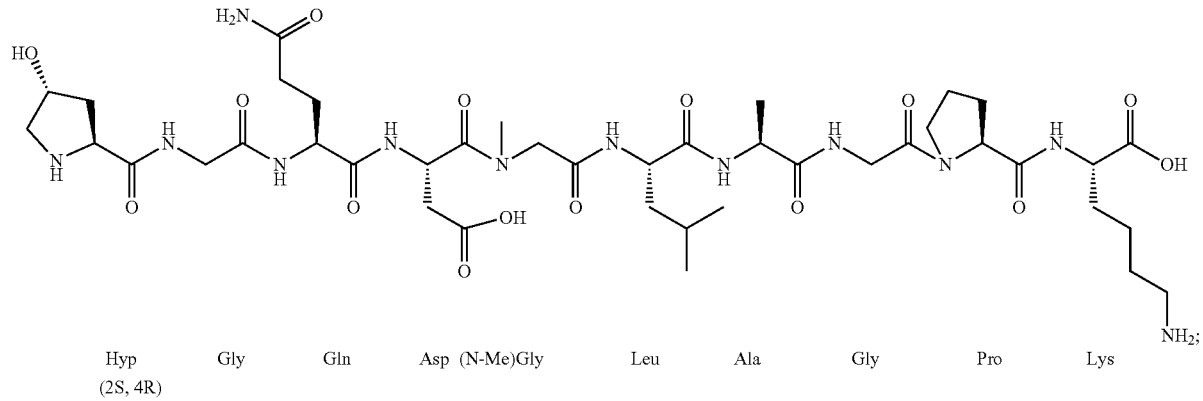

| Hyp | Gly | Gln | Asp | (N-Me)Gly | Leu | Ala | Gly | Pro | Lys |
| (2S, 4R) | | | | | | | | | | or a pharmaceutically acceptable salt thereof.

In certain embodiments, the compound may be a prodrug, e.g., wherein a hydroxyl in the parent compound is presented as an ester or a carbonate, a carboxylic acid present in the parent compound is presented as an ester, or an amino group is presented as an amide. In certain such embodiments, the prodrug is metabolized to the active parent compound in vivo (e.g., the ester is hydrolyzed to the corresponding hydroxyl or carboxylic acid).

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee.

The compounds of the invention have more than one stereocenter. Accordingly, the compounds of the invention may be enriched in one or more diastereomers. For example, a compound of the invention may have greater than 30% de, 40% de, 50% de, 60% de, 70% de, 80% de, 90% de, or even 95% or greater de. In certain embodiments, the compounds of the invention have substantially one isomeric configuration at one or more stereogenic centers, and have multiple isomeric configurations at the remaining stereogenic centers.

In certain embodiments, the enantiomeric excess of a given stereocenter in the compound is at least 40% ee, 50% ee, 60% ee, 70% ee, 80% ee, 90% ee, 92% ee, 94% ee, 95% ee, 96% ee, 98% ee or greater ee.

As used herein, single bonds drawn without stereochemistry do not indicate the stereochemistry of the compound. The compound of formula (I) provides an example of a compound for which no stereochemistry is indicated.

As used herein, hashed or bolded wedge bonds indicate absolute stereochemical configuration.

In certain embodiments, a therapeutic preparation of the compound of the invention may be enriched to provide predominantly one enantiomer of a compound. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, a therapeutic preparation may be enriched to provide predominantly one diastereomer of the compound of the invention. A diastereomerically enriched mixture may comprise, for example, at least 60 mol percent of one diastereomer, or more preferably at least 75, 90, 95, or even 99 mol percent.

Pharmaceutical Compositions

In certain embodiments, the invention provides a pharmaceutical composition comprising a compound of the invention, or a pharmaceutically acceptable salt thereof; and a pharmaceutically acceptable carrier.

In certain embodiments, the pharmaceutical composition is formulated for topical administration to the eye, e.g., as eye drops.

In certain embodiments at least 50%, 60%, 70%, 80%, or 90% of the compound is present as a salt. Preferably, at least 95% of the compound is present as a salt. Even more preferably, at least 99% of the compound is present as a salt.

In certain embodiments, the present invention provides a pharmaceutical preparation suitable for use in a human patient, comprising any salt or compound of the invention, and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

One embodiment of the present invention provides a pharmaceutical kit comprising a salt or compound of the invention, or a pharmaceutically acceptable salt thereof, and optionally directions on how to administer the compound.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In certain preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ (e.g., wheat germ), olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the invention with one or more additional therapeutic agent(s) provides improved efficacy relative to each individual administration of the compound of the invention (e.g., a compound of formula I, V, VI, or VII) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, oxalic, mandelic and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I, V, VI, or VII. As another example, the salt may comprise less than one inorganic or organic acid molecule per molecule of base, such as two molecules of compound of Formula I, V, VI, or VII per molecule of tartaric acid.

In further embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Methods of Treatment

The present invention also provides methods of treating eye disease, comprising administering to a subject in need thereof a compound of the invention or a pharmaceutical composition comprising a compound of the invention.

Specifically, the eye disease may be selected from retinopathy, keratitis, dry-macular degeneration, wet-macular degeneration, dry eye syndrome, keratoconjunctival epithelium disorder, proliferative vitreoretinopathy, pigmentary retinopathy, diabetic retinopathy, retinopathy of prematurity, retinopathy of immaturity, proliferative retinopathy, ischemic retinopathy, epidemic keratoconjunctivitis, atopic keratitis, superior limbic keratitis, pterygium keratitis sicca, phlyctenular keratoconjunctivitis, scleritis, corneal transplant rejection, choroidal neovascularization, neovascular glaucoma, ischemic optic neuropathy, retrolental fibroplasias, diabetic macula, neovascular iris disease, erythrosis, myopia, Von Hippel-Lindau syndrome, ocular histoplasmosis, central retinal vein occlusion, Sjogren syndrome and Stevens-Johnson syndrome. Preferably, the eye disease may be selected from retinopathy, keratitis, macular degeneration, dry eye syndrome and keratoconjunctival epithelium disorder.

In certain preferred embodiments, the eye disease is selected from retinopathy, keratitis, dry-macular degeneration, wet-macular degeneration, dry eye syndrome, heratoconjunctivitis sicca and keratoconjunctival epithelium disorder.

The pharmaceutical composition for treating an eye disease, which comprises a compound of the invention as an active pharmaceutical ingredient, may further comprise at least one additive selected from the group consisting of a carrier, an excipient, a disintegrant, a sweetener, a coating agent, a swelling agent, a lubricant, a slip agent, a flavor, an antioxidant, a buffer, a bacteriostat, a diluent, a dispersant, a surfactant, and a binder. Specifically, a formulation for parenteral administration may be a sterilized aqueous solution, a non-aqueous solution, a suspension, an emulsion, a lyophilized preparation, a suppository, or the like.

The dose of the compound of the invention that is administered to the subject may be adjusted depending on such various factors as the kind of the disease, the severity of the disease, the kinds and amounts of the active pharmaceutical ingredient and other ingredients contained in the pharmaceutical composition, the type of the formulation, the age, body weight, general health condition, sex, and diet of the patient, the time and the route of administration, the duration of treatment, and the drugs concurrently used.

However, for the desired effect, the effective amount of the compound contained in the pharmaceutical composition may be 0.0001 µg/day to 100 µg/day. In such event, the administration may be carried out once a day, or divided into several doses. Specifically, the concentration of the compound contained in the pharmaceutical composition may be 1000 µM to 0.001 µM. Also, the concentration of or compound contained in the pharmaceutical composition may be 100 µM to 0.005 µM or 50 µM to 0.02 µM.

In addition, if necessary, the concentration of the compound contained in the pharmaceutical composition may be 30 µM to 1 µM. Further, the concentration of the compound or the peptide contained in the pharmaceutical composition may be 0.01 µM to 1 µM.

In addition, the subject may be a mammal, particularly a human. The administration route may be appropriately selected by a person skilled in the art in consideration of the administration method, the volume and viscosity of the body fluid, and the like. Specifically, the administration may be carried out through any one route selected from the group consisting of an application, intravenous, intraarterial, intraperitoneal, intramuscular, intrasternal, percutaneous, intranasal, inhalation, topical, rectal, oral, intraocular, and intradermal. Preferably, the administration comprises topical administration to the eye of the subject.

In particular, it may preferably be applied to the eye for use as an eye drop.

The invention now being generally described, it will be more readily understood by reference to the following examples which are included merely for purposes of illustration of certain aspects and embodiments of the present invention, and are not intended to limit the invention.

EXAMPLES

Example 1: Preparation of YDE Derivatives

A protein analysis of the extracellular matrix derived from animal chondrocytes was performed in Baek's group of Center of Biomedical Mass Spectrometry (Diatech Korea Co., Ltd., Seoul, Korea). Proline-GQDGLAGPK (P-GQDG-LAGPK (SEQ ID NO: 123)), which is a part of the amino acid sequence of the collagen type II α1 protein, was obtained through the above protein analysis.

An exemplary protein synthesis for YDE-011 follows (SEQ ID NOS 124-131 and 131, respectively in order of appearance). The other compounds of the invention (e.g., YDE-001-YDE-086) are made through an analogous procedure by, e.g., substituting in a different amino acid building block reagent in a desired step.

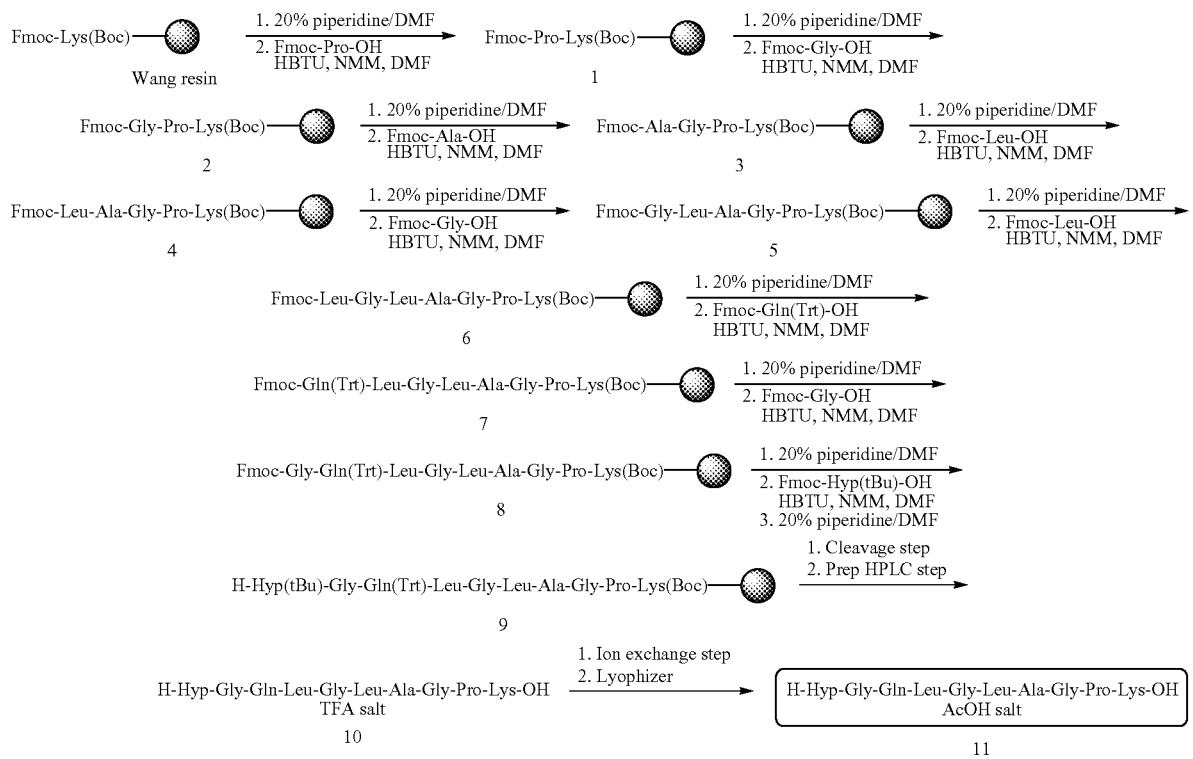

Exemplary Procedure for YDE-011

Solid Phase Synthesis

Fmoc-Pro-Lys(Boc)-Wang Resin (1)

To a solid phase synthesis reactor equipped with filtration membrane was added Fmoc-Lys(Boc)-Wang Resin (1.75 g, 1 mmole) in DCM (30 mL) then swelled for 30 min then the resin was drained. To the resin, a solution of piperidine (10 mL) in DMF (40 mL) was added and stirred for 5 minutes then the resin was drained. The resin was washed 6 times with DMF (50 mL). To the resin, a solution of Fmoc-Pro-OH (3.37 g, 10 mmole) in DMF (25 mL) and a solution of HBTU (3.8 g, 10 mmole) and N-Methylmorpholine (2.0 g, 20 mmole) in DMF (25 mL) were added respectively. The reaction mixture was stirred for 1 h and the resin was drained. The resin was used to next step without further purification.

Fmoc-Gly-Pro-Lys(Boc)-Wang Resin (2)

To Fmoc-Pro-Lys(Boc)-Wang resin (1), a solution of piperidine (10 mL) in DMF (40 mL) was added and stirred for 5 minutes then the resin was drained. The resin was washed 6 times with DMF (50 mL). To the resin, a solution of Fmoc-Gly-OH (3.0 g, 10 mmole) in DMF (25 mL) and a solution of HBTU (3.8 g, 10 mmole) and N-Methylmorpholine (2.0 g, 20 mmole) in DMF (25 mL) were added respectively. The reaction mixture was stirred for 1 h and the resin was drained. The resin was used to next step without further purification.

Fmoc-Ala-Gly-Pro-Lys(Boc)-Wang Resin (3) (SEQ ID NO: 124)

To Fmoc-Gly-Pro-Lys(Boc)-Wang resin (2), a solution of piperidine (10 mL) in DMF (40 mL) was added and stirred for 5 minutes then the resin was drained. The resin was washed 6 times with DMF (50 mL). To the resin, a solution of Fmoc-Ala-OH (3.1 g, 10 mmole.) in DMF (25 mL) and a solution of HBTU (3.8 g, 10 mmole) and N-Methylmorpholine (2.0 g, 20 mmole) in DMF (25 mL) were added respectively. The reaction mixture was stirred for 1 h and the resin was drained. The resin was used to next step without further purification.

Fmoc-Leu-Ala-Gly-Pro-Lys(Boc)-Wang Resin (4) (SEQ ID NO: 125)

To Fmoc-Ala-Gly-Pro-Lys(Boc)-Wang resin (3) (SEQ ID NO: 124), a solution of piperidine (10 mL) in DMF (40 mL) was added and stirred for 5 minutes then the resin was drained. The resin was washed 6 times with DMF (50 mL). To the resin, a solution of Fmoc-Leu-OH (3.5 g, 10 mmole) in DMF (25 mL) and a solution of HBTU (3.8 g, 10 mmole) and N-Methylmorpholine (2.0 g, 20 mmole) in DMF (25 mL) were respectively. The reaction mixture was stirred for 1 h and the resin was drained. The resin was used to next step without further purification.

Fmoc-Gly-Leu-Ala-Gly-Pro-Lys(Boc)-Wang Resin (5) (SEQ ID NO: 126)

To Fmoc-Leu-Ala-Gly-Pro-Lys(Boc)-Wang resin (4) (SEQ ID NO: 125), 10 mL piperidine in DMF (40 mL) was added and stirred for 5 minutes then the resin was drained. The resin was washed 6 times with DMF (50 mL). To the resin, a solution of Fmoc-Gly-OH (3.0 g, 10 mmole) in DMF (25 mL) and a solution of HBTU (3.8 g, 10 mmole) and N-Methylmorpholine (2.0 g, 20 mmole) in DMF (25 mL) were respectively. The reaction mixture was stirred for 1 h and the resin was drained. The resin was used to next step without further purification.

Fmoc-Leu-Gly-Leu-Ala-Gly-Pro-Lys(Boc)-Wang Resin (6) (SEQ ID NO: 127)

To Fmoc-Gly-Leu-Ala-Gly-Pro-Lys(Boc)-Wang resin (5) (SEQ ID NO: 126), a solution of piperidine (10 mL) in DMF (40 mL) was added and stirred for 5 minutes then the resin was drained. The resin was washed 6 times with DMF (50 mL). To the resin, a solution of Fmoc-Leu-OH (3.5 g, 10 mmole) in DMF (25 mL) and a solution of HBTU (3.8 g, 10 mmole) and N-Methylmorpholine (2.0 g, 20 mmole) in DMF (25 mL) were respectively. The reaction mixture was stirred for 1 h and the resin was drained. The resin was used to next step without further purification.

Fmoc-Gln(Trt)-Leu-Gly-Leu-Ala-Gly-Pro-Lys(Boc)-Wang Resin (7) (SEQ ID NO: 128)

To Fmoc-Leu-Gly-Leu-Ala-Gly-Pro-Lys(Boc)-Wang resin (6) (SEQ ID NO: 127), a solution of piperidine (10 mL) in DMF (40 mL) was added and stirred for 5 minutes then the resin was drained. The resin was washed 6 times with DMF (50 mL). To the resin, a solution of Fmoc-Gln(Trt)-OH (6.1 g, 10 mmole) in DMF (25 mL) and a solution of HBTU (3.8 g, 10 mmole) and N-Methylmorpholine (2.0 g, 20 mmole) in DMF (25 mL, 10 eq) were respectively. The reaction mixture was stirred for 1 h and the resin was drained. The resin was used to next step without further purification.

Fmoc-Gly-Gln(Trt)-Leu-Gly-Leu-Ala-Gly-Pro-Lys(Boc)-Wang Resin (8) (SEQ ID NO: 129)

To Fmoc-Gln(Trt)-Leu-Gly-Leu-Ala-Gly-Pro-Lys(Boc)-Wang resin (7) (SEQ ID NO: 128), a solution of piperidine (10 mL) in DMF (40 mL) was added and stirred for 5 minutes then the resin was drained. The resin was washed 6 times with DMF (50 mL). To the resin, a solution of Fmoc-Gly-OH (3.0 g, 10 mmole) in DMF (25 mL) and a solution of HBTU (3.8 g, 10 mmole) and N-Methylmorpholine (2.0 g, 20 mmole) in DMF (25 mL) were added respectively. The reaction mixture was stirred for 1 h and the resin was drained. The resin was used to next step without further purification.

H-Hyp(tBu)-Gly-Gln(Trt)-Leu-Gly-Leu-Ala-Gly-Pro-Lys(Boc)-Wang Resin (9) (SEQ ID NO: 130)

To Fmoc-Gly-Gln(Trt)-Leu-Gly-Leu-Ala-Gly-Pro-Lys(Boc)-Wang resin (8) (SEQ ID NO: 129), a solution of piperidine (10 mL) in DMF (40 mL) was added and stirred for 5 minutes then the resin was drained The resin was washed for 6 times with DMF (50 mL). To the resin, a solution of Fmoc-Hyp(tBu)-OH (4.2 g, 10 mmole) in DMF (25 mL) and a solution of HBTU (3.8 g, 10 mmole) and N-Methylmorpholine (2.0 g, 20 mmole) in DMF (25 mL) were added and the reaction mixture was stirred for 1 h and the resin was drained. To Fmoc-Hyp(tBu)-Gly-Gln(Trt)-Leu-Gly-Leu-Ala-Gly-Pro-Lys(Boc)-Wang resin (SEQ ID NO: 142), a solution of piperidine (10 mL) in DMF (40 mL) was added. The reaction mixture was stirred for 5 minutes then the resin was drained. The resin was washed 6 times with DMF (50 mL).

Removal from Resin

H-Hyp-Gly-Gln-Leu-Gly-Leu-Ala-Gly-Pro-Lys-OH TFA Salt (10) (SEQ ID NO: 131)

To the 1 mmole H-Hyp(tBu)-Gly-Gln(Trt)-Leu-Gly-Leu-Ala-Gly-Pro-Lys(Boc)-Wang Resin (9) (SEQ ID NO: 130), 30 mL of cocktail solution (87.5% TFA/2.5% 1,2-ethandithiol/2.5% H$_2$O/5.0% thioanisole) were added and the reaction mixture was stirred for 2 h and monitored the reaction mixture by HPLC. To filtered solution was added cold diethyl ether (500 mL) to precipitate crude peptide. The precipitated peptide was filtered through a filtration apparatus and washed with 500 mL of diethyl ether. The crude peptide was dried under vacuum to give 105% (1 g).

Purification Step

H-Hyp-Gly-Gln-Leu-Gly-Leu-Ala-Gly-Pro-Lys-OH TFA salt(10) (SEQ ID NO: 131)

The crude compound was purified by Prep HPLC system

Salt Exchange Step

H-Hyp-Gly-Gln-Leu-Gly-Leu-Ala-Gly-Pro-Lys-OH AcOH salt (11) (SEQ ID NO: 131)

The Purified compound was exchanged from TFA salt to AcOH salt by Ion Exchange resin. The Ion exchanged peptide was dried by lyophilizer.

YDE-001 to YDE-092 peptides were synthesized by ANYGEN (Gwangju, Korea) in a manner analogous to the exemplary procedure shown above, by substituting one or more different amino acid residues into the peptide Proline-GQDGLAGPK (SEQ ID NO: 123) (FIG. 1 and Table 1).

Figure 2:
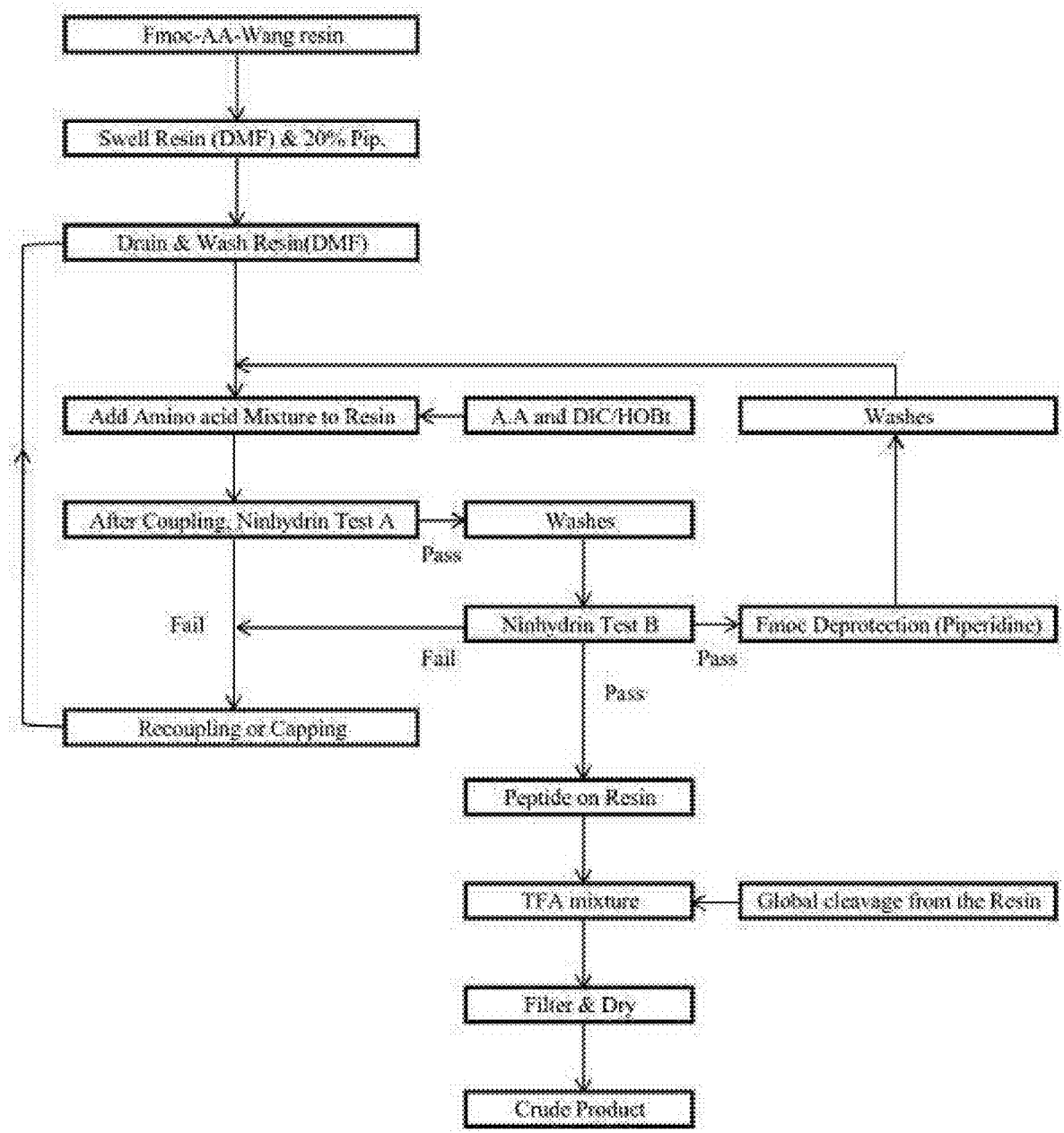
FIG. 2 is a diagram showing a process for synthesizing the peptides prepared according to an embodiment of the present invention.
Figure 3:
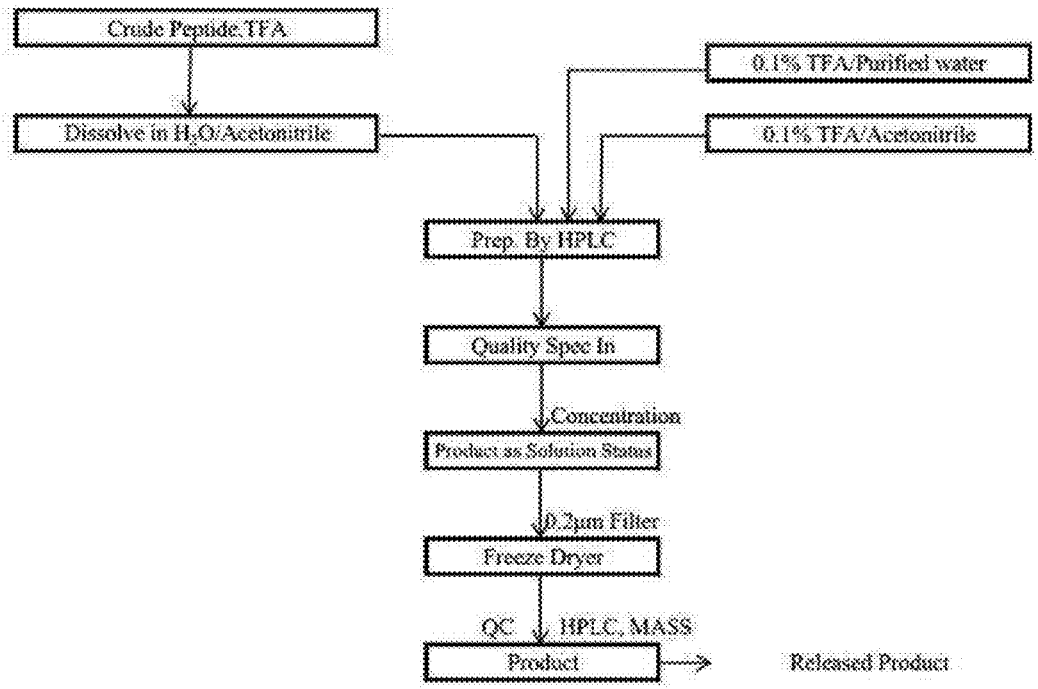
FIG. 3 is a diagram showing a purification procedure of the peptides prepared according to an embodiment of the present invention.

The process for synthesizing the YDE-001 to YDE-075 peptides and the purification procedure thereof conducted by ANYGEN are depicted in FIGS. 2 and 3.

TABLE 1

| No. | Chemical structure | SEQ ID NO. |
|---|---|---|
| YY-101 | Hyp(2S,4R) — Gly — Gln — Asp — Gly — Leu — Ala — Gly — Pro — Lys | SEQ ID NO: 101 |
| YY-102 | Hyp(2S,4R) — Gly — Gln — Aspatimide — Gly — Leu — Ala — Gly — Pro — Lys | SEQ ID NO: 102 |
| YDE-001 | Hyp(2S,4R) — Gly — Gln — Glu — Gly — Leu — Ala — Gly — Pro — Lys | SEQ ID NO: 1 |
| YDE-002 | Hyp(2S,4R) — Gly — Gln — Asn — Gly — Leu — Ala — Gly — Pro — Lys | SEQ ID NO: 2 |

TABLE 1-continued

| No. | Chemical structure | SEQ ID NO. |
|---|---|---|
| YDE-003 | Hyp(2S,4R) - Gly - Gln - Gln - Gly - Leu - Ala - Gly - Pro - Lys | SEQ ID NO: 3 |
| YDE-004 | Hyp(2S,4R) - Gly - Gln - His - Gly - Leu - Ala - Gly - Pro - Lys | SEQ ID NO: 4 |
| YDE-005 | Hyp(2S,4R) - Gly - Gln - Asp - Gly - Leu - Ala - Gly - Pro - Lys | SEQ ID NO: 5 |
| YDE-006 | Hyp(2S,4R) - Gly - Gln - Ser - Gly - Leu - Ala - Gly - Pro - Lys | SEQ ID NO: 6 |

TABLE 1-continued
| No. | Chemical structure | SEQ ID NO. |
|---|---|---|
| YDE-007 | 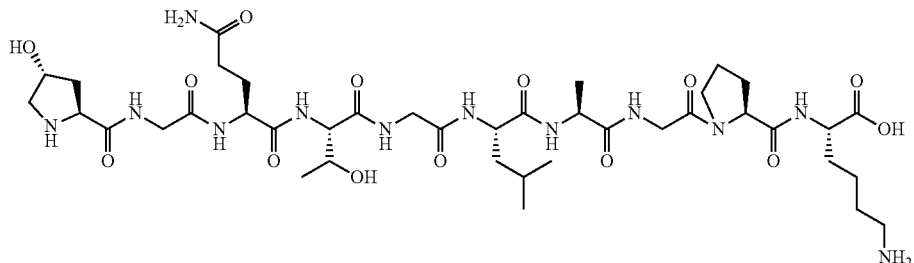 Hyp(2S,4R) Gly Gln Thr Gly Leu Ala Gly Pro Lys | SEQ ID NO: 7 |
| YDE-008 | 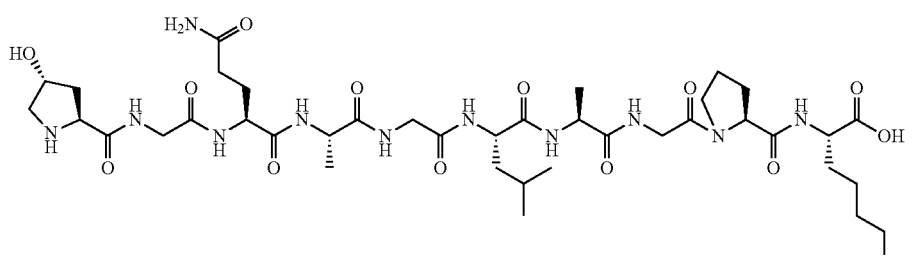 Hyp(2S,4R) Gly Gln Ala Gly Leu Ala Gly Pro Lys | SEQ ID NO: 8 |
| YDE-009 | 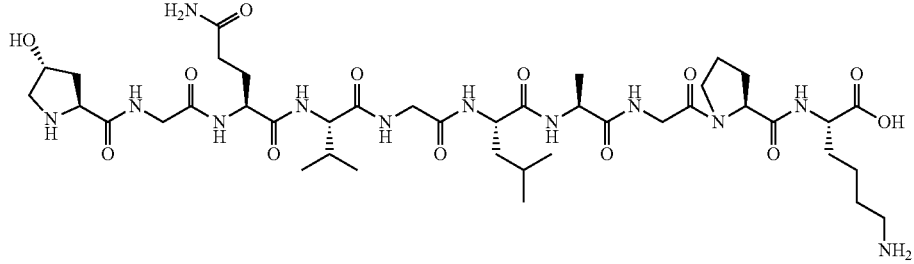 Hyp(2S,4R) Gly Gln Val Gly Leu Ala Gly Pro Lys | SEQ ID NO: 9 |
| YDE-010 | 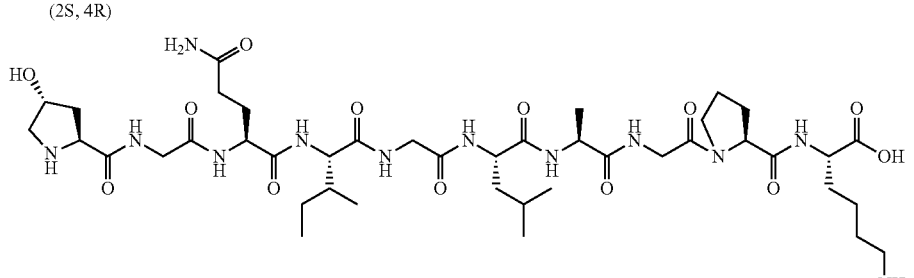 Hyp(2S,4R) Gly Gln Ile Gly Leu Ala Gly Pro Lys | SEQ ID NO: 10 |

TABLE 1-continued

| No. | Chemical structure | SEQ ID NO. |
|---|---|---|
| YDE-011 | Hyp(2S,4R) Gly Gln Leu Gly Leu Ala Gly Pro Lys | SEQ ID NO: 11 |
| YDE-012 | Hyp(2S,4R) Gly Gln Phe Gly Leu Ala Gly Pro Lys | SEQ ID NO: 12 |
| YDE-013 | Hyp(2S,4R) Gly Gln Tyr Gly Leu Ala Gly Pro Lys | SEQ ID NO: 13 |
| YDE-014 | Hyp(2S,4R) Gly Gln Trp Gly Leu Ala Gly Pro Lys | SEQ ID NO: 14 |

TABLE 1-continued
| No. | Chemical structure | SEQ ID NO. |
|---|---|---|
| YDE-015 | 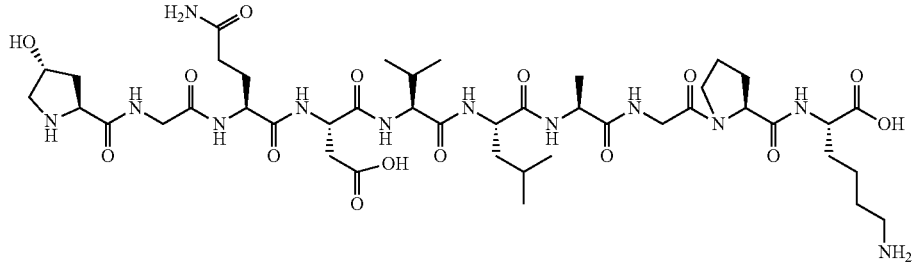<br>Hyp (2S, 4R)　Gly　Gln　Asp　Val　Leu　Ala　Gly　Pro　Lys | SEQ ID NO: 15 |
| YDE-016 | 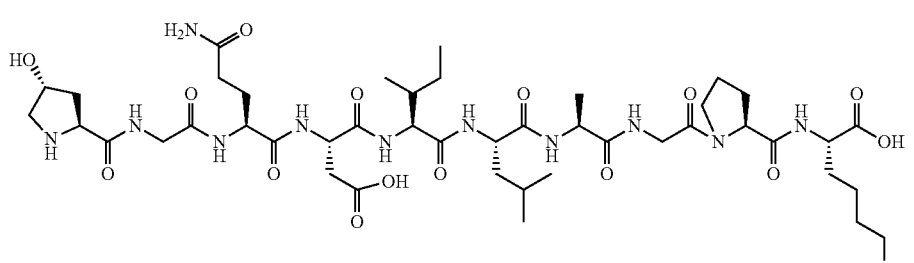<br>Hyp (2S, 4R)　Gly　Gln　Asp　Ile　Leu　Ala　Gly　Pro　Lys | SEQ ID NO: 16 |
| YDE-017 | 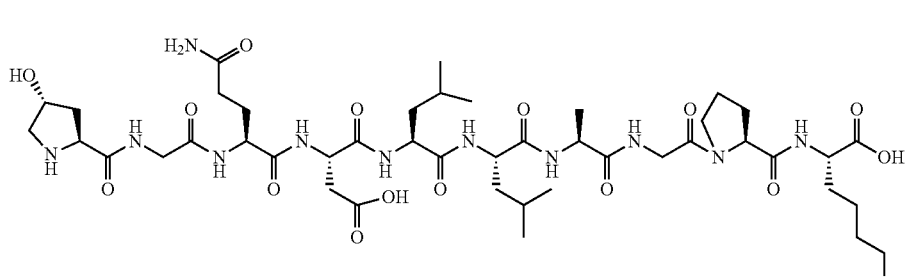<br>Hyp (2S, 4R)　Gly　Gln　Asp　Leu　Leu　Ala　Gly　Pro　Lys | SEQ ID NO: 17 |
| YDE-018 | 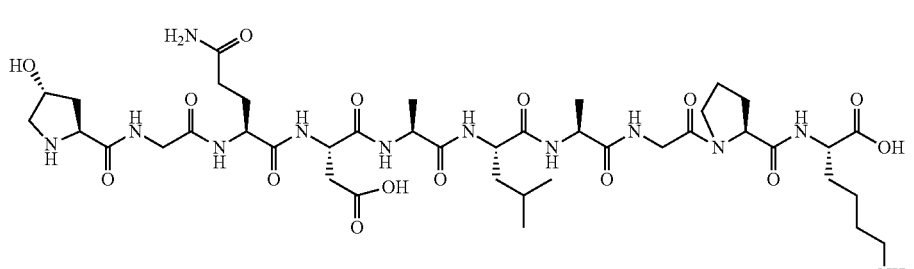<br>Hyp (2S, 4R)　Gly　Gln　Asp　Ala　Leu　Ala　Gly　Pro　Lys | SEQ ID NO: 18 |

TABLE 1-continued

| No. | Chemical structure | SEQ ID NO. |
|---|---|---|
| YDE-019 | Hyp (2S, 4R) — Gly — Gln — Asp — Phe — Leu — Ala — Gly — Pro — Lys | SEQ ID NO: 19 |
| YDE-020 | Hyp (2S, 4R) — Gly — Gln — Asp — Tyr — Leu — Ala — Gly — Pro — Lys | SEQ ID NO: 20 |
| YDE-021 | Hyp (2S, 4R) — Gly — Gln — Asp — Trp — Leu — Ala — Gly — Pro — Lys | SEQ ID NO: 21 |
| YDE-022 | Hyp (2S, 4R) — Gly — Gln — Asp — His — Leu — Ala — Gly — Pro — Lys | SEQ ID NO: 22 |

TABLE 1-continued

| No. | Chemical structure | SEQ ID NO. |
|---|---|---|
| YDE-023 | Hyp(2S,4R) Gly Gln Asp Ser Leu Ala Gly Pro Lys | SEQ ID NO: 23 |
| YDE-024 | Hyp(2S,4R) Gly Gln Asp Thr Leu Ala Gly Pro Lys | SEQ ID NO: 24 |
| YDE-025 | Hyp(2S,4R) Gly Gln Asp (Me)Gly Leu Ala Gly Pro Lys | SEQ ID NO: 25 |
| YDE-026 | Hyp(2S,4R) Gly Gln Homo-Ser Gly Leu Ala Gly Pro Lys | SEQ ID NO: 26 |

TABLE 1-continued

| No. | Chemical structure | SEQ ID NO. |
|---|---|---|
| YDE-027 | Hyp (2S, 4R) — Gly — Gln — Asp(Me) — Gly — Leu — Ala — Gly — Pro — Lys | SEQ ID NO: 27 |
| YDE-028 | Hyp (2S, 4R) — Gly — Gln — Asn(Me) — Gly — Leu — Ala — Gly — Pro — Lys | SEQ ID NO: 28 |
| YDE-029 | Hyp (2S, 4R) — Gly — Gln — Leu — Gly — Leu — Ala — Gly — Pro — Tyr | SEQ ID NO: 29 |
| YDE-030 | Hyp (2S, 4R) — Gly — Gln — Leu — Gly — Leu — Ala — Gly — Pro — Leu | SEQ ID NO: 30 |
| YDE-031 | Hyp (2S, 4R) — Gly — Gln — Leu — Gly — Leu — Ala — Gly — Pro — Glu | SEQ ID NO: 31 |

TABLE 1-continued
| No. | Chemical structure | SEQ ID NO. |
|---|---|---|
| YDE-032 | 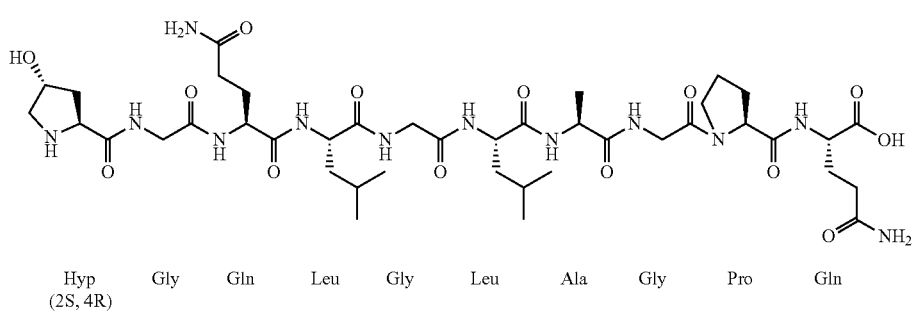 [SMILES: CC(C)C[C@H](NC(=O)CNC(=O)[C@H](CC(C)C)NC(=O)[C@H](CCC(N)=O)NC(=O)CNC(=O)[C@@H]1C[C@@H](O)CN1)C(=O)N[C@@H](C)C(=O)NCC(=O)N1CCC[C@H]1C(=O)N[C@@H](CCC(N)=O)C(=O)O]<br>Hyp (2S, 4R) — Gly — Gln — Leu — Gly — Leu — Ala — Gly — Pro — Gln | SEQ ID NO: 32 |
| YDE-033 | 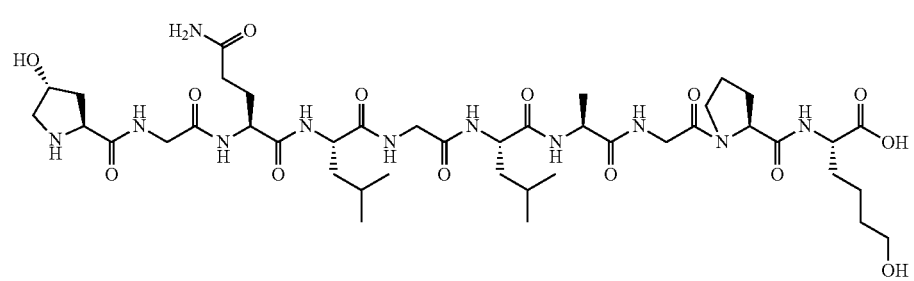<br>Hyp (2S, 4R) — Gly — Gln — Leu — Gly — Leu — Ala — Gly — Pro — Nle(6-OH) | SEQ ID NO: 33 |
| YDE-034 | 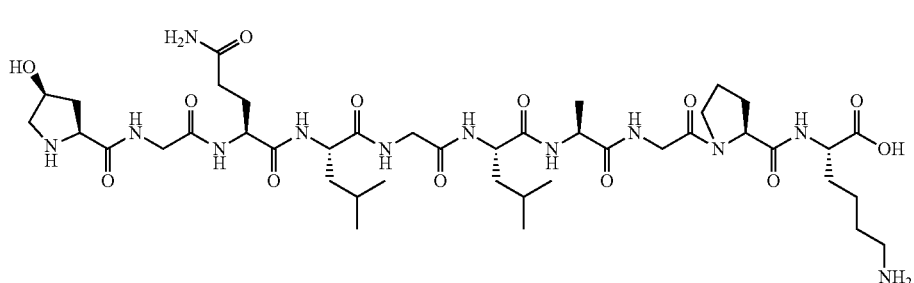<br>Hyp (2S, 4R) — Gly — Gln — Leu — Gly — Leu — Ala — Gly — Pro — Lys | SEQ ID NO: 34 |
| YDE-035 | 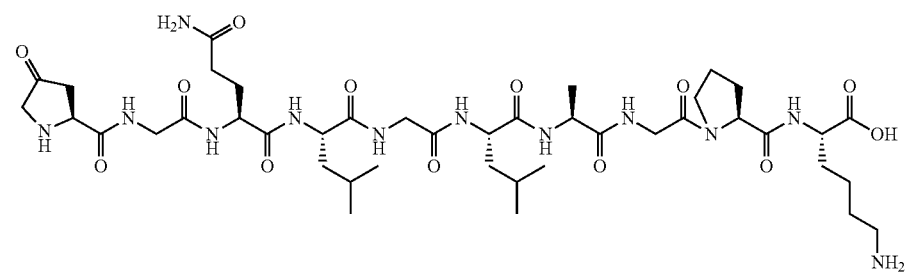<br>(4-oxo)Pro — Gly — Gln — Leu — Gly — Leu — Ala — Gly — Pro — Lys | SEQ ID NO: 35 |

TABLE 1-continued

| No. | Chemical structure | SEQ ID NO. |
|---|---|---|
| YDE-036 | (5-oxo)Pro — Gly — Gln — Leu — Gly — Leu — Ala — Gly — Pro — Lys | SEQ ID NO: 36 |
| YDE-037 | Pro — Gly — Gln — Leu — Gly — Leu — Ala — Gly — Pro — Lys | SEQ ID NO: 37 |
| YDE-038 | (4-hydrocyMe)Pro (4R) — Gly — Gln — Leu — Gly — Leu — Ala — Gly — Pro — Lys | SEQ ID NO: 38 |
| YDE-039 | (4-Fluoro)Pro (4R) — Gly — Gln — Leu — Gly — Leu — Ala — Gly — Pro — Lys | SEQ ID NO: 39 |

TABLE 1-continued
| No. | Chemical structure | SEQ ID NO. |
|---|---|---|
| YDE-040 | 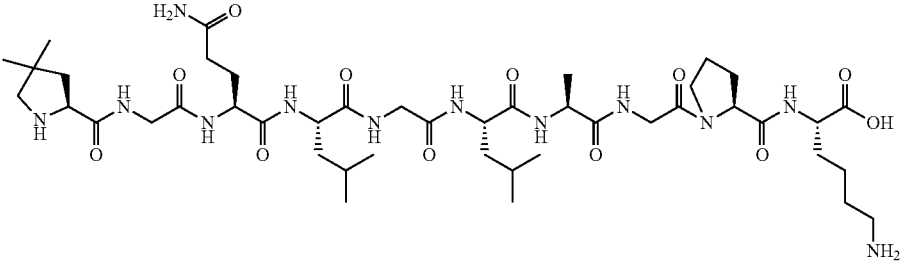<br>(4-Dimethyl)Pro  Gly  Gln  Leu  Gly  Leu  Ala  Gly  Pro  Lys | SEQ ID NO: 40 |
| YDE-041 | 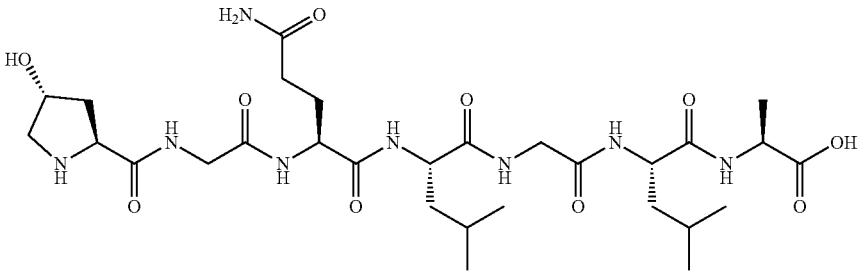<br>Hyp  Gly  Gln  Leu  Gly  Leu  Ala<br>(2S, 4R) | SEQ ID NO: 41 |
| YDE-042 | 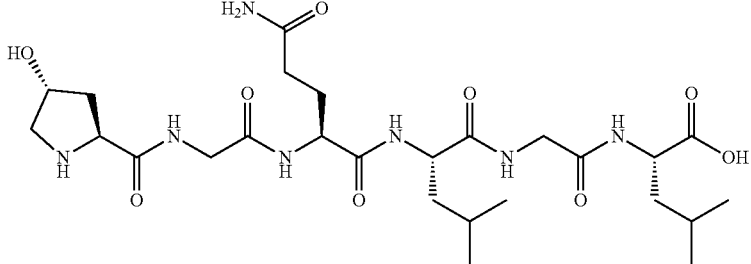<br>Hyp  Gly  Gln  Leu  Gly  Leu<br>(2S, 4R) | SEQ ID NO: 42 |
| YDE-043 | 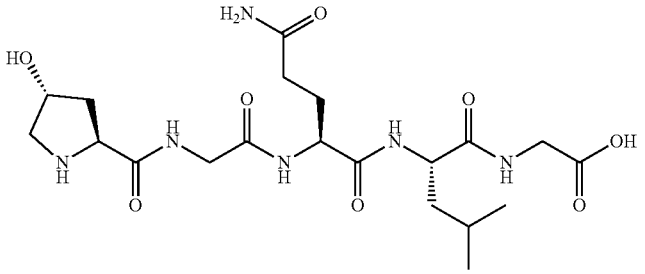<br>Hyp  Gly  Gln  Leu  Gly<br>(2S, 4R) | SEQ ID NO: 43 |

TABLE 1-continued
| No. | Chemical structure | SEQ ID NO. |
|---|---|---|
| YDE-044 | 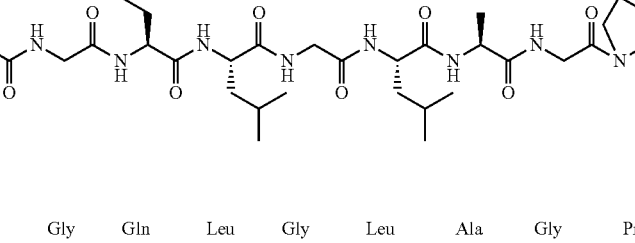<br>(4-Me)Pro (4R)   Gly   Gln   Leu   Gly   Leu   Ala   Gly   Pro   Lys | SEQ ID NO: 44 |
| YDE-045 | 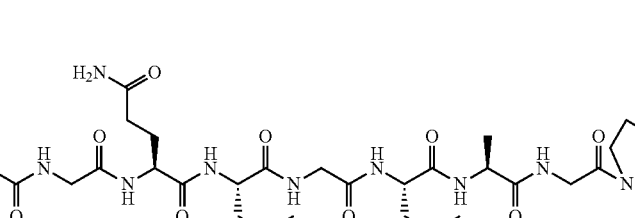<br>(5-Me)Pro (5R)   Gly   Gln   Leu   Gly   Leu   Ala   Gly   Pro   Lys | SEQ ID NO: 45 |
| YDE-047 | 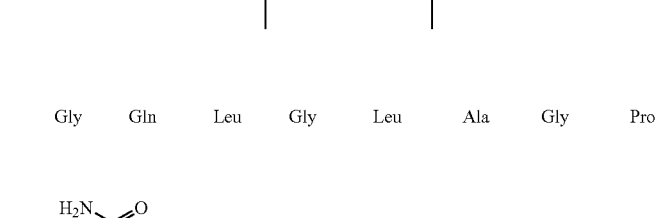<br>Ala   Gly   Gln   Leu   Gly   Leu   Ala   Gly   Pro   Lys | SEQ ID NO: 47 |
| YDE-048 | 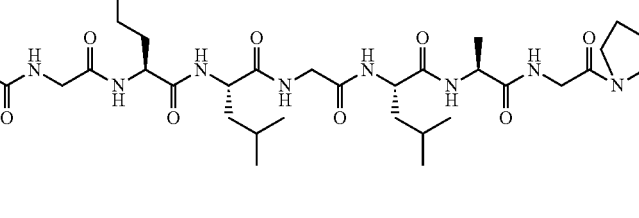<br>Hyp (2S, 4R)   Ala   Gln   Leu   Gly   Leu   Ala   Gly   Pro   Lys | SEQ ID NO: 48 |

TABLE 1-continued
| No. | Chemical structure | SEQ ID NO. |
|---|---|---|
| YDE-049 | 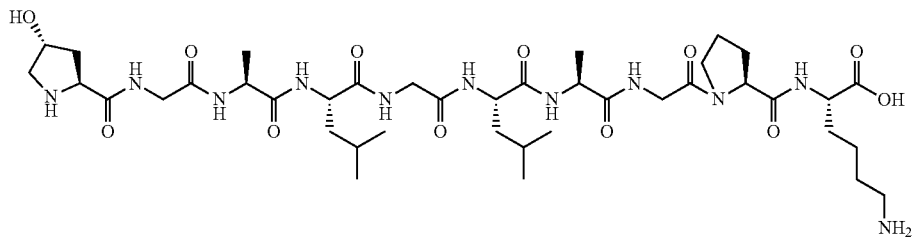<br>Hyp (2S, 4R) — Gly — Ala — Leu — Gly — Leu — Ala — Gly — Pro — Lys | SEQ ID NO: 49 |
| YDE-050 | 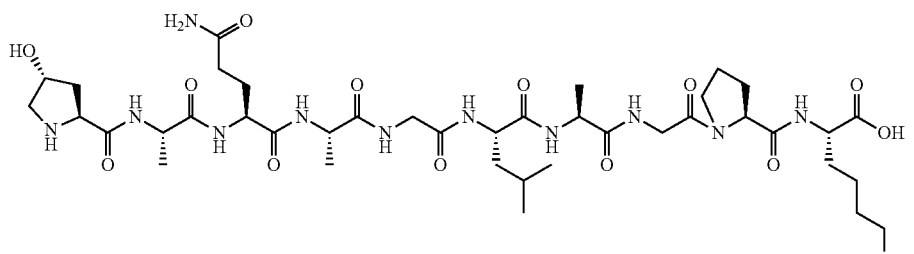<br>Hyp (2S, 4R) — Gly — Gln — Ala — Gly — Leu — Ala — Gly — Pro — Lys | SEQ ID NO: 8 |
| YDE-051 | 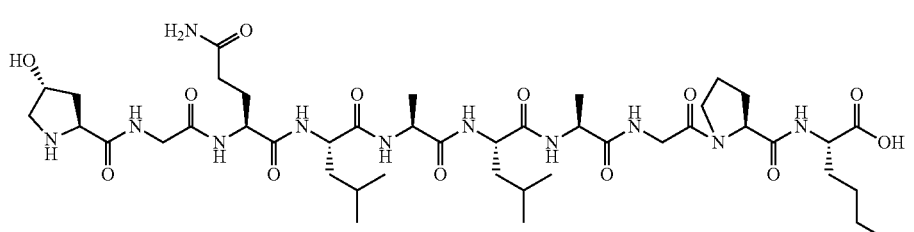<br>Hyp (2S, 4R) — Gly — Gln — Leu — Ala — Leu — Ala — Gly — Pro — Lys | SEQ ID NO: 51 |
| YDE-052 | 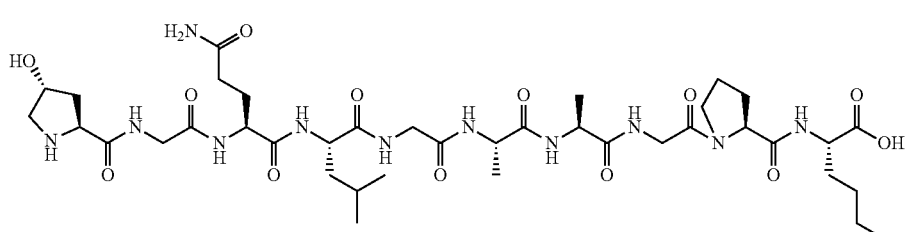<br>Hyp (2S, 4R) — Gly — Gln — Leu — Gly — Ala — Ala — Gly — Pro — Lys | SEQ ID NO: 52 |

TABLE 1-continued
| No. | Chemical structure | SEQ ID NO. |
|---|---|---|
| YDE-053 | 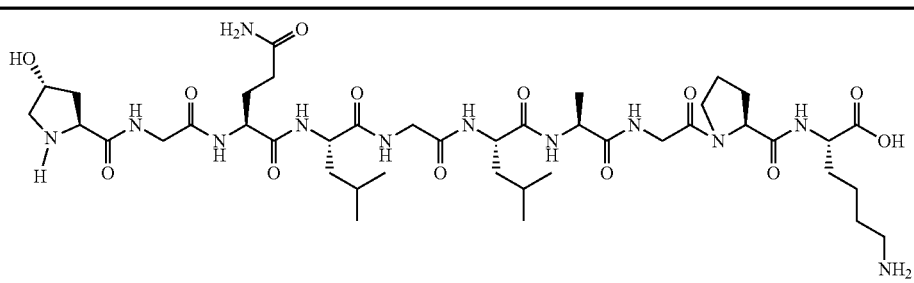<br>Hyp  Gly  Gln  Leu  Gly  Leu  Ala  Gly  Pro  Lys | SEQ ID NO: 11 |
| YDE-054 | 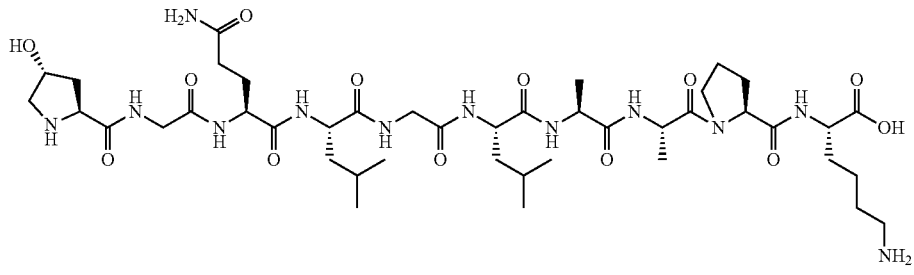<br>Hyp  Gly  Gln  Leu  Gly  Leu  Ala  Ala  Pro  Lys<br>(2S, 4R) | SEQ ID NO: 54 |
| YDE-055 | 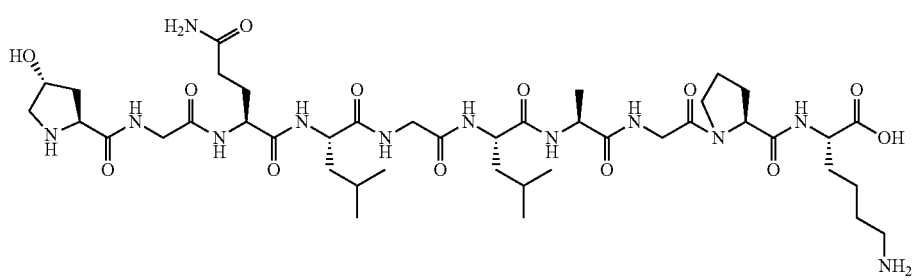<br>Hyp  Gly  Gln  Leu  Gly  Leu  Ala  Gly  Pro  Lys<br>(2S, 4R) | SEQ ID NO: 55 |
| YDE-056 | 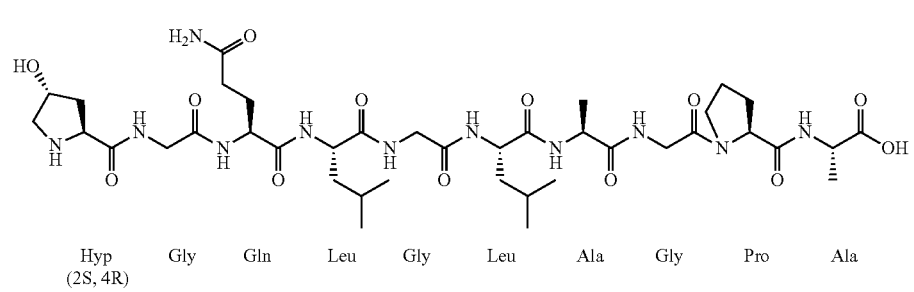 [SMILES: CC(C)C[C@H](NC(=O)CNC(=O)[C@H](CC(C)C)NC(=O)[C@H](CCC(N)=O)NC(=O)CNC(=O)[C@@H]1C[C@@H](O)CN1)C(=O)N[C@@H](C)C(=O)NCC(=O)N1CCC[C@H]1C(=O)N[C@@H](C)C(=O)O]<br>Hyp  Gly  Gln  Leu  Gly  Leu  Ala  Gly  Pro  Ala<br>(2S, 4R) | SEQ ID NO: 56 |
| YDE-057 | 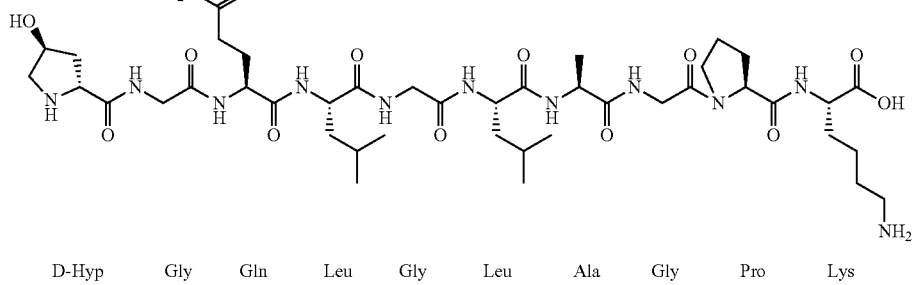<br>D-Hyp  Gly  Gln  Leu  Gly  Leu  Ala  Gly  Pro  Lys<br>(2R, 4S) | SEQ ID NO: 57 |

TABLE 1-continued
| No. | Chemical structure | SEQ ID NO. |
|---|---|---|
| YDE-058 | 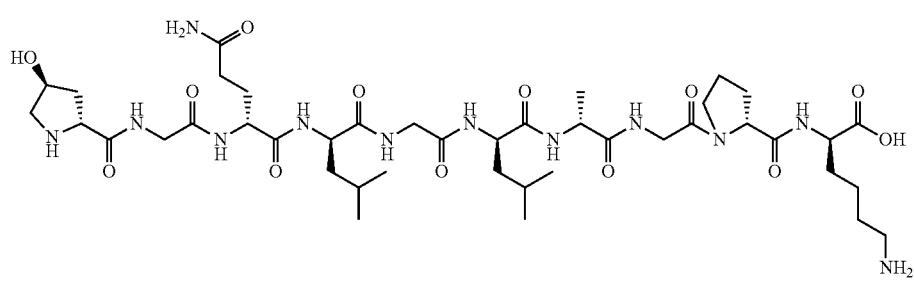<br>D-Hyp (2R, 4S) — Gly — D-Gln — D-Leu — Gly — D-Leu — D-Ala — Gly — D-Pro — D-Lys | SEQ ID NO: 58 |
| YDE-059 | 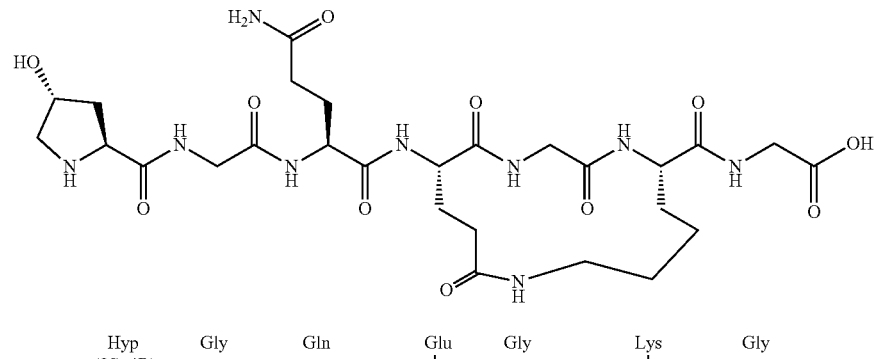<br>Hyp (2S, 4R) — Gly — Gln — Glu — Gly — Lys — Gly<br>                        amine bond | SEQ ID NO: 59 |
| YDE-060 | 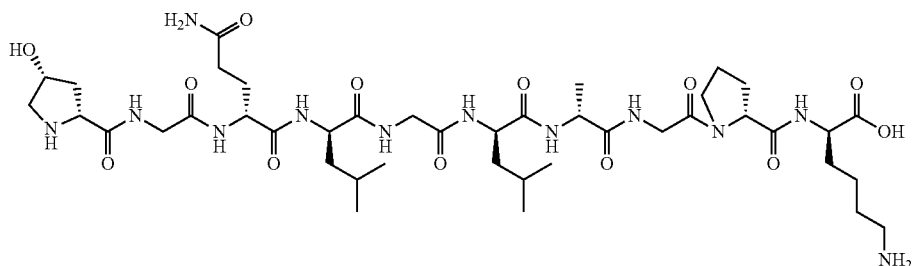<br>D-Hyp (2R, 4R) — Gly — D-Gln — D-Leu — Gly — D-Leu — D-Ala — Gly — D-Pro — D-Lys | SEQ ID NO: 60 |
| YDE-064 | 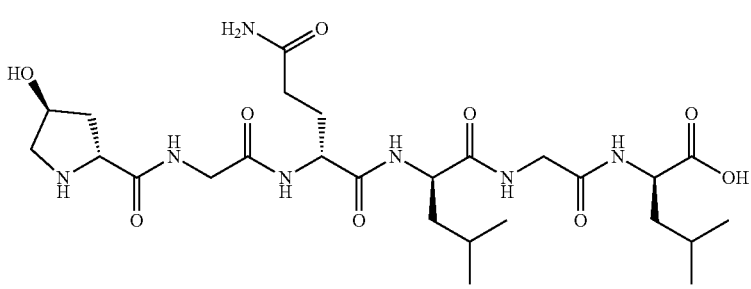<br>D-Hyp (2R, 4S) — Gly — D-Gln — D-Leu — Gly — D-Leu | SEQ ID NO: 64 |

TABLE 1-continued

| No. | Chemical structure | SEQ ID NO. |
|---|---|---|
| YDE-066 | Hyp (2S, 4R) — Gly — Gln — D-Leu — Gly | SEQ ID NO: 66 |
| YDE-072 | D-Hyp (2R, 4S) — Ala — Gln — Leu — Gly — Leu — Ala — Gly — Pro — Lys | SEQ ID NO: 72 |
| YDE-073 | D-Hyp (2R, 4S) — Gly — Gln — Leu — Gly — Leu — Ala — Gly — Pro — Ala | SEQ ID NO: 73 |
| YDE-074 | D-Hyp (2R, 4S) — Ala — Gln — Leu — Gly — Leu — Ala — Gly — Pro — Ala | SEQ ID NO: 74 |
| YDE-075 | D-Hyp (2R, 4S) — Gly — Gln — Leu — Gly | SEQ ID NO: 75 |

TABLE 1-continued

| No. | Chemical structure | SEQ ID NO. |
|---|---|---|
| YDE-078 | Hyp(2S, 4R) – Gly – Gln – Leu – Gly – Leu – Ala – Gly – Pro – Lys(Ac) | SEQ ID NO: 78 |
| YDE-080 | Hyp(2S, 4R) – Gly – Gln – D-Leu – Gly – D-Leu – D-Ala – Gly – Pro – Lys | SEQ ID NO: 80 |
| YDE-081 | D-Hyp(2R, 4S) – Gly – D-Gln – D-Leu – Gly | SEQ ID NO: 81 |
| YDE-083 | Hyp(2S, 4R) – Gly – D-Gln – Leu – Gly | SEQ ID NO: 83 |

TABLE 1-continued
| No. | Chemical structure | SEQ ID NO. |
|---|---|---|
| YDE-084 | 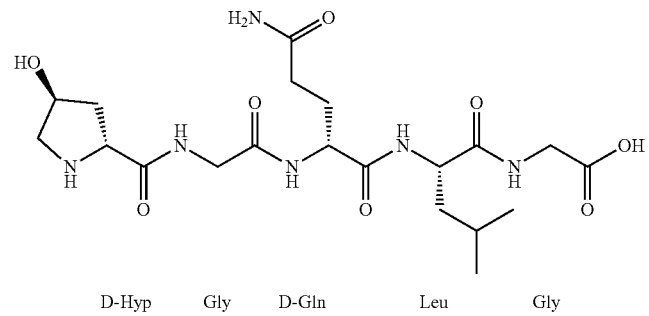\n\nD-Hyp (2R, 4S) — Gly — D-Gln — Leu — Gly | SEQ ID NO: 84 |
| YDE-085 | 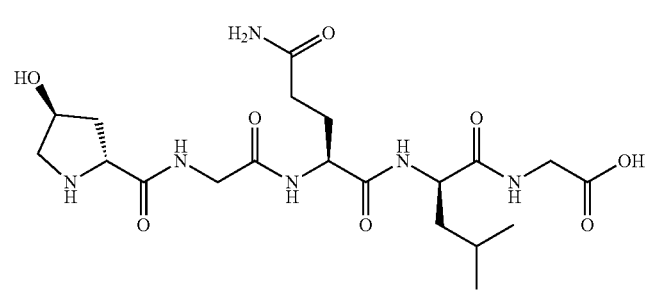\n\nD-Hyp (2R, 4S) — Gly — Gln — D-Leu — Gly | SEQ ID NO: 85 |
| YDE-086 | 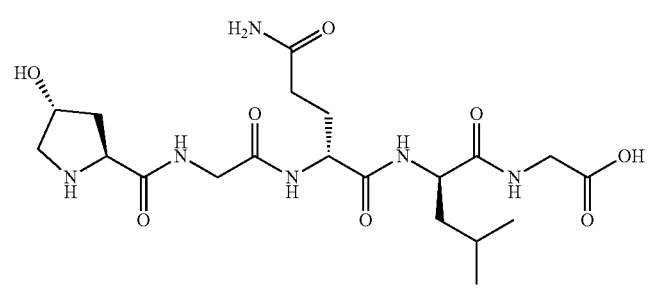\n\nHyp (2S, 4R) — Gly — D-Gln — D-Leu — Gly | SEQ ID NO: 86 |
| YDE-092 | 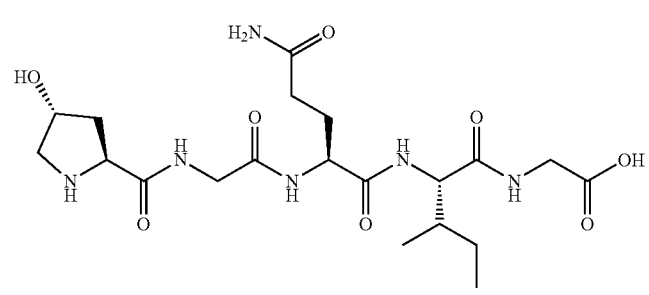\n\nHyp (2S, 4R) — Gly — Gln — Ile — Gly | SEQ ID NO: 92 |

TABLE 1-continued

| No. | Chemical structure | SEQ ID NO. |
|---|---|---|
| YDE-094 | 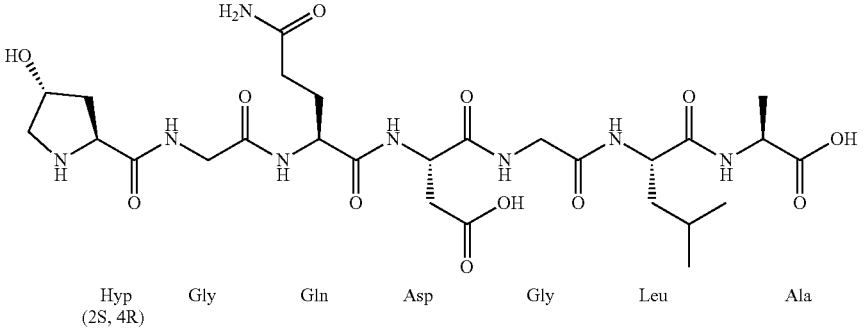 [SMILES: CC(C)C[C@H](NC(=O)CNC(=O)[C@H](CC(=O)O)NC(=O)[C@H](CCC(N)=O)NC(=O)CNC(=O)[C@@H]1C[C@@H](O)CN1)C(=O)N[C@@H](C)C(=O)O]<br>Hyp (2S, 4R)　　Gly　　Gln　　Asp　　Gly　　Leu　　Ala | SEQ ID NO: 94 |
| YDE-100 | 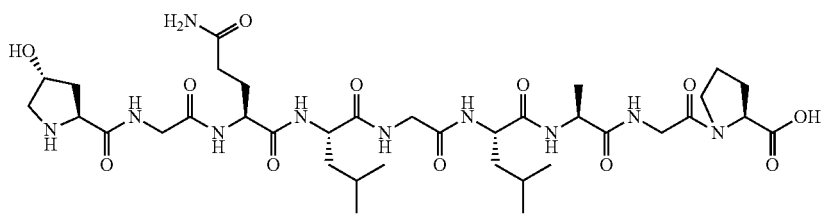<br>Hyp (2S, 4R)　　Gly　　Gln　　Leu　　Gly　　Leu　　Ala　　Gly　　Pro | SEQ ID NO: 100 |

Analysis of YDE Derivatives

The YDE derivatives prepared in Example 1 were analyzed by HPLC. As a result, it was confirmed that the purities of YDE-001, YDE-002, YDE-003, YDE-004, YDE-005, YDE-006, YDE-007, YDE-008, YDE-009, YDE-010, YDE-011, YDE-012, YDE-013, YDE-014, YDE-015, YDE-016, YDE-017, YDE-018, YDE-019, YDE-020, YDE-021, YDE-022, YDE-023, YDE-024, YDE-025, YDE-026, YDE-027, YDE-028, YDE-029, YDE-030, YDE-031, YDE-032, YDE-033, YDE-034, YDE-035, YDE-036, YDE-037, YDE-038, YDE-039, YDE-040, YDE-041, YDE-042, YDE-043, YDE-044, YDE-045, YDE-047, YDE-048, YDE-049, YDE-050, YDE-051, YDE-052, YDE-053, YDE-054, YDE-055, YDE-056, YDE-057, YDE-058, YDE-059, YDE-060, YDE-064, YDE-066, YDE-072, YDE-073, YDE-074, YDE-075, YDE-078, YDE-080, YDE-081, YDE-083, YDE-084, YDE-085, YDE-086, YDE-092, YDE-094, and YDE-100 synthesized were 98.3%, 98.9%, 98.7%, 98.5%, 99.1%, 99.4%, 98.0%, 99.6%, 99.6%, 99.2%, 98.1%, 98.3%, 96.1%, 98.9%, 95.1%, 98.6%, 96.9%, 99.5%, 98.0%, 98.1%, 98.8%, 98.2%, 97.2%, 98.6%, 98.8%, 98.7%, 99.2%, 98.7%, 98.1%, 97.5%, 96.5%, 97.4%, 98.7%, 97.8%, 95.5%, 97.5%, 97.2%, 96.9%, 99.3%, 98.0%, 99.4%, 96.4%, 95.1%, 98.6%, 97.4%, 98.8%, 97.4%, 95.8%, 98.9%, 96.9%, 98.8%, 97.7%, 95.0%, 97.9%, 96.3%, 97.8%, 99.2%, 98.6%, 95.9%, 99.2%, 99.0%, 95.1%, 95.0%, 97.4%, and 98.7%, respectively.

In addition, the YDE derivatives prepared in Example 1 were analyzed by Ion-Mass. As a result, it was confirmed that the molecular weights of YDE-001, YDE-002, YDE-003, YDE-004, YDE-005, YDE-006, YDE-007, YDE-008, YDE-009, YDE-010, YDE-011, YDE-012, YDE-013, YDE-014, YDE-015, YDE-016, YDE-017, YDE-018, YDE-019, YDE-020, YDE-021, YDE-022, YDE-023, YDE-024, YDE-025, YDE-026, YDE-027, YDE-028, YDE-029, YDE-030, YDE-031, YDE-032, YDE-033, YDE-034, YDE-035, YDE-036, YDE-037, YDE-038, YDE-039, YDE-040, YDE-041, YDE-042, YDE-043, YDE-044, YDE-045, YDE-047, YDE-048, YDE-049, YDE-050, YDE-051, YDE-052, YDE-053, YDE-054, YDE-055, YDE-056, YDE-057, YDE-058, YDE-059, YDE-060, YDE-064, YDE-066, YDE-072, YDE-073, YDE-074, YDE-075, YDE-078, YDE-080, YDE-081, YDE-083, YDE-084, YDE-085, YDE-086, YDE-092, YDE-094, and YDE-100 synthesized were 969.6, 954.8, 967.7, 977.1, 968.1, 926.9, 941.1, 910.7, 939.7, 953.0, 953.7, 987.8, 1003.8, 1025.9, 996.7, 1011.0, 1011.4, 968.7, 1044.4, 1061.4, 1084.5, 1035.0, 984.9, 999.1, 969.7, 942.0, 937.6, 967.3, 988.1, 960.6, 954.2, 991.1, 954.4, 990.7, 950.9, 937.6, 968.1, 955.4, 966.0, 709.3, 622.2, 486.8, 951.3, 951.3, 911.4, 967.5, 896.5, 911.0, 967.3, 911.2, 953.2, 967.2, 927.4, 896.4, 952.8, 953.4, 670.1, 953.3, 599.7, 486.5, 966.1, 895.8, 909.1, 486.4, 995.1, 953.1, 486.5, 486.5, 486.5, 486.5, 486.5, 486.5, 673.2, and 823.9, respectively.

Example 2: Preparation of YDE Derivatives with Modified C-Terminus

Preparation of YDE Peptides

YDE peptides (YDE-093, YDE-096, and YDE-101 through YDE-107), derivatives of the amino acid sequence of the YDE-011, were obtained through the C-terminal modification of a YDE peptide such as YDE-011.

In order to prepare C-terminal modified peptide, Fmoc solid-phase peptide synthesis (SPPS) was conducted, based on a standard procedure described in WO 2018/225961 and further a C-terminal amidation reaction was carried out.

The peptides of the invention are made through an analogous procedure by, e.g., substituting in a different amino acid building block reagent in a desired step.

Exemplary Preparation of YDE-093

To prepare C-terminal amidated peptide YDE-093, a synthetic process was conducted as depicted in Scheme A, below. The Fmoc protected 10-mer peptide (Fmoc-Hyp-H-Gly-Gln-Leu-Gly-Ala-Leu-Gly-Pro-Lys(Dde)-OH (SEQ ID NO: 133)) was prepared according to the procedure described in WO 2018/225961.

Based on the selected amino acid sequence, a chain reaction was conducted in this order as below:
1) Fmoc-Lys(Dde)-OH
2) Fmoc-Pro-OH
3) Fmoc-Gly-OH
4) Fmoc-Ala-OH
5) Fmoc-Leu-OH
6) Fmoc-Gly-OH
7) Fmoc-Leu-OH
8) Fmoc-Gln(Trt)-OH
9) Fmoc-Gly-OH
10) Fmoc-Hyp(tBu)-OH Scheme A (Scheme A discloses SEQ ID NOS 134-140, 140-141, 141, 113-114, 114 and 114, respectively, in order of appearance)

Resin Loading

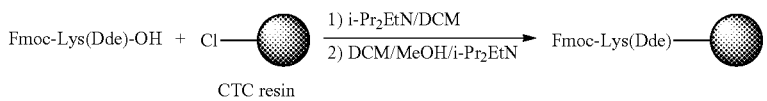

CTC resin

Coupling the Building Blocks

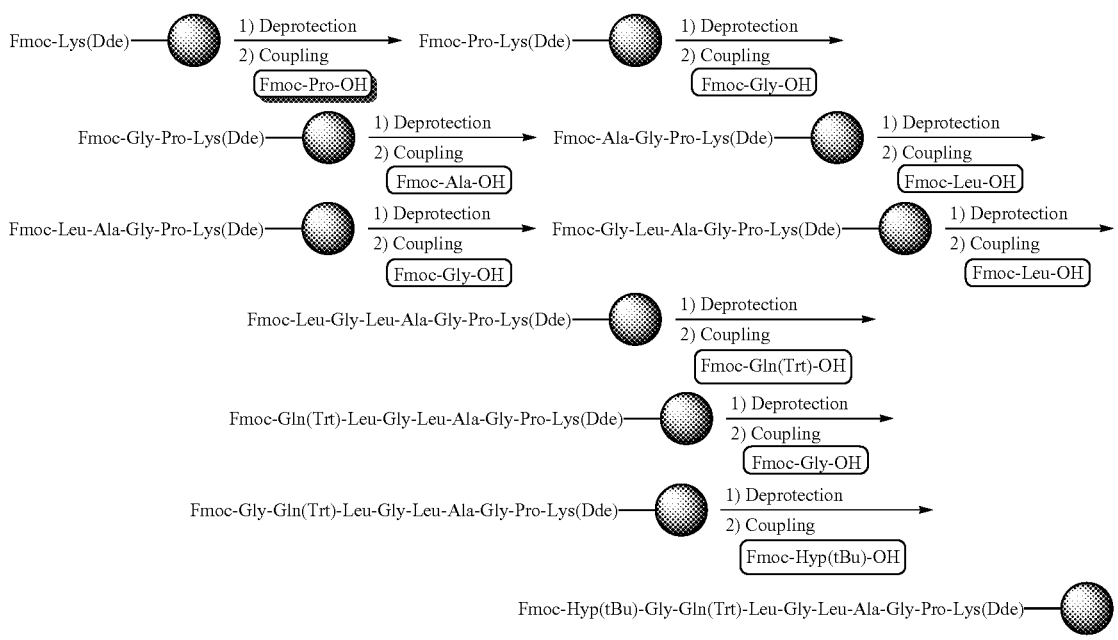

Resin Cleavage

C-terminal Amidation & Deprotection

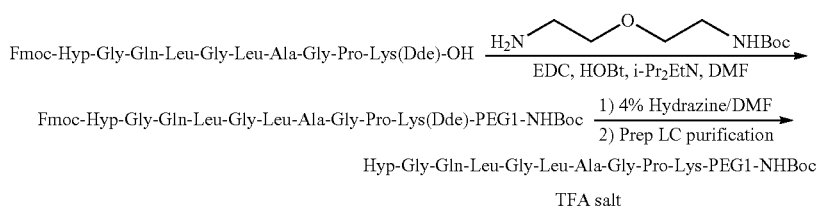

Hyp-Gly-Gln-Leu-Gly-Leu-Ala-Gly-Pro-Lys-PEG1-NHBoc
TFA salt

Salt Exchange

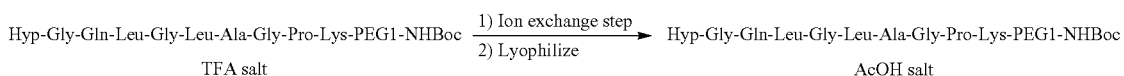

= resin

Deprotection = 20% piperidine/DMF
Coupling = HBTU, NMM, DMF

To a solution of Fmoc-Hyp-Gly-Gln-Leu-Gly-Ala-Leu-Gly-Pro-Lys(Dde)-OH (S EQ ID NO: 133) (500 mg, 0.37 mmol) and tert-butyl (2-(2-aminoethoxy)ethyl)carbamate (91 mg, 0.44 mmol) in DMF (10 mL) was added HOBt (76 mg, 0.56 mmol), EDCI (107 mg, 0.56 mmol) and i-Pr₂EtN (24 μL, 0.136 mmol) at 0° C. and stirred for 1 hour at same temperature. After 1 hour, the reaction mixture was allowed to warm to room temperature and stirred for 16 hours. After the reaction was completed, the reaction mixture was poured into water (20 mL) and extracted with DCM (20 mL×2). The combined organic layers were further washed with water (20 mL×2) and concentrated in vacuo. The residue was precipitation from diethyl ether to afford a desired Fmoc-protected peptide (400 mg, 71%) as a white solid.

Fmoc-Hyp-Gly-Gln-Leu-Gly-Ala-Leu-Gly-Pro-Lys (Dde)-PEG1-NHBoc (SEQ ID NO: 115) (400 mg, 0.26 mmol) was put into a reaction vessel and 4% Hydrazine in DMF solution (10 mL) was added and stirred for 30 min, then diethyl ether (40 mL) was added to induce precipitation. Thereafter, the precipitates were collected by filtration, followed by washing twice with excess ether to afford the crude peptide YDE-093 (quantitative yield) as a white solid. The crude YDE-093 was purified by Preparative HPLC system. The purified peptide was exchanged from TFA salt to AcOH salt by ion exchange resin. The ion exchanged peptide was dried by lyophilizer.

YDE-093, YDE-096, and YDE-101 through YDE-107 are depicted in Table A below.

TABLE 1A

| No. | Chemical structure | SEQ ID NO. |
|---|---|---|
| YDE-093 | 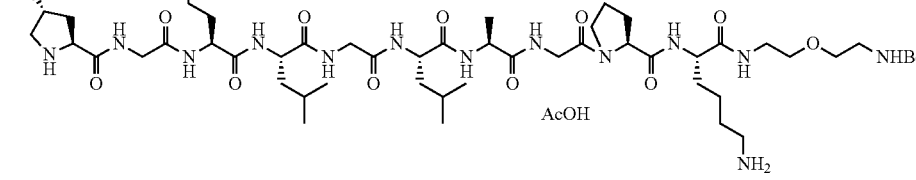 Hyp (2S, 4R)   Gly   Gln   Leu   Gly   Leu   Ala   Gly   Pro   Lys-NH-PEG-NHBoc | SEQ ID NO: 93 |
| YDE-096 | 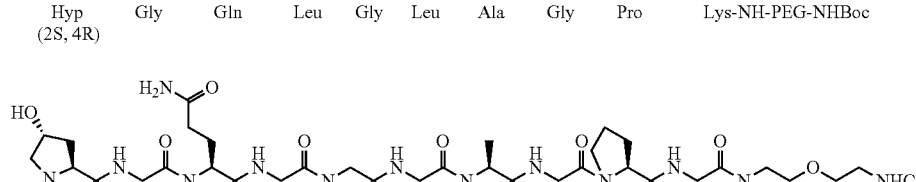 Hyp (2S, 4R)   Gly   Gln   Leu   Gly   Leu   Ala   Gly   Pro   Lys-NH-PEG1-NHCbz | SEQ ID NO: 96 |
| YDE-101 | 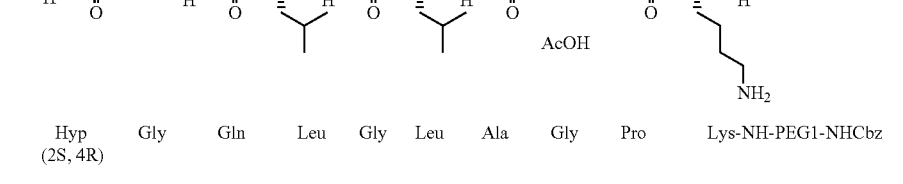 Hyp (2S, 4R)   Gly   Gln   Leu   Gly   Leu   Ala   Gly   Pro (dimethyl) | SEQ ID NO: 116 |
| YDE-102 | 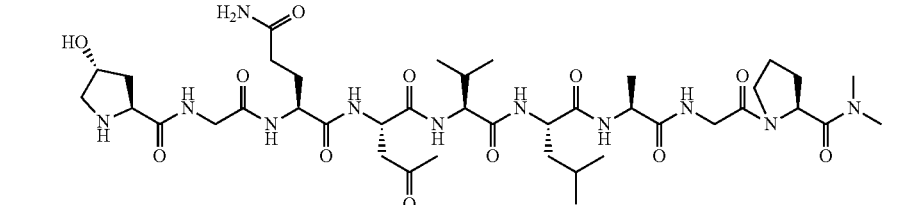 Hyp (2S, 4R)   Gly   Gln   Leu   Gly   Leu   Ala   Gly   Pro (diethyl) | SEQ ID NO: 132 |

TABLE 1A-continued

| No. | Chemical structure | SEQ ID NO. |
|---|---|---|
| YDE-103 | Hyp Gly Gln Leu Gly Leu Ala Gly Pro (azetidine) (2S, 4R) | SEQ ID NO: 103 |
| YDE-105 | Hyp Gly Gln Leu Gly Leu Ala Gly Pro (methylethyl) (2S, 4R) | SEQ ID NO: 105 |
| YDE-106 | Hyp Gly Gln Leu Gly Leu Ala Gly Pro (pyrrolidine) (2S, 4R) | SEQ ID NO: 106 |
| YDE-107 | Hyp Gly Gln Leu Gly Leu Ala Gly Pro (isopropylethyl) (2S, 4R) | SEQ ID NO: 107 |

Analysis of YDE Peptides

The YDE peptides prepared in Example 2 were analyzed by HPLC. As a result, it was confirmed that the purities of YDE-093, YDE-096, YDE-101, YDE-102, YDE-103, YDE-105, YDE-106 and YDE-107 synthesized were 99.1%, 95.4%, 96.7%, 97.2%, 97.9%, 97.4%, 97.2% and 98.2%, respectively.

In addition, the YDE derivatives prepared in Example 2 were analyzed by Ion-Mass. As a result, it was confirmed that the molecular weights of YDE-093, YDE-096, YDE-101, YDE-102, YDE-103, YDE-105, YDE-106 and YDE-107 synthesized were 1139.0, 1173.6, 851.9, 880.1, 864.5, 866.1, 878.4 and 894.3, respectively.

Example 3: Evaluation of the Eye Protection Effect on Dry Eye Syndrome by the YDE Derivatives Preparation of Rats with Dry Eye Syndrome In order to evaluate the eye protection effect on dry eye syndrome by YDE-001 to YDE-028 prepared in Example 1, a total of 320 Sprague-Dawley-type male rats (OrientBio, Seungnam, Korea) were adapted for 7 days. Thereafter, dry eye syndrome was induced in 264 test rats through extra-orbital lacrimal gland excision (hereinafter, ELGE). 8 test rats without the eye abnormality were subjected to a sham operation as a control group.

Figure 4:
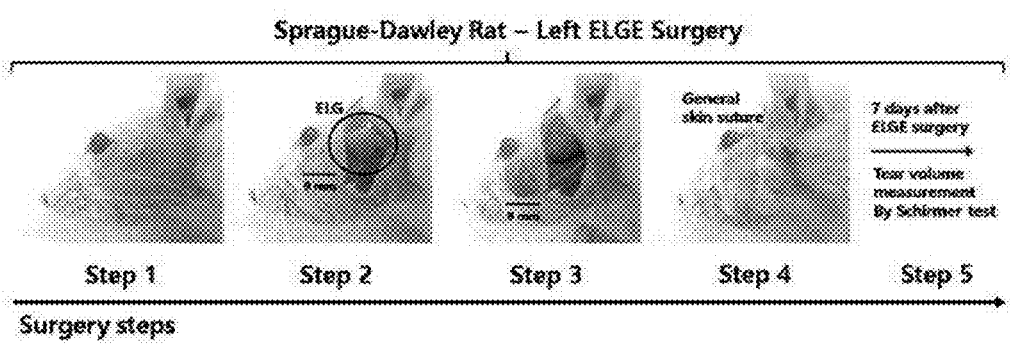
FIG. 4 is a photograph showing a procedure of extraorbital lacrimal gland excision.

The rat was systemically anesthetized by inhaling a mixed gas of 2% to 3% of isoflurane (Hana Pharm. Co., Hwasung, Korea), 70% of $N_2O$, and 28.6% of $O_2$ using a rodent anesthesia machine (Surgivet, Waukesha, Wis., USA) and a ventilator (Model 687, Harvard Apparatus, Cambridge, UK). Thereafter, the extraorbital lacrimal gland located in the subdermal area above the masseter muscle and under the optic nerve was excised through a transverse incision in a size of 10 mm on the anterior part of the left ear tragus. The skin was sutured by a general method. The ELGE operation time did not exceed 5 minutes for each rat. After 6 days from the ELGE operation, it was checked through the Schirmer test by measuring the amount of tear secretion whether dry eye syndrome had been induced. Meanwhile, each rat of the control group with the sham operation was checked for the presence and location of the extraorbital lacrimal gland through a skin incision, and the skin was then sutured without the excision thereof (FIG. 4).

The average weight of the ELGE test group measured before the ELGE operation was 241.59±13.56 g, and the average weight measured after 6 days from the ELGE operation was 297.38±34.02 g. The average weight of the control group measured before the sham operation was 240.13±25.63 g, and the average weight measured after 6 days from the sham operation was 297.38±34.02 g (FIG. 5).

The average amount of tear secretion of the control group was 8.34±0.73 mm$^3$, and the average amount of tear secretion of the ELGE test group was 3.55±0.70 mm$^3$. 8 rats per group and a total of 32 groups were selected based on the average amount of tear secretion.

As a reference drug, 3% diquafosol sodium (Santen, Tokyo, Japan; hereinafter, DS), which is currently on the market, was used.

The present animal tests were conducted with a prior approval of the Animal Experimental Ethics Committee of Daegu Haany University (Approval No. DHU2017-003, Jan. 12, 2017). All test animals were fasted for 18 hours before the ELGE operation and final sacrifice except for feeding water.

The 32 groups were summarized in Table 2.

TABLE 2

| Group classification | 32 groups in total; 8 rats per group |
|---|---|
| Sham control group | Group administered with physiological saline after the sham operation |
| ELGE control group | Group administered with physiological saline after the ELGE operation |
| Reference | Group administered with DS after the ELGE operation |
| YY-102 | Group administered with a 0.3% YY-102 solution after the ELGE operation |
| YDE series | Group administered with any of 0.3% YDE-01 to YDE-28 solutions (28 groups in total) |

In addition, in order to evaluate the eye protection effect on dry eye syndrome by YDE-029 to YDE-043 prepared in Example 1, a total of 200 Sprague-Dawley-type male rats (OrientBio, Seungnam, Korea) were adapted for 7 days. Dry eye syndrome was induced in 165 test rats through the ELGE. 8 test rats without the eye abnormality were subjected to the sham operation as a control group. The ELGE was carried out as described above.

The average weight of the ELGE test group measured before the ELGE operation was 264.09±11.53 g, and the average weight measured after 6 days from the ELGE operation was 316.13±15.77 g. The average weight of the control group measured before the sham operation was 263.50±9.24 g, and the average weight measured after 6 days from the sham operation was 315.25±10.85 g (FIG. 6).

The average amount of tear secretion of the control group was 10.90±1.69 mm$^3$, and the average amount of tear secretion of the ELGE test group was 4.83±0.99 mm$^3$. 8 rats per group and a total of 20 groups were selected based on the average amount of tear secretion.

As a reference drug, 3% DS, which is currently on the market, was used.

The present animal tests were conducted with a prior approval of the Animal Experimental Ethics Committee of Daegu Haany University (Approval No. DHU2017-050, Jun. 8, 2017). All test animals were fasted for 18 hours before the ELGE operation and final sacrifice except for feeding water.

The 20 groups were summarized in Table 3.

TABLE 3

| Group classification | 20 groups in total; 8 rats per group |
|---|---|
| Sham control group | Group administered with physiological saline after the sham operation |
| ELGE control group | Group administered with physiological saline after the ELGE operation |
| Reference | Group administered with DS after the ELGE operation |
| YY-101 | Group administered with a 0.3% YY-101 solution after the ELGE operation |
| YY-102 | Group administered with a 0.3% YY-102 solution after the ELGE operation |
| YDE series | Group administered with any of 0.3% YDE-01 to YDE-28 solutions (15 groups in total) |

Administration of the YDE Derivatives

For YDE-001 to YDE-028, YY-102 and the 28 YDE-series were each dissolved in physiological saline at a concentration of 3 mg/ml and administered at a dose of 5 µl/eye at 9:30 am and 3:30 pm daily for 14 days after 7 days from the ELGE operation for a total of 28 times. The DS solution was dissolved in physiological saline at a concentration of 30 mg/ml and administered at a dose of 5/eye twice a day for 14 days after 7 days from the ELGE operation for a total of 28 times. For the sham control and the ELGE control groups, the same stimulation as the administration was applied. In order to prevent excessive eye dryness, the same volume of physiological saline was applied in the same manner in place of the test substances.

Further, for YDE-029 to YDE-043, YY-102 and the 15 YDE-series were each dissolved in physiological saline at a concentration of 3 mg/ml and administered at a dose of 5 µl/eye at 9:30 am and 3:30 pm daily for 14 days after 7 days from the ELGE operation for a total of 28 times. The DS solution was dissolved in physiological saline at a concentration of 30 mg/ml and administered at a dose of 5/eye twice a day for 14 days after 7 days from the ELGE operation for a total of 28 times. For the sham control and the ELGE control groups, the same stimulation as the administration was applied. In order to prevent excessive eye dryness, the same volume of physiological saline was applied in the same manner in place of the test substances (FIG. 7).

Confirmation of the Changes in the Amount of Tear Secretion by the YDE Derivatives After 6 days from the ELGE surgery, the changes in the amount of tear secretion were measured at day 7 and day 14 after the administration of YDE-001 to YDE-043. The amount of tear secretion was measured by the decrease in the travel distance of tears absorbed by cobalt chloride paper in a size of 1×15 mm (Toyo Roshi Kaisha, Japan).

The cobalt chloride paper was placed in the lateral canthus of a rat for 60 seconds to absorb tears (FIG. 9). The length of the area absorbed from the corner of the cobalt chloride paper was measured with an electronic digital caliper (Mytutoyo, Tokyo, Japan) (FIG. 8).

FIG. 9 shows the results of the test, wherein A is for the sham control group, B is for the ELGE control group, C is for the DS reference group, D is for the YY-102 administered group, and E to AF are for the YDE-001 to YDE-028 administered groups in order.

As a result, it was confirmed that the amount of tear secretion was decreased after 6 days from the ELGE operation at days 7 and 14 after the application of physiological saline in the ELGE control group as compared with the sham control group. In the groups treated with YDE derivatives and the DS reference group, the amount of tear secretion was increased as compared with the ELGE control group, except for the groups treated with a 3% solution of YDE-9, YDE-10, YDE-17, YDE-19, YDE-20, YDE-21, YDE-22, YDE-25, YDE-27, and YDE-28, which did not show any significant changes in the amount of tear secretion after the administration thereof for 14 days. Especially, the amount of tear secretion was increased by more than 20% in the groups treated with a 3% solution of YDE-15, YDE-11, YDE-08, YDE-26, YDE-16, YDE-01, YDE-23, and YY-102 as compared with the DS reference group.

The specific amounts of tear secretion are shown in FIG. 10 and Table 4.

TABLE 4

| No. | Tear Volumes (mm$^3$) | |
| --- | --- | --- |
|  | Day 7 | Day 14 |
| YY-101 | 7.66 ± 0.61 | 6.00 ± 0.69 |
| YY-102 | 4.59 ± 1.43 | 5.77 ± 1.99 |
| YDE-001 | 4.88 ± 1.62 | 5.92 ± 2.19 |
| YDE-002 | 3.84 ± 1.16 | 5.01 ± 1.67 |
| YDE-003 | 4.13 ± 1.76 | 4.88 ± 1.57 |
| YDE-004 | 3.42 ± 1.06 | 5.19 ± 1.84 |
| YDE-005 | 3.85 ± 0.93 | 5.08 ± 1.91 |
| YDE-006 | 3.44 ± 1.69 | 5.35 ± 1.68 |
| YDE-007 | 3.91 ± 1.28 | 5.45 ± 1.26 |
| YDE-008 | 4.57 ± 1.25 | 6.10 ± 2.36 |
| YDE-009 | 3.76 ± 1.21 | 4.54 ± 1.11 |
| YDE-010 | 3.42 ± 1.31 | 4.35 ± 1.36 |
| YDE-011 | 4.22 ± 1.45 | 6.16 ± 2.16 |
| YDE-012 | 3.68 ± 0.99 | 5.67 ± 1.86 |
| YDE-013 | 5.27 ± 1.50 | 5.49 ± 1.92 |
| YDE-014 | 3.81 ± 1.21 | 5.62 ± 1.85 |
| YDE-015 | 4.03 ± 2.19 | 6.65 ± 2.13 |
| YDE-016 | 4.59 ± 1.13 | 5.98 ± 2.27 |
| YDE-017 | 4.00 ± 1.22 | 4.89 ± 1.50 |
| YDE-018 | 3.75 ± 1.54 | 4.99 ± 1.60 |
| YDE-019 | 4.84 ± 1.39 | 4.52 ± 1.07 |
| YDE-020 | 3.41 ± 1.47 | 4.20 ± 1.35 |
| YDE-021 | 4.08 ± 1.33 | 4.90 ± 1.13 |
| YDE-022 | 3.19 ± 0.67 | 4.10 ± 0.95 |
| YDE-023 | 5.32 ± 2.30 | 5.78 ± 2.23 |
| YDE-024 | 3.85 ± 1.30 | 5.72 ± 1.36 |
| YDE-025 | 3.21 ± 0.72 | 4.72 ± 2.19 |
| YDE-026 | 4.32 ± 1.47 | 6.01 ± 1.83 |
| YDE-027 | 2.82 ± 0.86 | 3.95 ± 1.52 |
| YDE-028 | 4.04 ± 0.99 | 4.73 ± 1.18 |

FIG. 11 shows the results of the test, wherein A is for the sham control group, B is for the ELGE control group, C is for the DS reference group, D is for the YY-102 administered group, and E to S are for the YDE-029 to YDE-043 administered groups in order.

As a result, it was confirmed that the amount of tear secretion was decreased after 6 days from the ELGE operation at days 7 and 14 after the application of physiological saline in the ELGE control group as compared with the sham control group. In the groups treated with YDE derivatives and the DS reference group, the amount of tear secretion was increased as compared with the ELGE control group, except for the groups treated with a 3% solution of YDE-029, YDE-030, YDE-032, YDE-033, YDE-034, YDE-036, and YDE-41, which did not show any significant changes in the amount of tear secretion after the administration thereof for 14 days. Especially, the amount of tear secretion was increased by more than 20% in the groups treated with a 3% solution of YDE-040, YDE-043, and YDE-042 in order as compared with the DS reference group.

The specific amounts of tear secretion are shown in FIG. 12 and Table 5.

TABLE 5

| No. | Tear Volumes (mm$^3$) | |
| --- | --- | --- |
|  | Day 7 | Day 14 |
| YY-101 | 5.36 ± 0.68 | 6.25 ± 0.68 |
| YY-102 | 5.77 ± 1.01 | 6.60 ± 0.64 |
| YDE-029 | 5.33 ± 1.43 | 6.03 ± 1.71 |
| YDE-030 | 5.69 ± 1.79 | 6.65 ± 2.17 |
| YDE-031 | 5.63 ± 1.97 | 5.91 ± 0.85 |
| YDE-032 | 5.58 ± 0.80 | 5.03 ± 0.93 |
| YDE-033 | 4.99 ± 1.20 | 4.54 ± 1.16 |
| YDE-034 | 6.16 ± 1.01 | 6.43 ± 1.86 |
| YDE-035 | 4.96 ± 0.96 | 6.25 ± 0.79 |
| YDE-036 | 4.95 ± 1.05 | 5.13 ± 1.03 |
| YDE-037 | 4.98 ± 0.66 | 5.80 ± 0.90 |
| YDE-039 | 6.04 ± 1.01 | 6.44 ± 1.96 |
| YDE-040 | 5.77 ± 1.05 | 8.63 ± 1.53 |
| YDE-041 | 5.01 ± 1.26 | 6.25 ± 2.15 |
| YDE-042 | 6.30 ± 1.08 | 7.97 ± 1.48 |
| YDE-043 | 5.90 ± 1.06 | 8.16 ± 1.42 |

Confirmation of the Changes in the Corneal Damage by the YDE Derivatives

After YDE-001 to YDE-028 were each administered to the eyes 14 times, the changes in the corneal permeability were checked.

In order to measure the corneal permeability, Zolethyl 50™ (Virbac Lab., Carros, France), an animal anesthetic, was intraperitoneally injected at a dose of 25 mg/kg. Thereafter, saline containing a 1% (v/v) fluorescent solution (fluorescein sodium salt, Tokyo Kasei Kogyo Co., Tokyo, Japan) was applied to the eyes at a dose of 5 µl/eye. The eyes thus treated were closed and fixed with a tape. After 1 hour, the remaining fluorescent solution was removed using a cotton swab (FIG. 12). After 12 hours to 24 hours, the corneal permeability was measured using a blue light tungsten lamp and an ophthalmic slit lamp table top model biomicroscope (Model SM-70N; Takaci Seiko Co., Nakano, Japan) (FIG. 13).

FIG. 14 shows the results of the test, wherein A is for the sham control group, B is for the ELGE control group, C is for the DS reference group, D is for the YY-102 administered group, and E to AF are for the YDE-001 to YDE-028 administered groups in order.

As a result, the permeability of the fluorescent dye was increased in the ELGE control group as compared with the sham control group. The permeability of the fluorescent dye was not decreased in the groups treated with a 3% solution of YDE-10, YDE-20, YDE-22, YDE-25, YDE-27, and YDE-28 as compared with the ELGE control group at day 14 after the administration. In the groups treated with YDE derivatives and the DS reference group, the corneal permeability of the fluorescent dye was decreased as compared with the ELGE control group, except for the groups treated with a 3% solution of YDE-10, YDE-20, YDE-22, YDE-25, YDE-27, and YDE-28. Especially, the permeability of the fluorescent dye was decreased by more than 20% in the groups treated with a 3% solution of YDE-15, YDE-11, YDE-08, YDE-26, YDE-16, YDE-01, YDE-23, and YY-102, as compared with the DS reference group.

The specific permeabilities of the fluorescent dye are shown in FIG. 15 and Table 6.

TABLE 6

| No. | Permeability of fluorescent dye (%) |
|---|---|
| YY-101 | 27.53 ± 5.62 |
| YY-102 | 27.48 ± 14.37 |
| YDE-001 | 25.49 ± 11.62 |
| YDE-002 | 38.26 ± 11.25 |
| YDE-003 | 40.45 ± 6.46 |
| YDE-004 | 35.05 ± 11.74 |
| YDE-005 | 37.98 ± 11.53 |
| YDE-006 | 33.23 ± 13.26 |
| YDE-007 | 32.79 ± 10.77 |
| YDE-008 | 20.32 ± 11.87 |
| YDE-009 | 41.50 ± 7.86 |
| YDE-010 | 49.29 ± 12.06 |
| YDE-011 | 18.11 ± 11.61 |
| YDE-012 | 31.01 ± 11.38 |
| YDE-013 | 32.24 ± 7.84 |
| YDE-014 | 31.15 ± 10.87 |
| YDE-015 | 15.95 ± 6.48 |
| YDE-016 | 24.57 ± 10.34 |
| YDE-017 | 39.76 ± 7.42 |
| YDE-018 | 38.19 ± 10.96 |
| YDE-019 | 40.39 ± 12.57 |
| YDE-020 | 47.84 ± 13.47 |
| YDE-021 | 37.00 ± 10.49 |
| YDE-022 | 47.82 ± 10.01 |
| YDE-023 | 26.51 ± 8.18 |
| YDE-024 | 30.63 ± 10.41 |
| YDE-025 | 47.10 ± 11.45 |
| YDE-026 | 22.63 ± 11.23 |
| YDE-027 | 50.24 ± 11.94 |
| YDE-028 | 41.17 ± 10.25 |

In addition, YDE-029 to YDE-043 were each administered to the eyes 14 times, and the changes in the corneal permeability were then checked. The measurement of the corneal permeability was carried out in the same manner as described above (FIG. 16).

As a result, the permeability of the fluorescent dye was increased in the ELGE control group as compared with the sham control group. The permeability of the fluorescent dye was not decreased in the groups treated with a 3% solution of YDE-29, YDE-32, YDE-33, YDE-36, and YDE-41 as compared with the ELGE control group at day 14 after the administration. In the groups treated with YDE derivatives and the DS reference group, the corneal permeability of the fluorescent dye was decreased as compared with the ELGE control group, except for the groups treated with a 3% solution of YDE-29, YDE-32, YDE-33, YDE-36, and YDE-41. Especially, the permeability of the fluorescent dye was decreased by more than 20% in the groups treated with a 3% solution of YDE-40, YDE-43, and YDE-42, as compared with the DS reference group.

The specific permeabilities of the fluorescent dye are shown in FIG. 17 and Table 7.

TABLE 7

| No. | Permeability of fluorescent dye (%) |
|---|---|
| YY-101 | 33.80 ± 11.11 |
| YY-102 | 27.89 ± 7.10 |
| YDE-029 | 63.45 ± 11.57 |
| YDE-030 | 30.60 ± 13.61 |
| YDE-031 | 33.35 ± 11.01 |
| YDE-032 | 58.90 ± 19.81 |
| YDE-033 | 60.55 ± 21.22 |
| YDE-034 | 32.17 ± 12.94 |
| YDE-035 | 27.62 ± 6.51 |
| YDE-036 | 57.87 ± 22.91 |
| YDE-037 | 36.30 ± 9.75 |
| YDE-039 | 29.94 ± 11.40 |
| YDE-040 | 18.33 ± 9.41 |
| YDE-041 | 46.38 ± 26.65 |
| YDE-042 | 20.72 ± 11.37 |
| YDE-043 | 19.04 ± 7.36 |

Example 4: Evaluation of the Stability of the YDE Derivatives

In order to confirm the stability of each test substance in an aqueous solution, 10 mg of each sample was dissolved in 1 ml of water to a concentration of 1 mg/ml, which was then charged to a glass vial, plugged with a rubber cap, sealed with an aluminum cap, and stored under long-term storage conditions (25° C., 75% RH). The stability of the test substance was evaluated by measuring the amount of related substances at the time of one week, two weeks, four weeks, eight weeks, and twelve weeks under the long-term storage conditions.

As a result, 66.5% of related substances was generated in YY-101 after two weeks. In contrast, 1.1% to 30.6% of related substances was generated in YDE-001 to YDE-028 after 12 weeks. The specific amounts are shown in Table 8.

TABLE 8

| No. | Amount of related substances (%; after 12 weeks) |
|---|---|
| YY-101 | 66.51 (after 2 weeks) |
| YDE-001 | 3.92 |
| YDE-002 | 4.93 |
| YDE-003 | 6.86 |
| YDE-004 | 2.11 |
| YDE-005 | 2.97 |
| YDE-006 | 3.67 |
| YDE-007 | 3.76 |
| YDE-008 | 4.42 |
| YDE-009 | 4.71 |
| YDE-010 | 4.39 |
| YDE-011 | 3.83 |
| YDE-012 | 3.57 |
| YDE-013 | 5.92 |
| YDE-014 | 6.72 |
| YDE-015 | 13.05 |
| YDE-016 | 11.33 |
| YDE-017 | 11.88 |
| YDE-018 | 25.39 |
| YDE-019 | 13.43 |
| YDE-020 | 21.54 |
| YDE-021 | 21.33 |
| YDE-022 | 19.23 |
| YDE-023 | 30.66 |
| YDE-024 | 20.59 |
| YDE-025 | 5.17 |
| YDE-026 | 10.15 |
| YDE-027 | 12.74 |
| YDE-028 | 1.15 |
| YDE-029 | 2.77 |
| YDE-030 | 2.74 |

TABLE 8-continued

| No. | Amount of related substances (%; after 12 weeks) |
|---|---|
| YDE-031 | 34.82 |
| YDE-032 | 6.16 |
| YDE-033 | 5.6 |
| YDE-034 | 1.25 |
| YDE-035 | 3.89 |
| YDE-036 | 8.77 |
| YDE-037 | 2.88 |
| YDE-039 | 2.19 |
| YDE-040 | 3.58 |
| YDE-041 | 3.04 |
| YDE-042 | 3.98 |
| YDE-043 | 3.43 |

Example 5: Evaluation of Recovery of Corneal Damage by the YDE Derivatives

In order to confirm whether the YDE derivatives could recover corneal damage, the cellular growth rate of human primary corneal epithelial cells was checked.

Specifically, primary corneal epithelial cells (ATCC, ATCC PCS-700-010) were seeded on a 96-well culture plate (Perkin Elmer, 6005680) containing the Corneal Epithelial Cell Basal Medium (ATCC, ATCC PCS-700-030) in the Corneal Epithelial Cell Growth Kit (ATCC, ATCC PCS-700-040) in an amount of $5\times10^3$ cells per well, which was then cultured for 24 hours under the conditions of 37° C. and 5% $CO_2$.

YDE-001 to YDE-075 were each dissolved in 100% DMSO (Sigma, D2660) to a concentration of 10 mM, which was then diluted with 100% DMSO to a concentration of the compound of 6, 1.9, 0.6, 0.2, 0.06, 0.02, 0.006, and 0.002 mM. 20 μl of the diluted YDE derivative was added to a 96-well microplate (Greiner Bio-One, 651201) containing 380 μl of the Corneal Epithelial Cell Basal Medium such that the concentration of DMSO was diluted to 5%.

After 24 hours, 20 μl of each of the YDE derivatives diluted in the 96-well microplate was added to the 96-well culture plate containing the cells. As a control group, hEGF (Sigma, E9644) was treated at the same concentration as the YDE derivatives. The cells treated with the YDE-derivatives or hEGF were cultured for 48 hours and 72 hours under the conditions of 37° C. and 5% $CO_2$ (FIGS. 18 to 25).

The cultured cells were treated with the CellTiter-Glo luminescent reagent (Promega, G7573) according to the manufacturer's instructions and reacted for 30 minutes at room temperature. Thereafter, the fluorescent signal (or luminescence signal) was checked using an Envision 2014 Multi-label plate reader. The measured values were normalized using a vehicle control (100% proliferation cell).

As a result, the cell proliferation was observed at concentrations of 0.3 μM or less in YY-101, YY-102, YDE-011, YDE-038, YDE-042, YDE-043, YDE-044, YDE-045, YDE-049, YDE-054, YDE-057, YDE-058, YDE-059, and YDE-060. Especially, a high cell proliferation rate was shown in YY-102, YDE-011, YDE-045, YDE-057, and YDE-060 (FIGS. 26 to 43).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound represented by Formula (I):

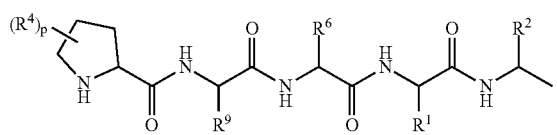

(I)

or a pharmaceutically acceptable salt thereof; wherein:

$R^1$ is unsubstituted alkyl, arylalkyl, or heteroarylalkyl;

$R^2$ and $R^3$ are each independently H or substituted or unsubstituted alkyl, alkoxy, haloalkyl, alkenyl, alkynyl, aryl, arylalkyl, arylalkenyl, arylalkynyl, heteroalkyl, cycloalkyl, heterocycloalkyl, heteroaryl, or heteroarylalkyl;

$R^4$, independently for each occurrence, is selected from substituted or unsubstituted alkyl, aryl, arylalkyl, heterocycloalkyl, oxo, —$OR^b$, —$CH_2OR^b$, halo, hydroxyl, and hydroxyalkyl;

$R^b$ is substituted or unsubstituted alkyl, aryl, arylalkyl, or heterocycloalkyl;

p is 1 or 2;

$R^6$ is hydrogen or substituted or unsubstituted alkyl; and $R^7$, $R^8$, and $R^9$ are each independently hydrogen or alkyl;

wherein when a group is substituted, it is substituted with halogen, hydroxyl, carboxyl (—COOH), alkoxycarbonyl, alkoxyl, amino, amido, heterocyclyl, aralkyl, heteroaryl; and wherein the compound is not:

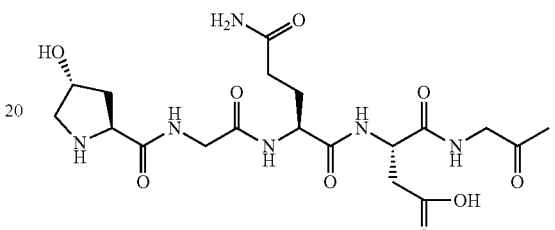

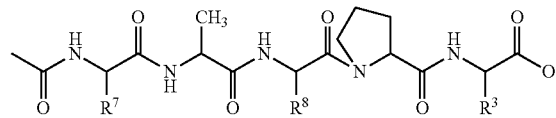

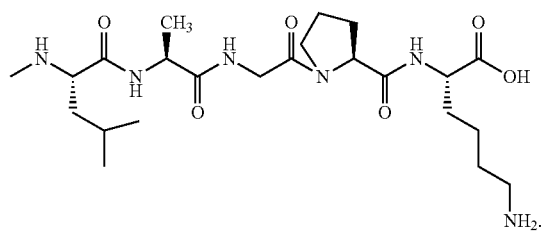

2. The compound of claim 1, wherein:

$R^2$ and $R^3$ are each independently H or substituted or unsubstituted alkyl, arylalkyl, or heteroarylalkyl; and $R^4$, independently for each occurrence, is selected from substituted or unsubstituted alkyl, oxo, hydroxyl, —$OR^b$, hydroxyalkyl, —$CH_2OR^b$, and halo.

3. The compound of claim 1, wherein $R^1$ is selected from

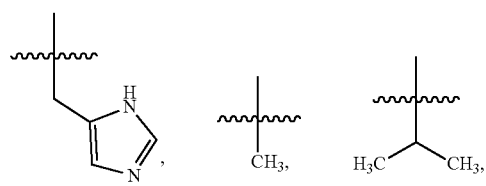

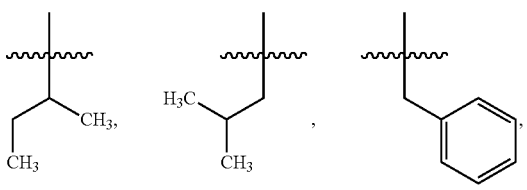

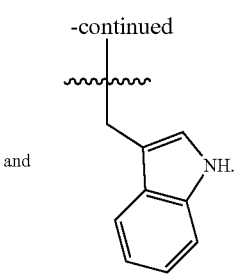
and

4. The compound of claim 1, wherein $R^2$ is hydrogen.

5. The compound of claim 1, wherein $R^3$ is

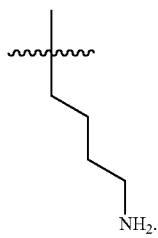 [SMILES: *CCCCN]

6. The compound of claim 1, wherein p is 1; and $R^4$ is hydroxyl.

7. The compound of claim 1, wherein $R^6$ is

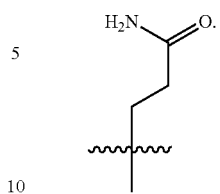

8. The compound of claim 1, wherein $R^7$ is

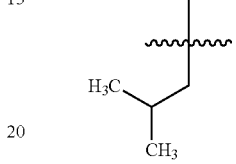

9. The compound of claim 1, wherein $R^8$ is —H.

10. The compound of claim 1, wherein $R^9$ is —CH$_3$ or —H.

11. The compound of claim 1, selected from the following:

(SEQ ID NO: 4)

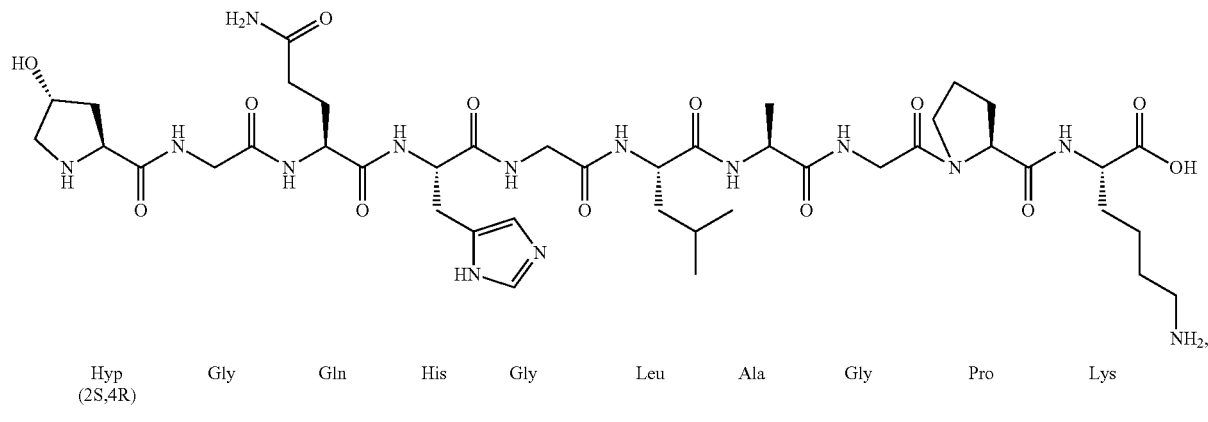

Hyp (2S,4R) — Gly — Gln — His — Gly — Leu — Ala — Gly — Pro — Lys (SEQ ID NO: 8)

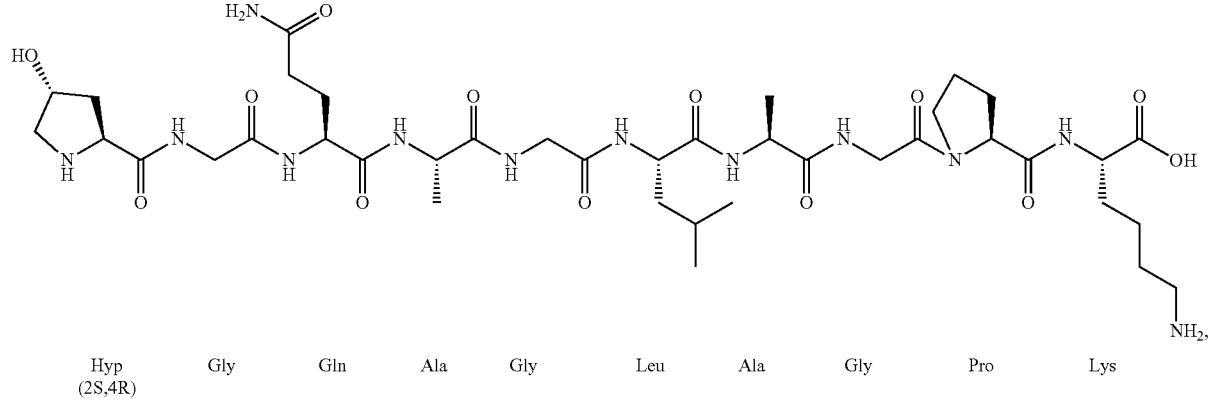

Hyp (2S,4R) — Gly — Gln — Ala — Gly — Leu — Ala — Gly — Pro — Lys (SEQ ID NO: 9)
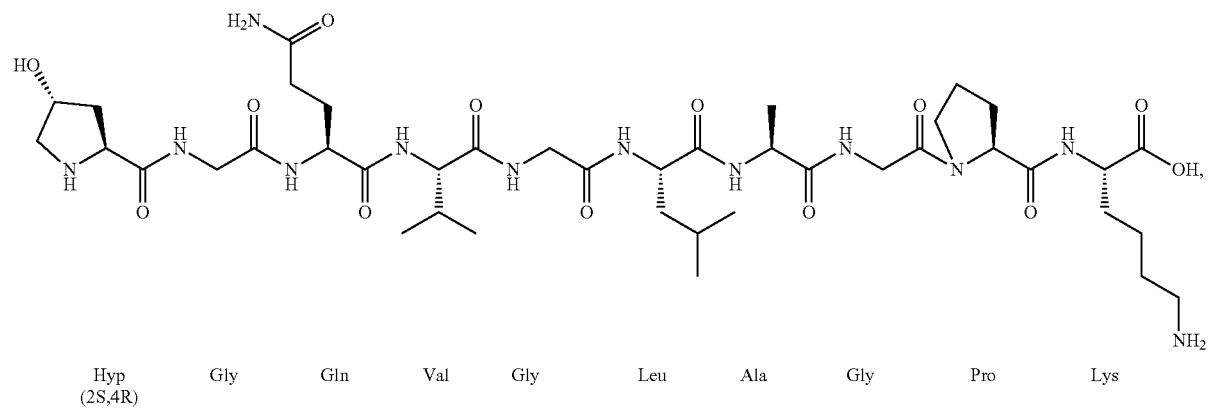
Hyp (2S,4R) — Gly — Gln — Val — Gly — Leu — Ala — Gly — Pro — Lys
(SEQ ID NO: 10)
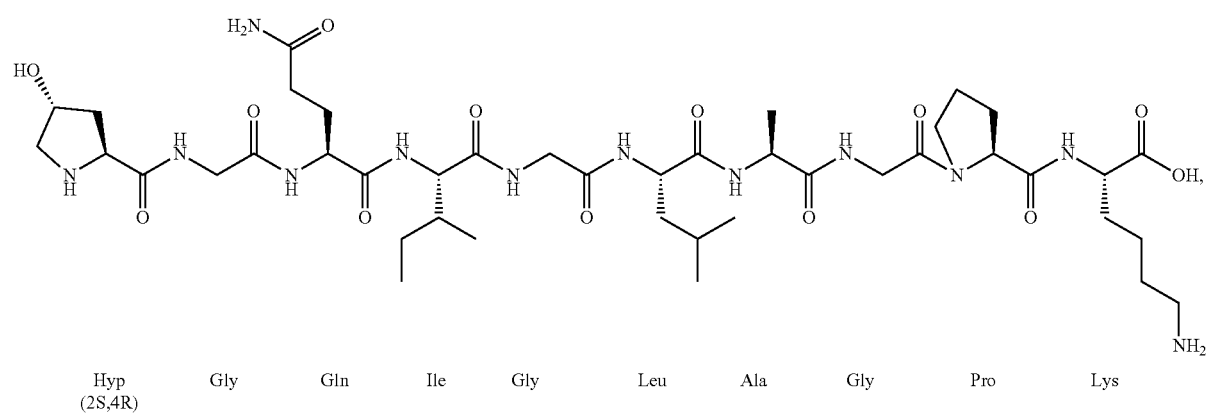
Hyp (2S,4R) — Gly — Gln — Ile — Gly — Leu — Ala — Gly — Pro — Lys
(SEQ ID NO: 11)
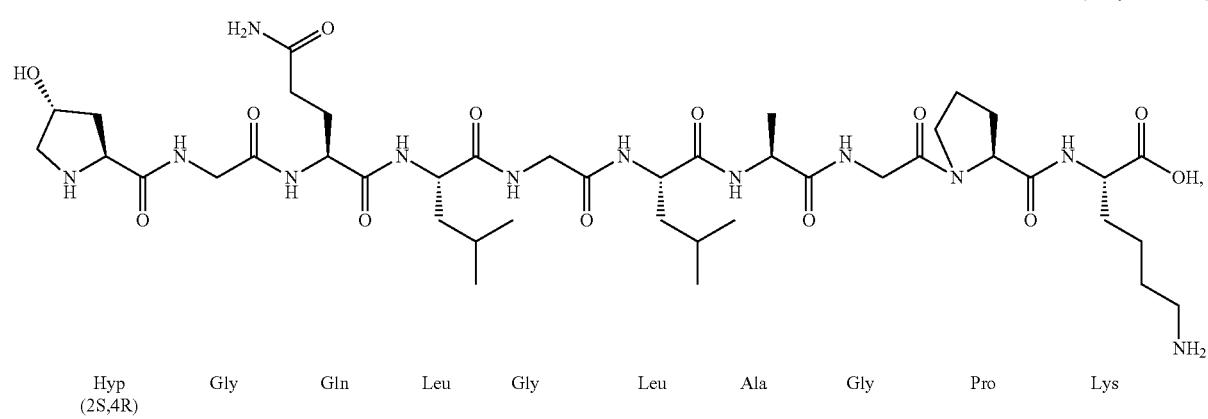
Hyp (2S,4R) — Gly — Gln — Leu — Gly — Leu — Ala — Gly — Pro — Lys (SEQ ID NO: 12)
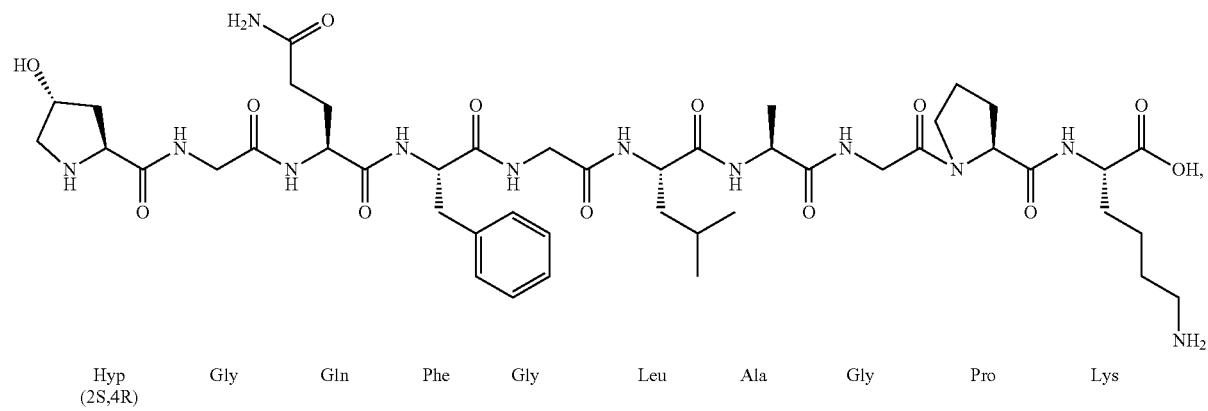
| Hyp (2S,4R) | Gly | Gln | Phe | Gly | Leu | Ala | Gly | Pro | Lys |
(SEQ ID NO: 14)
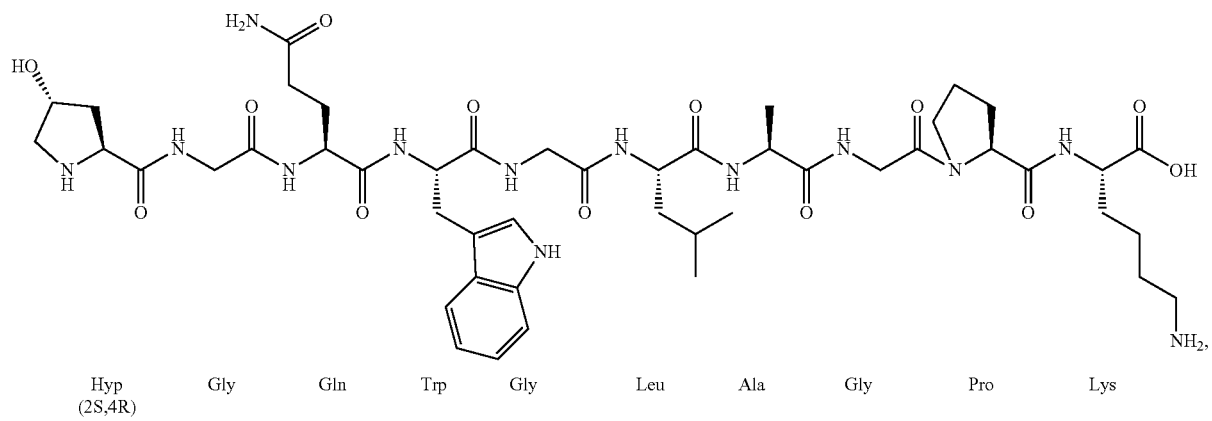
| Hyp (2S,4R) | Gly | Gln | Trp | Gly | Leu | Ala | Gly | Pro | Lys |
(SEQ ID NO: 29)
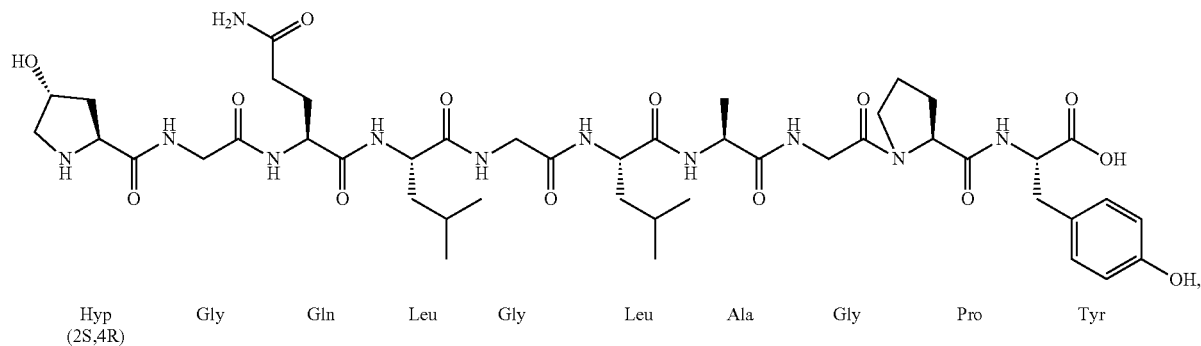
| Hyp (2S,4R) | Gly | Gln | Leu | Gly | Leu | Ala | Gly | Pro | Tyr |
(SEQ ID NO: 30)
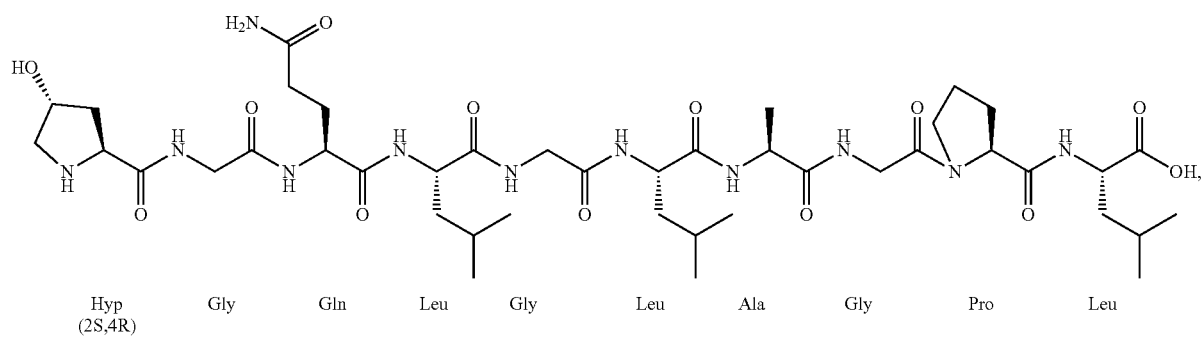
| Hyp (2S,4R) | Gly | Gln | Leu | Gly | Leu | Ala | Gly | Pro | Leu |

(SEQ ID NO: 31)
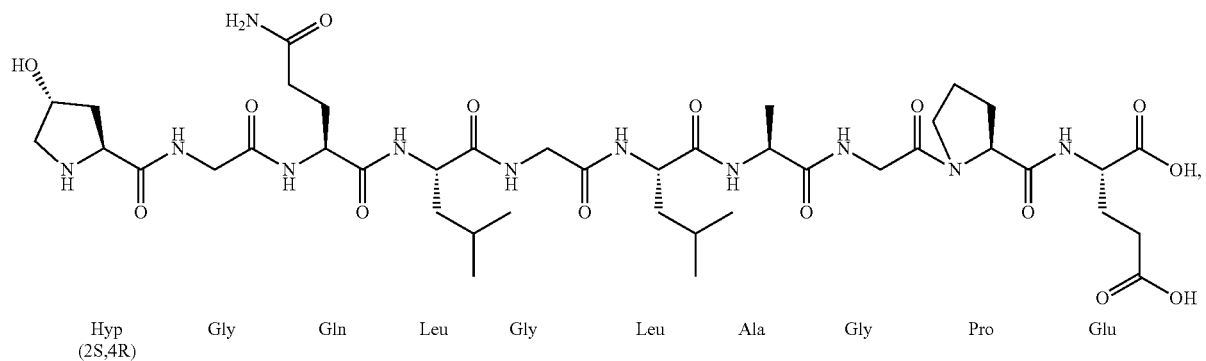
| Hyp (2S,4R) | Gly | Gln | Leu | Gly | Leu | Ala | Gly | Pro | Glu |
(SEQ ID NO: 32)
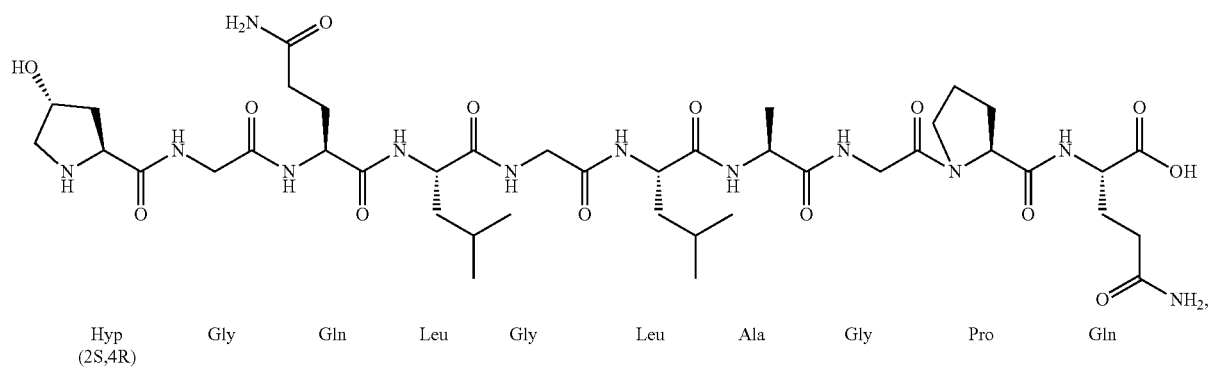
| Hyp (2S,4R) | Gly | Gln | Leu | Gly | Leu | Ala | Gly | Pro | Gln |
(SEQ ID NO: 33)
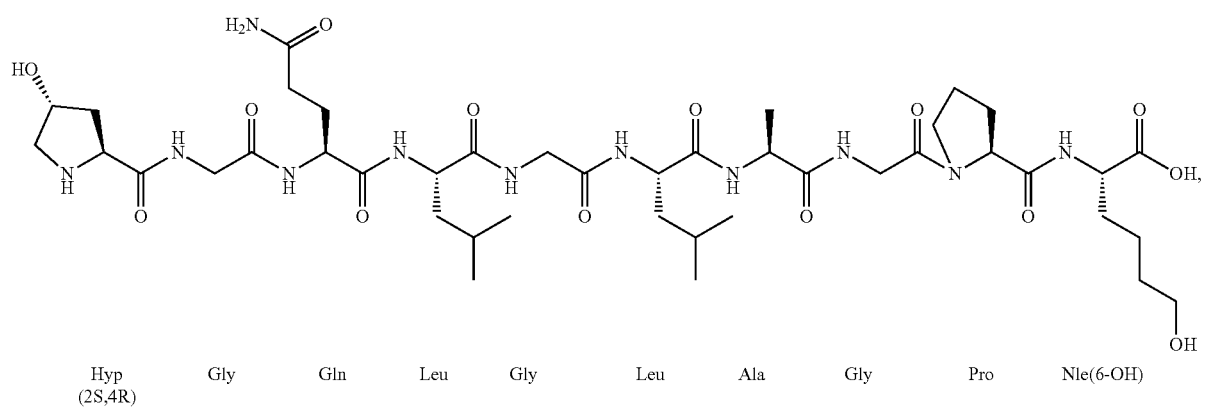
| Hyp (2S,4R) | Gly | Gln | Leu | Gly | Leu | Ala | Gly | Pro | Nle(6-OH) |
(SEQ ID NO: 34)
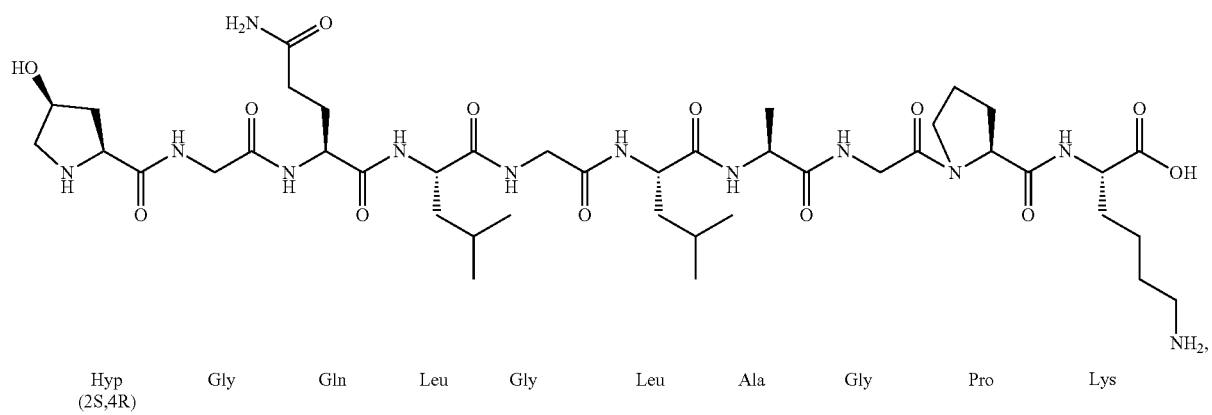
| Hyp (2S,4R) | Gly | Gln | Leu | Gly | Leu | Ala | Gly | Pro | Lys |

-continued
(SEQ ID NO: 35)
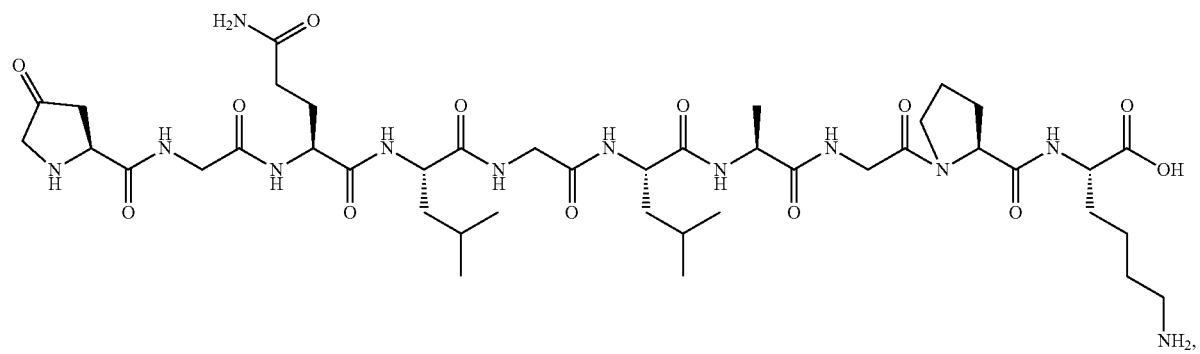
(4-oxo)Pro Gly Gln Leu Gly Leu Ala Gly Pro Lys
(SEQ ID NO: 36)
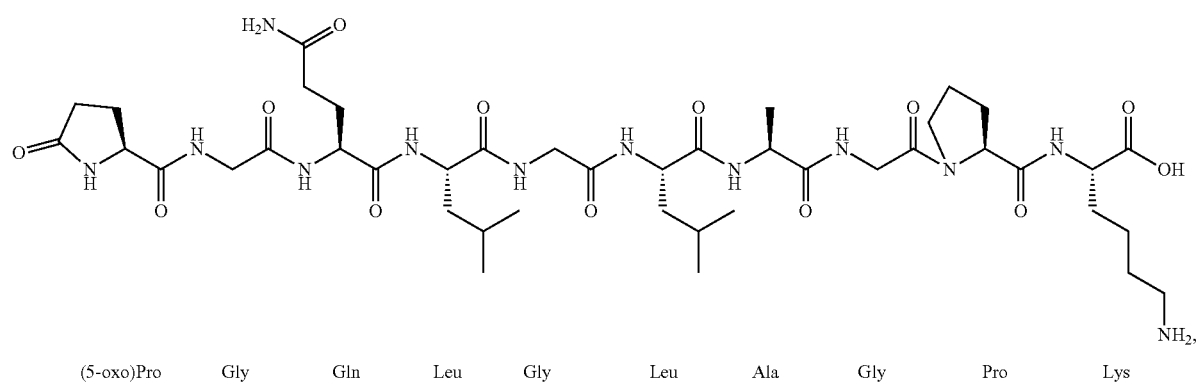
(5-oxo)Pro Gly Gln Leu Gly Leu Ala Gly Pro Lys
(SEQ ID NO: 38)
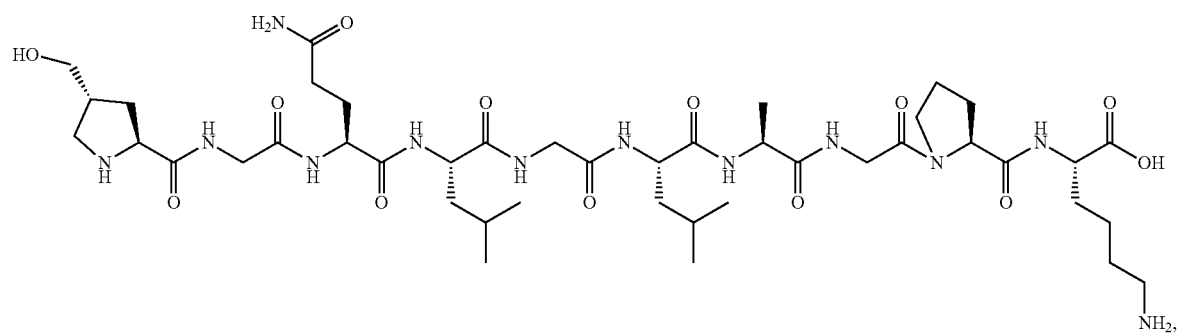
(4-hydroxyMe)Pro Gly Gln Leu Gly Leu Ala Gly Pro Lys
(4R)
(SEQ ID NO: 39)
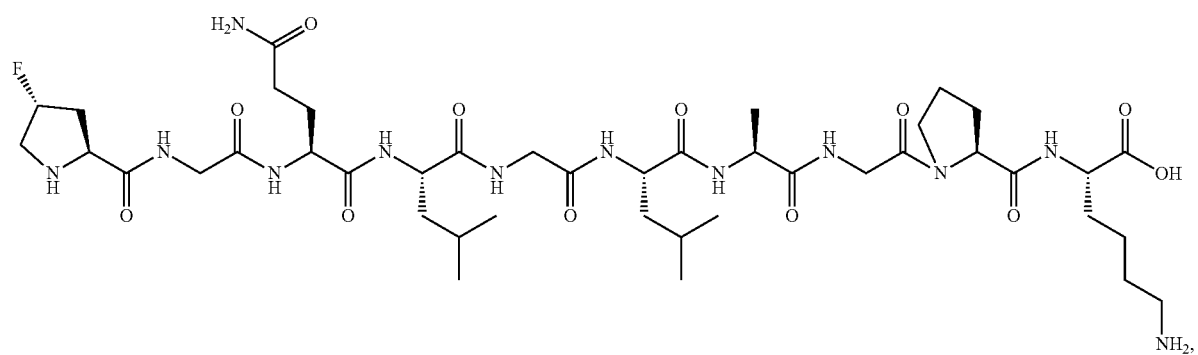
(4-Fluoro)Pro Gly Gln Leu Gly Leu Ala Gly Pro Lys
(4R)

(SEQ ID NO: 40)
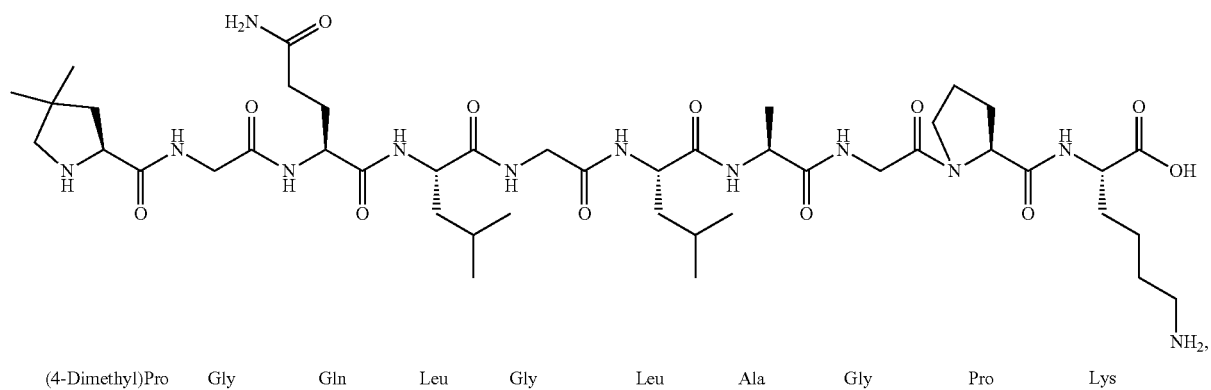
| (4-Dimethyl)Pro | Gly | Gln | Leu | Gly | Leu | Ala | Gly | Pro | Lys |
(SEQ ID NO: 44)
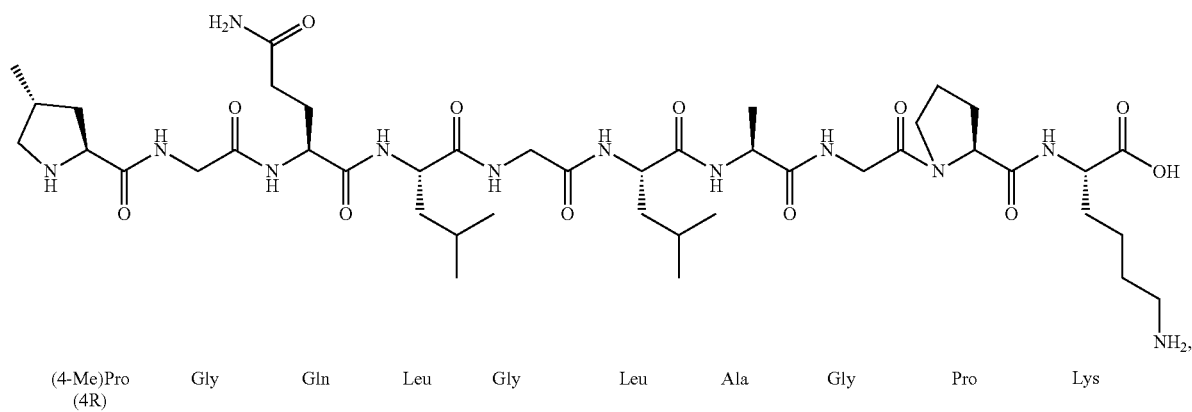
| (4-Me)Pro (4R) | Gly | Gln | Leu | Gly | Leu | Ala | Gly | Pro | Lys |
(SEQ ID NO: 45)
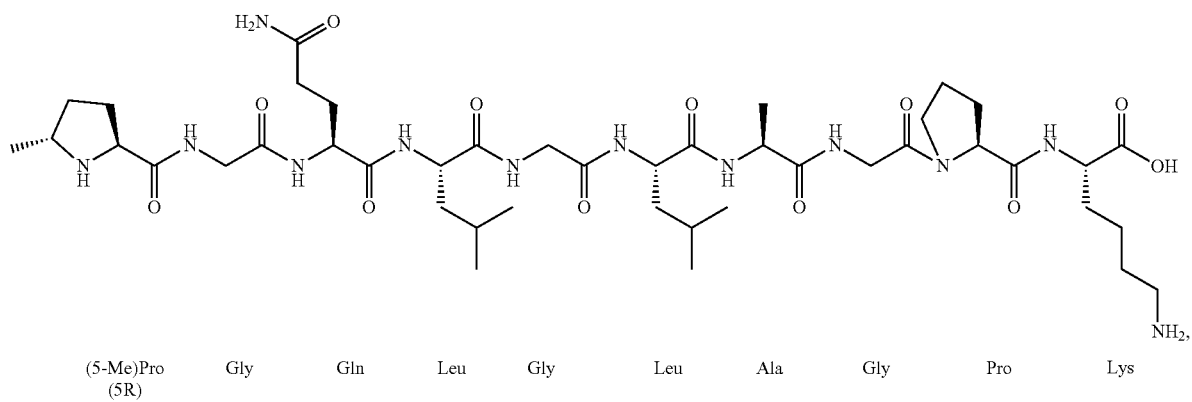
| (5-Me)Pro (5R) | Gly | Gln | Leu | Gly | Leu | Ala | Gly | Pro | Lys |

(SEQ ID NO: 48)
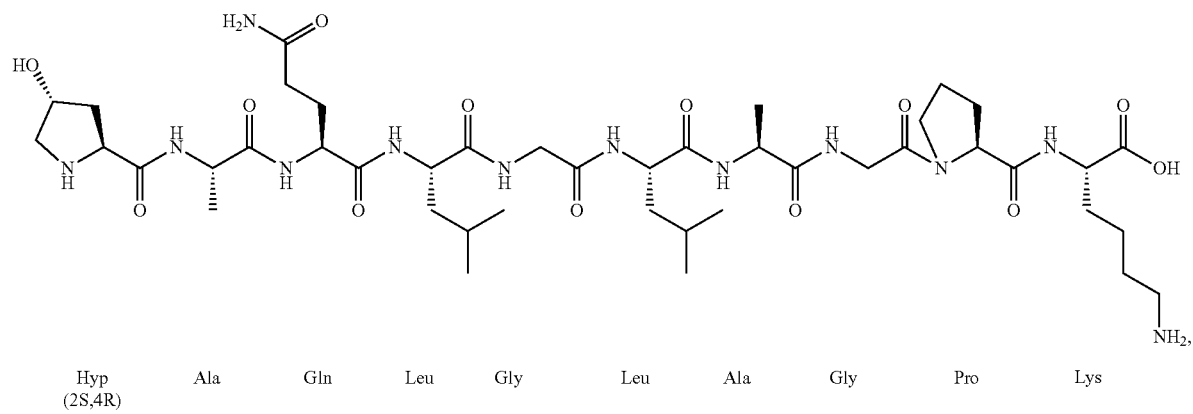
Hyp (2S,4R) — Ala — Gln — Leu — Gly — Leu — Ala — Gly — Pro — Lys
(SEQ ID NO: 49)
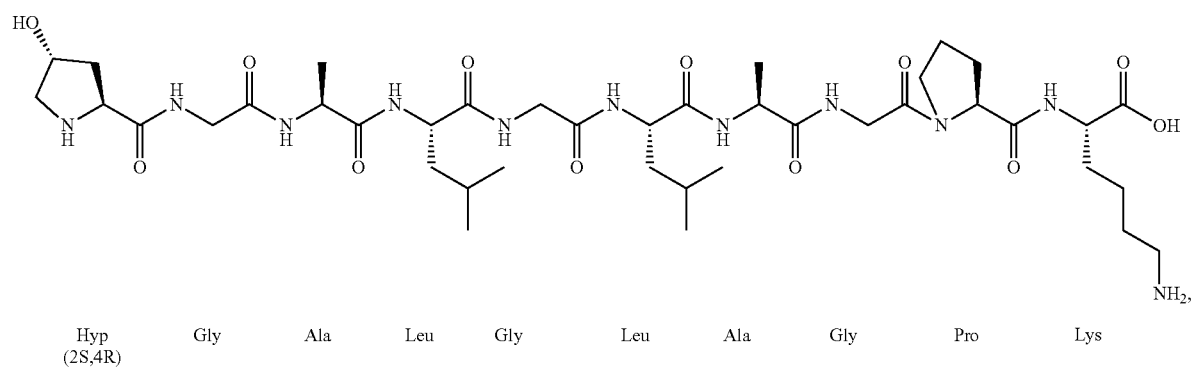
Hyp (2S,4R) — Gly — Ala — Leu — Gly — Leu — Ala — Gly — Pro — Lys
(SEQ ID NO: 8)
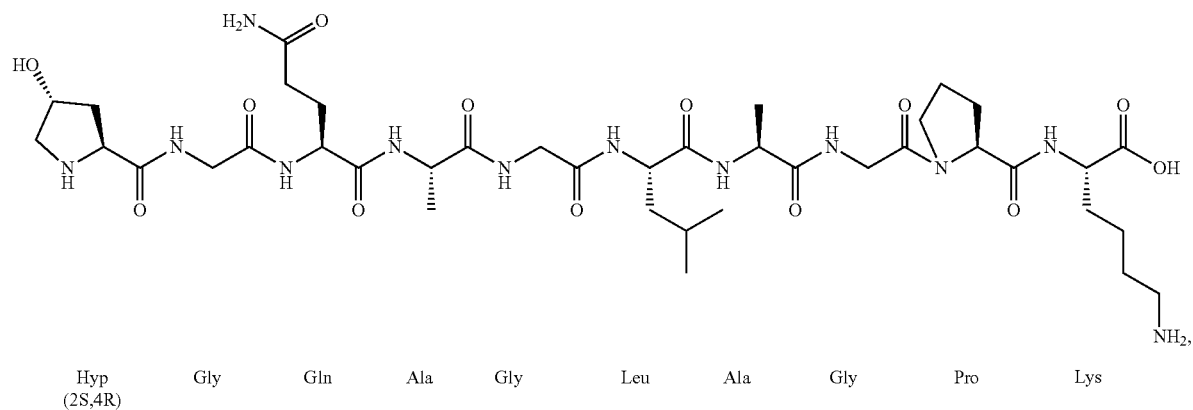
Hyp (2S,4R) — Gly — Gln — Ala — Gly — Leu — Ala — Gly — Pro — Lys (SEQ ID NO: 51)
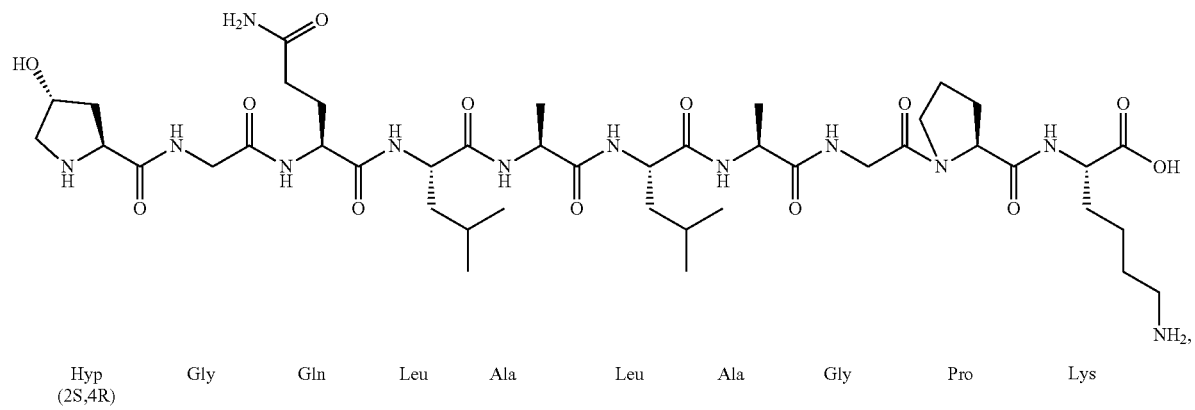
| Hyp (2S,4R) | Gly | Gln | Leu | Ala | Leu | Ala | Gly | Pro | Lys |
(SEQ ID NO: 52)
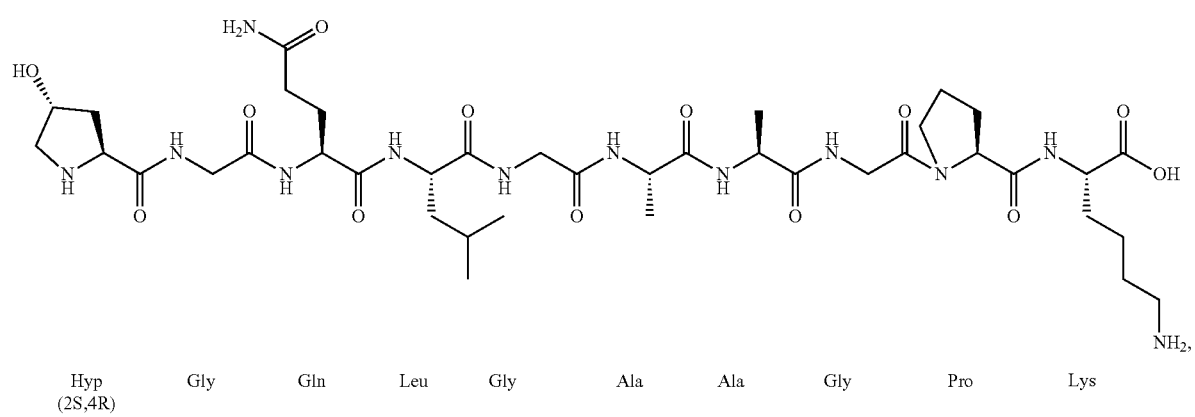
| Hyp (2S,4R) | Gly | Gln | Leu | Gly | Ala | Ala | Gly | Pro | Lys |
(SEQ ID NO: 54)
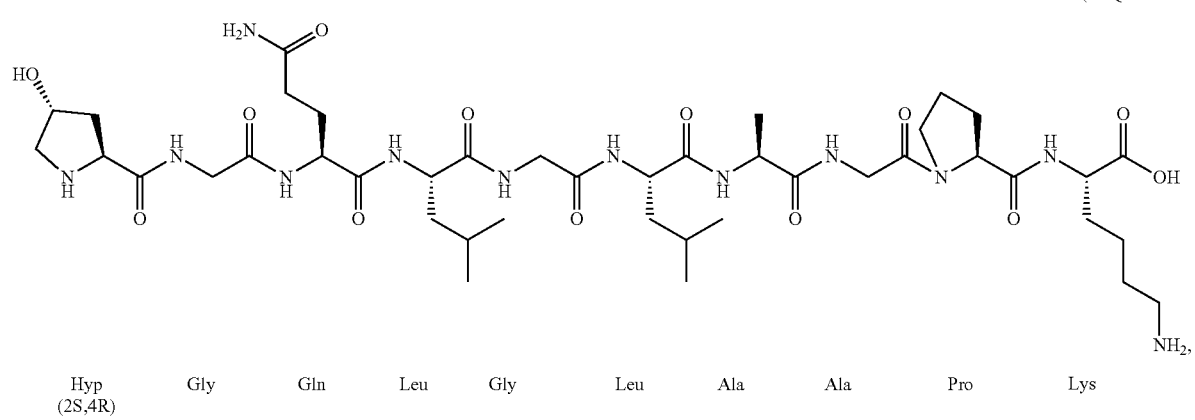
| Hyp (2S,4R) | Gly | Gln | Leu | Gly | Leu | Ala | Ala | Pro | Lys |
(SEQ ID NO: 56)
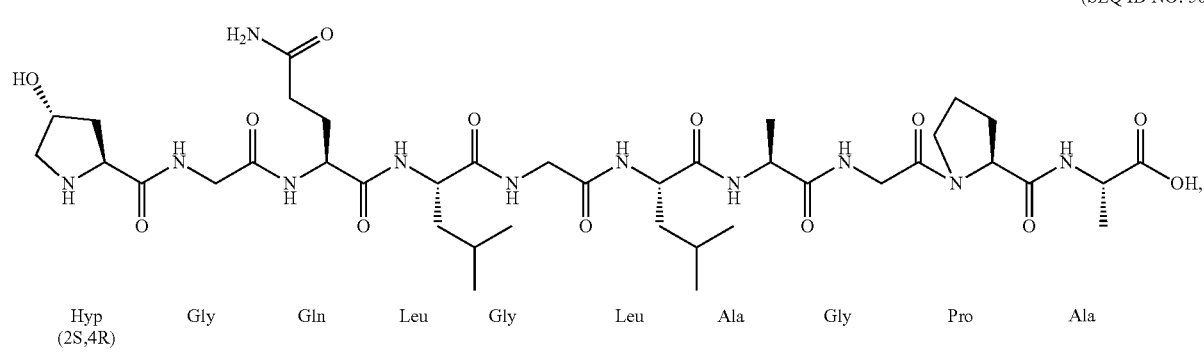
| Hyp (2S,4R) | Gly | Gln | Leu | Gly | Leu | Ala | Gly | Pro | Ala |

(SEQ ID NO: 57)
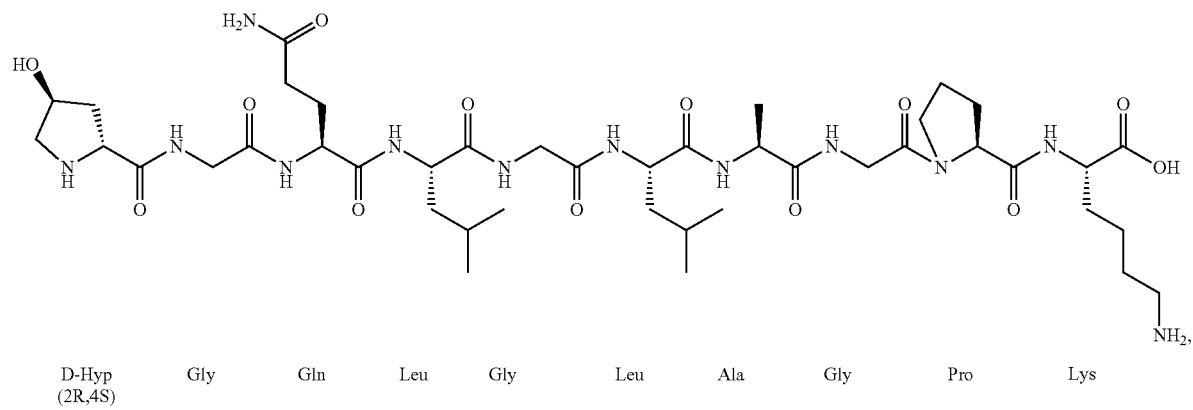
| D-Hyp (2R,4S) | Gly | Gln | Leu | Gly | Leu | Ala | Gly | Pro | Lys |
(SEQ ID NO: 58)
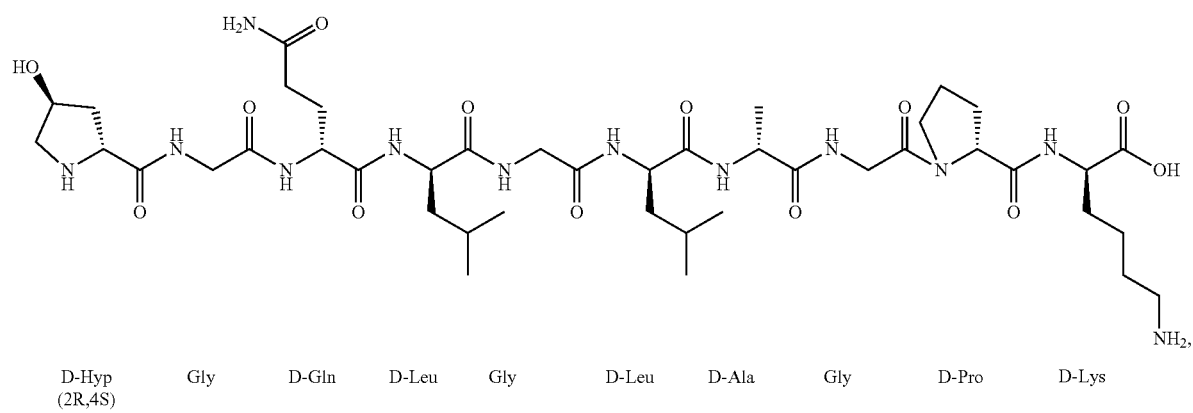
| D-Hyp (2R,4S) | Gly | D-Gln | D-Leu | Gly | D-Leu | D-Ala | Gly | D-Pro | D-Lys |
(SEQ ID NO: 60)
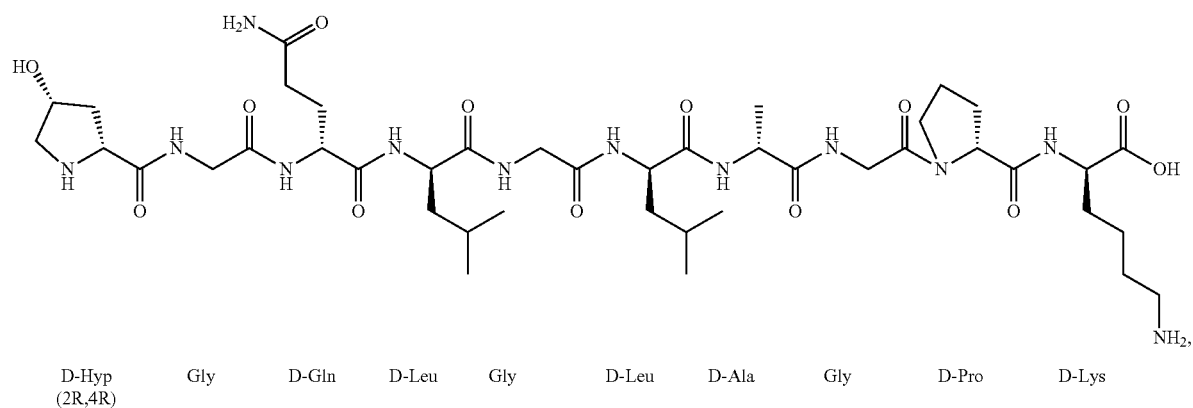
| D-Hyp (2R,4R) | Gly | D-Gln | D-Leu | Gly | D-Leu | D-Ala | Gly | D-Pro | D-Lys |

(SEQ ID NO: 72)
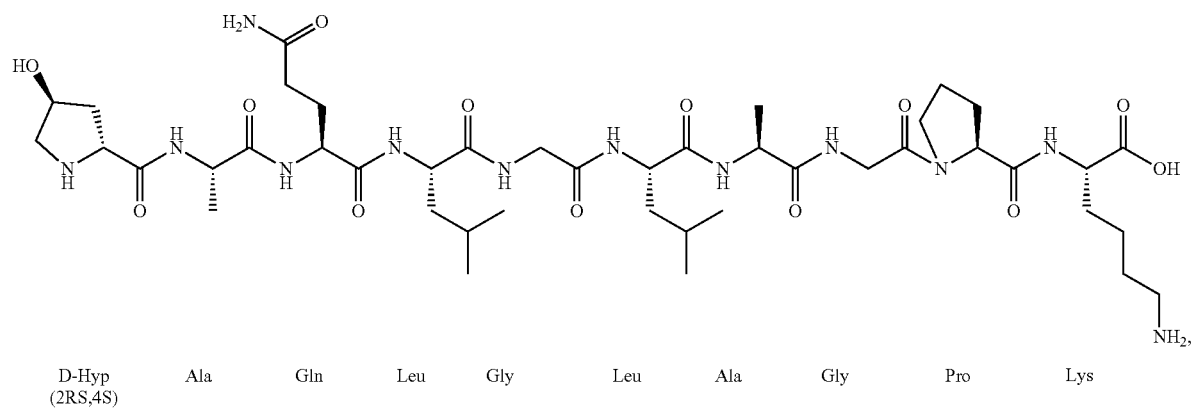
D-Hyp (2RS,4S) — Ala — Gln — Leu — Gly — Leu — Ala — Gly — Pro — Lys
(SEQ ID NO: 73)
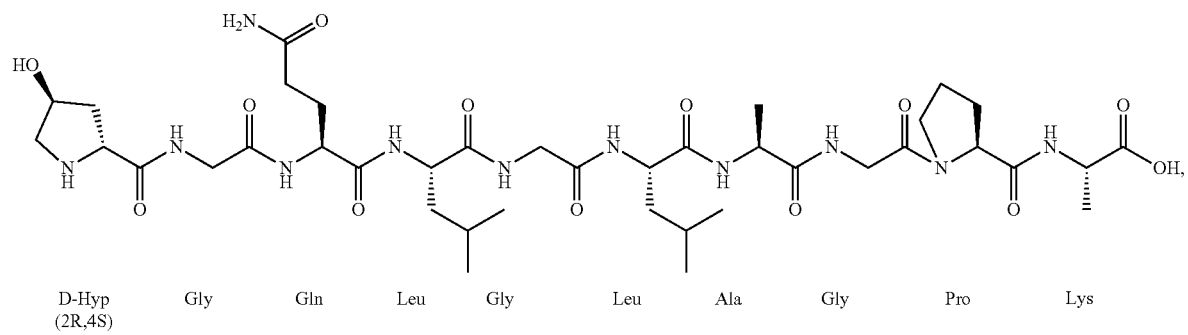
D-Hyp (2R,4S) — Gly — Gln — Leu — Gly — Leu — Ala — Gly — Pro — Lys
(SEQ ID NO: 74)
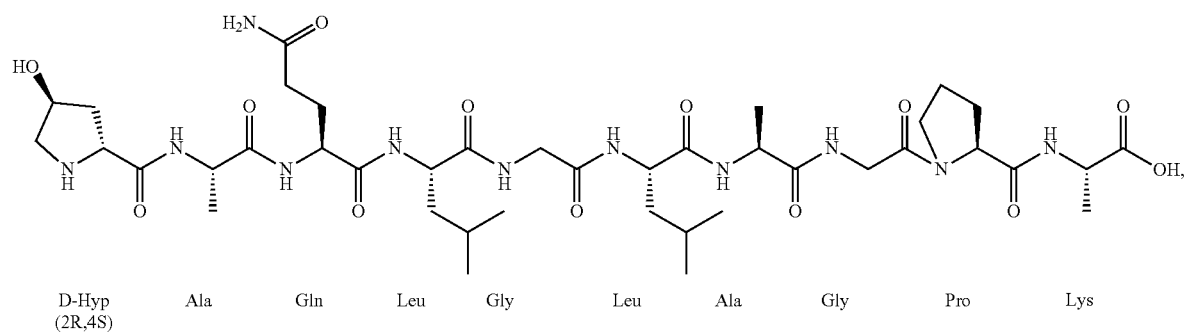
D-Hyp (2R,4S) — Ala — Gln — Leu — Gly — Leu — Ala — Gly — Pro — Lys
(SEQ ID NO: 78)
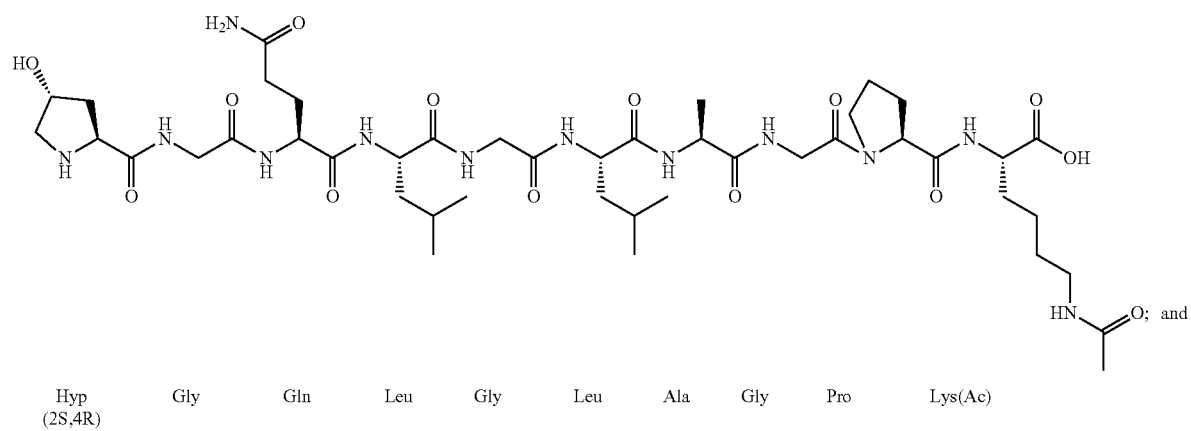
Hyp (2S,4R) — Gly — Gln — Leu — Gly — Leu — Ala — Gly — Pro — Lys(Ac)

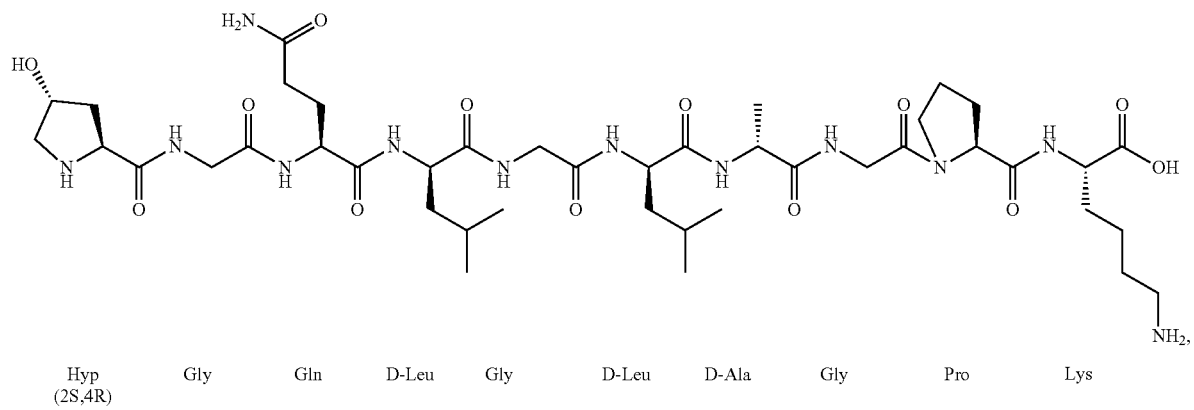

(SEQ ID NO: 80)

| Hyp (2S,4R) | Gly | Gln | D-Leu | Gly | D-Leu | D-Ala | Gly | Pro | Lys | or a pharmaceutically acceptable salt thereof.

12. A pharmaceutical composition comprising a compound of claim 1 and a pharmaceutically acceptable carrier.

13. A method of treating eye disease, comprising administering to a subject in need thereof a compound of claim 1.

14. The compound of claim 1, wherein $R^1$ is unsubstituted alkyl or arylalkyl.

15. The compound of claim 1, wherein $R^1$ is selected from

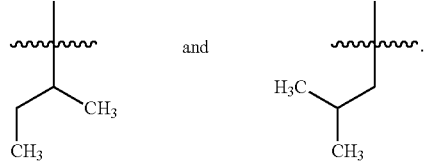

16. The compound of claim 1, wherein $R^1$ is

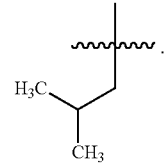

17. The compound of claim 1, wherein the compound is:

(SEQ ID NO: 10)

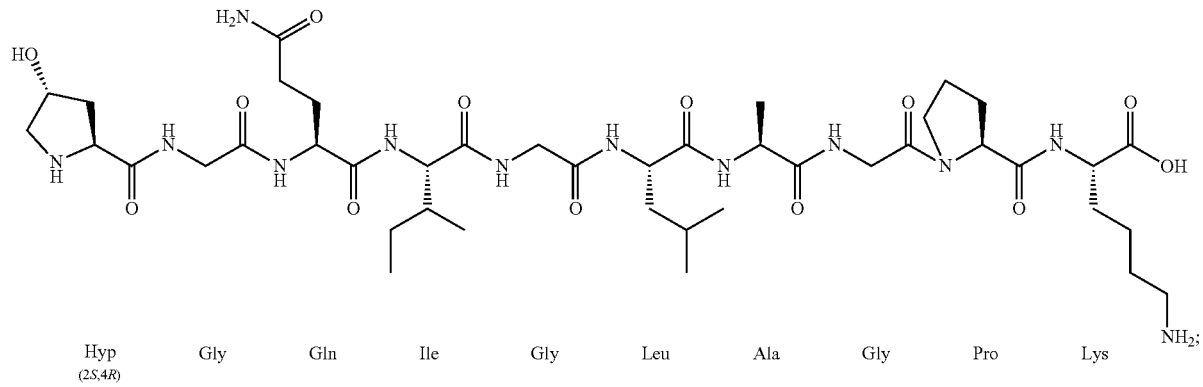

| Hyp (2S,4R) | Gly | Gln | Ile | Gly | Leu | Ala | Gly | Pro | Lys | or a pharmaceutically acceptable salt thereof.

18. The compound of claim 1, wherein the compound is:

(SEQ ID NO: 11)

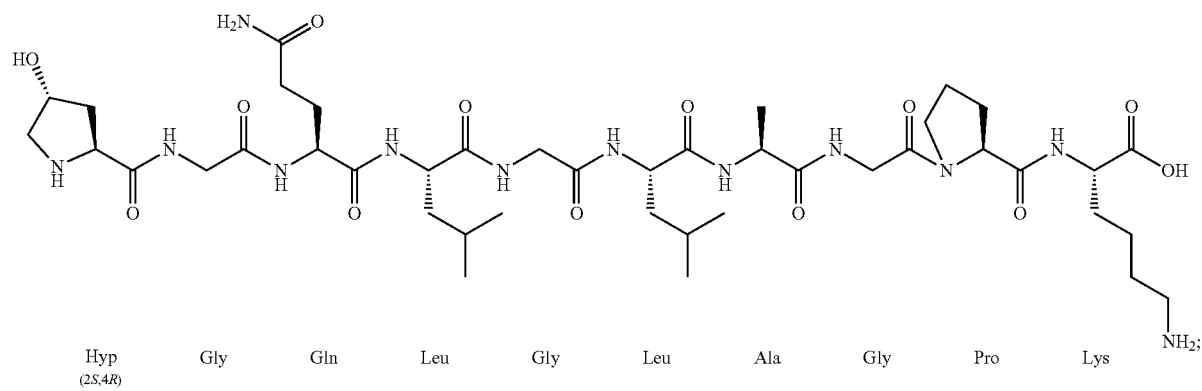

Hyp (2S,4R) — Gly — Gln — Leu — Gly — Leu — Ala — Gly — Pro — Lys or a pharmaceutically acceptable salt thereof.

19. The compound of claim 1, wherein the compound is:

(SEQ ID NO: 48)

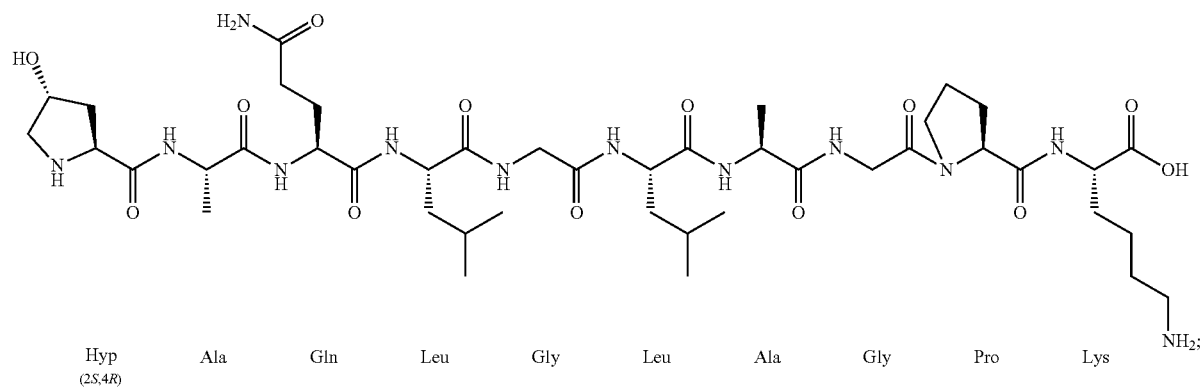

Hyp (2S,4R) — Ala — Gln — Leu — Gly — Leu — Ala — Gly — Pro — Lys or a pharmaceutically acceptable salt thereof.

20. The compound of claim 1, wherein the compound is:

(SEQ ID NO: 60)

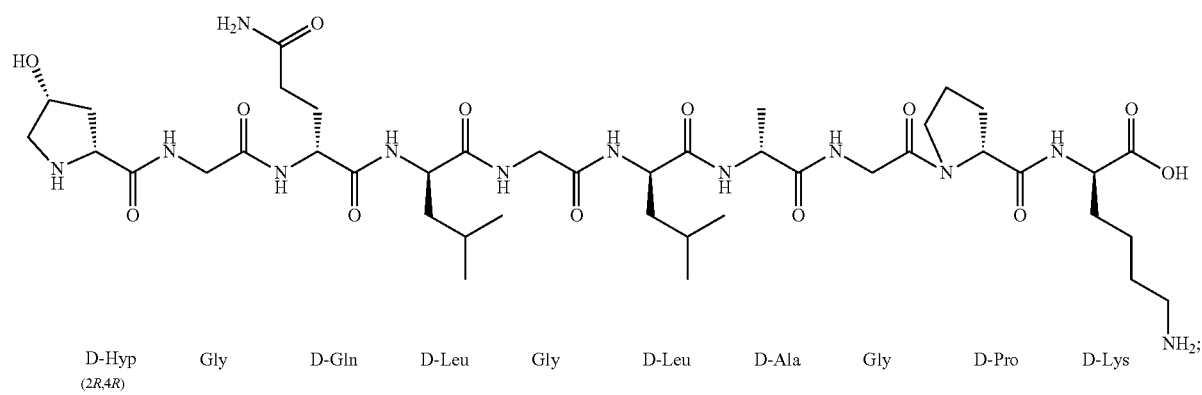

D-Hyp (2R,4R) — Gly — D-Gln — D-Leu — Gly — D-Leu — D-Ala — Gly — D-Pro — D-Lys or a pharmaceutically acceptable salt thereof.

21. The compound of claim 1, wherein the compound is a pharmaceutically acceptable salt of:

(SEQ ID NO: 10)

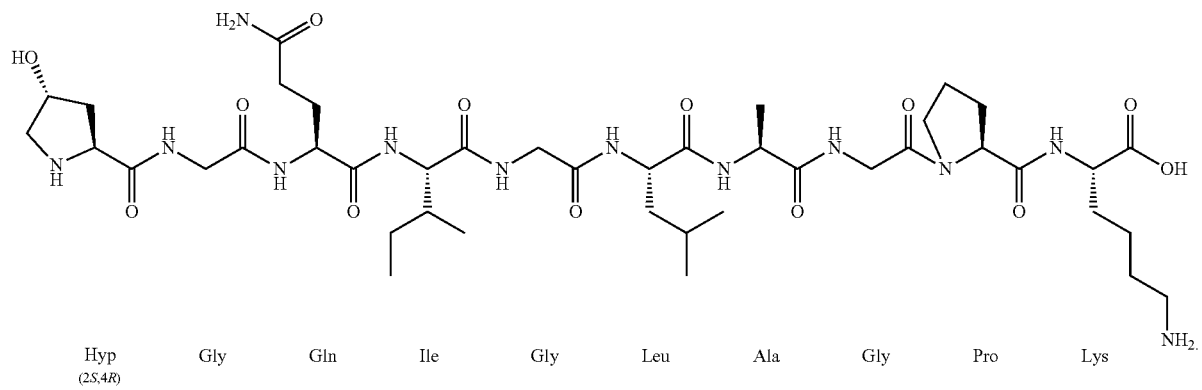

| Hyp (2S,4R) | Gly | Gln | Ile | Gly | Leu | Ala | Gly | Pro | Lys |

22. The compound of claim 1, wherein the compound is a pharmaceutically acceptable salt of:

(SEQ ID NO: 11)

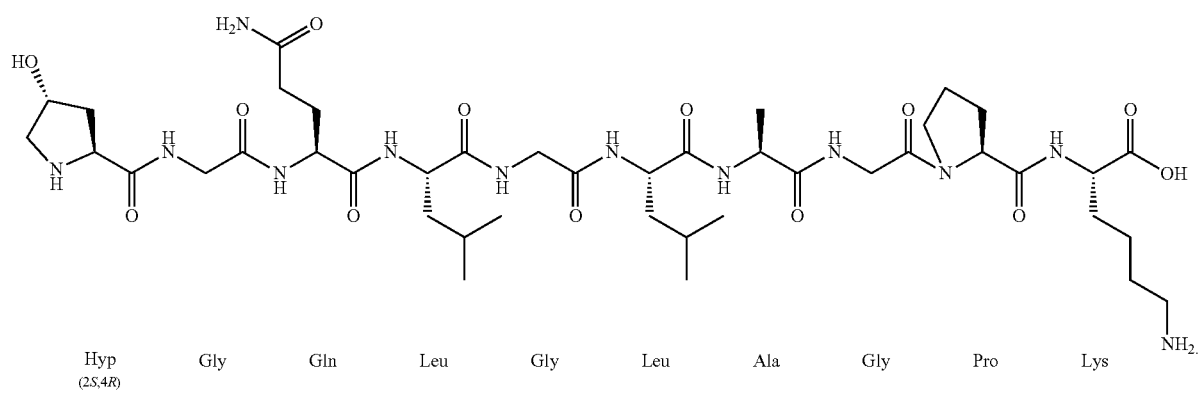

| Hyp (2S,4R) | Gly | Gln | Leu | Gly | Leu | Ala | Gly | Pro | Lys |

23. The compound of claim 1, wherein the compound is a pharmaceutically acceptable salt of:

(SEQ ID NO: 48)

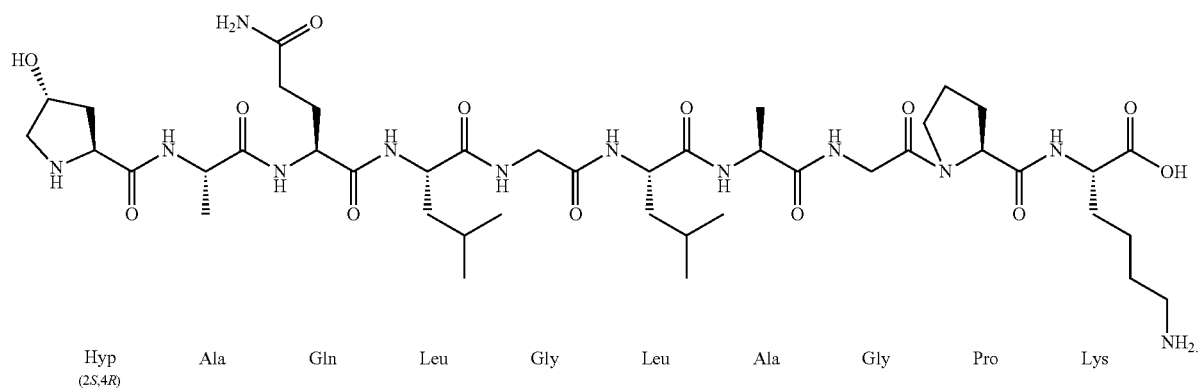

| Hyp (2S,4R) | Ala | Gln | Leu | Gly | Leu | Ala | Gly | Pro | Lys |

24. The compound of claim 1, wherein the compound is a pharmaceutically acceptable salt of:
(SEQ ID NO: 60)
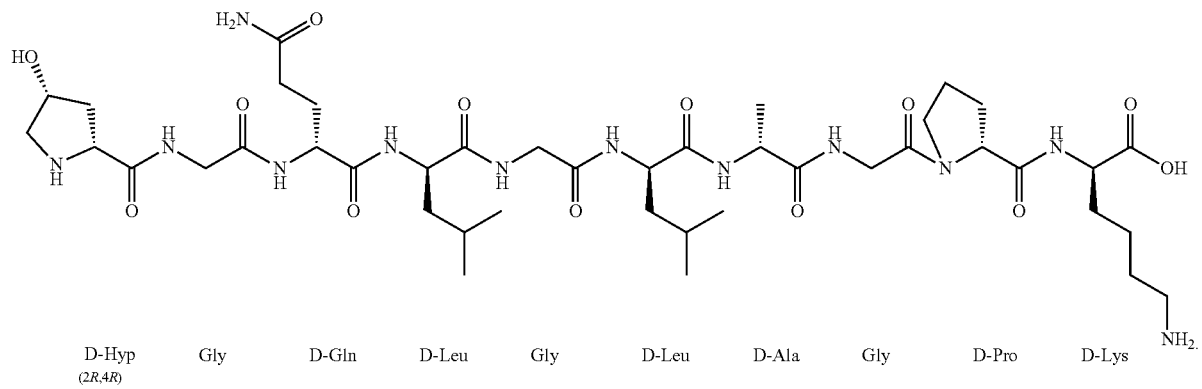
| D-Hyp (2R,4R) | Gly | D-Gln | D-Leu | Gly | D-Leu | D-Ala | Gly | D-Pro | D-Lys |
* * * * *

SEQUENCE LISTING

```
<160> NUMBER OF SEQ ID NOS: 142

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 1

Pro Gly Gln Glu Gly Leu Ala Gly Pro Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Hyp(2S,4R)

<400> SEQUENCE: 2

Pro Gly Gln Asn Gly Leu Ala Gly Pro Lys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 3

Pro Gly Gln Gln Gly Leu Ala Gly Pro Lys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 4

Pro Gly Gln His Gly Leu Ala Gly Pro Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 5

Pro Gly Gln Lys Gly Leu Ala Gly Pro Lys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 6

Pro Gly Gln Ser Gly Leu Ala Gly Pro Lys
```

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 7

Pro Gly Gln Thr Gly Leu Ala Gly Pro Lys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 8

Pro Gly Gln Ala Gly Leu Ala Gly Pro Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 9

Pro Gly Gln Val Gly Leu Ala Gly Pro Lys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 10

Pro Gly Gln Ile Gly Leu Ala Gly Pro Lys
1               5                   10

<210> SEQ ID NO 11
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 11

Pro Gly Gln Leu Gly Leu Ala Gly Pro Lys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 12

Pro Gly Gln Phe Gly Leu Ala Gly Pro Lys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 13

Pro Gly Gln Tyr Gly Leu Ala Gly Pro Lys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 14

Pro Gly Gln Trp Gly Leu Ala Gly Pro Lys
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
```

```
<400> SEQUENCE: 15

Pro Gly Gln Asp Val Leu Ala Gly Pro Lys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 16

Pro Gly Gln Asp Ile Leu Ala Gly Pro Lys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 17

Pro Gly Gln Asp Leu Leu Ala Gly Pro Lys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 18

Pro Gly Gln Asp Ala Leu Ala Gly Pro Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 19

Pro Gly Gln Asp Phe Leu Ala Gly Pro Lys
1               5                   10
```

```
<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 20

Pro Gly Gln Asp Tyr Leu Ala Gly Pro Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 21

Pro Gly Gln Asp Trp Leu Ala Gly Pro Lys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 22

Pro Gly Gln Asp His Leu Ala Gly Pro Lys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 23

Pro Gly Gln Asp Ser Leu Ala Gly Pro Lys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Hyp(2S,4R)

<400> SEQUENCE: 24

Pro Gly Gln Asp Thr Leu Ala Gly Pro Lys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (5)..(5)
<223> OTHER INFORMATION: (Me)Gly

<400> SEQUENCE: 25

Pro Gly Gln Asp Gly Leu Ala Gly Pro Lys
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (4)..(4)
<223> OTHER INFORMATION: Homo-Ser

<400> SEQUENCE: 26

Pro Gly Gln Ser Gly Leu Ala Gly Pro Lys
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (4)..(4)
<223> OTHER INFORMATION: Asp(Me)

<400> SEQUENCE: 27

Pro Gly Gln Asp Gly Leu Ala Gly Pro Lys
1               5                   10

<210> SEQ ID NO 28
<211> LENGTH: 10
```

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (4)..(4)
<223> OTHER INFORMATION: Asn(Me)

<400> SEQUENCE: 28

Pro Gly Gln Asn Gly Leu Ala Gly Pro Lys
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 29

Pro Gly Gln Leu Gly Leu Ala Gly Pro Tyr
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 30

Pro Gly Gln Leu Gly Leu Ala Gly Pro Leu
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 31

Pro Gly Gln Leu Gly Leu Ala Gly Pro Glu
1               5                   10

<210> SEQ ID NO 32
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 32

Pro Gly Gln Leu Gly Leu Ala Gly Pro Gln
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (10)..(10)
<223> OTHER INFORMATION: Nle(6-OH)

<400> SEQUENCE: 33

Pro Gly Gln Leu Gly Leu Ala Gly Pro Leu
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4S)

<400> SEQUENCE: 34

Pro Gly Gln Leu Gly Leu Ala Gly Pro Lys
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-oxo)Pro

<400> SEQUENCE: 35

Pro Gly Gln Leu Gly Leu Ala Gly Pro Lys
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: (5-oxo)Pro

<400> SEQUENCE: 36

Pro Gly Gln Leu Gly Leu Ala Gly Pro Lys
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Pro Gly Gln Leu Gly Leu Ala Gly Pro Lys
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-hydroxyMe)Pro(4R)

<400> SEQUENCE: 38

Pro Gly Gln Leu Gly Leu Ala Gly Pro Lys
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Fluoro)Pro(4R)

<400> SEQUENCE: 39

Pro Gly Gln Leu Gly Leu Ala Gly Pro Lys
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-DiMethyl)Pro

<400> SEQUENCE: 40

Pro Gly Gln Leu Gly Leu Ala Gly Pro Lys
1               5                   10

<210> SEQ ID NO 41
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 41

Pro Gly Gln Leu Gly Leu Ala
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 42

Pro Gly Gln Leu Gly Leu
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 43

Pro Gly Gln Leu Gly
1               5

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Me)Pro(4R)

<400> SEQUENCE: 44

Pro Gly Gln Leu Gly Leu Ala Gly Pro Lys
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: (5-Me)Pro(5R)

<400> SEQUENCE: 45

Pro Gly Gln Leu Gly Leu Ala Gly Pro Lys
1               5                   10

<210> SEQ ID NO 46

<400> SEQUENCE: 46

000

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Gly Gln Leu Gly Leu Ala Gly Pro Lys
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 48

Pro Ala Gln Leu Gly Leu Ala Gly Pro Lys
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 49

Pro Gly Ala Leu Gly Leu Ala Gly Pro Lys
1               5                   10

<210> SEQ ID NO 50

<400> SEQUENCE: 50

000

<210> SEQ ID NO 51
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 51

Pro Gly Gln Leu Ala Leu Ala Gly Pro Lys
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 52

Pro Gly Gln Leu Gly Ala Ala Gly Pro Lys
1               5                   10

<210> SEQ ID NO 53

<400> SEQUENCE: 53

000

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 54

Pro Gly Gln Leu Gly Leu Ala Ala Pro Lys
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 55

Pro Gly Gln Leu Gly Leu Ala Gly Ala Lys
1               5                   10

<210> SEQ ID NO 56
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 56

Pro Gly Gln Leu Gly Leu Ala Gly Pro Ala
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Hyp(2R,4S)

<400> SEQUENCE: 57

Pro Gly Gln Leu Gly Leu Ala Gly Pro Lys
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Hyp(2R,4S)
<220> FEATURE:
<221> NAME/KEY: MOD_RES
<222> LOCATION: (3)..(3)
<223> OTHER INFORMATION: D-Gln
<220> FEATURE:
<221> NAME/KEY: MOD_RES
<222> LOCATION: (4)..(4)
<223> OTHER INFORMATION: D-Leu
<220> FEATURE:
<221> NAME/KEY: MOD_RES
<222> LOCATION: (6)..(6)
<223> OTHER INFORMATION: D-Leu
<220> FEATURE:
<221> NAME/KEY: MOD_RES
<222> LOCATION: (7)..(7)
<223> OTHER INFORMATION: D-Ala
<220> FEATURE:
<221> NAME/KEY: MOD_RES
<222> LOCATION: (9)..(9)
<223> OTHER INFORMATION: D-Pro
<220> FEATURE:
<221> NAME/KEY: MOD_RES
<222> LOCATION: (10)..(10)
<223> OTHER INFORMATION: D-Lys

<400> SEQUENCE: 58

Pro Gly Gln Leu Gly Leu Ala Gly Pro Lys
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MISC_FEATURE
<222> LOCATION: (4)..(6)
<223> OTHER INFORMATION: Amide bond

<400> SEQUENCE: 59

Pro Gly Gln Glu Gly Lys Gly
1               5

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Hyp(2R,4R)
<220> FEATURE:
<221> NAME/KEY: MOD_RES
<222> LOCATION: (3)..(3)
<223> OTHER INFORMATION: D-Gln
<220> FEATURE:
<221> NAME/KEY: MOD_RES
<222> LOCATION: (4)..(4)
<223> OTHER INFORMATION: D-Leu
<220> FEATURE:
<221> NAME/KEY: MOD_RES
<222> LOCATION: (6)..(6)
<223> OTHER INFORMATION: D-Leu
<220> FEATURE:
<221> NAME/KEY: MOD_RES
<222> LOCATION: (7)..(7)
<223> OTHER INFORMATION: D-Ala
<220> FEATURE:
<221> NAME/KEY: MOD_RES
<222> LOCATION: (9)..(9)
<223> OTHER INFORMATION: D-Pro
<220> FEATURE:
<221> NAME/KEY: MOD_RES
<222> LOCATION: (10)..(10)
<223> OTHER INFORMATION: D-Lys

<400> SEQUENCE: 60

Pro Gly Gln Leu Gly Leu Ala Gly Pro Lys
1               5                   10

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000
```

```
<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Hyp(2R,4S)
<220> FEATURE:
<221> NAME/KEY: MOD_RES
<222> LOCATION: (3)..(3)
<223> OTHER INFORMATION: D-Gln
<220> FEATURE:
<221> NAME/KEY: MOD_RES
<222> LOCATION: (4)..(4)
<223> OTHER INFORMATION: D-Leu
<220> FEATURE:
<221> NAME/KEY: MOD_RES
<222> LOCATION: (6)..(6)
<223> OTHER INFORMATION: D-Leu

<400> SEQUENCE: 64

Pro Gly Gln Leu Gly Leu
1               5

<210> SEQ ID NO 65

<400> SEQUENCE: 65

000

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (4)..(4)
<223> OTHER INFORMATION: D-Leu

<400> SEQUENCE: 66

Pro Gly Gln Leu Gly
1               5

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000
```

<210> SEQ ID NO 70

<400> SEQUENCE: 70

000

<210> SEQ ID NO 71

<400> SEQUENCE: 71

000

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Hyp(2R,4S)

<400> SEQUENCE: 72

Pro Ala Gln Leu Gly Leu Ala Gly Pro Lys
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Hyp(2R,4S)

<400> SEQUENCE: 73

Pro Gly Gln Leu Gly Leu Ala Gly Pro Ala
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Hyp(2R,4S)

<400> SEQUENCE: 74

Pro Ala Gln Leu Gly Leu Ala Gly Pro Ala
1               5                   10

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)

```
<223> OTHER INFORMATION: D-Hyp(2R,4S)

<400> SEQUENCE: 75

Pro Gly Gln Leu Gly
1               5

<210> SEQ ID NO 76

<400> SEQUENCE: 76

000

<210> SEQ ID NO 77

<400> SEQUENCE: 77

000

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (10)..(10)
<223> OTHER INFORMATION: Lys(Ac)

<400> SEQUENCE: 78

Pro Gly Gln Leu Gly Leu Ala Gly Pro Lys
1               5                   10

<210> SEQ ID NO 79

<400> SEQUENCE: 79

000

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (4)..(4)
<223> OTHER INFORMATION: D-Leu
<220> FEATURE:
<221> NAME/KEY: MOD_RES
<222> LOCATION: (6)..(6)
<223> OTHER INFORMATION: D-Leu
<220> FEATURE:
<221> NAME/KEY: MOD_RES
<222> LOCATION: (7)..(7)
<223> OTHER INFORMATION: D-Ala

<400> SEQUENCE: 80

Pro Gly Gln Leu Gly Leu Ala Gly Pro Lys
1               5                   10
```

```
<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Hyp(2R,4S)
<220> FEATURE:
<221> NAME/KEY: MOD_RES
<222> LOCATION: (3)..(3)
<223> OTHER INFORMATION: D-Gln
<220> FEATURE:
<221> NAME/KEY: MOD_RES
<222> LOCATION: (4)..(4)
<223> OTHER INFORMATION: D-Leu

<400> SEQUENCE: 81

Pro Gly Gln Leu Gly
1               5

<210> SEQ ID NO 82

<400> SEQUENCE: 82

000

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (3)..(3)
<223> OTHER INFORMATION: D-Gln

<400> SEQUENCE: 83

Pro Gly Gln Leu Gly
1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Hyp(2R,4S)
<220> FEATURE:
<221> NAME/KEY: MOD_RES
<222> LOCATION: (3)..(3)
<223> OTHER INFORMATION: D-Gln

<400> SEQUENCE: 84

Pro Gly Gln Leu Gly
1               5
```

```
<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Hyp(2R,4S)
<220> FEATURE:
<221> NAME/KEY: MOD_RES
<222> LOCATION: (4)..(4)
<223> OTHER INFORMATION: D-Leu

<400> SEQUENCE: 85

Pro Gly Gln Leu Gly
1               5

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (3)..(3)
<223> OTHER INFORMATION: D-Gln
<220> FEATURE:
<221> NAME/KEY: MOD_RES
<222> LOCATION: (4)..(4)
<223> OTHER INFORMATION: D-Leu

<400> SEQUENCE: 86

Pro Gly Gln Leu Gly
1               5

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91
```

000

```
<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 92

Pro Gly Gln Ile Gly
1               5

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (10)..(10)
<223> OTHER INFORMATION: Lys-NH-PEG-NHBoc

<400> SEQUENCE: 93

Pro Gly Gln Leu Gly Leu Ala Gly Pro Lys
1               5                   10

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 94

Pro Gly Gln Asp Gly Leu Ala
1               5

<210> SEQ ID NO 95

<400> SEQUENCE: 95

000

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Hyp(2S,4R)
<220> FEATURE:
<221> NAME/KEY: MOD_RES
<222> LOCATION: (10)..(10)
<223> OTHER INFORMATION: Lys-NH-PEG1-NHCbz

<400> SEQUENCE: 96

Pro Gly Gln Leu Gly Leu Ala Gly Pro Lys
1               5                   10

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 100

Pro Gly Gln Leu Gly Leu Ala Gly Pro
1               5

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)

<400> SEQUENCE: 101

Pro Gly Gln Asp Gly Leu Ala Gly Pro Lys
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Hyp(2S,4R)
<220> FEATURE:
<221> NAME/KEY: MOD_RES
<222> LOCATION: (4)..(4)
<223> OTHER INFORMATION: Aspartimide

<400> SEQUENCE: 102

Pro Gly Gln Asp Gly Leu Ala Gly Pro Lys
1               5                   10

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (9)..(9)
<223> OTHER INFORMATION: Pro(azetidine)

<400> SEQUENCE: 103

Pro Gly Gln Leu Gly Leu Ala Gly Pro
1               5

<210> SEQ ID NO 104

<400> SEQUENCE: 104

000

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (9)..(9)
<223> OTHER INFORMATION: Pro(Methylethyl)

<400> SEQUENCE: 105

Pro Gly Gln Leu Gly Leu Ala Gly Pro
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (9)..(9)
<223> OTHER INFORMATION: Pro(pyrrolidine)
```

```
<400> SEQUENCE: 106

Pro Gly Gln Leu Gly Leu Ala Gly Pro
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (9)..(9)
<223> OTHER INFORMATION: Pro(isopropylethyl)

<400> SEQUENCE: 107

Pro Gly Gln Leu Gly Leu Ala Gly Pro
1               5

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp
<220> FEATURE:
<221> NAME/KEY: MOD_RES
<222> LOCATION: (4)..(4)
<223> OTHER INFORMATION: Glu, Asn, Gln, His, Lys, Ser, Thr, Ala, Val,
      Ile, Leu, Phe, Tyr, Trp, Homo-Ser, Asp(Me) or Asn(Me)
<220> FEATURE:
<223> OTHER INFORMATION: See specification as filed for detailed
      description of substitutions and preferred embodiments

<400> SEQUENCE: 108

Pro Gly Gln Xaa Gly Leu Ala Gly Pro Lys
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp
<220> FEATURE:
<221> NAME/KEY: MOD_RES
<222> LOCATION: (5)..(5)
<223> OTHER INFORMATION: Val, Ile, Leu, Ala, Phe, Tyr, Trp, Ser,
      Thr or (NMe)Gly
<220> FEATURE:
<223> OTHER INFORMATION: See specification as filed for detailed
      description of substitutions and preferred embodiments

<400> SEQUENCE: 109

Pro Gly Gln Asp Xaa Leu Ala Gly Pro Lys
1               5                   10
```

```
<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp
<220> FEATURE:
<221> NAME/KEY: MOD_RES
<222> LOCATION: (10)..(10)
<223> OTHER INFORMATION: Tyr, Leu, Glu, Gln, Ala or Nle(6OH)
<220> FEATURE:
<223> OTHER INFORMATION: See specification as filed for detailed
      description of substitutions and preferred embodiments

<400> SEQUENCE: 110

Pro Gly Gln Leu Gly Leu Ala Gly Pro Xaa
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Modified Pro
<220> FEATURE:
<223> OTHER INFORMATION: See specification as filed for detailed
      description of substitutions and preferred embodiments

<400> SEQUENCE: 111

Xaa Gly Gln Leu Gly Leu Ala Gly Pro Lys
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (5)..(5)
<223> OTHER INFORMATION: (N-Me)Gly

<400> SEQUENCE: 112

Pro Gly Gln Asp Gly Leu Ala Gly Pro Lys
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
```

-continued

```
<221> NAME/KEY: MOD_RES
<222> LOCATION: (1)..(1)
<223> OTHER INFORMATION: Hyp
<220> FEATURE:
<221> NAME/KEY: MOD_RES
<222> LOCATION: (10)..(10)
<223> OTHER INFORMATION: Lys(Dde)-PEG1-NHBoc

<400> SEQUENCE: 113

Pro Gly Gln Leu Gly Leu Ala Gly Pro Lys
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp
<220> FEATURE:
<221> NAME/KEY: MOD_RES
<222> LOCATION: (10)..(10)
<223> OTHER INFORMATION: Lys-PEG1-NHBoc

<400> SEQUENCE: 114

Pro Gly Gln Leu Gly Leu Ala Gly Pro Lys
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (1)..(1)
<223> OTHER INFORMATION: Hyp
<220> FEATURE:
<221> NAME/KEY: MOD_RES
<222> LOCATION: (10)..(10)
<223> OTHER INFORMATION: Lys(Dde)-PEG1-NHBoc

<400> SEQUENCE: 115

Pro Gly Gln Leu Gly Ala Leu Gly Pro Lys
1               5                   10

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp(2S,4R)
<220> FEATURE:
<221> NAME/KEY: MOD_RES
<222> LOCATION: (9)..(9)
<223> OTHER INFORMATION: Pro(diMethyl)

<400> SEQUENCE: 116

Pro Gly Gln Leu Gly Leu Ala Gly Pro
```

```
1               5
```

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp

<400> SEQUENCE: 117

```
Pro Gly Gln Leu Gly Leu Ala Gly Ala Lys
1               5                   10
```

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp

<400> SEQUENCE: 118

```
Pro Gly Gln Leu Gly Leu Ala
1               5
```

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp

<400> SEQUENCE: 119

```
Pro Gly Gln Glu Gly Leu Gly
1               5
```

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp

<400> SEQUENCE: 120

```
Pro Gly Gln Leu Gly Leu
1               5
```

<210> SEQ ID NO 121
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp

<400> SEQUENCE: 121

Pro Gly Gln Leu Gly
1               5

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp
<220> FEATURE:
<221> NAME/KEY: MOD_RES
<222> LOCATION: (4)..(4)
<223> OTHER INFORMATION: D-Leu

<400> SEQUENCE: 122

Pro Gly Gln Leu Gly
1               5

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Pro Gly Gln Asp Gly Leu Ala Gly Pro Lys
1               5                   10

<210> SEQ ID NO 124
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (4)..(4)
<223> OTHER INFORMATION: Lys(boc)

<400> SEQUENCE: 124

Ala Gly Pro Lys
1

<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
```

```
<220> FEATURE:
<221> NAME/KEY: MOD_RES
<222> LOCATION: (5)..(5)
<223> OTHER INFORMATION: Lys(boc)

<400> SEQUENCE: 125

Leu Ala Gly Pro Lys
1               5

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (6)..(6)
<223> OTHER INFORMATION: Lys(boc)

<400> SEQUENCE: 126

Gly Leu Ala Gly Pro Lys
1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (7)..(7)
<223> OTHER INFORMATION: Lys(boc)

<400> SEQUENCE: 127

Leu Gly Leu Ala Gly Pro Lys
1               5

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (1)..(1)
<223> OTHER INFORMATION: Gln(trt)
<220> FEATURE:
<221> NAME/KEY: MOD_RES
<222> LOCATION: (8)..(8)
<223> OTHER INFORMATION: Lys(boc)

<400> SEQUENCE: 128

Gln Leu Gly Leu Ala Gly Pro Lys
1               5

<210> SEQ ID NO 129
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (2)..(2)
<223> OTHER INFORMATION: Gln(trt)
<220> FEATURE:
<221> NAME/KEY: MOD_RES
<222> LOCATION: (9)..(9)
<223> OTHER INFORMATION: Lys(boc)

<400> SEQUENCE: 129

Gly Gln Leu Gly Leu Ala Gly Pro Lys
1               5

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (1)..(1)
<223> OTHER INFORMATION: Hyp(tBu)
<220> FEATURE:
<221> NAME/KEY: MOD_RES
<222> LOCATION: (3)..(3)
<223> OTHER INFORMATION: Gln(trt)
<220> FEATURE:
<221> NAME/KEY: MOD_RES
<222> LOCATION: (10)..(10)
<223> OTHER INFORMATION: Lys(boc)

<400> SEQUENCE: 130

Pro Gly Gln Leu Gly Leu Ala Gly Pro Lys
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (1)..(1)
<223> OTHER INFORMATION: Hyp
<220> FEATURE:
<223> OTHER INFORMATION: C-term OH

<400> SEQUENCE: 131

Pro Gly Gln Leu Gly Leu Ala Gly Pro Lys
1               5                   10

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Hyp(2S,4R)
<220> FEATURE:
<221> NAME/KEY: MOD_RES
<222> LOCATION: (9)..(9)
<223> OTHER INFORMATION: Pro(diethyl)

<400> SEQUENCE: 132

Pro Gly Gln Leu Gly Leu Ala Gly Pro
1               5

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (1)..(1)
<223> OTHER INFORMATION: Hyp
<220> FEATURE:
<221> NAME/KEY: MOD_RES
<222> LOCATION: (10)..(10)
<223> OTHER INFORMATION: Lys(Dde)
<220> FEATURE:
<223> OTHER INFORMATION: C-term OH

<400> SEQUENCE: 133

Pro Gly Gln Leu Gly Ala Leu Gly Pro Lys
1               5                   10

<210> SEQ ID NO 134
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (4)..(4)
<223> OTHER INFORMATION: Lys(Dde)

<400> SEQUENCE: 134

Ala Gly Pro Lys
1

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (5)..(5)
<223> OTHER INFORMATION: Lys(Dde)

<400> SEQUENCE: 135

Leu Ala Gly Pro Lys
1               5
```

```
<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (6)..(6)
<223> OTHER INFORMATION: Lys(Dde)

<400> SEQUENCE: 136

Gly Leu Ala Gly Pro Lys
1               5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (7)..(7)
<223> OTHER INFORMATION: Lys(Dde)

<400> SEQUENCE: 137

Leu Gly Leu Ala Gly Pro Lys
1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (1)..(1)
<223> OTHER INFORMATION: Gln(trt)
<220> FEATURE:
<221> NAME/KEY: MOD_RES
<222> LOCATION: (8)..(8)
<223> OTHER INFORMATION: Lys(Dde)

<400> SEQUENCE: 138

Gln Leu Gly Leu Ala Gly Pro Lys
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (2)..(2)
<223> OTHER INFORMATION: Gln(trt)
<220> FEATURE:
<221> NAME/KEY: MOD_RES
```

```
<222> LOCATION: (9)..(9)
<223> OTHER INFORMATION: Lys(Dde)

<400> SEQUENCE: 139

Gly Gln Leu Gly Leu Ala Gly Pro Lys
1               5

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (1)..(1)
<223> OTHER INFORMATION: Hyp(tBu)
<220> FEATURE:
<221> NAME/KEY: MOD_RES
<222> LOCATION: (3)..(3)
<223> OTHER INFORMATION: Gln(trt)
<220> FEATURE:
<221> NAME/KEY: MOD_RES
<222> LOCATION: (10)..(10)
<223> OTHER INFORMATION: Lys(Dde)

<400> SEQUENCE: 140

Pro Gly Gln Leu Gly Leu Ala Gly Pro Lys
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (1)..(1)
<223> OTHER INFORMATION: Hyp
<220> FEATURE:
<221> NAME/KEY: MOD_RES
<222> LOCATION: (10)..(10)
<223> OTHER INFORMATION: Lys(Dde)
<220> FEATURE:
<223> OTHER INFORMATION: C-term OH

<400> SEQUENCE: 141

Pro Gly Gln Leu Gly Leu Ala Gly Pro Lys
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (1)..(1)
<223> OTHER INFORMATION: Hyp(tBu)
<220> FEATURE:
<221> NAME/KEY: MOD_RES
<222> LOCATION: (3)..(3)
```

```
<223> OTHER INFORMATION: Gln(trt)
<220> FEATURE:
<221> NAME/KEY: MOD_RES
<222> LOCATION: (10)..(10)
<223> OTHER INFORMATION: Lys(boc)

<400> SEQUENCE: 142

Pro Gly Gln Leu Gly Leu Ala Gly Pro Lys
 1               5                  10
```